(12) United States Patent
Suzuki et al.

(10) Patent No.: US 7,402,696 B2
(45) Date of Patent: Jul. 22, 2008

(54) BENZENE COMPOUNDS

(75) Inventors: Nobuyasu Suzuki, Kawasaki (JP); Yukio Nihei, Kawasaki (JP); Hidehiro Ichinose, Kawasaki (JP); Hideyuki Tanaka, Kawasaki (JP); Noriko Yasa, Kawasaki (JP); Toshihiro Hatanaka, Kawasaki (JP); Yoko Masuzawa, Kawasaki (JP); Eiji Nakanishi, Kawasaki (JP); Nobuo Kondo, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/549,450

(22) Filed: Oct. 13, 2006

(65) Prior Publication Data

US 2007/0105899 A1    May 10, 2007

Related U.S. Application Data

(63) Continuation of application No. PCT/JP2005/007392, filed on Apr. 18, 2005.

(30) Foreign Application Priority Data

| Apr. 16, 2004 | (JP) | ................ | 2004-122199 |
| Apr. 16, 2004 | (JP) | ................ | 2004-122200 |
| Apr. 16, 2004 | (JP) | ................ | 2004-122201 |
| Jan. 28, 2005 | (JP) | ................ | 2005-021616 |

(51) Int. Cl.
*C07C 311/00* (2006.01)
*C07D 333/36* (2006.01)
*C07D 307/02* (2006.01)

(52) U.S. Cl. ............... 564/86; 549/69; 549/493

(58) Field of Classification Search ........... 564/86; 549/69, 493
See application file for complete search history.

(56) References Cited

U.S. PATENT DOCUMENTS 5,382,502 A    1/1995    Lau et al. .................. 430/552

(Continued)

FOREIGN PATENT DOCUMENTS

EP    1630162 A    3/2006

(Continued)

OTHER PUBLICATIONS

Barashkov et al., Synthetic Metals, 75, 3, 241-248, 1995.

(Continued)

*Primary Examiner*—D. Margaret Seaman
*Assistant Examiner*—Nizal S Chandrakumar

(57) ABSTRACT

The present invention provides novel benzene compounds presented by the following formulas, and analogs thereof, that exert an ACC activity-inhibiting effect that is effective in the treatment of obesity, hyperlipemia, fatty liver, hyperglycemia, impaired glucose tolerance, diabetes, diabetic complications (diabetic peripheral neuropathy, diabetic nephropathy, diabetic retinopathy, and diabetic macroangiopathy, hypertension, arteriosclerosis), hypertension, and arteriosclerosis.

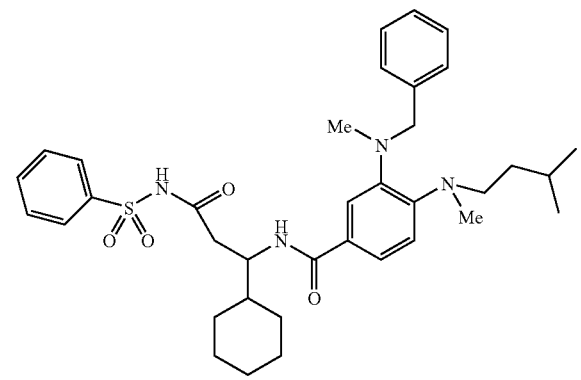

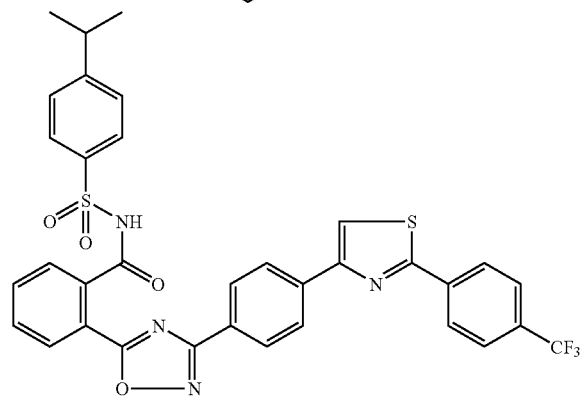

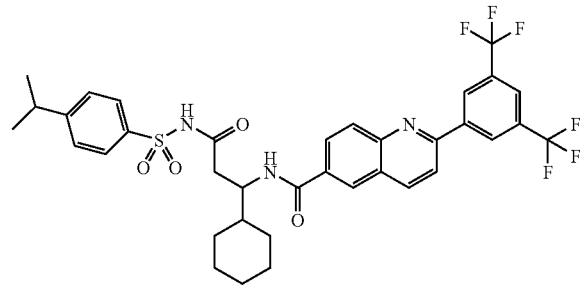

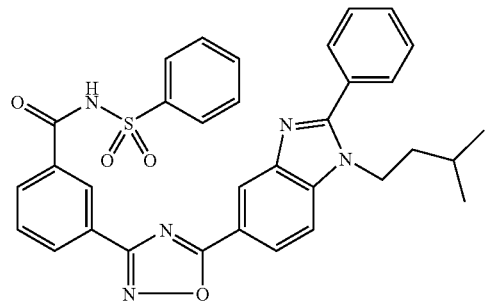

7 Claims, No Drawings

U.S. PATENT DOCUMENTS

| | | | |
|---|---|---|---|
| 5,627,181 A | 5/1997 | Riedl et al. | 514/236.8 |
| 6,096,735 A | 8/2000 | Ogawa et al. | 514/213.01 |
| 2002/0025976 A1 | 2/2002 | Chu et al. | 514/370 |
| 2002/0103203 A1 | 8/2002 | Bender et al. | 514/252.02 |
| 2003/0162818 A1 | 8/2003 | Ikawa et al. | 514/354 |
| 2003/0181764 A1 | 9/2003 | Ikawa et al. | 564/86 |
| 2003/0191323 A1 | 10/2003 | Ikawa et al. | 548/530 |
| 2004/0077628 A1 | 4/2004 | Ishihara et al. | 514/214.03 |
| 2004/0092521 A1 | 5/2004 | Altenbach et al. | 514/243 |
| 2004/0171634 A1 | 9/2004 | Kania et al. | 514/303 |
| 2005/0009815 A1 | 1/2005 | DeVita et al. | 514/227.5 |
| 2005/0026915 A1 | 2/2005 | DeVita et al. | 514/227.8 |

FOREIGN PATENT DOCUMENTS

| | | |
|---|---|---|
| JP | 60-190734 A | 9/1985 |
| JP | 11-171847 A | 6/1999 |
| JP | 11-171848 A | 6/1999 |
| WO | WO 99/26943 | 6/1999 |
| WO | WO 03/043991 | 5/2003 |
| WO | WO 03/059871 | 7/2003 |
| WO | WO 03/059886 | 7/2003 |
| WO | WO 03/082350 | 10/2003 |
| WO | WO 2004/031145 A2 * | 10/2003 |
| WO | WO 03/094912 | 11/2003 |
| WO | WO 2004/014860 | 2/2004 |
| WO | WO 2004/033427 | 4/2004 |
| WO | WO 2004/052370 | 6/2004 |
| WO | WO 2005/042513 | 5/2005 |

OTHER PUBLICATIONS

Ferles Miloslav et al., Collection of Czechoslovak Chemical Communication, 44, 9, 2672-2676, 1979.
Levert et al., J. Biological Chemistry, 277, 19, 16347-16350, 2002.
Bianchi et al., J. Cellular Biochemistry, 48, 1, 86-97, 1992.
International Search Report of PCT/JP2005/007392.

* cited by examiner

BENZENE COMPOUNDS

CROSS REFERENCES TO RELATED APPLICATIONS

This application is a continuation of International Patent Application No. PCT/JP2005/007392, filed on Apr. 18, 2005, and claims priority to Japanese Patent Application No. 2004-122199, filed on Apr. 16, 2004, Japanese Patent Application No. 2004-122200, filed on Apr. 16, 2004, Japanese Patent Application No. 2004-122201, filed on Apr. 16, 2004, and Japanese Patent Application No. 2005-021616, filed on Jan. 28, 2005, all of which are incorporated herein by reference in their entireties

BACKGROUND OF THE INVENTION

1. Field of the Invention

The present invention relates to benzene compounds, and more particularly, to novel benzene compounds having inhibition activity on acetyl CoA carboxylase ("ACC" hereinafter).

2. Discussion of the Background

It has become clear in recent years that obesity is an important risk factor for arteriosclerosis, particularly coronary artery disease. That is, it has been reported that in obese individuals, various factors such as fatty acids and TNF-α are released from accumulated visceral fat tissue, inducing insulin resistance in skeletal muscle, the liver, and fat tissue, accelerating the synthesis of neutral fat in the liver, and inducing hyperlipemia. Further, the heightened level of insulin in the blood resulting from insulin resistance not only causes impaired glucose tolerance, especially diabetes, but also stimulates renal reabsorption of Na ions and activates the sympathetic nerves, thereby increasing peripheral vascular resistance and finally resulting in hypertensive symptoms. The hyperlipemia, diabetes, and hypertension resulting from obesity cause vascular blockage such as cerebrovascular blockage and coronary artery disease as a result of arteriosclerosis, and are thought to greatly affect an individual's life prognosis.

The foundations for treating obesity are kinetotherapy and dietetic therapy. However, due to conflict with basic human desires, the necessity of striking a balance with time spent working, increased stress, and a variety of other factors, numerous difficulties present themselves when trying to achieve set objectives. Extremely obese persons sometimes undergo surgical treatment such as stomach-reducing operations and stomach bypassing surgery. However, when an obese person undergoes an abdominal operation, complications such as infection and steatolysis often result, a great amount of time is lost, and pain is experienced. Accordingly, it is considered necessary to combine the use of drugs capable of safely and easily complementing exercise and diet therapies. Examples of pharmaceuticals currently employed as anti-obesity agents are central nervous system appetite depressants such as mazindol and sibutramine and pancreatic lipase inhibitors such as orlistat. Drugs acting on the central nervous system sometimes produce severe side effects such as thirst, constipation, stomach discomfort, and on occasion, auditory and visual hallucination. Orlistat has been found to have digestive tract side effects such as diarrhea, incontinence, and flatulence. In general, these anti-obesity drugs are only slightly effective at dosages that do not produce side effects, the safety of these drugs with long-term use has yet to be established, and they have seldom been found to have an advantageous effect with regard to insulin resistance, which is closely linked to obesity.

Treatments employing biguanide agents and agonists of peroxisome proliferator-activated receptor ("PPAR" hereinafter) γ are widely employed for insulin resistance. Biguanide agents are reported to afford improvement with regard to insulin resistance and have blood-glucose-lowering and hyperlipemia-improving actions, primarily in patients with non-insulin dependent diabetes. However, single-drug treatment is not adequately effective, and it has become clear that these drugs present life-threatening side effects such as lactic acid acidosis in addition to digestive organ symptoms such as upper abdominal discomfort, nausea, and diarrhea. Similar to biguanide agents, PPAR-γ agonists afford improvement in insulin resistance, hyperglycemia, and hyperlipemia in non-insulin dependent diabetes patients, but cannot yet be considered satisfactory with regard to side effects (obesity, severe hepatitis).

ACC, an enzyme catalyzing the synthesis of malonyl CoA from acetyl CoA, is a rate-determining enzyme in the synthesis of long-chain fatty acids. The malonyl CoA that is synthesized from acetyl CoA by ACC is known to negatively control carnitine acyltransferase involved in the consumption of free long-chain fatty acids as an energy source. ACC activation is also thought to contribute to fatty acid synthesis in visceral fat tissue. Accordingly, drugs that inhibit ACC may not only block the synthesis of new long-chain fatty acids and neutral fat in the body, but may also serve as treatment agents and preventive agents for obesity symptoms and various illnesses resulting from obesity-induced hyperlipemia and insulin resistance by reducing existing fat tissue. Examples of compounds known to block ACC in mammals are acylsulfonamide derivatives, 5-(tetradecyloxy)-2-furoic acid, and biotin derivatives. It has become clear that acylsulfonamide derivatives promote the glucose uptake by skeletal muscle cells in vitro and have an effect on reducing blood glucose in diabetic model animals. Their usefulness as pharmaceuticals in humans has also been prospective (see, JP-A-11-171847, JP-A-11-171848, JP-A-11-171856, WO02/02517, WO02/02101, WO03/59886, WO03/59871, *J. Biol. Chem.*, vol. 226, pp. 497-509 (1957), *J. Biol. Chem.*, vol. 77, pp 16347-16350 (2002)).

SUMMARY OF THE INVENTION

It is one object of the present invention is to provide novel compounds which inhibit ACC activity.

It is another object of the present invention is to provide novel pharmaceutical compositions which comprise such a compound.

It is another object of the present invention is to provide novel method for preventing and/or treating obesity, hyperlipemia, fatty liver, hyperglycemia, impaired glucose tolerance, diabetes, diabetic peripheral neuropathy, diabetic nephropathy, diabetic retinopathy, diabetic macroangiopathy, hypertension, and arteriosclerosis with such a compound or pharmaceutical composition.

It is another object of the present invention is to provide novel pharmaceutical compositions which comprise such a compound and any one or two of drugs which is selected from the group consisting of insulin, sulfonylurea agents, α-glucosidase inhibitors, biguanide agents, PPAR-γ agonists, PPAR-γ antagonists, PPAR-α agonists, SGLT inhibitors, GLP-1 receptor agonists, DPP-IV inhibitors, aldose reductase inhibitors, anti-diabetic neuropathy drugs, HMG-CoA reductase inhibitors, antioxidants, calcium antagonists, angiotensin converting enzyme inhibitors, angiotensin II receptor antagonists, beta blockers, α1 blockers, diuretics, anti-obesity drugs, and low energy foods.

It is another object of the present invention is to provide novel method for preventing and/or treating obesity, hyperlipemia, fatty liver, hyperglycemia, impaired glucose tolerance, diabetes, diabetic peripheral neuropathy, diabetic nephropathy, diabetic retinopathy, diabetic macroangiopathy, hypertension, and arteriosclerosis with combination of such a compound and any one or two of drugs which is selected from the group consisting of insulin, sulfonylurea agents, α-glucosidase inhibitors, biguanide agents, PPAR-γ agonists, PPAR-γ antagonists, PPAR-α agonists, SGLT inhibitors, GLP-1 receptor agonists, DPP-IV inhibitors, aldose reductase inhibitors, anti-diabetic neuropathy drugs, HMG-CoA reductase inhibitors, antioxidants, calcium antagonists, angiotensin converting enzyme inhibitors, angiotensin II receptor antagonists, beta blockers, α1 blockers, diuretics, anti-obesity drugs, and low energy foods.

These and other objects, which will become apparent during the following detailed description, have been achieved by the inventor's vigorous research that compounds which have a specific novel skeleton, have superior ACC inhibiting activities and are useful as pharmaceuticals.

Accordingly, the present invention provides novel quinoline compounds; benzimidazole compounds; acetylene compounds, oxazole compounds, thiazole compounds and benzenediamine compounds, pharmaceutical composition comprises such a compound, particularly ACC activity inhibitors, and method for preventing or/and treating diseases by employing such a compound, a pharmaceutical composition, or an inhibitor.

The present invention comprises the following Modes 1 through 4 below.

Mode 1:

(1) A compound of formula (I-I), a pharmaceutically acceptable salt thereof, or a solvate thereof:

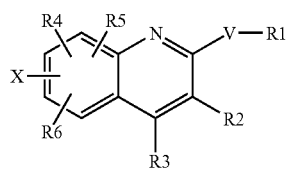

(I-I)

(wherein X represents formula (II-I) or (III-I):

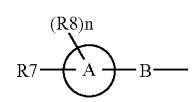

(II-I)

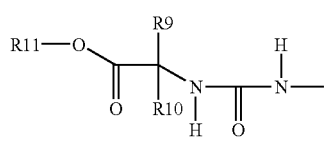

(III-I)

(wherein ring A represents a substituted or unsubstituted aromatic hydrocarbon ring, substituted or unsubstituted heteroaromatic ring, substituted or unsubstituted cycloalkene, or substituted or unsubstituted cycloalkane;

B represents a single bond or a group represented by any one of formulas (i) to (xiv):

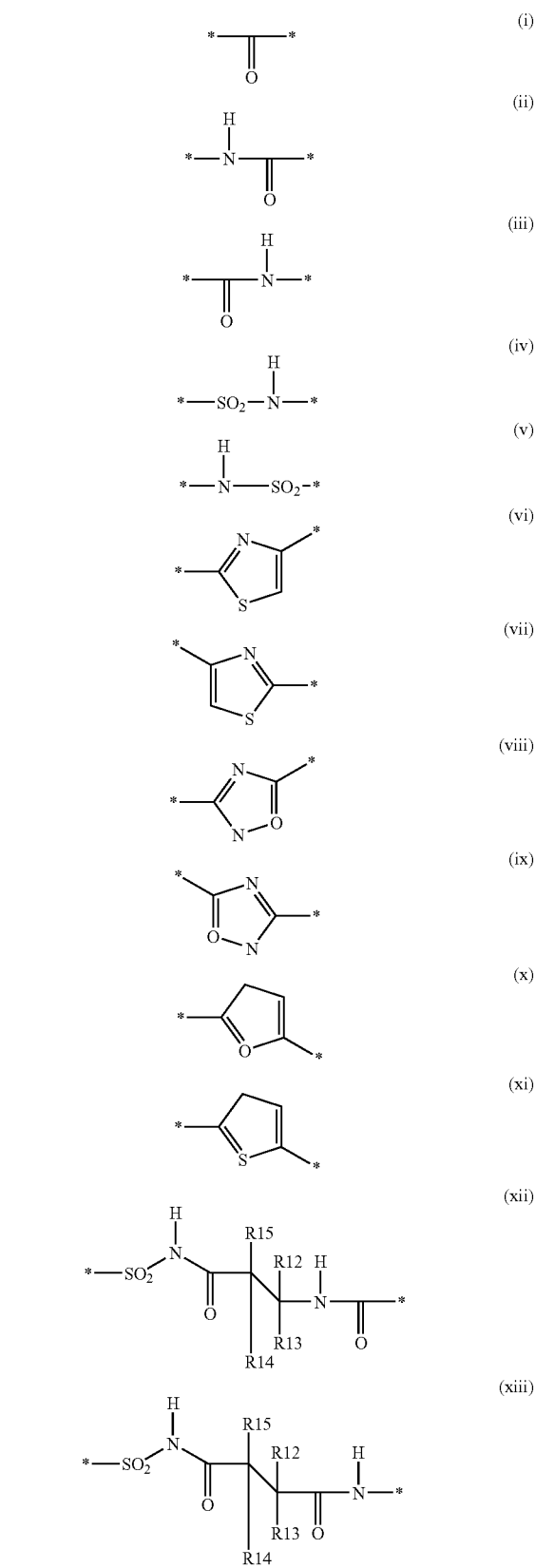

-continued (xiv)

$$*-SO_2-\underset{H}{\overset{R16}{N}}-\underset{O}{\overset{}{C}}-\underset{R17}{\overset{H}{C}}-\underset{H}{\overset{}{N}}-\underset{O}{\overset{}{C}}-N-*$$

(wherein R12 to R17, which may be the same or different, each independently represents a substituted or unsubstituted alkyl group with 1 to 12 carbon atoms, a substituted or unsubstituted alkenyl group with 2 to 12 carbon atoms, a substituted or unsubstituted alkynyl group with 2 to 12 carbon atoms, a substituted or unsubstituted alkoxy group with 1 to 12 carbon atoms, a substituted or unsubstituted acyl group with 1 to 12 carbon atoms, a substituted or unsubstituted aromatic hydrocarbon group, a substituted or unsubstituted aromatic heterocyclic group, a hydrogen atom, a hydroxyl group, a mercapto group, a substituted or unsubstituted amino group with 1 to 12 carbon atoms, a substituted or unsubstituted alkylthio group with 1 to 6 carbon atoms, a nitro group, a halogen atom, or a cyano group);

V represents a group represented by formula (x) or (xi), or a single bond;

each of R1 to R3, which may be the same or different, independently represents a substituted or unsubstituted alkyl group with 1 to 12 carbon atoms, a substituted or unsubstituted alkenyl group with 2 to 12 carbon atoms, a substituted or unsubstituted alkynyl group with 2 to 12 carbon atoms, a substituted or unsubstituted aromatic hydrocarbon group, or a substituted or unsubstituted aromatic heterocyclic group;

each of R4 to R6 and R8 to R10, which may be the same or different, independently represents a substituted or unsubstituted alkyl group with 1 to 12 carbon atoms, a substituted or unsubstituted alkenyl group with 2 to 12 carbon atoms, a substituted or unsubstituted alkynyl group with 2 to 12 carbon atoms, a substituted or unsubstituted alkoxy group with 1 to 12 carbon atoms, a substituted or unsubstituted acyl group with 1 to 12 carbon atoms, a substituted or unsubstituted aromatic hydrocarbon group, a substituted or unsubstituted aromatic heterocyclic group, a hydrogen atom, a hydroxyl group, a mercapto group, a substituted or unsubstituted amino group with 1 to 12 carbon atoms, a substituted or unsubstituted alkylthio group with 1 to 6 carbon atoms, a nitro group, a halogen atom, or a cyano group;

R7 represents a substituted or unsubstituted alkyl group with 1 to 12 carbon atoms, a substituted or unsubstituted alkenyl group with 2 to 12 carbon atoms, a substituted or unsubstituted alkynyl group with 2 to 12 carbon atoms, a substituted or unsubstituted aromatic hydrocarbon group, a substituted or unsubstituted aromatic heterocyclic group, a hydrogen atom, a hydroxyl group, a mercapto group, a nitro group, a halogen atom, a cyano group, a hydroxylamino group, a carboxyl group, the group represented by R18-W— (wherein R18 represents a substituted or unsubstituted alkyl group with 1 to 12 carbon atoms, a substituted or unsubstituted alkenyl group with 2 to 12 carbon atoms, a substituted or unsubstituted alkynyl group with 2 to 12 carbon atoms, a substituted or unsubstituted aromatic hydrocarbon group, a substituted or unsubstituted aromatic heterocyclic group and —W— represents —CH2NHCO—, —SO2NHCO—, NHCOCH2-, CONHCH2-, —NHCO—, —CONH—, —OCO—, —NHCON—, —CH2NHCS—, —SO2NHCS—, —NHCSCH2-, —CSNHCH2-, —NHCS—, —CSNH—, —NHCSNH—, —CH2NHSO2-, —CONHSO2-, —CSNHSO2-, —NHSO2CH2-, —SO2NHCH2-, —NHSO2-, —SO2NH—, —NHSO2NH—, —S—, —O—, or —NH—);

R11 represents a substituted or unsubstituted alkyl group with 1 to 12 carbon atoms, a substituted or unsubstituted alkenyl group with 2 to 12 carbon atoms, a substituted or unsubstituted alkynyl group with 2 to 12 carbon atoms, a substituted or unsubstituted acyl group with 1 to 12 carbon atoms, a substituted or unsubstituted aromatic hydrocarbon group, or a substituted or unsubstituted aromatic heterocyclic group; and n represents an integer of 0 to 5).

(2) The compound of (1), a pharmaceutically acceptable salt thereof, or a solvate thereof, wherein X is the group represented by formula (II-I).

(3) The compound of (1), a pharmaceutically acceptable salt thereof, or a solvate thereof, wherein X is the group represented by formula (III-I).

(4) The compound of (2), a pharmaceutically acceptable salt thereof, or a solvate thereof, wherein ring A represents an aromatic hydrocarbon ring substituted at positions 1 and 2, 1 and 3, or 1 and 4; an heteroaromatic ring substituted at positions 1 and 2, 1 and 3, or 1 and 4; a cycloalkene substituted at positions 1 and 2, 1 and 3, or 1 and 4; or a cycloalkane substituted at positions 1 and 1, 1 and 2, 1 and 3, or 1 and 4

(5) The compound of (4), a pharmaceutically acceptable salt thereof, or a solvate thereof, wherein ring A represents a substituted or unsubstituted benzene ring.

(6) The compound of (5), a pharmaceutically acceptable salt thereof, or a solvate thereof, wherein R7 represents a carboxyl group, hydrogen atom, or a group represented by R18-W— (wherein —W— represents —OCO—, —SO2NHCO—, or —CONHSO2-).

(7) The compound of (6), a pharmaceutically acceptable salt thereof, or a solvate thereof, wherein B is the group represented by formula (ii), (iii), (iv), (vi), (vii), (viii), (ix), or (xiv).

(8) The compound of (7), a pharmaceutically acceptable salt thereof, or a solvate thereof, wherein B is the group represented by formula (ii).

(9) The compound of (7), a pharmaceutically acceptable salt thereof, or a solvate thereof, wherein B is the group represented by formula (xiv).

(10) The compound of (8), a pharmaceutically acceptable salt thereof, or a solvate thereof, wherein R18 represents a substituted or unsubstituted alkyl group with 1 to 12 carbon atoms, a substituted or unsubstituted aromatic hydrocarbon group, or a substituted or unsubstituted aromatic heterocyclic group.

(11) The compound of (9), a pharmaceutically acceptable salt thereof, or a solvate thereof, wherein R7 represents R18-W— and R18 represents a substituted or unsubstituted alkyl group with 1 to 12 carbon atoms, a substituted or unsubstituted aromatic hydrocarbon group, or a substituted or unsubstituted aromatic heterocyclic group.

(12) The compound of (3) a pharmaceutically acceptable salt thereof, or a solvate thereof, wherein each of R9 and R10 independently represents substituted or unsubstituted alkyl groups with 1 to 12 carbon atoms, substituted or unsubstituted aromatic hydrocarbon groups, or substituted or unsubstituted aromatic heterocyclic groups.

(13) A method for preventing and/or treating hyperlipemia comprising administering to a subject in need thereof an effecting amount of a compound according to any one of (1) to (12), a pharmaceutically acceptable salt thereof, or a solvate thereof.

(14) A method for preventing and/or treating fatty liver comprising administering to a subject in need thereof an effecting amount of a compound according to any one of (1) to (12), a pharmaceutically acceptable salt thereof, or a solvate thereof.

(15) A method for preventing and/or treating hyperglycemia comprising administering to a subject in need thereof an effecting amount of a compound according to any one of (1) to (12), a pharmaceutically acceptable salt thereof, or a solvate thereof.

(16) A method for preventing and/or treating impaired glucose tolerance or diabetes comprising administering to a subject in need thereof an effecting amount of a compound according to any one of (1) to (12), a pharmaceutically acceptable salt thereof, or a solvate thereof.

(17) A method for preventing and/or treating diabetic complications, comprising administering to a subject in need thereof an effective amount of a compound according to any one of (1) to (12), a pharmaceutically acceptable salt thereof, or a solvate thereof;
wherein said diabetic complications represent diabetic peripheral neuropathy, diabetic nephropathy, diabetic retinopathy, diabetic macroangiopathy, hypertension, or arteriosclerosis.

(18) A method for preventing and/or treating hypertension and arteriosclerosis comprising administering to a subject in need thereof an effective amount of a compound according to any one of (1) to (12), a pharmaceutically acceptable salt thereof, or a solvate thereof.

(19) A method for preventing and/or treating obesity, hyperlipemia, fatty liver, impaired glucose tolerance, diabetes, diabetic complications, hypertension, arteriosclerosis, or hyperglycemia, comprising administering to a subject in need thereof an effective amount of i) a compound according to any one of (1) to (12), a pharmaceutically acceptable salt thereof, or a solvate thereof, and ii) any one or two of drugs which is selected from the group a:

a: insulin, sulfonylurea agents, α-glucosidase inhibitors, biguanide agents, PPAR-γ agonists, PPAR-γ antagonists, PPAR-α agonists, SGLT inhibitors, GLP-1 receptor agonists, DPP-IV inhibitors, aldose reductase inhibitors, anti-diabetic neuropathy drugs, HMG-CoA reductase inhibitors, antioxidants, calcium antagonists, angiotensin converting enzyme inhibitors, angiotensin II receptor antagonists, beta blockers, α1 blockers, diuretics, anti-obesity drugs, and low energy foods;
wherein said diabetic complications represent diabetic peripheral neuropathy, diabetic nephropathy, diabetic retinopathy, diabetic macroangiopathy, hypertension, or arteriosclerosis.

(20) A pharmaceutical composition comprising i) a compound according to any one of (1) to (12), a pharmaceutically acceptable salt thereof, or a solvate thereof, and ii) a pharmaceutical acceptable carrier.

(21) A pharmaceutical composition comprising i) a compound according to any one of (1) to (12), a pharmaceutically acceptable salt thereof, or a solvate thereof, and ii) any one or two of drugs which is selected from the group consisting of insulin, sulfonylurea agents, α-glucosidase inhibitors, biguanide agents, PPAR-γ agonists, PPAR-γ antagonists, PPAR-α agonists, SGLT inhibitors, GLP-1 receptor agonists, DPP-IV inhibitors, aldose reductase inhibitors, anti-diabetic neuropathy drugs, HMG-CoA reductase inhibitors, antioxidants, calcium antagonists, angiotensin converting enzyme inhibitors, angiotensin II receptor antagonists, beta blockers, α1 blockers, diuretics, anti-obesity drugs, and low energy foods.

Mode 2:

(1)' A compound of formula (I-II), a pharmaceutically acceptable salt thereof, or a solvate thereof:

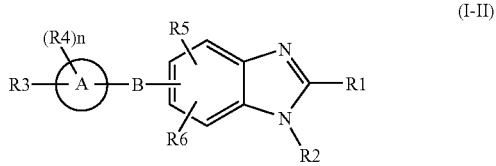

(wherein ring A represents a substituted or unsubstituted aromatic hydrocarbon ring, substituted or unsubstituted heteroaromatic ring, substituted or unsubstituted cycloalkane, or substituted or unsubstituted cycloalkene;

B represents a group represented by any one of formulas (i) to (viii):

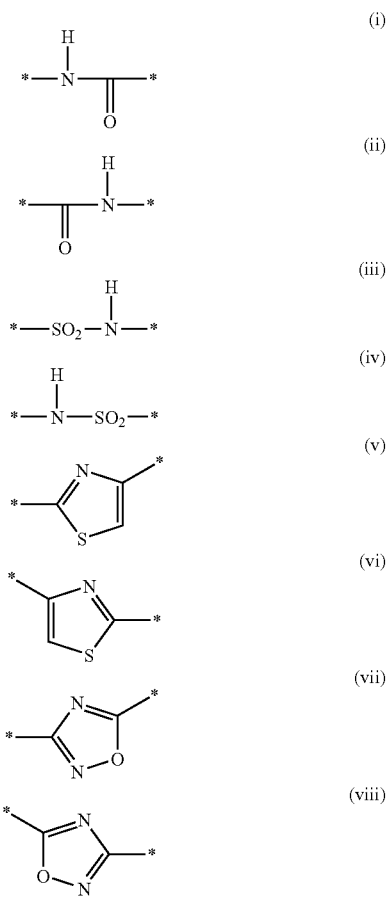

each of R1 and R2, which may be the same or different, independently represents a substituted or unsubstituted alkyl group with 1 to 12 carbon atoms, a substituted or unsubstituted alkenyl group with 2 to 12 carbon atoms, a substituted or unsubstituted alkynyl group with 2 to 12 carbon atoms, a substituted of unsubstituted aromatic hydrocarbon group, or a substituted or unsubstituted aromatic heterocyclic group;

R3 represents a substituted or unsubstituted alkyl group with 1 to 12 carbon atoms, a substituted or unsubstituted alkenyl group with 2 to 12 carbon atoms, a substituted or unsubstituted alkynyl group with 2 to 12 carbon atoms, a substituted or unsubstituted aromatic hydrocarbon group, a substituted or unsubstituted aromatic heterocyclic group, a hydrogen atom, a hydroxyl group, a mercapto group, a nitro group, a halogen atom, a cyano group, a hydroxylamino group, a carboxyl group, the group represented by R7-X— (wherein R7 represents a substituted or unsubstituted alkyl group with 1 to 12 carbon atoms, a substituted or unsubstituted alkenyl group with 2 to 12 carbon atoms, a substituted or unsubstituted alkynyl group with 2 to 12 carbon atoms, a substituted or unsubstituted aromatic hydrocarbon group, a substituted or unsubstituted aromatic heterocyclic group and —X— represents —CH2NHCO—, —SO2NHCO—, NHCOCH2-, CONHCH2-, —NHCO—, —CONH—, —OCO—, —NHCONH—, —CH2NHCS—, —SO2NHCS—, —NHCSCH2-, —CSNHCH2-, —NHCS—, —CSNH—, —NHCSNH—, —CH2NHSO2-, —CONHSO2-, —CS-NHSO2-, —NHSO2CH2-, —SO2NHCH2-, —NHSO2-, —SO2NH—, —NHSO2NH—, —S—, —O—, or —NH—);

R4, which may be the same or different, each independently represents a substituted or unsubstituted alkyl group with 1 to 12 carbon atoms, a substituted or unsubstituted alkenyl group with 2 to 12 carbon atoms, a substituted or unsubstituted alkynyl group with 2 to 12 carbon atoms, a substituted or unsubstituted alkoxy group with 1 to 12 carbon atoms, a substituted or unsubstituted acyl group with 1 to 12 carbon atoms, a substituted or unsubstituted aromatic hydrocarbon group, a substituted or unsubstituted aromatic heterocyclic group, a hydrogen atom, a hydroxyl group, a mercapto group, a substituted or unsubstituted amino group with 1 to 12 carbon atoms, a substituted or unsubstituted alkylthio group with 1 to 6 carbon atoms, a nitro group, a halogen atom, or a cyano group;

each of R5 and R6 independently represents a substituted or unsubstituted alkyl group with 1 to 12 carbon atoms, a substituted or unsubstituted alkenyl group with 2 to 12 carbon atoms, a substituted or unsubstituted alkynyl group with 2 to 12 carbon atoms, a substituted or unsubstituted alkoxy group with 1 to 12 carbon atoms, a substituted or unsubstituted acyl group with 1 to 12 carbon atoms, a substituted or unsubstituted aromatic hydrocarbon group, a substituted or unsubstituted aromatic heterocyclic group, a hydrogen atom, a hydroxyl group, a mercapto group, a substituted or unsubstituted amino group with 1 to 12 carbon atoms, a substituted or unsubstituted alkylthio group with 1 to 6 carbon atoms, a nitro group, a halogen atom, or a cyano group; and n represents an integer of 0 to 5).

(2)' The compound of (1)', a pharmaceutically acceptable salt thereof, or a solvate thereof, wherein ring A represents an aromatic hydrocarbon ring substituted at positions 1 and 2, 1 and 3, or 1 and 4; an heteroaromatic ring substituted at positions 1 and 2, 1 and 3, or 1 and 4; a cycloalkene substituted at positions 1 and 2, 1 and 3, or 1 and 4; or a cycloalkane substituted at positions 1 and 1, 1 and 2, 1 and 3, or 1 and 4.

(3)' The compound of (2)', a pharmaceutically acceptable salt thereof, or a solvate thereof, wherein ring A represents a substituted or unsubstituted benzene ring.

(4)' The compound of (3)', a pharmaceutically acceptable salt thereof, or a solvate thereof, wherein R3 represents either a carboxyl group or the group represented by R7-X— (wherein X represents any one of the groups represented by —OCO—, —SO2NHCO—, or — CONHSO2-).

(5)' The compound of (4)', a pharmaceutically acceptable salt thereof, or a solvate thereof, wherein B is the group represented by formula (i), (iii), or (vii).

(6)' The compound of (5)', a pharmaceutically acceptable salt thereof, or a solvate thereof, wherein each of R1 and R2 represents a substituted or unsubstituted alkyl group with 1 to 12 carbon atoms, a substituted or unsubstituted aromatic hydrocarbon group, or a substituted or unsubstituted aromatic heterocyclic group.

(7)' The compound of (6)', a pharmaceutically acceptable salt thereof, or a solvate thereof, wherein R3 represents the group represented by R7-X— (wherein X represents —CONHSO2-).

(8)' The compound of (7)', a pharmaceutically acceptable salt thereof, or a solvate thereof, wherein R7 represents a substituted or unsubstituted alkyl group with 1 to 12 carbon atoms, a substituted or unsubstituted aromatic hydrocarbon group, or a substituted or unsubstituted aromatic heterocyclic group.

(9)' A method for preventing and/or treating hyperlipemia comprising administering to a subject in need thereof an effecting amount of a compound according to any one of (1)' to (8)', a pharmaceutically acceptable salt thereof, or a solvate thereof.

(10)' A method for preventing and/or treating fatty liver comprising administering to a subject in need thereof an effecting amount of a compound according to any one of (1)' to (8)', a pharmaceutically acceptable salt thereof, or a solvate thereof.

(11)' A method for preventing and/or treating hyperglycemia comprising administering to a subject in need thereof an effecting amount of a compound according to any one of (1)' to (8)', a pharmaceutically acceptable salt thereof, or a solvate thereof.

(12)' A method for preventing and/or treating impaired glucose tolerance and/or diabetes comprising administering to a subject in need thereof an effecting amount of a compound according to any one of (1)' to (8)', a pharmaceutically acceptable salt thereof, or a solvate thereof.

(13)' A method for preventing and/or treating diabetic complications comprising administering to a subject in need thereof an effective amount of a compound according to any one of (1)' to (8)', a pharmaceutically acceptable salt thereof, or a solvate thereof;

wherein said diabetic complications represent diabetic peripheral neuropathy, diabetic nephropathy, diabetic retinopathy, diabetic macroangiopathy, hypertension, or arteriosclerosis (14)' A method for preventing and/or treating hypertension and arteriosclerosis comprising administering to a subject in need thereof an effective amount of a compound according to any one of (1)' to (8)', a pharmaceutically acceptable salt thereof; or a solvate thereof.

(15)' A method for preventing and/or treating obesity, hyperlipemia, fatty liver, impaired glucose tolerance, diabetes, diabetic complications, hypertension, arteriosclerosis, or hyperglycemia, comprising administering to a subject in need thereof an effective amount of i) a compound according to any one of (1)' to (8)', a pharmaceutically acceptable salt thereof, or a solvate thereof, and ii) any one or two of drugs which is selected from the group a:

a: insulin, sulfonylurea agents, α-glucosidase inhibitors, biguanide agents, PPAR-γ agonists, PPAR-γ antagonists, PPAR-α agonists, SGLT inhibitors, GLP-1 receptor agonists, DPP-1V inhibitors, aldose reductase inhibitors, anti-diabetic neuropathy drugs, HMG-CoA reductase inhibitors, antioxidants, calcium antagonists, angiotensin converting enzyme inhibitors, angiotensin II receptor antagonists, beta blockers, α1 blockers, diuretics, anti-obesity drugs, and low energy foods;

wherein said diabetic complications represent diabetic peripheral neuropathy, diabetic nephropathy, diabetic retinopathy, diabetic macroangiopathy, hypertension, or arteriosclerosis.

(16)' A pharmaceutical composition comprising i) a compound according to any one of (1)' to (8)', a pharmaceutically acceptable salt thereof, or a solvate thereof, and ii) a pharmaceutical acceptable carrier.

(17)' A pharmaceutical composition comprising i) a compound according to any one of (1)' to (8)', a pharmaceutically acceptable salt thereof, or a solvate thereof, and ii) any one or two of drugs which is selected from the group consisting of insulin, sulfonylurea agents, α-glucosidase inhibitors, biguanide agents, PPAR-γ agonists, PPAR-γ antagonists, PPAR-α agonists, SGLT inhibitors, GLP-1 receptor agonists, DPP-IV inhibitors, aldose reductase inhibitors, anti-diabetic neuropathy drugs, HMG-CoA reductase inhibitors, antioxidants, calcium antagonists, angiotensin converting enzyme inhibitors, angiotensin II receptor antagonists, beta blockers, α1 blockers, diuretics, anti-obesity drugs, and low energy foods.

Mode 3:

(1)" A compound of formula (1A-III), (1B-III), (1C-III), or (1D-III), a pharmaceutically acceptable salt thereof, or a solvate thereof:

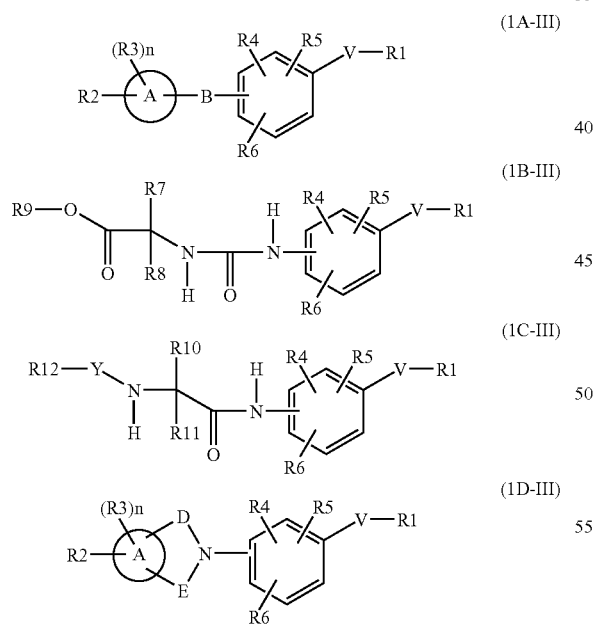

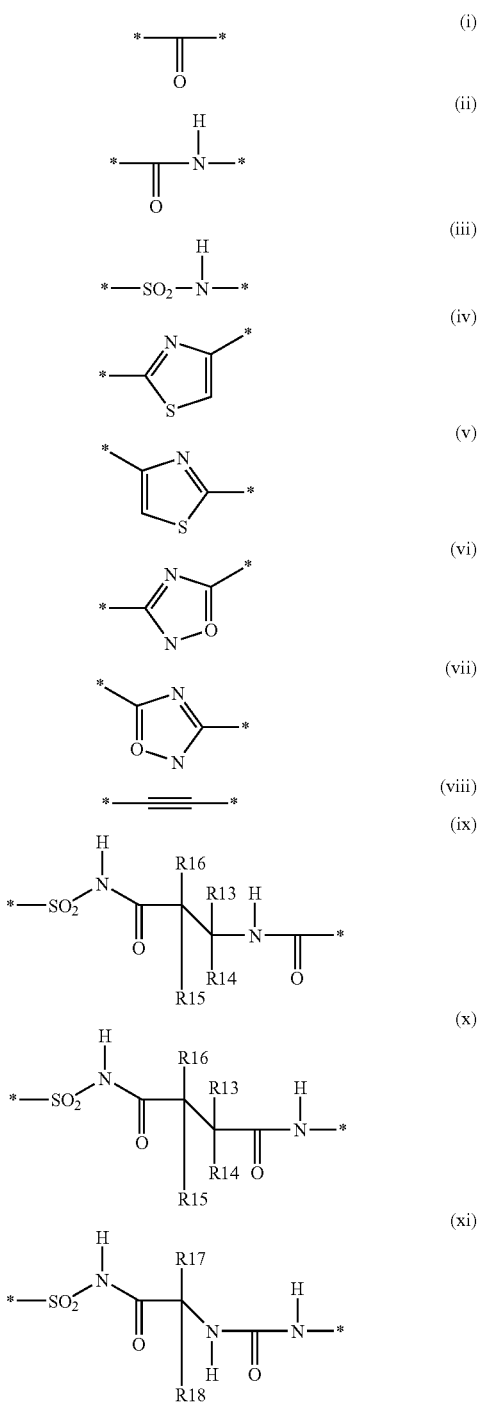

(wherein ring A represents a substituted or unsubstituted aromatic hydrocarbon ring, substituted or unsubstituted heteroaromatic ring, substituted or unsubstituted cycloalkene, or substituted or unsubstituted cycloalkane;

B represents a single bond or a group represented by formula (i), (ii), (iii), (iv), (v), (vi), (vii), (viii), (ix), (x), or (xi):

(wherein R13, R14, R15, R16, R17, and R18, which may be the same or different, each independently represents a substituted or unsubstituted alkyl group with 1 to 12 carbon atoms, substituted or unsubstituted alkenyl group with 2 to 12 carbon atoms, substituted or unsubstituted alkynyl group with 2 to 12 carbon atoms, substituted or unsubstituted alkoxy group with 1 to 12 carbon atoms, substituted or unsubstituted acyl group with 1 to 12 carbon atoms, substituted or unsubstituted aromatic hydrocarbon group, cyclic alkyl group with 3 to 8 carbon atoms, substituted or unsubstituted aromatic heterocyclic group, hydrogen atom, hydroxyl group, mercapto group, substituted or unsubstituted amino group with 1 to 12 carbon atoms, substituted or unsubstituted alkylthio group with 1 to 6 carbon atoms, nitro group, halogen atom, or cyano group, and R13 and R14, R14 and R15, or R17 and R18 may be joined together in a five- or six-membered ring);

R1 represents a substituted or unsubstituted aromatic hydrocarbon group or substituted or unsubstituted aromatic heterocyclic group;

R2 represents a substituted or unsubstituted alkyl group with 1 to 12 carbon atoms, a substituted or unsubstituted alkenyl group with 2 to 12 carbon atoms, a substituted or unsubstituted alkynyl group with 2 to 12 carbon atoms, a substituted or unsubstituted aromatic hydrocarbon group, a substituted or unsubstituted aromatic heterocyclic group, a hydrogen atom, a hydroxyl group, a mercapto group, a nitro group, a halogen atom, a cyano group, a hydroxylamino group, a carboxyl group, the group denoted by R19-X— (wherein R19 represents a substituted or unsubstituted alkyl group with 1 to 12 carbon atoms, a substituted or unsubstituted alkenyl group with 2 to 12 carbon atoms, a substituted or unsubstituted alkynyl group with 2 to 12 carbon atoms, a substituted or unsubstituted aromatic hydrocarbon group, a substituted or unsubstituted aromatic heterocyclic group and —X— represents —CH2NHCO—, —SO2NHCO—, NHCOCH2-, CONHCH2-, —NHCO—, —CONH—, —OCO—, —NHCONH—, —CH2NHCS—, —SO2NHCS—, NHCSCH2-, —CS-NHCH2-, —NHCS—, —CSNH—, —NHCSNH—, —CH2NHSO2-, —CONHSO2-, —CSNHSO2-, —NHSO2CH2-, —SO2NHCH2-, —NHSO2-, —SO2NH—, —NHSO2NH—, —S—, —O—, or —NH—); R19 and X being optionally joined by an alkylene group having 1 to 12 carbon atoms or an alkenylene groups having 2 to 12 carbon atoms;

R3 represents a substituted or unsubstituted alkyl group with 1 to 12 carbon atoms, a substituted or unsubstituted alkenyl group with 2 to 12 carbon atoms, a substituted or unsubstituted alkynyl group with 2 to 12 carbon atoms, a substituted or unsubstituted alkoxy group with 1 to 12 carbon atoms, a substituted or unsubstituted acyl group with 1 to 12 carbon atoms, a substituted or unsubstituted aromatic hydrocarbon group, a substituted or unsubstituted aromatic heterocyclic group, a hydrogen atom, a hydroxyl group, a mercapto group, a substituted or unsubstituted amino group with 1 to 12 carbon atoms, a substituted or unsubstituted alkylthio group with 1 to 6 carbon atoms, a nitro group, a halogen atom, or a cyano group;

each of R4, R5, and R6 represents substituted or unsubstituted alkyl group with 1 to 12 carbon atoms, substituted or unsubstituted alkenyl group with 2 to 12 carbon atoms, substituted or unsubstituted alkynyl group with 2 to 12 carbon atoms, substituted or unsubstituted alkoxy group with 1 to 12 carbon atoms, substituted or unsubstituted acyl group with 1 to 12 carbon atoms, substituted or unsubstituted aromatic hydrocarbon group, substituted or unsubstituted aromatic heterocyclic group, hydrogen atom, hydroxyl group, mercapto group, substituted or unsubstituted amino group with 1 to 12 carbon atoms, substituted or unsubstituted alkylthio group with 1 to 6 carbon atoms, nitro group, halogen atom, or cyano group;

V represents a group represented by formula (iv), (v), (vi), (vii), or (viii);

each of R7 and R8 represents substituted or unsubstituted alkyl group with 1 to 12 carbon atoms, substituted or unsubstituted alkenyl group with 2 to 12 carbon atoms, substituted or unsubstituted alkynyl group with 2 to 12 carbon atoms, substituted or unsubstituted alkoxy group with 1 to 12 carbon atoms, substituted or unsubstituted acyl group with 1 to 12 carbon atoms, substituted or unsubstituted aromatic hydrocarbon group, substituted or unsubstituted aromatic heterocyclic group, hydrogen atom, hydroxyl group, mercapto group, substituted or unsubstituted amino group with 1 to 12 carbon atoms, substituted or unsubstituted alkylthio groups with 1 to 6 carbon atoms, nitro group, halogen atom, or cyano group;

R9 represents a substituted or unsubstituted alkyl group with 1 to 12 carbon atoms, a substituted or unsubstituted alkenyl group with 2 to 12 carbon atoms, a substituted or unsubstituted alkynyl group with 2 to 12 carbon atoms, a substituted or unsubstituted acyl group with 1 to 12 carbon atoms, a substituted or unsubstituted aromatic hydrocarbon group, or a substituted or unsubstituted aromatic heterocyclic group; or R9 and an oxygen atom bonded thereto represent a group represented by Ra—X— (wherein Ra represents a substituted or unsubstituted aromatic hydrocarbon group and —X— represents SO2NH—);

each of R10 and R11 represents substituted or unsubstituted alkyl group with 1 to 12 carbon atoms, substituted or unsubstituted alkenyl group with 2 to 12 carbon atoms, substituted or unsubstituted alkynyl group with 2 to 12 carbon atoms, substituted or unsubstituted alkoxy group with 1 to 12 carbon atoms, substituted or unsubstituted acyl group with 1 to 12 carbon atoms, substituted or unsubstituted aromatic hydrocarbon group, substituted or unsubstituted aromatic heterocyclic group, hydrogen atom, hydroxyl group, mercapto group, substituted or unsubstituted amino group with 1 to 12 carbon atoms, substituted or unsubstituted alkylthio group with 1 to 6 carbon atoms, nitro group, halogen atom, or cyano group;

Y represents a group represented by —NHCO—, —OCO—, —NHCS—, —SO2NHCS—, —SO2-, —CONHSO2-, —CSNHSO2-, or —NHSO2-;

R12 represents a substituted or unsubstituted alkyl group with 1 to 12 carbon atoms, a substituted or unsubstituted alkenyl group with 2 to 12 carbon atoms, a substituted or unsubstituted alkynyl group with 2 to 12 carbon atoms, a substituted or unsubstituted aromatic hydrocarbon group, or a substituted or unsubstituted aromatic heterocyclic group;

each of D and E represents any one of the groups represented by —CO—, —CS—, —CH2-, —NHCO—, —N(R20)CO—, —OCO—, —NHCS—, —N(R20)CS—, —SO2-, —NHSO2-, and —N(R20)SO2- (wherein R20 represents a substituted or unsubstituted allyl group with 1 to 12 carbon atoms, a substituted or unsubstituted alkenyl group with 2 to 12 carbon atoms, a substituted or unsubstituted alkynyl with 2 to 12 carbon atoms, a substituted or unsubstituted aromatic hydrocarbon group, or a substituted or unsubstituted aromatic heterocyclic group); and n represents 1, 2, 3, 4, or 5).

(2)" The compound of (1)", a pharmaceutically acceptable salt thereof, or a solvate thereof, wherein the compound is the group represented by formula (1A-III).

(3)" The compound of (1)", a pharmaceutically acceptable salt thereof, or a solvate thereof, wherein the compound is the group represented by formula (1B-III).

(4)" The compound of (1)", a pharmaceutically acceptable salt thereof, or a solvate thereof, wherein the compound is the group represented by formula (1C-III).

(5)" The compound of (1)", a pharmaceutically acceptable salt thereof, or a solvate thereof, wherein the compound is the group represented by formula (1D-III).

(6)" The compound of (2)", a pharmaceutically acceptable salt thereof, or a solvate thereof, wherein ring A represents an aromatic hydrocarbon ring substituted at positions 1 and 2, 1 and 3, or 1 and 4; an heteroaromatic ring substituted at positions 1 and 2, 1 and 3, or 1 and 4; a cycloalkene substituted at positions 1 and 2, 1 and 3, or 1 and 4; or a cycloalkane substituted at positions 1 and 1, 1 and 2, 1 and 3, or 1 and 4.

(7)" The compound of (5)", a pharmaceutically acceptable salt thereof, or a solvate thereof, wherein ring A represents a substituted or unsubstituted benzene ring.

(8)" The compound of (7)", a pharmaceutically acceptable salt thereof, or a solvate thereof, wherein R2 represents a carboxyl group, hydrogen atom, or the group represented by R19-X— (wherein —X— represents —OCO—, —SO2NHCO—, or —CONHSO2-).

(9)" The compound of (8)", a pharmaceutically acceptable salt thereof, or a solvate thereof, wherein B is the group represented by formula (ii), (iii), (iv), (v), (vi), (vii), (viii), or (xi).

(10)" The compound of (8)", a pharmaceutically acceptable salt thereof, or a solvate thereof, wherein B is the group represented by formula (ii), (iii), (iv), (v), (vi), (vii), or (viii).

(11)" The compound of (8)", a pharmaceutically acceptable salt thereof, or a solvate thereof, wherein B is the group represented by formula (xi).

(12)" The compound of (10)", a pharmaceutically acceptable salt thereof, or a solvate thereof, wherein R19 is a substituted or unsubstituted alkyl group with 1 to 12 carbon atoms, a substituted or unsubstituted aromatic hydrocarbon group, or a substituted or unsubstituted aromatic heterocyclic group.

(13)" The compound of (11)", a pharmaceutically acceptable salt thereof, or a solvate thereof, wherein R19 is a substituted or unsubstituted alkyl group with 1 to 12 carbon atoms, a substituted or unsubstituted aromatic hydrocarbon group, or a substituted or unsubstituted aromatic heterocyclic group.

(14)" The compound of (3)", a pharmaceutically acceptable salt thereof, or a solvate thereof, wherein each of R7 and R8 in formula (1B-III) represents a substituted or unsubstituted alkyl group with 1 to 12 carbon atoms, a substituted or unsubstituted aromatic hydrocarbon group, or a substituted or unsubstituted aromatic heterocyclic group.

(15)" The compound of (4)", a pharmaceutically acceptable salt thereof, or a solvate of thereof, wherein each of R10 and R11 in formula (1C-III) represents a substituted or unsubstituted alkyl group with 1 to 12 carbon atoms, a substituted or unsubstituted aromatic hydrocarbon group, or a substituted or unsubstituted aromatic heterocyclic group.

(16)" The compound of (5)", a pharmaceutically acceptable salt thereof, or a solvate thereof, wherein each of D and E in formula (1D-III) represents the group represented by —CO— or —CH2- and R2 represents a carboxyl group, hydrogen atom, or the group represented by R19-X— (wherein X— represents —OCO—, SO2NHCO—, or —CONHSO2-).

(17)" A method for preventing and/or treating hyperlipemia comprising administering to a subject in need thereof an effecting amount of a compound according to any one of (1)" to (16)", a pharmaceutically acceptable salt thereof, or a solvate thereof.

(18)" A method for preventing and/or treating fatty liver comprising administering to a subject in need thereof an effecting amount of a compound according to any one of (1)" to (16)", a pharmaceutically acceptable salt thereof, or a solvate thereof.

(19)" A method for preventing and/or treating hyperglycemia comprising administering to a subject in need thereof an effecting amount of a compound according to any one of (1)" to (16)", a pharmaceutically acceptable salt thereof, or a solvate thereof.

(20)" A method for preventing and/or treating impaired glucose tolerance or diabetes comprising administering to a subject in need thereof an effecting amount of a compound according to any one of (1)" to (16)", a pharmaceutically acceptable salt thereof, or a solvate thereof.

(21)" A method for preventing and/or treating diabetic complications comprising administering to a subject in need thereof an effective amount of a compound according to any one of (1)" to (16)", a pharmaceutically acceptable salt thereof, or a solvate thereof;

wherein said diabetic complications represent diabetic peripheral neuropathy, diabetic nephropathy, diabetic retinopathy, diabetic macroangiopathy, hypertension, or arteriosclerosis.

(22)" A method for preventing and/or treating hypertension and arteriosclerosis comprising administering to a subject in need thereof an effective amount of a compound according to any one of (1)" to (16)" a pharmaceutically acceptable salt thereof, or a solvate thereof;

(23)" A method for preventing and/or treating obesity, hyperlipemia, fatty liver, impaired glucose tolerance, diabetes, diabetic complications, hypertension, arteriosclerosis, or hyperglycemia, comprising administering to a subject in need thereof an effective amount of i) a compound according to any one of (1)" to (16)", a pharmaceutically acceptable salt thereof, or a solvate thereof, and ii) any one or two of drugs which is selected from the group A:

A: insulin, sulfonylurea agents, α-glucosidase inhibitors, biguanide agents, PPAR-γ agonists, PPAR-γ antagonists, PPAR-α agonists, SGLT inhibitors, GLP-1 receptor agonists, DPP-IV inhibitors, aldose reductase inhibitors, anti-diabetic neuropathy drugs, HMO-CoA reductase inhibitors, antioxidants, calcium antagonists, angiotensin converting enzyme inhibitors, angiotensin II receptor antagonists, beta blockers, α1 blockers, diuretics, anti obesity drugs, and low energy foods;

wherein said diabetic complications represent diabetic peripheral neuropathy, diabetic nephropathy, diabetic retinopathy, diabetic macroangiopathy, hypertension, or arteriosclerosis.

(24)" A pharmaceutical composition comprising i) a compound according to any one of (1)" to (16)", a pharmaceutically acceptable salt thereof, or a solvate thereof, and ii) a pharmaceutical acceptable carrier.

(25)" A pharmaceutical composition comprising i) a compound according to any one of (1)" to (16)", a pharmaceutically acceptable salt thereof, or a solvate thereof, and ii) any one or two of drugs which is selected from the group consisting of insulin, sulfonylurea agents, α-glucosidase inhibitors, biguanide agents, PPAR-γ agonists, PPAR-γ antagonists, PPAR-α agonists, SGLT inhibitors, GLP-1 receptor agonists, DPP-IV inhibitors, aldose reductase inhibitors, anti-diabetic neuropathy drugs, HMG-CoA reductase inhibitors, antioxidants, calcium antagonists, angiotensin converting enzyme inhibitors, angiotensin II receptor antagonists, beta blockers, α1 blockers, diuretics, anti-obesity drugs, and low energy foods.

Mode 4:

(1)''' A compound of formula (1A-IV), a pharmaceutically acceptable salt thereof, or a solvate thereof:

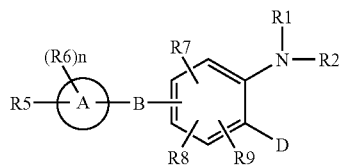

(1A-IV)

(wherein ring A represents a substituted or unsubstituted aromatic hydrocarbon ring, substituted or unsubstituted heteroaromatic ring, substituted or unsubstituted cycloalkene, or substituted or unsubstituted cycloalkane;

B represents a group represented by any one of formulas (i), (ii), (iii), (iv), (v), (vi), (vii), (viii), (ix), and (x):

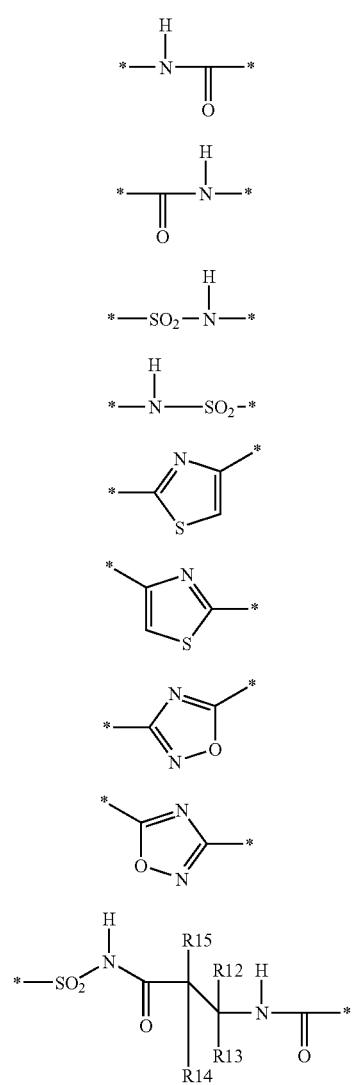

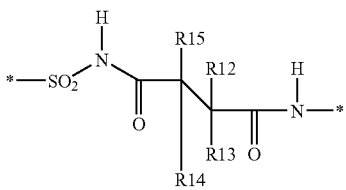

(wherein each of R12, R13, R14, and R15 represents a hydrogen atom, substituted or unsubstituted alkyl group with 1 to 12 carbon atoms, or a substituted or unsubstituted aromatic hydrocarbon group or cyclic alkyl group, R12 and R13 may be joined in a five- or six-membered ring);

D represents a hydrogen atom, nitro group, or amino group substituted with R3 and R4;

each of R1, R2, R3, and R4 represents a hydrogen atom, a substituted or unsubstituted alkyl group with 1 to 12 carbon atoms, a substituted or unsubstituted alkenyl group with 2 to 12 carbon atoms, a substituted or unsubstituted alkynyl group with 2 to 12 carbon atoms, a substituted or unsubstituted aromatic hydrocarbon group, a substituted or unsubstituted acyl group with 1 to 18 carbon atoms, a substituted or unsubstituted aromatic heterocyclic group, a cyclic alkyl group; with R1, R2, R3, and R4 being the same or different, it being possible for R1, R-2, R3, and R4 may be joined together to form a five-, six-, or seven-membered ring which may comprise nitrogen atoms, oxygen atoms, or sulfur atoms;

R5 represents a substituted or unsubstituted alkyl group with 1 to 12 carbon atoms, a substituted or unsubstituted alkenyl group with 2 to 12 carbon atoms, a substituted or unsubstituted alkynyl group with 2 to 12 carbon atoms, a substituted or unsubstituted aromatic hydrocarbon group, a substituted or unsubstituted aromatic heterocyclic group, a hydrogen atom, a hydroxyl group, a mercapto group, a nitro group, a halogen atom, a cyano group, a hydroxylamino group, a carboxyl group, the group represented by R10-X— (wherein R10 represents a hydrogen atom, a substituted or unsubstituted alkyl group with 1 to 12 carbon atoms, a substituted or unsubstituted alkenyl group with 2 to 12 carbon atoms, a substituted or unsubstituted alkynyl group with 2 to 12 carbon atoms, a substituted or unsubstituted aromatic hydrocarbon group, a substituted or unsubstituted aromatic heterocyclic group and —X— represents —CH2NHCO—, —SO2NHCO—, NHCOCH2-, —CONHCH2-, —NHCO—, —CONH—, —OCO—, —NHCONH—, —CH2NHCS—, —SO2NHCS—, —NHCSCH2-, —CSNHCH2-, —NHCS—, —CSNH—, —NHCSNH—, —CH2NHSO2-, —CONHSO2-, —CSNHSO2-, —NHSO2CH2-, —SO2NHCH2-, —NHSO2-, —SO2NH—, —NHSO2NH—, —S—, —O—, or —NH—);

R6 in (R6)n (wherein n is the number of substitutions of R6 and represents 1, 2, 3, 4, or 5, it being possible for these substituents to be the same or different) represents a substituted or unsubstituted alkyl group with 1 to 12 carbon atoms, a substituted or unsubstituted alkenyl group with 2 to 12 carbon atoms, a substituted or unsubstituted alkynyl group with 2 to 12 carbon atoms, a substituted or unsubstituted alkoxy group with 1 to 12 carbon atoms, a substituted or unsubstituted acyl group with 1 to 12 carbon atoms, a substituted or unsubstituted aromatic hydrocarbon group, a substituted or unsubstituted aromatic heterocyclic group, a hydrogen atom, a hydroxyl group, a mercapto group, a substituted or unsubstituted amino group with 1 to 12 carbon atoms, a substituted or unsubstituted alkylthio group with 1 to 6 carbon atoms, a nitro group, a halogen atom, or a cyano group; and each of R7, R8, and R9 represents a substituted or unsubstituted alkyl group with 1 to 12 carbon atoms, a substituted or unsubstituted alkenyl group with 2 to 12 carbon atoms, a substituted or unsubstituted alkynyl group with 2 to 12 carbon atoms, a substituted or unsubstituted alkoxy group with 1 to 12 carbon atoms, a substituted or unsubstituted acyl group with 1 to 12 carbon atoms, a substituted or unsubstituted aromatic hydrocarbon group, a substituted or unsubstituted aromatic heterocyclic group, a hydrogen atom, a hydroxyl group, a mercapto group, a substituted or unsubstituted amino group with 1 to 12 carbon atoms, a substituted or unsubstituted alkylthio group with 1 to 6 carbon atoms, a nitro group, a halogen atom, or a cyano group).

(2)''' The compound of (1)''', a pharmaceutically acceptable salt thereof, or a solvate thereof, wherein D represents an amino group substituted with R3 and R4.

(3)''' The compound of (1)''', a pharmaceutically acceptable salt thereof, or a solvate thereof, wherein D represents a nitro group.

(4)''' The compound of (2)''', a pharmaceutically acceptable salt thereof, or a solvate thereof, wherein A represents an aromatic hydrocarbon ring substituted at positions 1 and 2, 1 and 3, or 1 and 4; an heteroaromatic ring substituted at positions 1 and 2, 1 and 3, or 1 and 4; a cycloalkene substituted at positions 1 and 2, 1 and 3, or 1 and 4; or a cycloalkane substituted at positions 1 and 1, 1 and 2, 1 and 3, or 1 and 4.

(5)''' The compound of (3)''', a pharmaceutically acceptable salt thereof, or a solvate thereof, wherein A represents an aromatic hydrocarbon ring substituted at positions 1 and 2, 1 and 3, or 1 and 4; an heteroaromatic ring substituted at positions 1 and 2, 1 and 3, or 1 and 4; a cycloalkene substituted at positions 1 and 2, 1 and 3, or 1 and 4; or a cycloalkane substituted at positions 1 and 1, 1 and 2, 1 and 3, or 1 and 4.

(6)''' The compound of (4)''', a pharmaceutically acceptable salt thereof, or a solvate thereof, wherein A represents a substituted or unsubstituted benzene ring.

(7)''' The compound of (5)''', a pharmaceutically acceptable salt thereof, or a solvate thereof, wherein A represents a substituted or unsubstituted benzene ring.

(8)''' The compound of (6)''', a pharmaceutically acceptable salt thereof, or a solvate thereof, wherein R5 represents a hydrogen atom, carboxyl group, or the group represented by R10-X— (wherein —X— represents —OCO—, —SO2NHCO—, or —CONHSO2-).

(9)''' The compound of (7)''', a pharmaceutically acceptable salt thereof, or a solvate thereof, wherein R5 represents a hydrogen atom, carboxyl group, or the group represented by R10-X— (wherein —X— represents —OCO—, —SO2NHCO—, or —CONHSO2-).

(10)''' The compound of (8)''', a pharmaceutically acceptable salt thereof, or a solvate thereof, wherein B is the group represented by formula (i), (vii), (viii), or (ix).

(11)''' The compound of (9)''', a pharmaceutically acceptable salt thereof, or a solvate thereof, wherein B is the group represented by formula (i), (vii), (viii), or (ix).

(12)''' The compound of (10)''', a pharmaceutically acceptable salt thereof, or a solvate thereof; wherein B is the group represented by formula (ix).

(13)''' A method for preventing and/or treating hyperlipemia comprising administering to a subject in need thereof an effecting amount of a compound according to any one of (1)''' to (12)''', a pharmaceutically acceptable salt thereof, or a solvate thereof.

(14)''' A method for preventing and/or treating fatty liver comprising administering to a subject in need thereof an effecting amount of a compound according to any one of (1)''' to (12)''', a pharmaceutically acceptable salt thereof or a solvate thereof.

(15)''' A method for preventing and/or treating hyperglycemia comprising administering to a subject in need thereof an effecting amount of a compound according to any one of (1)''' to (12)''', a pharmaceutically acceptable salt thereof, or a solvate thereof.

(16)''' A method for preventing and/or treating impaired glucose tolerance or diabetes comprising administering to a subject in need thereof an effecting amount of a compound according to any one of (1)''' to (12)''', a pharmaceutically acceptable salt thereof, or a solvate thereof.

(17)''' A method for preventing and/or treating diabetic complications comprising administering to a subject in need thereof an effective amount of a compound according to any one of (1)''' to (12)''', a pharmaceutically acceptable salt thereof, or a solvate thereof;

wherein said diabetic complications represent diabetic peripheral neuropathy, diabetic nephropathy, diabetic retinopathy, diabetic macroangiopathy, hypertension, or arteriosclerosis.

(18)''' A method for preventing and/or treating hypertension and arteriosclerosis comprising administering to a subject in need thereof an effective amount of a compound according to any one of (1)''' to (12)''', a pharmaceutically acceptable salt thereof or a solvate thereof.

(19)''' A method for preventing and/or treating obesity, hyperlipemia, fatty liver, impaired glucose tolerance, diabetes, diabetic complications, hypertension, arteriosclerosis, or hyperglycemia, comprising administering to a subject in need thereof an effective amount of i) a compound according to any one of (1)''' to (12)''', a pharmaceutically acceptable salt thereof, or a solvate thereof, and ii) any one or two of drugs which is selected from the group E:

E: insulin, sulfonylurea agents, α-glucosidase inhibitors, biguanide agents, PPAR-γ agonists, PPAR-γ antagonists, PPAR-α agonists, SGLT inhibitors, GLP-1 receptor agonists, DPP-IV inhibitors, aldose reductase inhibitors, anti-diabetic neuropathy drugs, HMG-CoA reductase inhibitors, antioxidants, calcium antagonists, angiotensin converting enzyme inhibitors, angiotensin II receptor antagonists, beta blockers, α1 blockers, diuretics, anti-obesity drugs, and low energy foods;

wherein said diabetic complications represent diabetic peripheral neuropathy, diabetic nephropathy, diabetic retinopathy, diabetic macroangiopathy, hypertension, or arteriosclerosis.

(20)''' A pharmaceutical composition comprising i) a compound according to any one of (1)''' to (12)''', a pharmaceutically acceptable salt thereof, or a solvate thereof, and ii) a pharmaceutical acceptable carrier.

(21)''' A pharmaceutical composition comprising i) a compound according to any one of (1)''' to (12)''', a pharmaceutically acceptable salt thereof, or a solvate thereof, and ii) any one or two of drugs which is selected from the group consisting of insulin, sulfonylurea agents, α-glucosidase inhibitors, biguanide agents, PPAR-γ agonists, PPAR-γ antagonists, PPAR-α agonists, SGLT inhibitors, GLP-1 receptor agonists, DPP-IV inhibitors, aldose reductase inhibitors, anti-diabetic neuropathy drugs, HMG-CoA reductase inhibitors, antioxidants, calcium antagonists, angiotensin converting enzyme inhibitors, angiotensin II receptor antagonists, beta blockers, α1 blockers, diuretics, anti-obesity drugs, and low energy foods.

The present invention further provides ACC inhibitors comprising the benzene compounds of the present invention; that is, the quinoline compounds of formula (I-I); the benzimidazole compounds of formula (I-II); the acetylene, oxadiazole, or thiazole compounds of formula (1A-III), (1B-III), (1C-III), or (1D-III); the benzenediamine compounds of formula (1A-IV); pharmaceutically acceptable salts thereof; and solvates thereof.

EFFECT OF THE INVENTION

The quinoline compound of formula (I-I); the benzimidazole compound of formula (I-II); the acetylene, oxadiazole, or thiazole compound of formula (1A-III), (1B-III), (1C-III), or (1D-III); the benzenediamine compound of formula (1A-IV); pharmaceutically acceptable salts thereof, and solvates thereof can be used to treat obesity, hyperlipemia (especially obesity-induced hyperlipemia), fatty liver, and various diseases caused by insulin resistance (hyperglycemia, impaired glucose tolerance, diabetes, diabetic peripheral neuropathy, diabetic nephropathy, diabetic retinopathy, diabetic macroangiopathy), hypertension, and arteriosclerosis, rendering the present invention extremely effective as a drug for preventing, treating, and arresting the development of these diseases and as a treatment method.

Further, the compounds of the present invention have excellent ACC inhibiting activity and exhibit good solubility and internal dynamics as drugs

DETAILED DESCRIPTION OF THE PREFERRED EMBODIMENTS

The quinoline compound of formula (I-I); the benzimidazole compound of formula (I-II); the acetylene, oxadiazole, or thiazole compound of formula (1A-III), (1B-III), (1C-III), or (1D-III); the benzenediamine compound of formula (1A-IV); pharmaceutically acceptable salts thereof; and solvates thereof of the present invention will be described in detail.

In the present Specification, the term "alkyl group with 1 to 12 carbon atoms" means a straight-chain, branched chain, or cyclic alkyl group. Examples are: methyl, ethyl, n-propyl, n-butyl, 2-methylpropyl, 1-methylpropyl, 1,1-dimethylethyl, cyclobutyl, n-pentyl, 1-methylbutyl, 2-methylbutyl, 3-methylbutyl, cyclopentyl, 2,2-dimethylpropyl, n-hexyl, 1-methylpentyl, 4-methylpentyl, 1-ethylbutyl, 2-ethylbutyl, 3,3-dimethylbutyl, cyclohexyl, n-heptyl, 1-methylhexyl, 2-methylhexyl, 5-methylhexyl, 4,4-dimethylpentyl, 1-propylbutyl, 2-ethylpentyl, cyclohexylmethyl, 1,1-diethylpropyl, cycloheptyl, n-octyl, 1-methyloctyl, 6-methylheptyl, 1-ethylhexyl, 2-ethylhexyl, 2-hexylethyl, 5,5-dimethylhexyl, cyclooctyl, n-nonyl, 1-methyloctyl, 7-methyloctyl, 6,6-dimethylheptyl, n-decyl, 1-methylnonyl, 8-methylnonyl, 7,7-dimethyloctyl, n-undecyl, 1-methyldecyl, 1-methyldecyl, 9-methyldecyl, 8,8-dimethylnonyl, n-dodecyl, 1-methylundecyl, 10-methylundecyl, 5-methylundecyl, of 9,9-dimethyldecyl. These alkyl groups may be further substituted with various substituents. Examples of such substituents are: halogen atoms such as chlorine, bromine, iodine, and fluorine; silyl groups; nitro groups; amino groups; cyano groups; hydroxyl groups; alkoxy groups; thiol groups; trichloromethyl groups; trifluoromethyl groups; aromatic hydrocarbon groups such as phenyl or naphthyl groups; aromatic heterocyclic groups such as thienyl, furyl, pyridyl, isothiazolyl, or imidazolyl groups; cyclic alkyl (cycloalkyl) groups such as cyclopropyl, cyclobutyl, cyclopentyl, or cyclohexyl groups; cycloalkenyl groups such as cyclohexenyl groups; heterocyclic groups such as piperidyl or piperadyl groups; benzyloxy groups; and carboxyl groups. These may have further substituents such as halogen atoms, halogenated alkyl groups, halogenated alkoxy groups, alkyl groups, alkoxy groups, thiol groups, nitro groups, alkylamino groups, amino groups, cyano groups, hydroxyl groups, alkylthio groups, carboxyl groups, alkoxycarbonyl groups, acetamide groups, 3-(2-oxopyrrolidine-1-yl)propyl groups, 4-(3-dimethylaminopropoxy)benzyl groups, 4-(2-hydroxyethoxy)benzyl groups, and 4-(2-(diethoxyphosphoryl)vinyl)benzyl groups.

The term "alkyl groups with 1 to 12 carbon atoms" means a straight chain, branched chain, or cyclic alkyl group such as the examples given above, as well as dodecyl, tetradecyl, pentadecyl, hexadecyl, heptadecyl, octadecyl, nonadecyl, and icosyl group. These alkyl groups may be substituted with various substituents. Examples of these substituents are the same as those given above for "alkyl groups with 1 to 12 carbon atoms".

The terms "alkenyl group, alkynyl group, alkoxy group, and alkylthio group with 2 to 12 carbon atoms, 1 to 6 carbon atoms" means straight chain, cyclic, or branched chain, examples of which are the same as those given for the alkyls. These alkenyl groups, alkynyl groups, alkoxy groups, and alkylthio groups may be further substituted with various substituents. These substituents are exemplified by the same substituents given by way of example above for the substituents of alkyl groups having 1 to 12 carbon atoms.

Examples of alkenyl groups; 1-methyl-1-propenyl, 1-hexenyl, ethenyl, 4,4-dimethyl-1-pentenyl, decenyl, and icosenyl.

Examples of alkynyl groups: 1-propynyl, 2-propynyl, 1,3-hexadiynyl, 2-hexynyl, and icosatriynyl.

Examples of alkoxy groups: methoxy, ethoxy, n-hexyloxy, 1-methylbutoxy, icosyloxy, and nonadecyloxy.

Examples of alkylthio groups: methylthio, ethylthio, 2-methyl-2-propylthio, 3-methylbutylthio, and n-hexylthio.

The term "acyl group with 1 to 12 carbon atoms" means straight chain, cyclic, or branched chain, examples of which are the same as those given for the alkyls. Examples are: formyl, acetyl, propionyl, butyryl, isobutyryl, valeryl, isovaleryl, pivaloyl, lauryl, acroyl, propioloyl, methacroyl, crotonoyl, benzoyl, naphthoyl, cinnamoyl, furoyl, thienoyl, nicotinoyl, isonicotinoyl, oxalyl, malonyl, succinyl, maleoyl, fumaroyl, myristoyl, palmitoyl, and steroyl. These acyl groups may be further substituted with various substituents. These substituents are exemplified by the same substituents given by way of example above for the substituents of alkyl groups having 1 to 12 carbon atoms.

The term "substituted amino group" means a amino group which has been substituted with one or two of the substituted or unsubstituted alkyl groups, substituted or unsubstituted alkenyl groups, substituted or unsubstituted alkynyl groups, substituted or unsubstituted aromatic hydrocarbon groups, or substituted or unsubstituted aromatic heterocyclic groups represented in the present Specification. These alkyl and alkenyl groups may bond together with nitrogen atoms to form five-membered, six-membered, or seven-membered heterocycles that may contain nitrogen atoms, oxygen atoms, or sulfur atoms. Examples of such substituted amino groups are: methylamino, ethyl amino, propylamino, diethylamino, 2-propenylamino, 1-piperazinyl, morpholino, thiomorpholino, perhydroazepinyl, phenylamino, naphthylamino, pyridylamino, furylamino, thienylamino, piperidino, 1-pyrrolidinyl, and 3-butenylamino.

The term "substituted or unsubstituted aromatic hydrocarbon group" means a monocyclic or polycyclic aromatic hydrocarbon group which may have one or more of various substituents on the ring. Examples are: phenyl, methylphenyl, dimethylphenyl, methoxyphenyl, dimethoxyphenyl, fluorophenyl, dinitrophenyl, trifluoromethylphenyl, dimethylaminophenyl, mercaptophenyl, α-naphthyl, and β-naphthyl groups. The group shown below is an example of substituted aromatic hydrocarbon group:

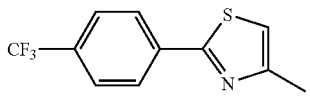

The term "substituted or unsubstituted aromatic heterocyclic group" means a group in the form of a tour-membered, five-membered, six-membered, seven-membered, eight-membered, or nine-membered ring comprising one or more hetero atoms such as nitrogen atoms, sulfur atoms, oxygen atoms, phosphorus atoms. These may be condensed into a benzene ring. There may be one or more of a variety of substituents on the ring. Examples are: pyridyl, furyl, thienyl, indolyl, quinolyl, isoquinolyl, benzofuranyl, benzothienyl, imidazolyl, benzimidazolyl, thiazolyl, oxazolyl, pyrazolyl, pyrimidyl, pyradinyl, pyridazyl, isooxazolyl, isoindolyl, and pyrrolyl.

The term "substituted or unsubstituted cyclic alkyl group" means a cyclic alkyl group having 3 to 20 carbon atoms, preferably 3 to 12 carbon atoms, that is monocyclic or polycyclic and may have one or more of various substituents on the ring. Examples are: cyclopropyl, cyclohexyl, cyclopentyl, cyclobutyl, bicyclo[1.0.1]butyl, bicyclo[3.2.1]octyl, spirobicyclohexyl, and 1,1,3-trimethylcyclohexyl groups.

The term "substituted or unsubstituted cyclic alkenyl group" means a cyclic alkenyl group having 3 to 20 carbon atoms, preferably 3 to 12 carbon atoms, that is monocyclic or polycyclic and may have one or more of various substituents on the ring. Examples are: cyclohexenyl, 1,3-cyclohexadienyl, 2,5-cyclohexadienyl, cyclopentenyl, bicyclo[2,2,2]oct-5-en-2-yl, bicyclo[5,5,1]tridec-1(12)-en-3-yl, 2-cyclohexanespiro-3'-cyclohexenyl, and 1,3,3-trimethyl-1-cyclohexenyl groups.

In the present Specification, the term "substituted or unsubstituted aromatic hydrocarbon ring" means an aromatic hydrocarbon ring that is monocyclic or polycyclic and may have one or more of various substituents on the ring. Examples are: benzene, methylbenzene, dimethylbenzene, methoxybenzene, dimethoxybenzene, fluorobenzene, dinitrobenzene, trifluoromethylbenzene, dimetlhylaminobenzene, mercaptobenzene, and naphthalene. Examples of substituents are: alkyl groups with 1 to 12 carbon atoms, alkoxy groups with 1 to 12 carbon atoms, halogeno groups, halogenated alkyl groups with 1 to 12 carbon atoms, nitro groups, substituted amino groups, and mercapto groups.

The term "substituted or unsubstituted heteroaromatic ring" means a four-membered, five-membered, six-membered, seven-membered, eight-membered, or nine-membered ring comprising one or more hetero atoms in the form of nitrogen atoms, sulfur atoms, oxygen atoms, phosphorus atoms, or the like as structural atoms. These may be condensed into a benzene ring. There may be one or more of a variety of substituents on the ring. Examples are: pyridine, furan, thiol, indole, quinoline, isoquinoline, benzofuran, benzothiol, imidazole, benzimidazole, thiazole, oxazole, pyrazole, pyrimidine, pyrazine, pyridazine, isoxazole, isoindole, and pyrrole.

The term "substituted or unsubstituted cycloalkane" means a cyclic alkane having 3 to 20 carbon atoms, preferably 3 to 12 carbon atoms, that is monocyclic or polycyclic and may have one or more of various substituents on the ring. Examples are: cyclopropane, cyclohexane, cyclopentane, cyclobutane, bicyclo[1.1.0]butane, bicyclo[3.2.1]octane, spirobicyclohexane, and 1,1,3-trimethylcyclohexane.

The term "substituted or unsubstituted cycloalkene" means a cyclic alkene group having 3 to 20 carbon atoms, preferably 3 to 12 carbon atoms, that is monocyclic or polycyclic and may have one or more of various substituents on the ring. Examples are: cyclohexene, 1,3-cyclohexadiene, 2,5-cyclohexadiene, cyclopentene, bicyclo[2,2,2]octa-5-ene, bicyclo[5,5,1]trideca-1 (12)-ene, 2-cyclohexanespiro-3'-cyclohexene, and 1,3,3-trimethyl-1-cyclohexene.

Preferred compounds of Mode 1 of the present invention will be described.

In the quinoline compound of formula (I-I), X is desirably (II-I).

When X is (II-I) in the quinoline compound of formula (I-I) that is provided by the present invention, ring A desirably comprises an aromatic hydrocarbon ring substituted at positions 1 and 2, 1 and 3, and 1 and 4; an heteroaromatic ring substituted at positions 1 and 2, 1 and 3, or 1 and 4; a cycloalkene substituted at positions 1 and 2, 1 and 3, or 1 and 4; or a cycloalkane substituted at positions 1 and 1, 1 and 2, 1 and 0.3 or 1 and 4

Of these, a monocyclic aromatic hydrocarbon ring substituted at positions 1 and 2, 1 and 3, or 1 and 4, or a cycloalkane having 6 to 8 carbon atoms that is substituted at positions 1 and 1, 1 and 2, 1 and 3, or 1 and 4 is preferred.

A quinoline compound in which ring A is a substituted or unsubstituted benzene ring is desirable.

In the quinoline compound of formula (I-I), R1 desirably represents a substituted or unsubstituted alkyl having 1 to 12 carbon atoms, a substituted or unsubstituted alkenyl having 2 to 12 carbon atoms, a substituted or unsubstituted alkynyl having 2 to 12 carbon atoms, a substituted or unsubstituted aromatic hydrocarbon group, or a substituted or unsubstituted aromatic heterocyclic group.

A substituted or unsubstituted alkyl group having 1 to 12 carbon atoms or a substituted or unsubstituted aromatic hydrocarbon group is particularly preferred. The aromatic hydrocarbon group is desirably monocyclic. Preferred substituents are halogenated alkyl groups with 1 to 12 carbon atoms, preferably trifluoromethyl groups. A halogenated alkyl group with 1 to 12 carbon atoms is desirable and di(trifluoromethyl)phenyl group is most preferred as R1.

In the quinoline compound of formula (I-I), each of R2, R3, R8, R4, R5, or R6 desirably represents hydrogen atom or substituted or unsubstituted amino group having 1 to 12 carbon atoms, with hydrogen atom being most preferred.

In the quinoline compound of formula (I-I), R7 desirably represents a carboxyl group, hydrogen atom, or the group represented by R18-W— (wherein —W— represents —OCO—, —SO2NHCO—, or CONHSO2-, preferably —SO2NHCO—). The group represented by R18-W— is particularly preferred. R18 desirably represents a substituted or unsubstituted alkyl group with 1 to 12 carbon atoms, a substituted or unsubstituted alkenyl group with 2 to 12 carbon atoms, a substituted or unsubstituted alkynyl group with 2 to 12 carbon atoms, a substituted or unsubstituted aromatic hydrocarbon group, or a substituted or unsubstituted aromatic heterocyclic group. A substituted or unsubstituted alkyl group with 1 to 12 carbon atoms or substituted or unsubstituted aromatic hydrocarbon group is preferred, A straight chain or branched chain alkyl group with 1 to 12 carbon atoms is preferred, while a straight chain or branched chain alkyl group with 3 to 6 carbon atoms is particularly preferred.

In the quinoline compound of formula (I-I) that is provided by the present invention, when X is (II-I), B desirably represents the group of formula (ii), (iii), (iv), (vi), (vii), (viii), (ix), or (xiv). The group of formula (xii) is also desirable. It is also desirable for each of R12 and R13 to represent a hydrogen atom, straight chain or cyclic alkyl group with 1 to 12 carbon atoms, or a phenyl group, it being preferable for R12 and R13 to form a ring and for both R14 and R15 to be hydrogen atoms.

In the quinoline compound that is provided by the present invention, when X is (II-I), ring A desirably represents a substituted or unsubstituted phenyl group; R1 desirably represents a substituted or unsubstituted aromatic hydrocarbon group; R2, R3, R8, R4, R5, and R6 desirably represent hydrogen atoms; B is desirably the group of formula (ii), (iii), (iv), (vii), (viii), (ix), or (xiv); and R7 is desirably the group represented by R18-W— (where —W— is the group represented by —OCO—, —SO2NHCO—, or CONHSO2-) or a hydrogen atom.

In the quinoline compound of formula (I-I), V desirably represents a single bond.

Examples of preferred quinoline compounds of the present invention represented by (I-I) are given below:

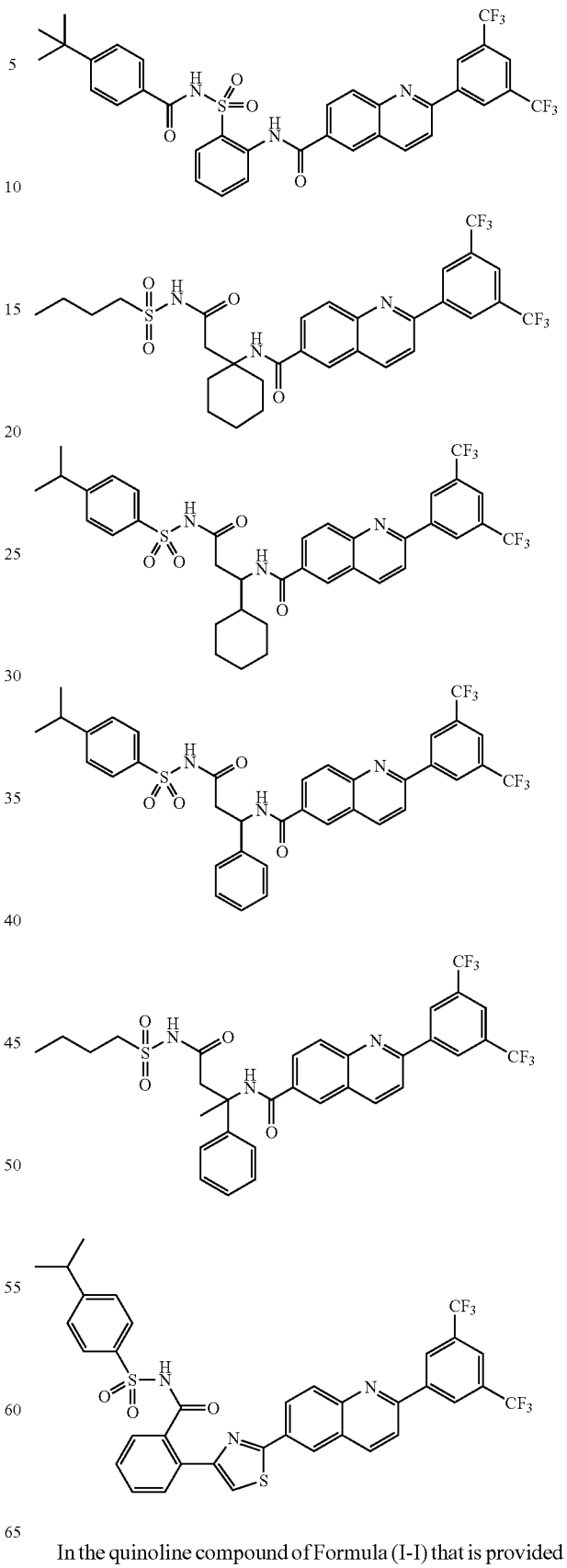

In the quinoline compound of Formula (I-I) that is provided by the present invention, when X is (III-I), R1 desirably represents a substituted or unsubstituted aromatic hydrocarbon group; R1, R3, R8, R4, R5, and R6 desirably represent hydrogen atoms; and R9 and R10 desirably represent substituted or unsubstituted alkyl groups with 1 to 12 carbon atoms, substituted or unsubstituted aromatic hydrocarbon groups, or substituted or unsubstituted aromatic heterocyclic groups.

Preferred compounds of Mode 2 of the present invention will be described.

In the benzimidazole compound of formula (I-II) that is provided by the present invention, ring A desirably represents an aromatic hydrocarbon ring substituted at positions 1 and 2, 1 and 3, or 1 and 4; an heteroaromatic ring substituted at positions 1 and 2, 1 and 3, or 1 and 4; a cycloalkene substituted at positions 1 and 2, 1 and 3, and 1 and 4; or a cycloalkane substituted at positions 1 and 1, 1 and 2, 1 and 3, or 1 and 4.

Of these, an aromatic hydrocarbon ring substituted at positions 1 and 2, 1 and 3, or 1 and 4 is preferred, with a monocyclic aromatic hydrocarbon being of even greater preference. A cycloalkane or cycloalkene desirably has 5 or more carbon atoms.

A benzimidazole compound in which ring A is a substituted or unsubstituted benzene ring is desirable.

In the benzimidazole compound of formula (I-II), each of R1 and R2 desirably represents substituted or unsubstituted alkyl group with 1 to 12 carbon atoms, a substituted or unsubstituted aromatic hydrocarbon group, or a substituted or unsubstituted aromatic heterocyclic group. Of these, a substituted or unsubstituted aromatic hydrocarbon group is preferred, with a substituted or unsubstituted phenyl group being of even greater preference. The substituent is desirably a halogenated alkyl group with 1 to 12 carbon atoms, preferably a trifluoromethyl group. The substitution positions are not specifically limited, but monosubstituted or disubstituted phenyl group is desirable.

In the benzimidazole compound of formula (I-II), R3 desirably represents a carboxyl group or the group represented by R7-X—. Of these, R7 desirably represents a substituted or unsubstituted alkyl group with 1 to 12 carbon atoms, a substituted or unsubstituted aromatic hydrocarbon group, or a substituted or unsubstituted aromatic heterocyclic group. In the formula, X desirably represents —OCO—, —SO2NHCO—, or —CONHSO2-, preferably —CONHSO2-. A substituted phenyl group is desirable as the substituted or unsubstituted aromatic hydrocarbon group, with a phenyl group substituted with an alkyl group having 1 to 12 carbon atoms being preferred.

In the benzimidazole compound of formula (I-II), B is desirably one of the groups represented by formulas (i), (iii), and (vii).

In the benzimidazole compound of formula (I-II), each of R4, R5, and R6 desirably represents hydrogen atom or substituted or unsubstituted amino group with 1 to 12 carbon atoms.

Of the compounds of formula (I-II), those in which ring A represents a substituted or unsubstituted benzene ring; each of R1 and R2 represents substituted or unsubstituted alkyl group with 1 to 12 carbon atoms or substituted or unsubstituted aromatic hydrocarbon groups; B represents the group represented by formula (i), (iii), or (vii); and R3 is the group represented by formula R7-X— (wherein X represents —CONHSO2- and R7 represents a substituted or unsubstituted alkyl with 1 to 12 carbon atoms or a substituted or unsubstituted aromatic hydrocarbon group) are preferred.

Examples of preferred benzimidazole compounds of formula (I-II) are given below:

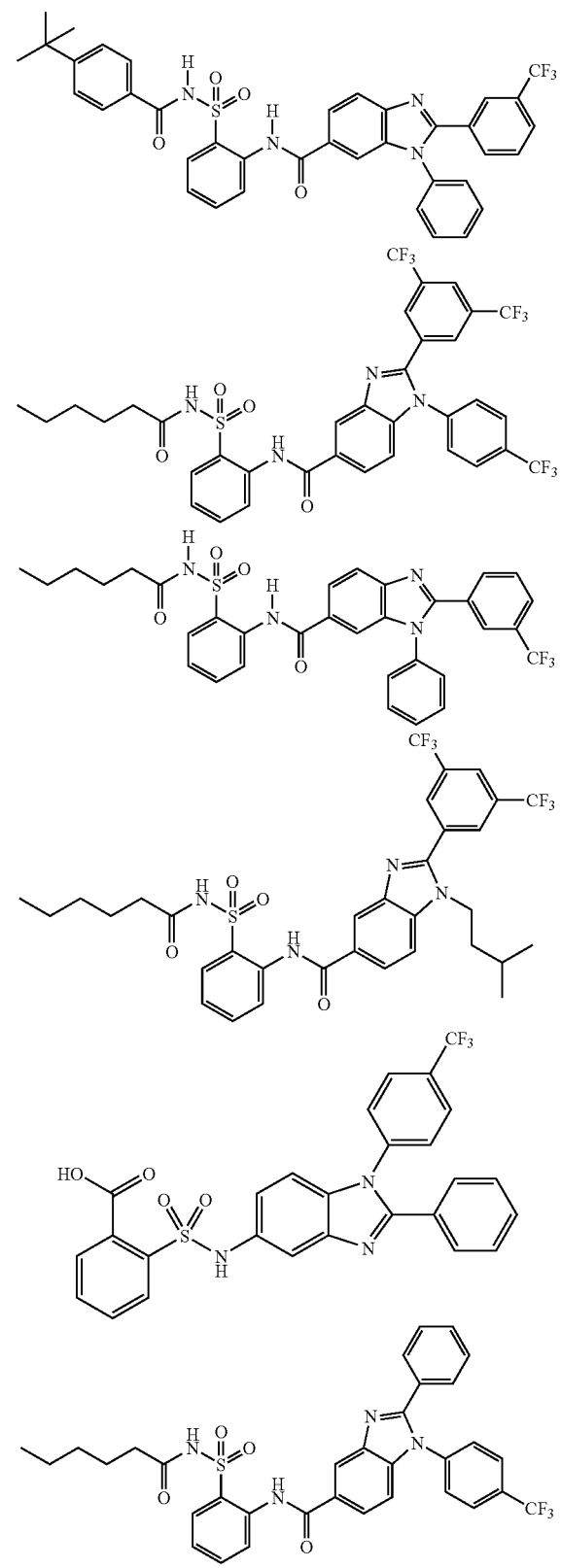

-continued

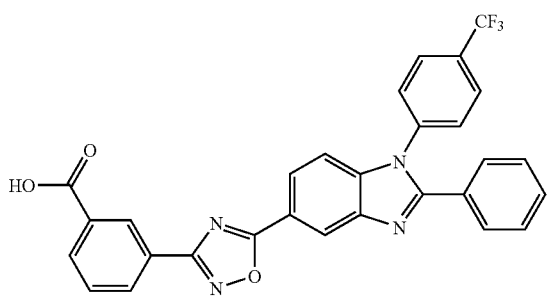

Preferred compounds of Mode 3 of the present invention will be described.

In the acetylene, oxadiazole, thiazole compound of formula (1A-III) that is provided by the present invention, ring A desirably represents an aromatic hydrocarbon ring substituted at positions 1 and 2, 1 and 3, or 1 and 4; an heteroaromatic ring substituted at positions 1 and 2, 1 and 3, or 1 and 4; a cycloalkene substituted at positions 1 and 2, 1 and 3, or 1 and 4; or a cycloalkane substituted at positions 1 and 1, 1 and 2, 1 and 3, or 1 and 4. A monocyclic aromatic hydrocarbon group substituted at positions 1 and 2, 1 and 3, or 1 and 4 is preferred. An acetylene, oxadiazole, or thiazole compound in which ring A is a substituted or unsubstituted phenyl group is desirable.

In formula (1A-III), R1 desirably represents a substituted or unsubstituted aromatic hydrocarbon group or substituted or unsubstituted aromatic heterocyclic group. A nitro group or amino group is also desirable. A substituted or unsubstituted aromatic hydrocarbon group is particularly preferred. The aromatic hydrocarbon group is desirably monocyclic. The substituent is desirably a halogenated alkyl group with 1 to 12 carbon atoms, preferably a trifluoromethyl group.

In formula (1A-III), R2 desirably represents a carboxyl group, hydrogen atom, or the group represented by R19-X— (wherein R19 desirably represents a substituted or unsubstituted alkyl group with 1 to 12 carbon atoms, a substituted or unsubstituted aromatic hydrocarbon group, or a substituted or unsubstituted aromatic heterocyclic group, with hydrogen atom also being desirable, and —X— represents —SO2NHCO—, —OCO—, or —CONHSO2-). It is also desirable for R19 and X to be joined by an alkylene group with 1 to 12 carbon atoms, an alkenylene group with 2 to 12 carbon atoms, or the like. R2 is preferably a group represented by R19-X—. Here, R19 desirably represents a hydrogen atom, substituted or unsubstituted aromatic hydrocarbon group, or substituted or unsubstituted aromatic heterocyclic group. Desirable substituents on the aromatic hydrocarbon group include straight chain and branched chain alkyl groups with 1 to 12 carbon atoms, nitro groups, and substituted or unsubstituted amino groups, such as amino groups substituted with one or two straight chain or branched chain alkyl groups with 1 to 12 carbon atoms, alkoxy groups with 1 to 12 carbon atoms, carboxyl groups, and alkoxycarbonyl groups with 1 to 12 carbon atoms. Preferred aromatic heterocyclic groups include pyridyl, thienyl, and pyrazolyl groups. Preferred substituents on the aromatic heterocyclic group are straight chain or branched chain alkyl groups with 1 to 12 carbon atoms. —X— desirably represents —SO2NHCO—, —OCO—, or NHSO2-.

In formula (1A-III), each of R3, R4, R5, and R6 desirably represents hydrogen atom or substituted or unsubstituted amino group with 1 to 12 carbon atoms. Optimally, R3, R4, R5, and R6 represent hydrogen atoms.

In formula (1A-III), B desirably represents the group represented by formula (ii), (iii), (iv), (v), (vi), (viii), or (xi). The group represented by formula (ii), (iii), (iv), (v), (vi), (vii), or (viii) is preferred.

In formula (1A-III), V desirably represents the group represented by formula (iv), (v), (vi), (vii), or (viii). The group represented by formula (iv), (v), (vi), or (vii) is particularly preferred.

Of the compounds of formula (1A-III), those in which ring A represents a substituted or unsubstituted benzene ring; R1 represents a substituted or unsubstituted aromatic hydrocarbon group; R2 represents a carboxyl group, hydrogen atom, or the group represented by R19-X— (wherein R19 represents a substituted or unsubstituted allyl group with 1 to 12 carbon atoms or a substituted or unsubstituted aromatic hydrocarbon group; —X— represents —SO2NHCO— or —CONHSO2-); R3, R5, R6, R7, and R8 represent hydrogen atoms; B represents the group of (ii), (iii), (iv), (v), (vi), (vii), (viii), or (xi); and V represents the group of (iv), (v), (vi), or (vii) are preferred.

Examples of preferred acetylene, oxadiazole, and thiazole compounds of formula (1A-III) are given below.

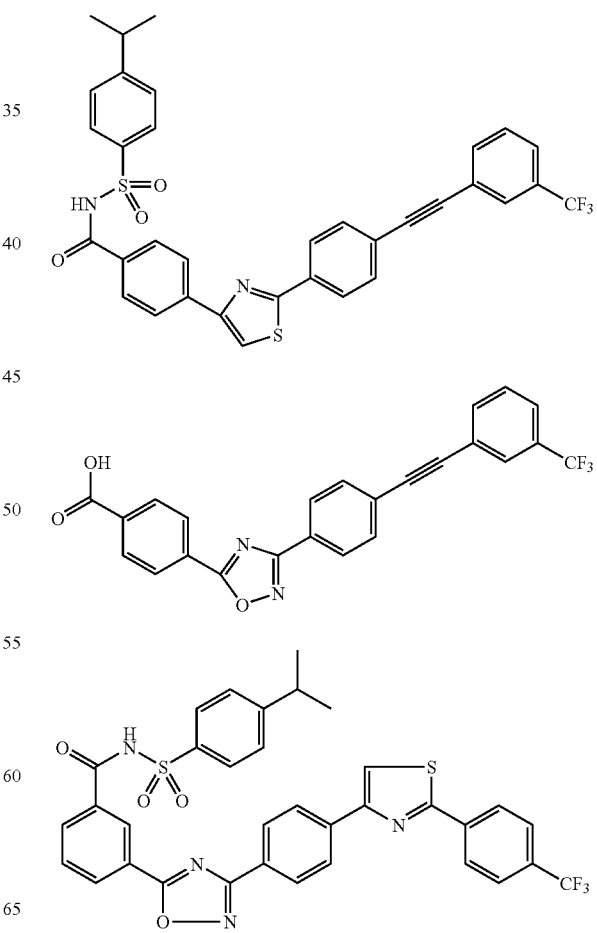

-continued
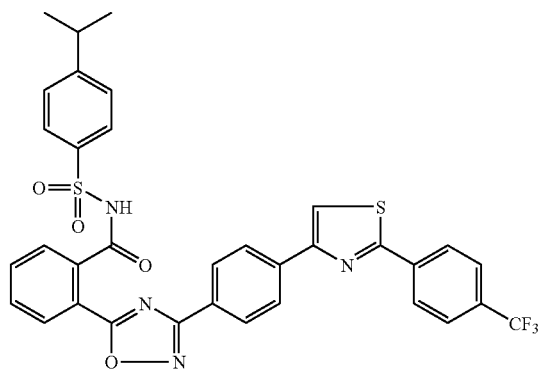
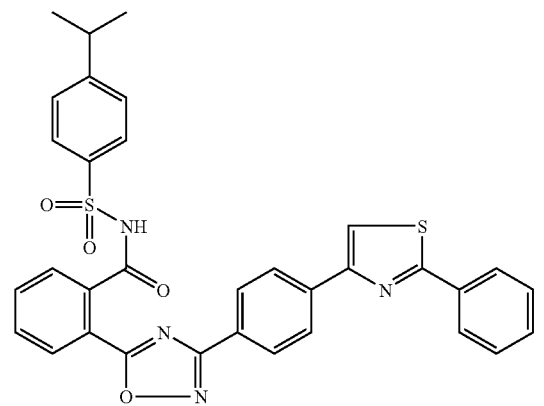
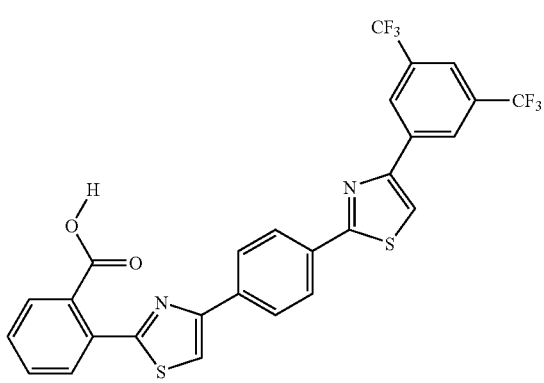
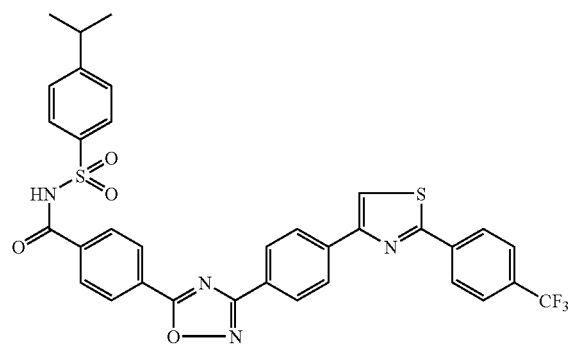
-continued
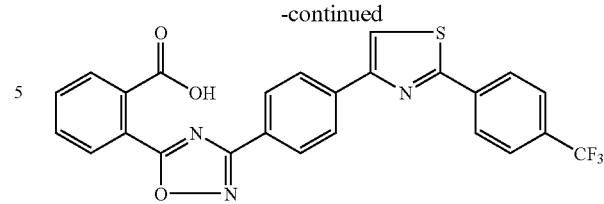
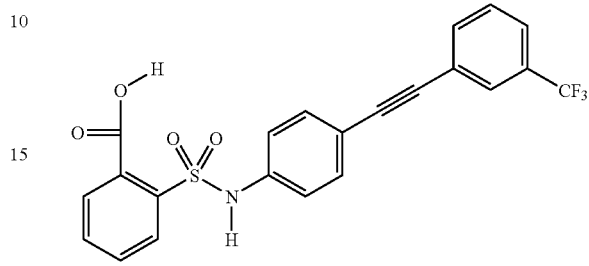
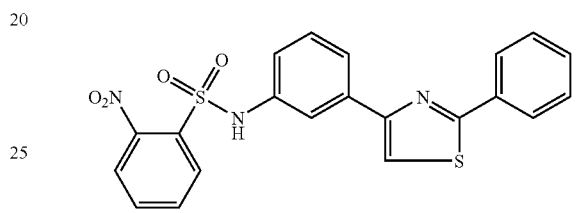
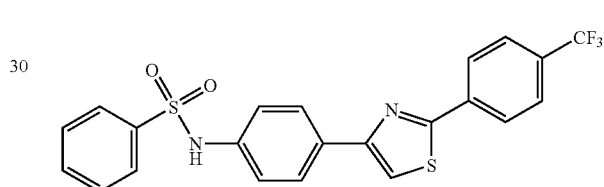
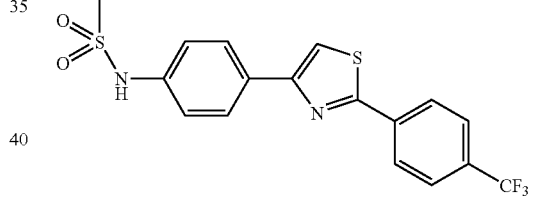
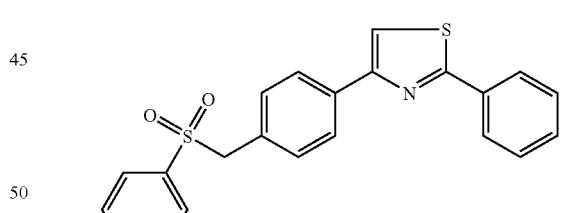
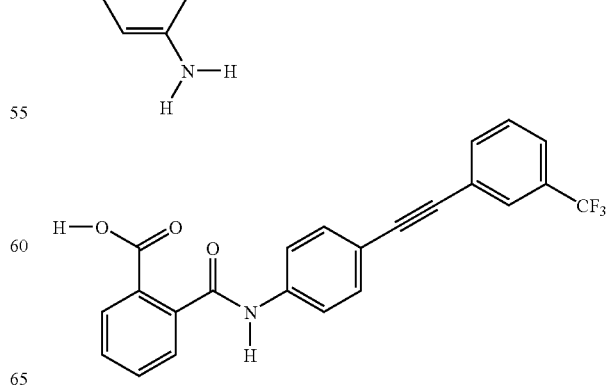

Further examples of preferred acetylene, oxadiazole, and thiazole compounds of formula (1A-III) are given below.

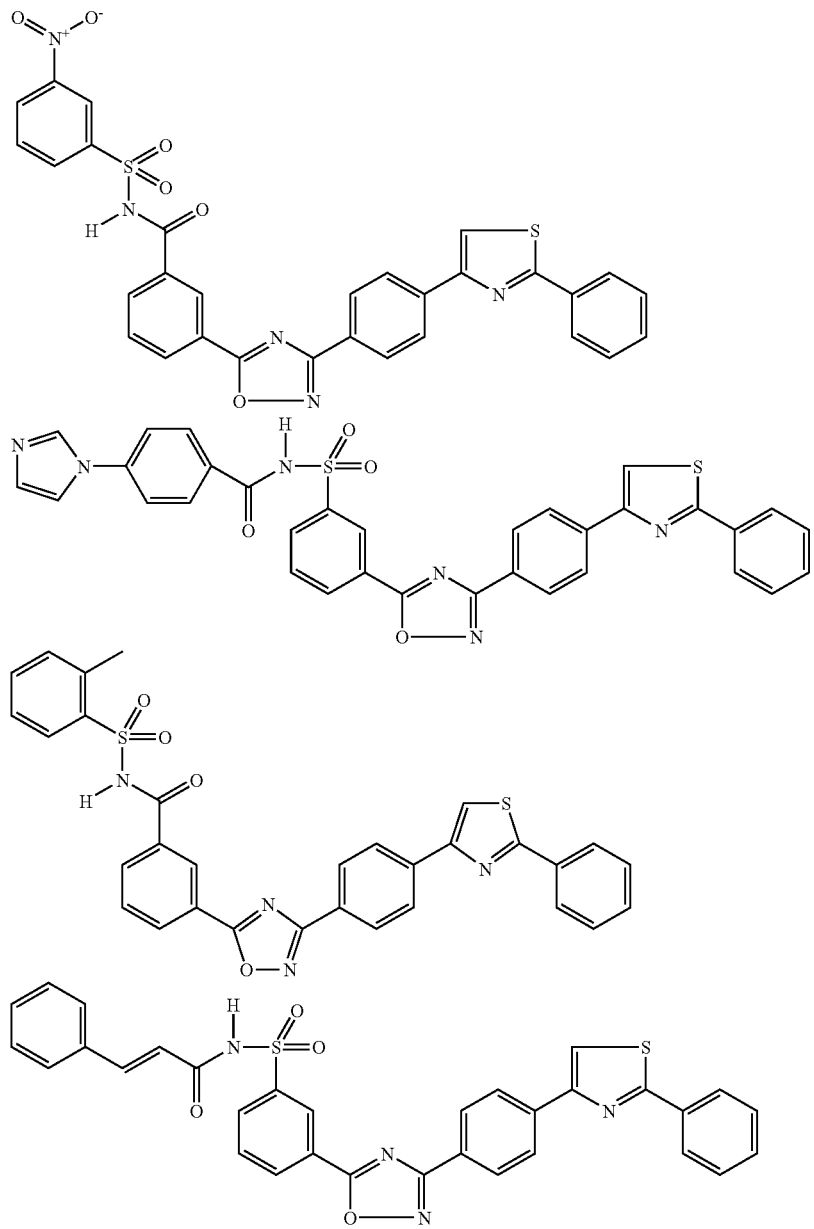

In formula (1B-III), R1 desirably represents a substituted or unsubstituted aromatic hydrocarbon group. This aromatic hydrocarbon group is desirably monocyclic. Preferred substituents are halogenated alkyl groups with 1 to 12 carbon atoms, particularly trifluoromethyl groups.

In formula (1B-III), R4, R5, and R6 are desirably hydrogen atoms.

In formula (1B-III), each of R7 and R8 desirably independently represents a substituted or unsubstituted alkyl group with 1 to 12 carbon atoms, a substituted or unsubstituted aromatic hydrocarbon group, or a substituted or unsubstituted aromatic heterocyclic group. It is desirable for either R7 or R8 to be a hydrogen atom and for one of the two to be a substituted or unsubstituted aromatic hydrocarbon group. Examples of preferred substituents on this aromatic hydrocarbon group are straight chain and branched chain alkyl groups with 1 to 12 carbon atoms.

In formula (1B-III), R9 desirably represents a hydrogen atom.

In formula (1B-III), V desirably represents the group represented by formula (iv), (v), (vi), or (vii).

In the acetylene, oxadiazole, thiazole compound represented by formula (1B-III) that is provided by the present invention, among compounds represented by general formula (1B-III), those in which R1 represents a substituted or unsubstituted aromatic hydrocarbon group; R4, R5, and R6 represent hydrogen atoms; and each of R7 and R8 represents a substituted or unsubstituted alkyl group with 1 to 12 carbon atoms, a substituted or unsubstituted aromatic hydrocarbon group, or a substituted or unsubstituted aromatic heterocyclic groups are preferred R9 desirably represents a hydrogen atom and V desirably represents the group represented by formula (iv), (v), (vi), or (vii).

Preferred examples of the acetylene, oxadiazole, thiazole compounds of formula (1B-III) are given below.

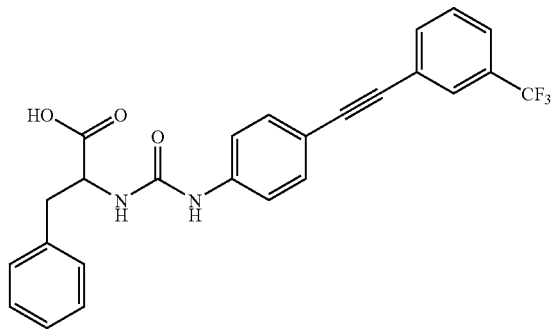

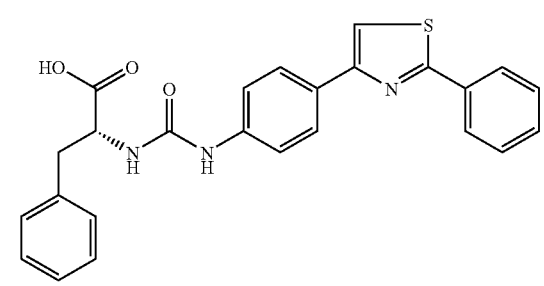

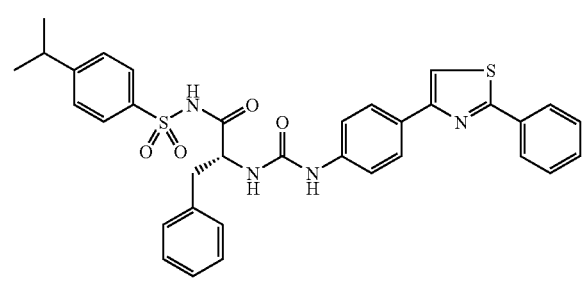

In formula (1C-III), R1 desirably represents a substituted or unsubstituted aromatic hydrocarbon group. An unsubstituted monocyclic aromatic hydrocarbon group is desirable, with a phenyl group being optimal.

In formula (1C-III), R4, R5, and R6 desirably represent hydrogen atoms.

In formula (1C-III), compounds in which each of R10 and R11 independently represents a substituted or unsubstituted alkyl group with 1 to 12 carbon atoms, a substituted or unsubstituted aromatic hydrocarbon group, or a substituted or unsubstituted aromatic heterocyclic group are preferred either R10 or R11 desirably represents a hydrogen atom, and one of two desirably represents a substituted or unsubstituted straight chain or branched chain alkyl group with 1 to 12 carbon atoms. The substituent is desirably a carboxyl group.

In formula (1C-III), V desirably represents the group represented by formula (iv), (v), (vi), or (vii). The group represented by formula (iv) or (v) is preferred.

In formula (1C-III), Y desirably represents —OCO—.

In formula (1C-III), R12 desirably represents a substituted or unsubstituted phenyl group. An unsubstituted phenyl group is optimal.

In the acetylene, oxadiazole, thiazole compounds of formula (1C-III) that is provided by the present invention, among compounds of formula (1C-III), those in which R1 represents a substituted or unsubstituted aromatic hydrocarbon group; R4, R5, and R6 denote hydrogen atoms; and each of R10 and R11 represents a substituted or unsubstituted alkyl group with 1 to 12 carbon atoms, substituted or unsubstituted aromatic hydrocarbon group, or substituted or unsubstituted aromatic heterocyclic group are preferred V desirably represents the group of formula (iv), (v), (vi), or (vii).

In formula (1C-III), Y desirably represents —OCO— and R12 desirably represents a substituted or unsubstituted phenyl group.

One of Example of preferred acetylene, oxadiazole, thiazole compounds of formula (1C-III) is given below.

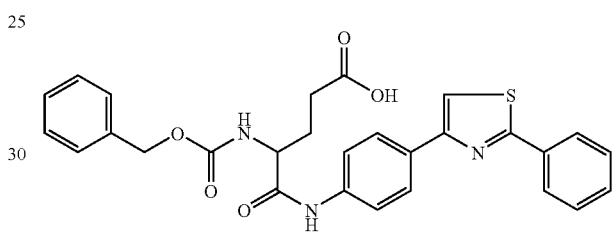

In the acetylene, oxadiazole, thiazole compound of formula (1D-III) that is provided by the present invention, among the compounds of formula (1D-III), those in which each of D and E represents —CO— or —CH2- are preferred.

In formula (1D-III), R2 desirably represents a carboxyl group, hydrogen atom, or group represented by R19-X— (where —X— represents —OCO—, —SO2NHCO—, or —CONHSO2-), A substituted or unsubstituted monocyclic aromatic hydrocarbon group is also desirable. A hydrogen atom, unsubstituted phenyl group, or R19-X— (where R19 represents a substituted or unsubstituted aromatic hydrocarbon group, preferably a phenyl group substituted with a straight chain or branched chain alkyl group with 1 to 12 carbon atoms, and X— represents —SO2NHCO—) is preferred.

In formula (1D-III), V desirably represents the group represented by formula (iv), (v), (vi), or (vii). The group represented by formula (viii) is also desirable. The groups represented by formulas (iv), (v), and (viii) are preferred.

In formula (1D-III), A desirably represents a substituted or unsubstituted aromatic hydrocarbon ring. Straight chain or branched chain alkenyl groups with 1 to 12 carbon atoms are desirable as substituents of the aromatic hydrocarbon ring.

In formula (1D-III), R1 desirably represents a substituted or unsubstituted aromatic hydrocarbon group. A phenyl group is desirable as this aromatic hydrocarbon group, with a halogenated alkyl group having 1 to 12 carbon atoms being desirable as a substituent.

In formula (1D-III), R4, R5, and R6 optimally represent hydrogen atoms.

Preferred examples of the acetylene, oxadiazole, thiazole compounds of formula (1D-III) are given below,

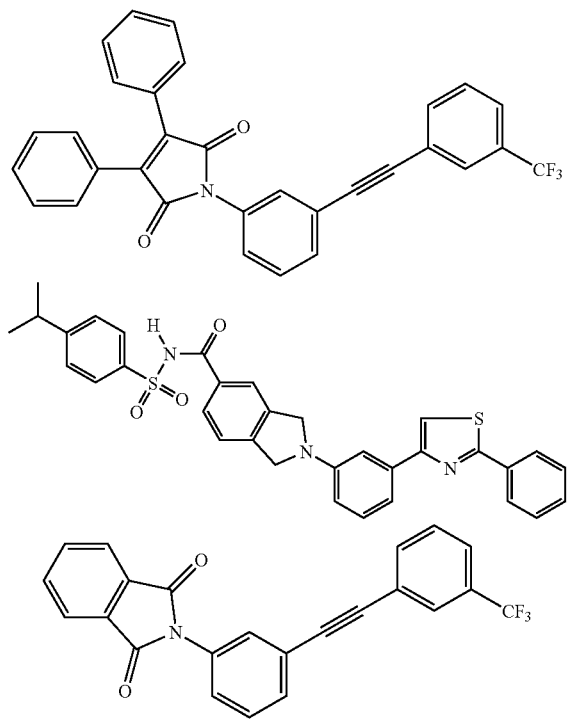

Preferred compounds of Mode 4 of the present invention will be described below.

In the benzenediamine compound of formula (1A-IV) that is provided by the present invention, ring A desirably represents an aromatic hydrocarbon ring substituted at positions 1 and 2, 1 and 3, or 1 and 4; an heteroaromatic ring substituted at positions 1 and 2, 1 and 3, or 1 and 4; a cycloalkene substituted at positions 1 and 2, 1 and 3, or 1 and 4; or a cycloalkane substituted at positions 1 and 1, 1 and 2, 1 and 3, or 1 and 4.

A benzenediamine compound in which ring A is a substituted or unsubstituted benzene ring is desirable.

D desirably represents a substituted or unsubstituted nitro group or —NR3R4.

Each of R1, R2, R3, and R4 desirably represents hydrogen atom; a substituted or unsubstituted alkyl group with 1 to 12 carbon atoms; a substituted or unsubstituted alkenyl group with 2 to 12 carbon atoms; a substituted or unsubstituted acyl group with 1 to 12 carbon atoms; substituted or unsubstituted alkynyl groups with 2 to 12 carbon atoms, cycloalkyl group, a substituted or unsubstituted aromatic hydrocarbon group, or a substituted or unsubstituted aromatic heterocyclic group. Hydrogen atoms, substituted or unsubstituted alkyl groups with 1 to 12 carbon atoms, substituted or unsubstituted acyl groups with 1 to 12 carbon atoms, and substituted or unsubstituted aromatic hydrocarbon groups are particularly preferred.

Hydrogen atoms; alkyl groups with 1 to 12 carbon atoms that are unsubstituted or substituted with aromatic hydrocarbon groups, aromatic heterocyclic groups, or cycloalkyl groups; or acyl groups with 1 to 12 carbon atoms that are unsubstituted or substituted with alkyl groups having 1 to 12 carbon atoms, aromatic hydrocarbon groups, aromatic heterocyclic groups, or cycloalkyl groups are particularly preferred.

Here, groups substituted with one or two substituted or unsubstituted alkyl groups, substituted or unsubstituted alkenyl groups, substituted or unsubstituted alkynyl groups, substituted or unsubstituted aromatic hydrocarbon groups, or substituted or unsubstituted aromatic heterocyclic groups are desirable as the substituents of the alkyl groups or the like. These alkyl and alkenyl groups can be joined by bonding nitrogen atoms to foil five-membered, six-membered, or seven-membered heterocyclic groups that may contain nitrogen atoms, oxygen atoms, or sulfur atoms.

Here, the aromatic hydrocarbon groups employed as substituents on alkyl groups and the like may be further substituted with halogen atoms, halogenated alkyl groups, halogenated alkoxy groups, alkyl groups, alkoxy groups, thiol groups, nitro groups, alkylamino groups, amino groups, cyano groups, hydroxyl groups, alkylthio groups, carboxyl groups, alkoxycarbonyl groups, and acetamide groups.

R5 desirably represents a hydrogen atom, carboxyl group, or the group represented by R10-X— (where —X— represents OCO—, —SO2NHCO—, or —CONHSO2-). R10 desirably represents a substituted or unsubstituted alkyl group with 1 to 12 carbon atoms, a substituted or unsubstituted alkenyl group with 2 to 12 carbon atoms, a substituted or unsubstituted alkynyl group with 2 to 12 carbon atoms, a substituted or unsubstituted aromatic hydrocarbon group, or a substituted or unsubstituted aromatic heterocyclic group, A substituted or unsubstituted alkyl group with 1 to 12 carbon atoms, or a substituted or unsubstituted aromatic hydrocarbon group is particularly preferred.

Each of R4, R5, and R6 desirably represents either of a hydrogen atom or a substituted or unsubstituted amino group with 1 to 12 carbon atoms.

R7, R8 and R9 desirably represent hydrogen atoms.

B desirably represents the group represented by formula (i), (ii), (iii), (v), (vi), (vii), (viii), or (ix). The group represented by formula (i), (vii), (viii), or (ix) is preferred. The group represented by formula (ix) is of even greater preference.

Among the compounds of formula (1A-IV), those in which Ring A represents a substituted or unsubstituted phenyl group; each of R1 and R2 represents a substituted or unsubstituted alkyl group with 1 to 12 carbon atoms or a substituted or unsubstituted aromatic hydrocarbon group; B represents the group represented by formula (i), (vii), (viii), or (ix); and R5 represents a hydrogen atom or the group represented by R10-X— (wherein —X— represents —OCO—, —SO2NHCO—, or —CONHSO2-) are preferred.

Examples of preferred benzenediamine compounds of formula (1A-IV) are given below.

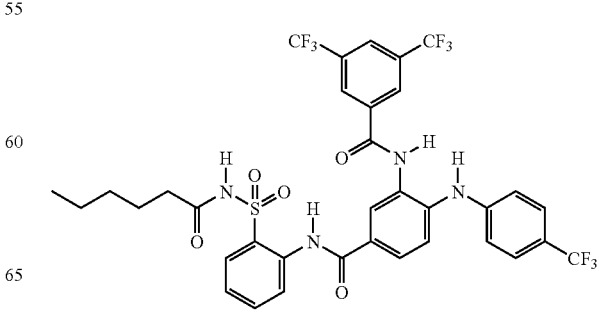

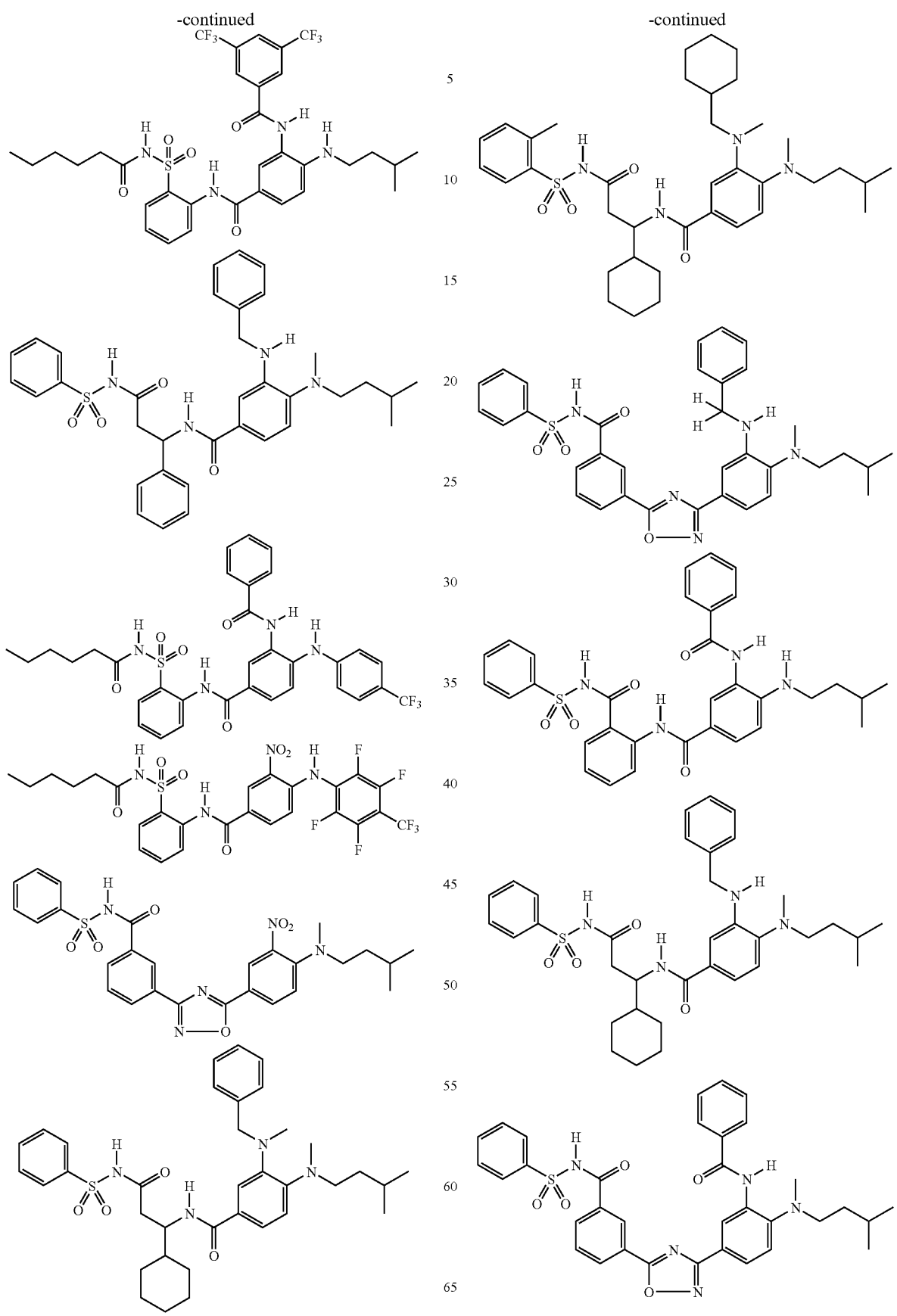

The method for manufacturing compounds of Mode 1 of the present invention will be described.

The quinoline compound of formula (I-I) can be synthesized by the methods described below. The method of synthesizing the quinoline compound (XV) will be given as an example thereof.

an acid such as TFA. Using the usual methods employed in the synthesis of amide compounds, the quinoline carboxylic acid (IIXI) is subjected to the amine compound (IIXII), yielding an amide compound. As required, R7 and R8 functional group conversion can be conducted, yielding the desired quinoline compound (XV).

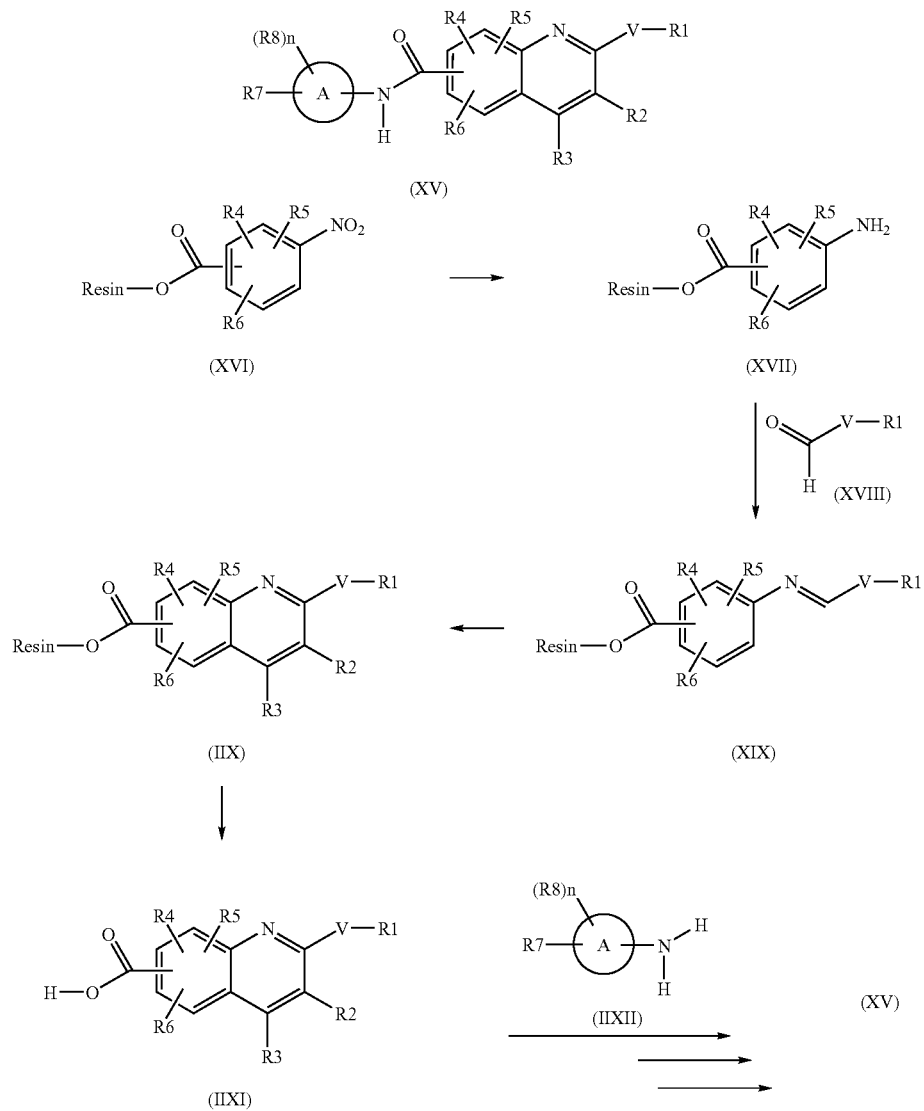

For example, a resin suited to solid phase synthesis, such as Wang resin, is employed. In the presence of a suitable base, 2,6-dichlorobenzoyl chloride or the like is employed to load 4-nitrobenzoic acid containing R4, R5, and R6 as substituents onto the resin, yielding an ester resin (XVI). The nitro group on the ester resin (XVI) is converted to an amino group with a reducing agent such as stannous chloride, yielding aniline resin (XVII). This is subjected to the aldehyde (XVIII), yielding an imine resin (XIX). A quinoline resin (IIX) can be obtained using the imine resin, an olefin comprising R2 and R3, and a Lewis acid catalyst such as Yb(OTf)3. Quinoline carboxylic acid (IIXI) can be cut out from the resin (IIX) with A method of synthesizing the quinoline compound represented by formula (IIXIII) will be described next by way of example. The Y—NH— moiety represents the partial structure defined by X— in the quinoline compound of formula (I).

The carboxyl group of quinoline caboxylic acid (IIXI) which is the synthetic intermediate of quinoline compound (XV) can be converted to an amino group (IIXIV), a cyano group (IIXVI), a thioamide group (IIXV), a hydroxyamidino group (IIXVII) or the like by the usual methods. Functional group conversion can be conducted as needed by the amine compound (IIXIV) is subjected to the compounds having various electrophilic functional groups to obtain the desired quinoline compound (IIXIII).

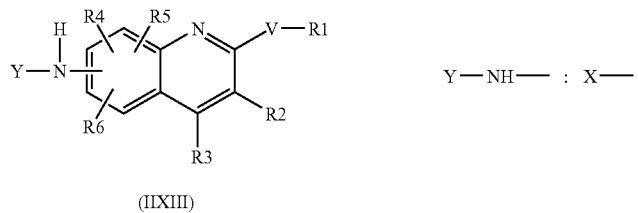

(IIXIII)

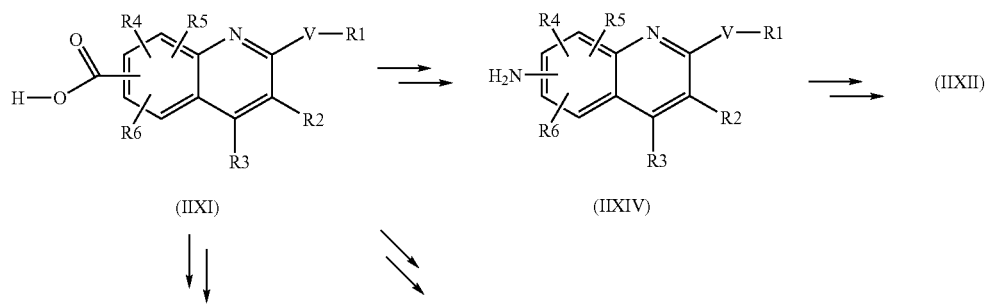

A method of synthesizing the quinoline compound of formula (IIXVIII) will be described next by way of example.

The thioamide compound (IIXV) described above is subjected to an α-halogenated ketone compound (IIXIX) to obtain a thiazole compound. Functional group conversion is conducted as needed, yielding the desired quinoline compound (IIXVIII).

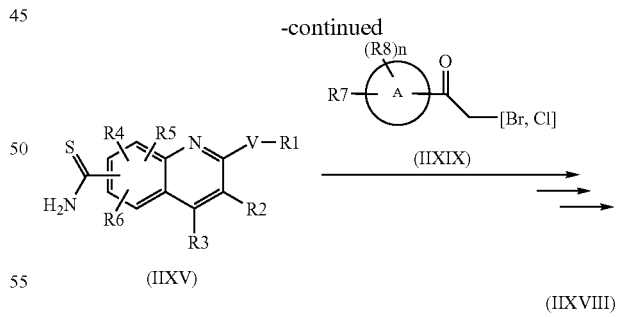

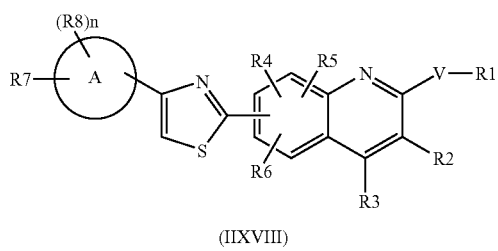

-continued

The method for manufacturing the compound of Mode 2 of the present invention will be described.

The benzimidazole compound of formula (I-II) can be synthesized by the method indicated by the following chemical equations, for example.

This is a method for general formula (I-II) when B represents formula (i), R3 represents R7-X— (where X represents —CONHSO2-), and R4, R5, and R6 represent hydrogen atoms.

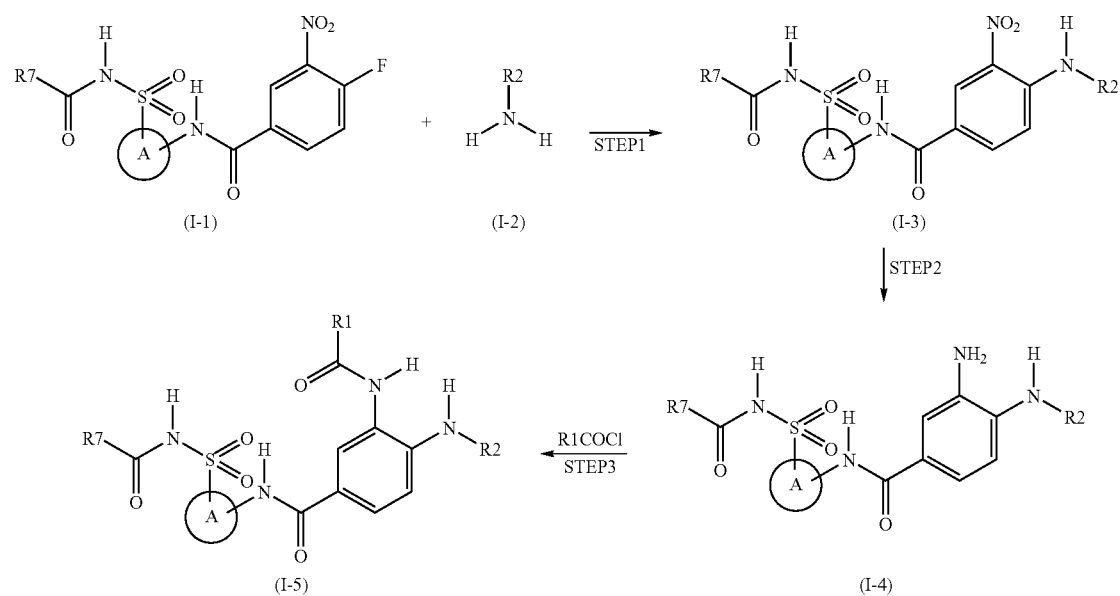
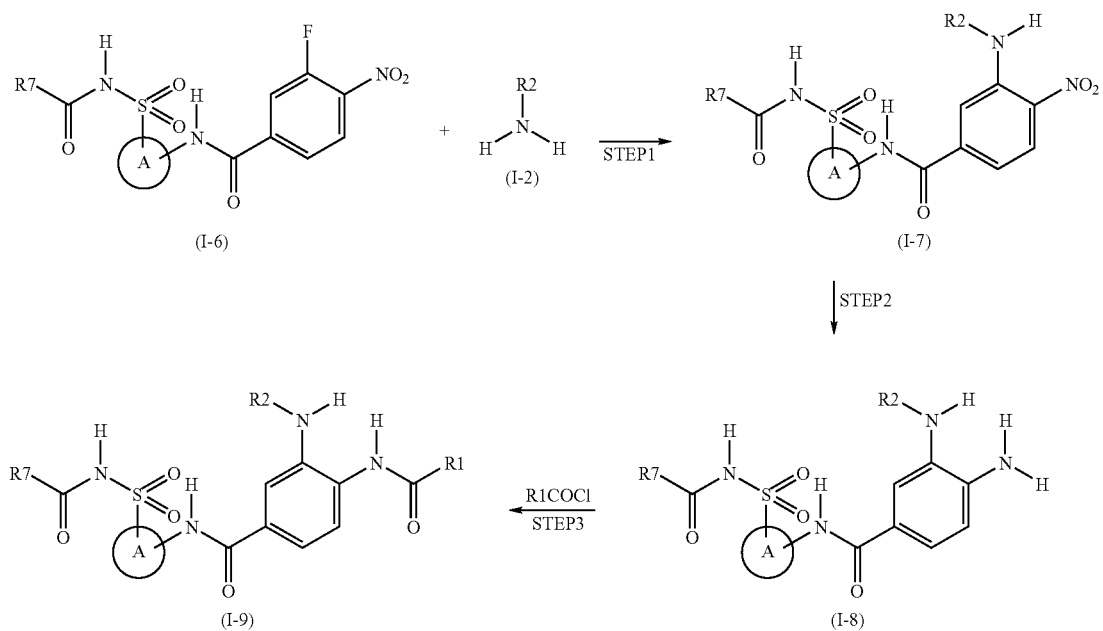

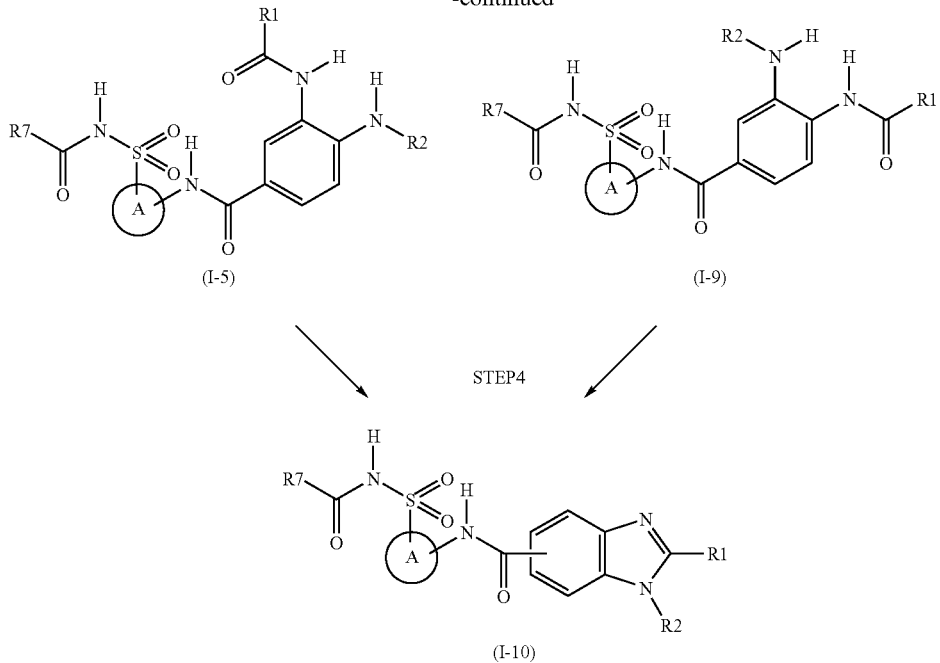

(I-5)      (I-9)

STEP4

(I-10)

In STEP 1, an aniline derivative (I-3) is manufactured from a fluoronitrobenzene compound (I-1) and an amine compound (I-2). For example, fluoronitrobenzene compound (I-1) and amine (I-2) are stirred with heating in the presence of a suitable base to yield aniline compound (I-3).

The base may be an inorganic base such as an alkali metal carbonate such as sodium carbonate or potassium carbonate; an organic base such as a trialkylamine such as trimethylamine or triethylamine; or a pyridine derivative such as pyridine, dimethylaminopyridine, picoline, or lutidine. The quantity of base is desirably 1 to 10 equivalents relative to amine compound (I-2).

In STEP 2, the nitro group of aniline compound (I-3) is reduced. Normally, iron powder is added to acetic acid under an argon gas flow, the mixture is heated to 60° C., the aniline compound (I-3) is added in small increments, and the mixture is stirred for about three hours. Subsequently, the iron powder is separated with a cotton plug, and NaHCO3 is added to the reaction solution obtained in small increments at about pH 5. The precipitating substance is filtered out, washed with water, diluted with ethyl acetate, washed with saturated brine, and dried with anhydrous sodium sulfate. The solvent is removed under reduced pressure, yielding the aniline compound (I-4).

The obtained aniline compound (I-4) is employed as starting material in STEP 3; it is stirred with a halogenated acyl compound (for example: acid chloride) using a suitable organic base in the form of a trialkylamine such as trimethylamine or triethylamine, or a pyridine derivative such as pyridine, dimethylaminopyridine, picoline, or lutidine. The NH2 group is thus monoacylated to obtain an aniline compound (I-5).

In STEP 4, the aniline compound (I-5) is cyclized. Normally, aniline compound (I-5) is dissolved in acetic acid, heated to 60° C., stirred for about three hours, and cooled to room temperature. The precipitate that forms is filtered out and washed with water, yielding benzimidazole compound (I-10).

Benzimidazole compound (I-10) can also be synthesized by employing fluoronitrobenzene compound (I-6) as starting material in STEPS 1, 2, 3 and 4 in the same mailer as above via aniline compounds (I-7), (I-8), and (I-9).

The method for manufacturing the compound of Mode 3 of the present invention will be described next.

The acetylene, oxadiazole, and thiazole compounds of the present invention represented by formulas (1A-III), (1B-III), (1C-III), and (1D-III) can be synthesized by the methods described below, for example.

Examples of methods for synthesizing oxadiazole compound (XII) and thiazole compound (XIII) will be described

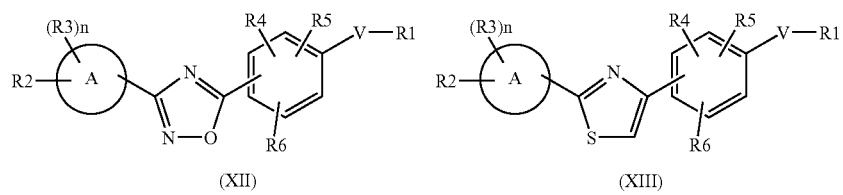

(XII)      (XIII)

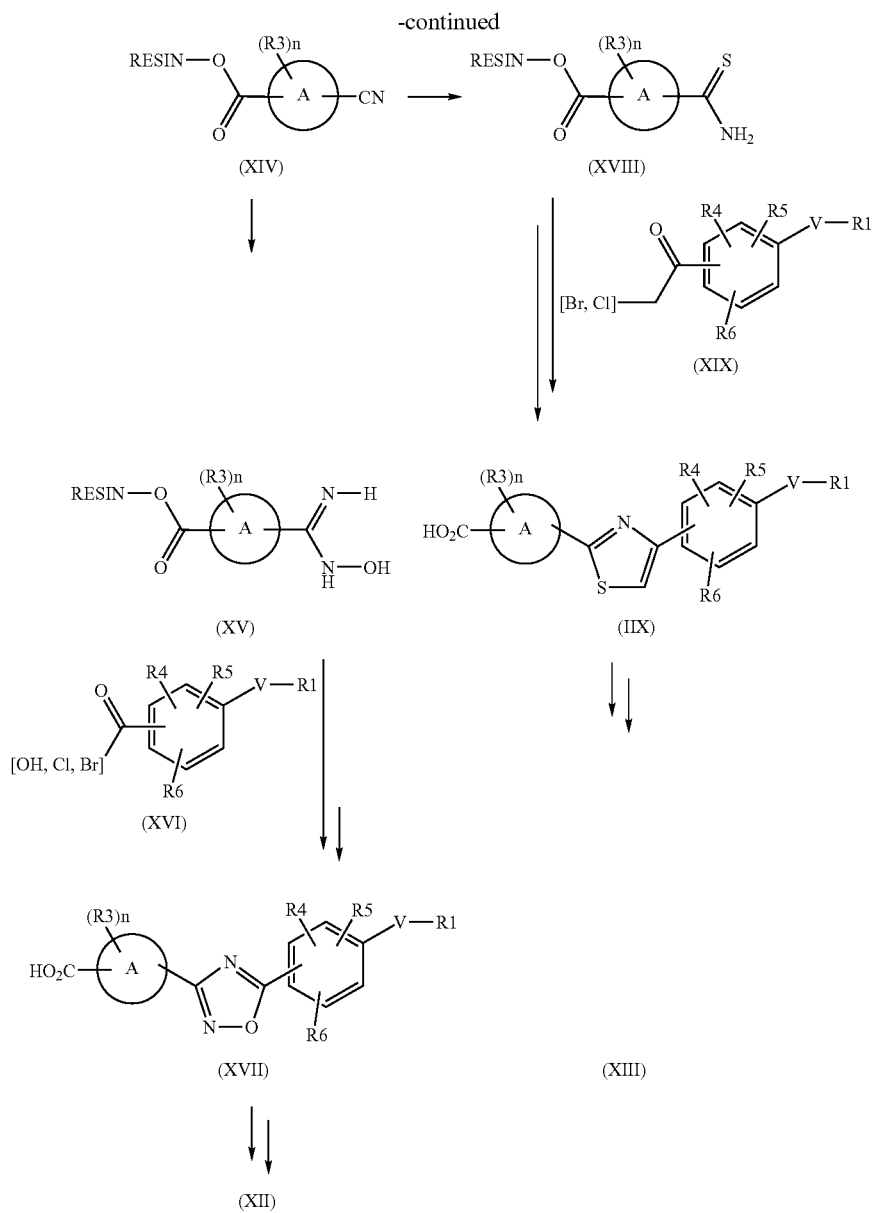

A resin suited to solid phase synthesis, such as Wang resin, is employed. In the presence of a suitable base, 2,6-dichlorobenzoyl chloride or the like containing substituents in the form of R3 and a cyano group is used to load the substituents onto the resin to obtain an ester resin (XIV). Hydroxylamine is added to the cyano group on the ester resin (XIV) to convert it to a hydroxyamidino group, yielding hydroxyamidine resin (XV). This is then subjected to an acid chloride or a carboxylic acid (XVI) to obtain oxadiazole resin (XVII). A suitable acid such as TFA is then used to cut the oxadiazole compound out of the oxadiazole resin (XVII), and as needed, the functional groups in the compound are converted to various substituents, yielding the desired oxadiazole compound (XII).

The cyano group on ester resin (XIV) is converted to a thioamide group with dithiophosphoric acid O,O-diethyl ester, yielding thioamide resin (XVIII). This is then subjected to an α-halogenated ketone compound (XIX) to obtain thiazole resin (IIX).

The thiazole compound is cut from thiazole resin (IIX) with a suitable acid such as TFA, and as needed, the functional groups in the compound are converted to various substituents, yielding the desired thiazole compound (XIII).

Methods for synthesizing sulfonamide compound (IIXI) and amide compound (IIXII) will be described next.

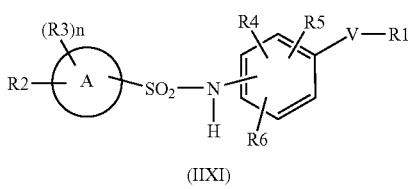

(IIXI)

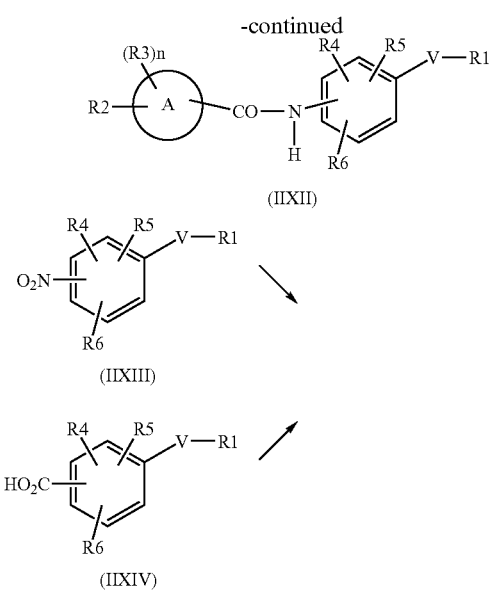

Aniline compound (IIXV) can be obtained by the usual methods from nitrobenzene compound (IIXIII) or benzoic acid compound (IIXIV). Sulfonamide compounds (IIXI) can be obtained by subjecting the aniline compound to various sulfonic acid chlorides in the presence of a suitable base, and amide compounds (IIXII) can be obtained by subjecting it to various acid chlorides in the presence of a suitable base. As needed, the functional groups in the compound can be converted to various substituents.

Methods for synthesizing aniline compound (IIXIV) and imide compound (IIXVII) will be described next.

Aniline compound (IIXVIII) is subjected to various halogenated methyl compounds (IIXIX) in the presence of a suitable base to obtain aniline compound (IIXVI), and is subjected to various acid anhydrides (IIIXI) in the presence of a suitable base to obtain imide compound (IIXVII). As needed, the functional groups in the compounds can be converted to various substituents. Imide compound (IIXVII) can also be synthesized by subjecting aniline derivative (IIXVIII) to various dicarboxylic acids (IIIX) in the presence of a suitable condensing agent to obtain an amide compound, and then conducting a suitable dehydration reaction. As needed, functional groups in the compound can be converted to various substituents.

Methods for synthesizing oxadiazole compound (IIIXII) and thiazole compound (IIIXIII) will be described next.

A hydroxylamine is added to the cyano group of a cyanobenzene compound (IIIXIV) to convert it to a hydroxyamidino group, yielding a hydroxyamidine compound (IIIXV). Next, an acid chloride or carboxylic acid (IIIXVI) is employed to obtain a oxadiazole compound (IIIXII). As needed, the functional groups in the compound can be converted to various substituents.

A cyanobenzene compound (IIIXIV) is subjected to a dithiophosphoric acid O,O-diethyl ether to obtain thioamide compound (IIIXVII). Next, this is subjected to an α-halogenated ketone compound (IIIXVIII) to obtain a thiazole compound (IIIXIII). As needed, the functional groups in the compound can be converted to various substituents.

A method for synthesizing an urea compound (IIIXIX) will be described next.

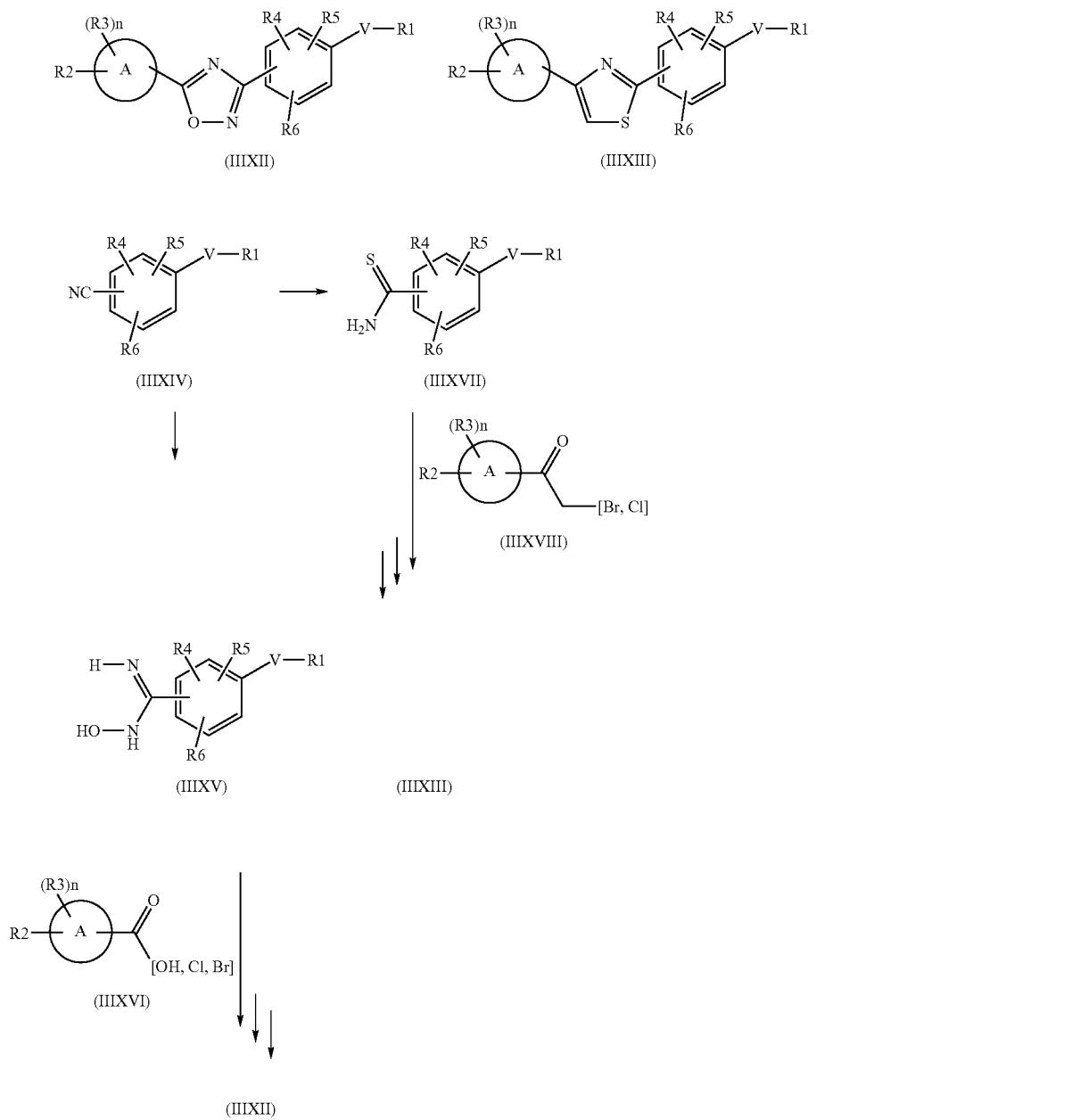

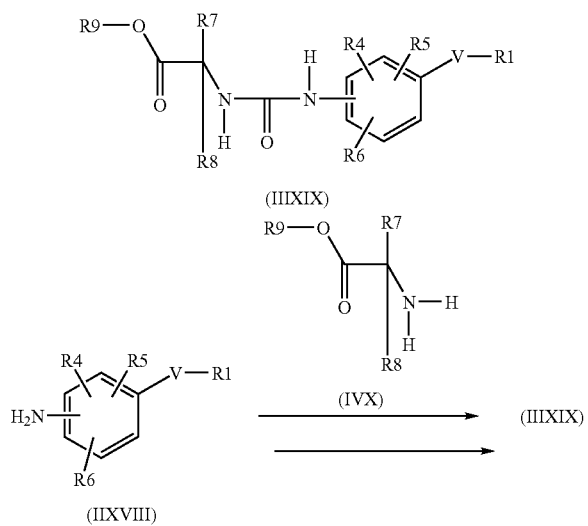

An aniline compound (IIXVIII) is subjected to phenyl chloroformate in the presence of a suitable base to obtain a phenyl carbamate derivative. This is then subjected to an amine compound (IVX) in the presence of a suitable base to obtain an urea compound (IIIXIX). As needed, the functional groups in the compound can be converted to various substituents.

Examples of the bases mentioned above are organic and inorganic bases such as alkali metal hydrides such as sodium hydride and potassium hydride; alkali metal hydroxides such as sodium hydroxide and potassium hydroxide; alkali metal carbonates such as sodium carbonate and potassium carbonate; alkali metal hydrogencarbonates such as sodium hydrogencarbonate and potassium hydrogencarbonate; alkali metal alkoxides such as sodium methoxide, sodium ethoxide, potassium methoxide, potassium tert-butoxide; trialkylamines such as trimethylamine and triethylamine; and pyridine derivatives such as pyridine, dimethylaminopyridine, picoline, and lutidine. The base is desirably employed in a quantity of 1 to 10 equivalents relative to the carboxylic acid compound.

Examples of the solvent employed in the reactions described above are: ethers such as diethylether, tetrahydrofuran (THF), and dioxane; aromatic hydrocarbons such as benzene, toluene, and xylene; hydrocarbons such as cyclopentane and cyclohexane; halogenated hydrocarbons such as dichloromethane, dichloroethane, trichloroethane, and chloroform; nitriles such as acetonitrile and propionitrile; esters such as ethyl acetate; N,N-dimethylformamide; dimethylsulfoxide; and mixtures of the foregoing with water.

A method for manufacturing the compound of Mode 4 of the present invention will be described next.

The benzenediamine compound of formula (1A-IV) can be synthesized by the method indicated by the following chemical equations, for example.

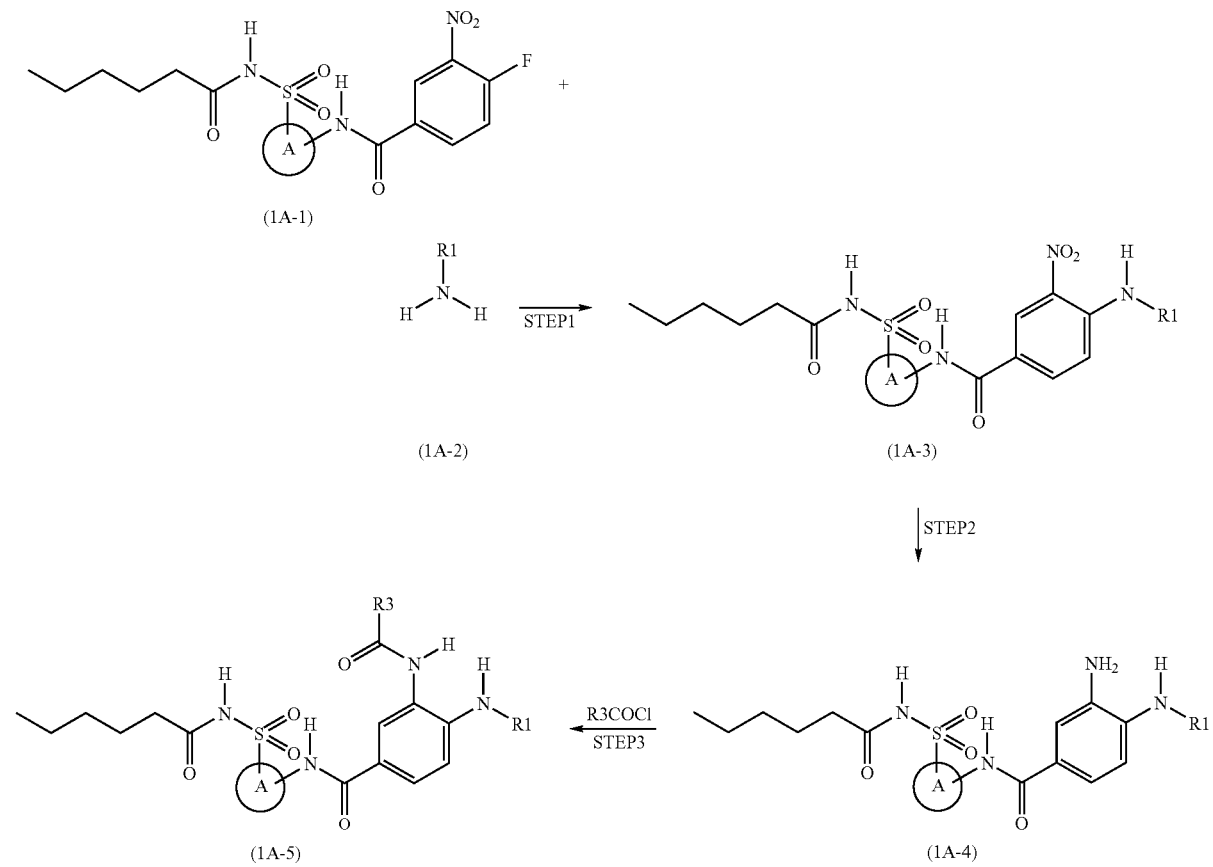

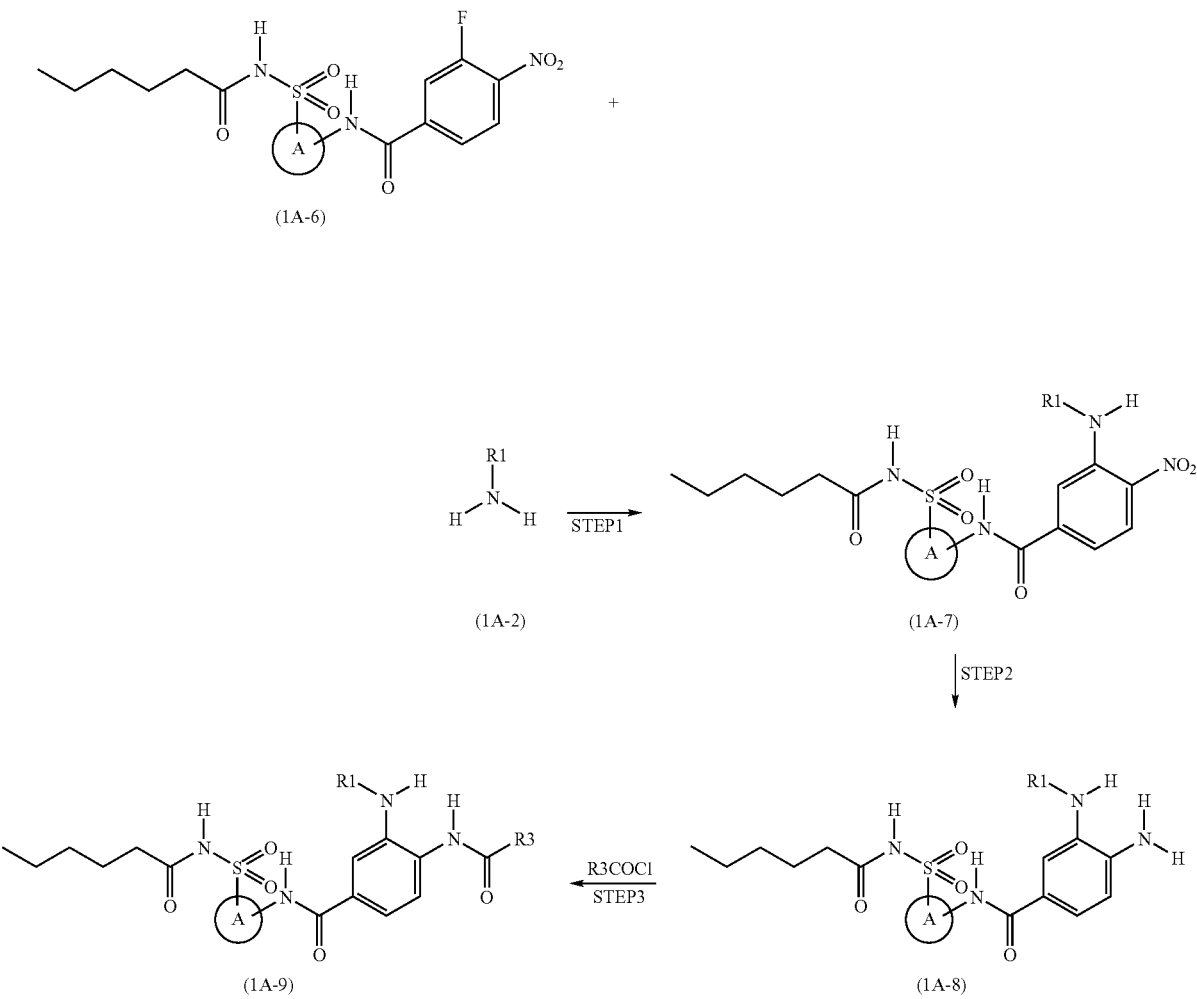

In STEP 1, an aniline compound is manufactured from a fluoronitrobenzene compound and an amine compound. For example, fluoronitrobenzene (1A-1) and amine (1A-2) are stirred with heating in the presence of a suitable base to yield aniline (1A-3). Further, fluoronitrobenzene (1A-6) and amine (1A-2) can be stirred with heating in the presence of a suitable base to yield aniline (1A-7). Examples of the bases employed are inorganic bases such as alkali metal carbonates such as sodium carbonate and potassium carbonate. Further examples are organic bases such as trialkylamines such as trimethylamine and triethyl amine, and pyridine derivatives such as pyridine, dimethylaminopyridine, picoline, and lutidine. Depending on the type of amine (1A-2), the reaction will sometimes proceed without the use of a base. In many cases, the quantity of base is desirably 1 to 10 equivalents relative to amine compound (1A-2).

In STEP 2, the nitro group of the aniline compound is reduced. Normally, iron powder is added to acetic acid under an argon gas flow, the mixture is heated to 60° C., the aniline compound is added in small increments, the mixture is stirred for about three hours, the iron powder is separated with a cotton plug, and NaHCO3 is added to the reaction solution obtained in small quantities at about pH 5. The precipitate that forms is filtered out, washed with water, diluted with ethyl acetate, washed with saturated brine, and dried with anhydrous sodium sulfate. The solvent is removed under reduced pressure, yielding aniline compounds (1A-4), (1A-8), and the like.

The obtained aniline is then employed as starting material in STEP 3. Using a suitable organic base; trialkylamine such as trimethylamine or triethylamine; or pyridine derivative such as pyridine, dimethylaminopyridine, picoline, or lutidine, the aniline is stirred with a halogenated acyl compound (such as acid chloride) to monoacylate the NH2 group, yielding aniline compound (1A-5), (1A-9), of the like.

A method for synthesizing the compound in which B represents the group of formula (viii) is given below.

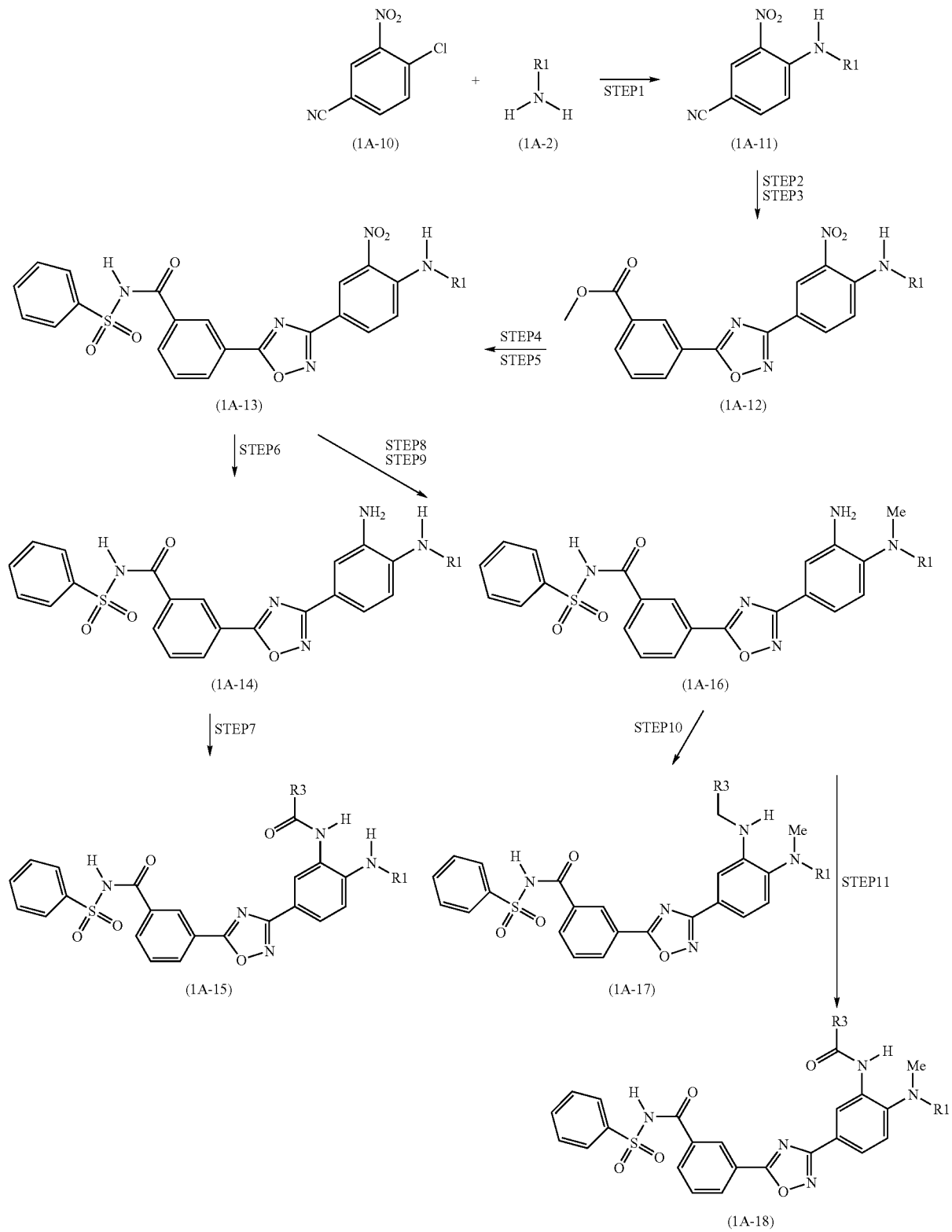

In STEP 1, an aniline compound is manufactured from 4-chloro-3-nitrobenzonitrile and an amine compound. For example, 4-chloro-3-nitrobenzonitrile (1A-10) and amine (1A-2) are stinted with heating in the presence of a suitable base to yield aniline (1A-11). Examples of the bases employed are inorganic bases such as alkali metal carbonates such as sodium carbonate and potassium carbonate. Further examples are organic bases such as trialkylamines such as trimethylamine and triethyl amine, and pyridine derivatives such as pyridine, dimethylaminopyridine, picoline, and lutidine. Depending on the type of amine (1A-2), the reaction will sometimes proceed without the use of a base. In many cases, the quantity of base is desirably 1 to 10 equivalents relative to amine compound (1A-2).

In STEP 2, an amideoxime compound is synthesized from benzonitrile compound (1A-11). Synthesis of amideoxime can be conducted by adding a hydroxylamine aqueous solution to a benzonitrile solution of tetrahydrofuran and ethanol and stirring with heating. In STEP 3, isophthalic acid monomethyl ester and water-soluble carbodiimide hydrochloride are added to a dioxane solution of the amideoxime compound and the mixture is stirred for several hours at room temperature. Next, the mixture is stirred for about 20 hours with heating to yield oxadiazole compound (1A-12).

In STEPS 4 and 5, oxadiazole compound (1A-12) is employed as a starting material to synthesize acylsulfonamide compound (1A-13). In STEP 4, methyl ester compound (1A-12) is hydrolyzed. Acylsulfonamide compound (1A-13) can be synthesized by employed a desired sulfonamide (benzenesulfonamide is described in the figure) and a suitable condensing agent.

In STEPS 6 and 9, the nitro group is reduced. Acylsulfonamide compound (1A-13) is employed as the starting material. Iron powder is added to acetic acid under an argon gas flow, the mixture is stirred with heating, an aniline compound is added incrementally, and the mixture is stirred for several hours. A cotton plug is used to separate the iron powder and NaHCO3 is added incrementally at about pH 5 to the reaction solution. The precipitate that forms is filtered out, washed with water, diluted with ethyl acetate, washed with saturated brine, and dried with anhydrous sodium sulfate. The solvent is removed under reduced pressure, yielding aniline compound (1A-14). In STEP 8, aniline compound (1A-13) is employed as starting material to conduct suitable methylation. Using the compound thus obtained as starting material in STEP 9, aniline compound (1A-16) can be synthesized.

The obtained anilines (1A-14) and (1A-16) are then employed as starting materials in STEPS 7 and 11, respectively. Employing a suitable organic base the aniline is stirred with a halogenated acyl compound (for example, acid chloride) to monoacylate the NH2 group, yielding acylsulfonamide compound (1A-15) and acylsulfonamide compound (1A-18). Examples of wherein said organic base are trialkylamines such as trimethylamine or triethylamine or pyridine derivatives such as pyridine, dimethylaminopyridine, picoline, or lutidine.

In STEP 10, aniline compound (1A-16) is employed as starting material. N-Alkylation is conducted by reductive amination or the like to synthesize acylsulfonamide compound (1A-17).

The description given below relates to a method for manufacturing the compound of Mode 1 to 4.

The reactions of STEPS 1, 2, 3, and 4 described above can be conducted in an inert solvent. Examples of the solvent are: ethers such as diethyl ether, tetrahydrofuran, and dioxane; aromatic hydrocarbons such as benzene, toluene, and xylene; hydrocarbons such as cyclopentane and cyclohexane; halogenated hydrocarbons such as dichloromethane, dichloroethane, trichloroethane, and chloroform; nitriles such as acetonitrile and propionitrile; esters such as ethyl acetate; N,N-dimethylformamide; dimethylsulfoxide; and mixtures of the foregoing with water.

In all of the above-described steps, as needed, the commonly employed means of purification, such as filtration, decantation, extraction, washing, solvent distillation, column and thin-layer chromatography, recrystallization, and distillation can be used for isolation and purification.

The benzene compound of the present invention includes the various salt, hydrate, and solvate forms thereof, particularly pharmaceutically acceptable forms thereof. Mixed formulations of the benzene compound of the present invention with other drugs such as anti-diabetic drugs and hypoglycemic agents, as well as combinations of two-drug formulations individually comprising these components, are also covered by the present invention.

Examples of drugs that can be combined with the benzene compound of the present invention for use ale insulin, insulin analogs such as lispro and glargine; insulin secretion promoters such as glibenclamide, tolbutamide, glipizide, and glimepiride; fast-acting insulin secretion promoters such as nateglinide and repaglinide; α-glucosidase inhibitors such as acarbose, voglibose, and miglitol; biguanide agents such as metformin and phenformin; insulin-resistance improving agents such as PPAR-γ antagonists and PPAR-γ agonists with nonthiazolidine skeletons such as GI-262570, JTT-501, and YM-440 and thiazolidine skeletons such as rosiglitazone, pioglitazone, and troglitazone; PPAR-α agonists such as chlofibrate; SGLT inhibitors such as T-1095; GLP-1 receptor agonists, DPP-IV inhibitors; and other hypoglycemic agents; aldose reductase inhibitors such as epalrestat, fidarestat, and zenarestat; anti-diabetic neuropathy agents such as mecobalamin and mexiletin; HMG-CoA reductase inhibitors such as pravastatin, simvastatin, fluvastatin, cerivastatin, atorvastatin, and itavastatin; antioxidants such as lipoic acid and probucol; antihypertensive agents such as calcium antagonists, angiotensin converting enzyme inhibitors, angiotensin II receptor antagonists, β blockers, α1 blockers, and diuretics; anti-obesity drugs such as orlistat and sibutramine; and low energy foods such as Optifast. Existing drugs and drugs currently under development or for which basic studies are being conducted, including dietetic therapies and kinetotherapies, are covered by the present invention when employed in combination with the compounds of formulas (1A-IV) and (1B-IV) in the same manner as the above pharmaceuticals with the objective of treating obesity, obesity-induced hyperlipemia, and various diseases (impaired glucose tolerance, diabetes, diabetic peripheral neuropathy, diabetic nephropathy, diabetic retinopathy, diabetic macroangiopathy, hyperlipemia, hypertension, and arteriosclerosis) caused by insulin resistance.

Although administration of drugs containing the benzene compound of the present invention to humans will vary with the age and disease of the patient, about 0.01 to 1,000 mg of the benzene compound of the present invention is desirably contained per formulation. The actual preferred method, procedure, and interval of administration can be suitably selected by making use of commonly employed techniques in consideration of the information recorded in the present specification based on the formulation of the various individual drugs employed, the timing of the drug effects, and the status of the individual patients being treated (weight, body fat ratio, body mass index, biochemical blood indications, and the like). More preferably, the benzene compound of the present invention is normally orally administered in an effective quantity of 1 to 100 mg divided into 1 to 3 administrations per day, for example.

When employing the benzene compound of the present invention in combination with another drug, the two may be administered simultaneously or at different times. Three or less daily administrations of each of the drugs is desirable. The treatment can be repeated so long as contraindications are not observed with continuous administration, or until a set objective is achieved in a individual patient.

The drug containing the benzene compound of the present invention as active ingredient may be formulated for oral administration in various forms, including as a tablet, a capsule, granules, a troche, or a liquid. These formulations can be achieved by known methods. For example, the benzene compound of the present invention can be suitably formulated with excipients such as starch, mannitol, and lactose; binders such as carboxymethylcellulose sodium and hydroxypropylcellulose; disintegrating agents such as crystalline cellulose and carboxymethylcellulose; lubricants such as talc and magnesium stearate; and fluidity-enhancing agents such as light silicic anhydride to manufacture tablets, capsules, granules, powders, and troches. The drug of the present invention may also be employed as an injection. For example, the formulation may be dispersed or solubilized in advance in an aqueous carrier such as normal saline by means of a surfactant, dispersing agent, or the like, or, when necessary, prepared as an injection-use crystal formulation or freeze-dried formulation for dispersion or dissolution at the time of use. Stabilizers and pH-adjusting agents may be added as optional components to the above aqueous carrier. The dosage and administration route of an injection is not specifically limited, but a safe, required dose can be administered in a single administration, dropwise, or the like based on the symptoms and characteristics of the patient, either intravenously, intra-arterially, subcutaneously, or intraperitoneally.

When employing the benzene compound of the present invention in combination with another drug, it is not necessary to incorporate all of the active ingredients into a single formulation. Each component, or multiple components, can be incorporated into a single or multiple suitable formulations. In such cases, the active ingredients can be prepared in the form of currently known or various fixture drug formulations yet to be developed, such as orally administered formulations and injections

EMBODIMENTS

The present invention will be described in greater detail below through embodiments.

Embodiments of the compound of Mode 1 of the present invention will be described first.

Table 1-I gives the molecular structure and mass spectrometry results for the compounds (1-I to 115-I) synthesized in Embodiments 1-I to 21-I below.

TABLE 1-I

| Compound No. | MOLSTRUCTURE | MS (ESI)(MH+) |
|---|---|---|
| 1 | | 465 |
| 2 | | 437 |
| 3 | | 505 |

TABLE 1-I-continued

| Compound No. | MOLSTRUCTURE | MS (ESI)(MH+) |
|---|---|---|
| 4 | | 624 |
| 5 | | 556 |
| 6 | | 540 |
| 7 | | 638 |
| 8 | | 533 |

TABLE 1-I-continued

| Compound No. | MOLSTRUCTURE | MS (ESI)(MH+) |
|---|---|---|
| 9 | | 481 |
| 10 | | 488 |
| 11 | | 435 |
| 12 | | 586 |
| 13 | | 572 |
| 14 | | 405 |

TABLE 1-I-continued
| Compound No. | MOLSTRUCTURE | MS (ESI)(MH+) |
|---|---|---|
| 15 | 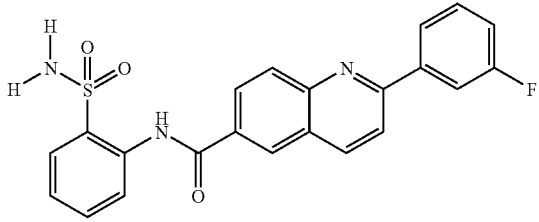 | 422 |
| 16 | 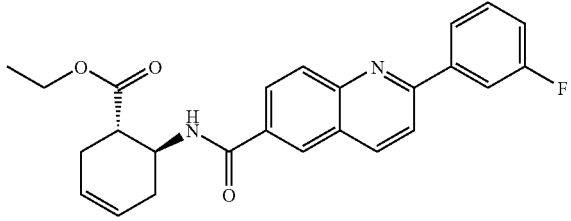 | 419 |
| 17 | 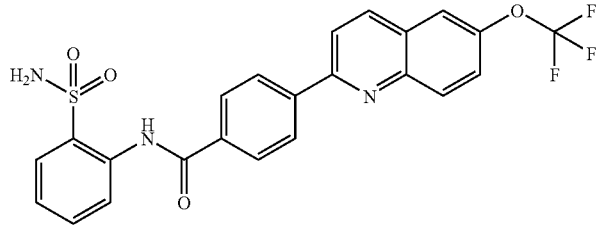 | |
| 18 | 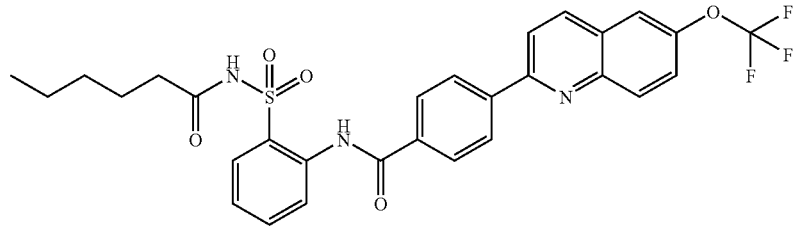 | |
| 19 | 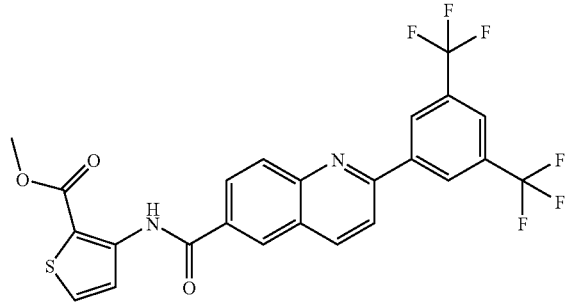 | 525 |

TABLE 1-I-continued

| Compound No. | MOLSTRUCTURE | MS (ESI)(MH+) |
|---|---|---|
| 20 | | 539 |
| 21 | | 582 |
| 22 | | 437 |
| 23 | | 451 |
| 24 | | 457 |

TABLE 1-I-continued

| Compound No. | MOLSTRUCTURE | MS (ESI)(MH+) |
|---|---|---|
| 25 | | 431 |
| 26 | | 459 |
| 27 | | 493 |
| 28 | | 429 |
| 29 | | 403 |
| 30 | | 431 |

TABLE 1-I-continued

| Compound No. | MOLSTRUCTURE | MS (ESI)(MH+) |
|---|---|---|
| 31 | | 465 |
| 32 | | 584 |
| 33 | | 520 |
| 34 | | 538 |
| 35 | | 510 |
| 36 | | 417 |

TABLE 1-I-continued

| Compound No. | MOLSTRUCTURE | MS (ESI)(MH+) |
|---|---|---|
| 37 | | 465 |
| 38 | | 499 |
| 39 | | 561 |
| 40 | | 485 |

TABLE 1-I-continued

| Compound No. | MOLSTRUCTURE | MS (ESI)(MH+) |
|---|---|---|
| 41 | | 567 |
| 42 | | |
| 43 | | |
| 44 | | |
| 45 | | |

TABLE 1-I-continued

| Compound No. | MOLSTRUCTURE | MS (ESI)(MH+) |
|---|---|---|
| 46 | | |
| 47 | | 525 |
| 48 | | 537 |
| 49 | | 714 |

TABLE 1-I-continued

| Compound No. | MOLSTRUCTURE | MS (ESI)(MH+) |
|---|---|---|
| 50 | | 720 |
| 51 | | 604 |
| 52 | | 618 |
| 53 | | 616 |

TABLE 1-I-continued

| Compound No. | MOLSTRUCTURE | MS (ESI)(MH+) |
|---|---|---|
| 54 | | 644 |
| 55 | | 658 |
| 56 | | 666 |
| 57 | | 678 |

TABLE 1-I-continued

| Compound No. | MOLSTRUCTURE | MS (ESI)(MH+) |
|---|---|---|
| 58 | (Chiral) | 684 |
| 59 | (Chiral) | 684 |
| 60 | | 630 |
| 61 | | 644 |

TABLE 1-I-continued

| Compound No. | MOLSTRUCTURE | MS (ESI)(MH+) |
|---|---|---|
| 62 | | 644 |
| 63 | | 525 |
| 64 | | 527 |
| 65 | | 568 |
| 66 | | 554 |

TABLE 1-I-continued
| Compound No. | MOLSTRUCTURE | MS (ESI)(MH+) |
|---|---|---|
| 67 | 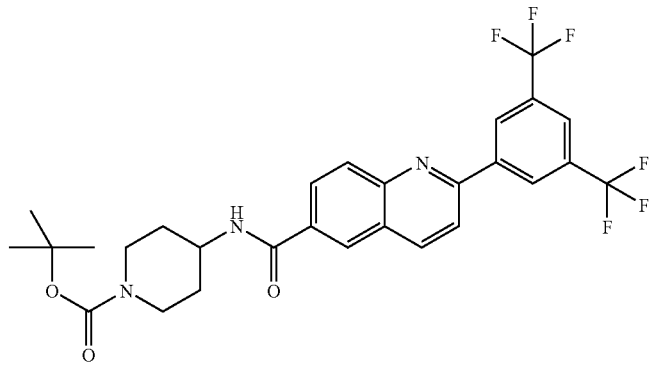 | 568 |
| 68 | 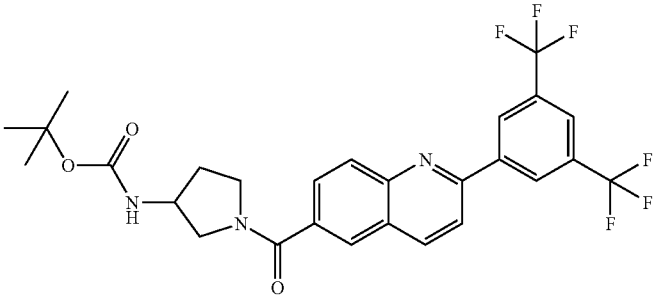 | 554 |
| 69 | 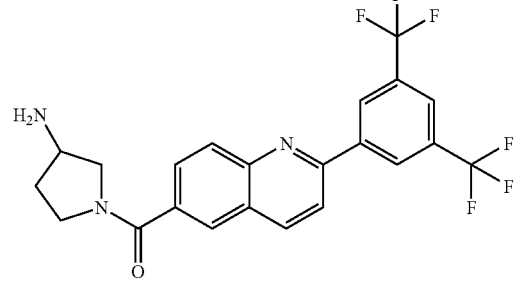 | 454 |
| 70 | 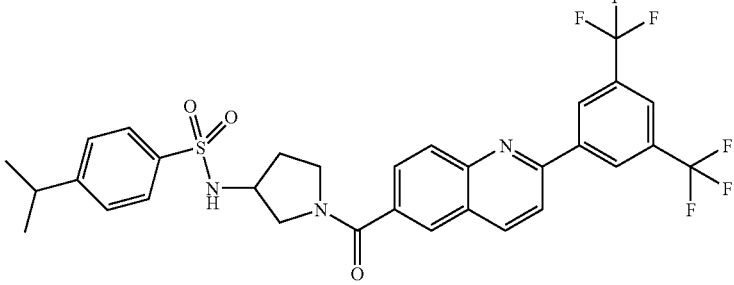 | 636 |

TABLE 1-I-continued

| Compound No. | MOLSTRUCTURE | MS (ESI)(MH+) |
|---|---|---|
| 71 | | 468 |
| 72 | | 454 |
| 73 | | 650 |
| 74 | | 636 |
| 75 | | 693 |

| Compound No. | MOLSTRUCTURE | MS (ESI)(MH+) |
|---|---|---|
| 76 | | 679 |
| 77 | | 679 |
| 78 | | 586 |
| 79 | | 505 |
| 80 | | 613 |

TABLE 1-I-continued

| Compound No. | MOLSTRUCTURE | MS (ESI)(MH+) |
|---|---|---|
| 81 | | 466 |
| 82 | | 452 |
| 83 | | 700 |
| 84 | | 571 |

TABLE 1-I-continued

| Compound No. | MOLSTRUCTURE | MS (ESI)(MH+) |
|---|---|---|
| 85 | | |
| 86 | | 610 |
| 87 | | 639 |

TABLE 1-I-continued

| Compound No. | MOLSTRUCTURE | MS (ESI)(MH+) |
| --- | --- | --- |
| 88 | | 574 |
| 89 | | 577 |
| 90 | | 583 |

TABLE 1-I-continued
| Compound No. | MOLSTRUCTURE | MS (ESI)(MH+) |
|---|---|---|
| 91 | 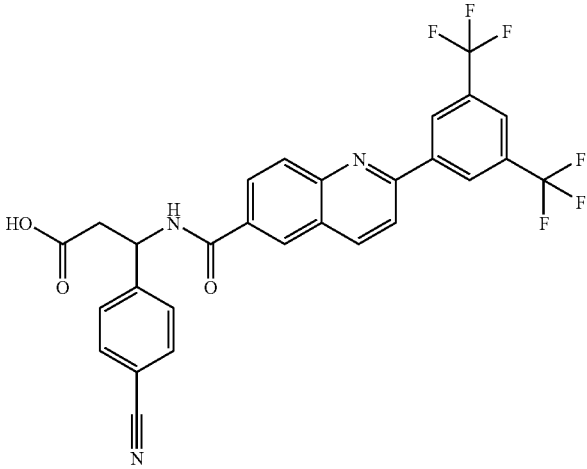 | 558 |
| 92 | 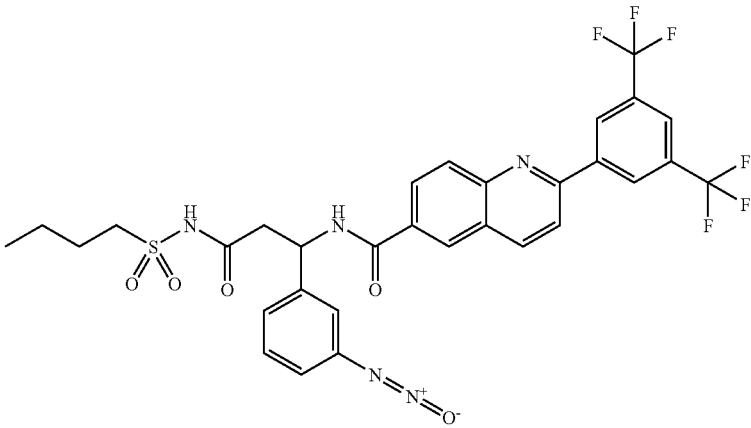 | 693 |
| 93 | 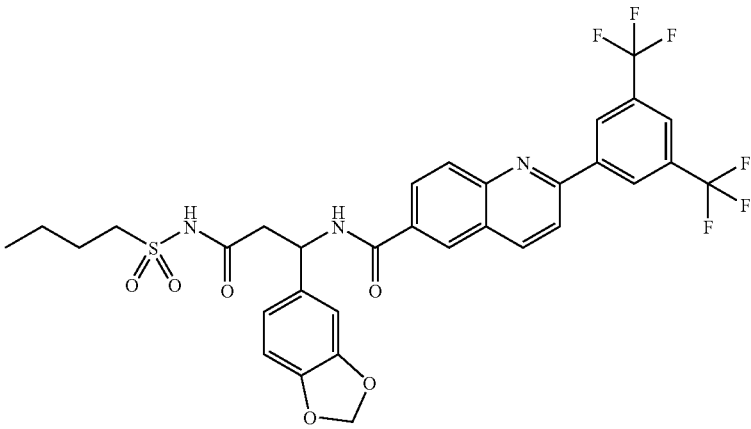 | 696 |

TABLE 1-I-continued
| Compound No. | MOLSTRUCTURE | MS (ESI)(MH+) |
|---|---|---|
| 94 | 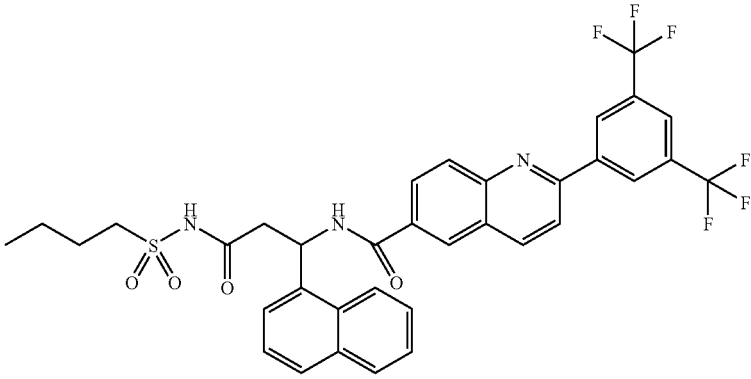 | 702 |
| 95 | 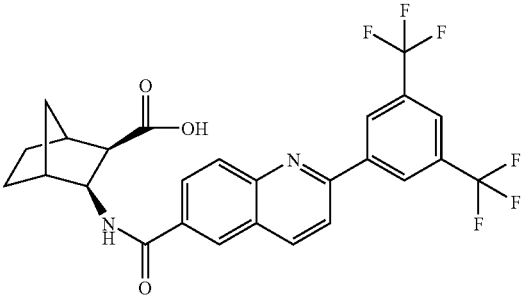 | 523 |
| 96 | 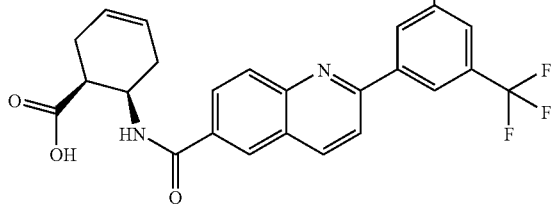 | 509 |
| 97 | 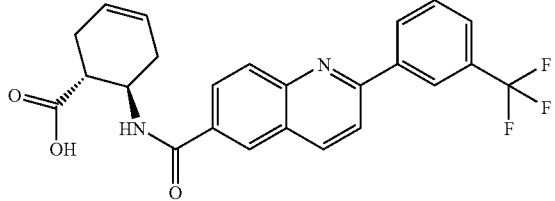 | 509 |

TABLE 1-I-continued

| Compound No. | MOLSTRUCTURE | MS (ESI)(MH+) |
|---|---|---|
| 98 | | 545 |
| 99 | | 523 |
| 100 | | 628 |
| 101 | | 628 |

TABLE 1-I-continued

| Compound No. | MOLSTRUCTURE | MS (ESI)(MH+) |
| --- | --- | --- |
| 102 | | 667 |
| 103 | | 701 |
| 104 | | |
| 105 | | |
| 106 | | |

TABLE 1-I-continued

| Compound No. | MOLSTRUCTURE | MS (ESI)(MH+) |
|---|---|---|
| 107 | | 588 |
| 108 | | 650 |
| 109 | | 602 |
| 110 | | 588 |
| 111 | | |

TABLE 1-I-continued

| Compound No. | MOLSTRUCTURE | MS (ESI)(MH+) |
|---|---|---|
| 112 | (structure) | 505 |
| 113 | (structure) | 541 |
| 114 | (structure) | 545 |
| 115 | (structure) | 726 |

Embodiment 1-I

Synthesis of Compound 1-I 4.0 g of commercial Wang resin (about 1.0 mmole/g) was suspended in NMP and left standing for three hours at room temperature. The excess solvent was removed. A 60 mL of NMP, 3.2 g of 4-nitrobenzoic acid, 2.9 mL of pyridine, and 3 mL of 2,6-dichlorobenzoyl chloride were added and the mixture was stirred for 20 hours at room temperature. The solvent was removed and the resin was washed twice with 60 mL of N-methylpyrrolidone (NMP hereinafter). The solvent was removed and the resin was sequentially washed three times each with 60 mL each of dichloromethane, NMP, and dichloromethane, and the resin was dried.

To the obtained resin were added 6 g of stannous chloride, 60 mL of NMP, and 3 mL of ethanol, and the mixture was stirred for 12 hours at room temperature. The solvent was removed and the resin was washed twice with 60 mL of NMP. The solvent was removed; the resin was sequentially washed three times each with 60 mL each of dichloromethane, NMP, and dichloromethane; and the resin was dried.

To the obtained aniline resin were added 2 mL of 4-trifluoromethylbenzaldehyde, 40 mL of toluene, and 0.5 mL of acetic acid and the mixture was stirred for 12 hours at 80° C. The solvent was removed, the resin was sequentially washed three times each with 60 mL each of dichloromethane, NMP, and dichloromethane, and the resin was dried.

To the obtained resin was added 40 mL of acetonitrile, followed by 6 mL of ethyl vinyl ether and 5.0 g of Yb(OTf)3, and the mixture was stirred for two hours at room temperature. The solvent was removed and the resin was washed twice with 60 mL of acetonitrile. The solvent was removed, the resin was sequentially washed three times each with 60 mL each of dichloromethane, NMP, and dichloromethane, and the resin was dried. To the obtained resin was added 100 mL of 100 percent trifluoroacetic acid, the mixture was left standing for one hour, and the reaction solution and resin were separated by filtration. The reaction solution was concentrated tinder reduced pressure to obtain 1.07 g of quinoline carboxylic acid, the synthetic intermediate of Embodiment Compound 3-I.

In an argon atmosphere, 3 mL of thionyl chloride was added to 516 mg (1.34 mmoles) of the obtained quinoline carboxylic acid and the mixture was stirred for 3 hours at 60° C. The thionyl chloride was then removed under reduced pressure. The residue was dissolved in 6 mL of methylene chloride, the solution was added dropwise at 0° C. to a 10 mL pyridine solution of 0.173 mL (1.34 mmoles) of anthranylic acid methyl ester; and the mixture was stirred for 24 hours at room temperature. The pyridine was removed under reduced pressure. The residue was dissolved in ethyl acetate, sequentially washed with 2N—HCl aqueous solution and saturated brine, and dried with anhydrous sodium sulfate. The solvent was removed under reduced pressure, yielding compound 1-I.

Embodiment 2-I

Synthesis of Compound 2-I

Compound 1-I obtained in Embodiment 1-I was dissolved in 10 mL of tetrahydrofuran and 10 mL of methanol, an excess quantity of 2N sodium hydroxide aqueous solution was added, and the mixture was stirred for 17 hours at room temperature. When the reaction had ended, the solution was acidified with 1N hydrochloric acid aqueous solution, and the methanol was removed. The residue was diluted with ethyl acetate and sequentially washed with 1N hydrochloric acid aqueous solution and saturated brine. Following drying with anhydrous sodium sulfate, the solvent was removed under reduced pressure. The residue was purified by recrystallization, yielding embodiment compound 2-I.

Embodiment 3-I

Synthesis of Compound 3-1

4.0 g of commercial Wang resin (about 10 mmole/g) was suspended in NMP and left standing for three hours at room temperature. The excess solvent was removed and 60 mL of NMP; 3.2 g of 4-nitrobenzoic acid, 2.9 mL of pyridine, and 3 mL of 2,6-dichlorobenzoyl chloride were added; and the mixture was stirred for 20 hours at room temperature. The solvent was removed and the resin was washed twice with 60 mL of NMP. The solvent was removed, the resin was sequentially washed three times each with 60 mL each of dichloromethane, NMP, and dichloromethane, and the resin was dried.

Next, 6 g of stannous chloride, 60 mL of NMP, and 3 mL of ethanol were added to the obtained resin and the mixture was stirred for 12 hours at room temperature. The solvent was removed and the resin was washed twice with 60 mL of NMP. The solvent was removed, the resin was sequentially washed three times each with 60 mL each of dichloromethane, NMP, and dichloromethane, and the resin was dried.

the obtained aniline resin were added 2 mL of 3,5-ditrifluoromethylbenzaldehyde, 40 mL of toluene, and 0.5 mL of acetic acid and the mixture was stirred for 12 hours at 80° C. The solvent was removed, the resin was sequentially washed three times each with 60 mL each of dichloromethane, NMP, and dichloromethane, and the resin was dried.

A 40 mL of acetonitrile was added to the obtained resin, followed by 6 mL of ethyl vinyl ether and 5.0 g of Yb(OTf)3, and the mixture was stirred for two hours at room temperature. The solvent was removed and the resin was washed twice with 60 mL of acetonitrile. The solvent was removed, the resin was sequentially washed three times with 60 mL each of dichloromethane, NMP, and dichloromethane, and the resin was dried. To the obtained resin was added 100 mL of 100 percent trifluoroacetic acid and the mixture was left standing for one hour. The reaction solution and the resin were separated by filtration and the reaction solution was concentrated under reduced pressure, yielding 27 g of quinoline carboxylic acid, the synthetic intermediate of Embodiment Compound 3-I.

In an argon atmosphere, 3 mL of thionyl chloride was added to 516 mg (1.34 mmoles) of the obtained quinoline carboxylic acid and the mixture was stirred for 3 hours at 60° C. The thionyl chloride was then removed under reduced pressure. The residue was dissolved in 6 mL of methylene chloride, the solution was added dropwise at 0° C. to a 10 mL pyridine solution of 0.173 mL (1.34 mmoles) of anthranilic acid ethyl ester, and the mixture was stirred for 24 hours at room temperature. The pyridine was removed under reduced pressure. The residue was dissolved in ethyl acetate, sequentially washed with 2N-HCl aqueous solution and saturated brine, and dried with anhydrous sodium sulfate. The solvent was removed under reduced pressure, yielding ester compound 1.

Next, the obtained residue was dissolved in 10 mL of tetrahydrofuran and 10 mL of methanol, excess 2N sodium hydroxide aqueous solution was added, and the mixture was stirred for, 17 hours at room temperature. When the reaction had ended, the solution was acidified with 1N hydrochloric acid aqueous solution, the methanol was removed, and the residue was diluted with ethyl acetate. The residue was then sequentially washed with 1N hydrochloric acid aqueous solution and saturated brine and dried with anhydrous sodium sulfate. The solvent was removed under reduced pressure. The residue was purified by recrystallization, yielding 333 mg of Compound 3-I.

Embodiment 4-I

Synthesis of Compound 4-I

Under argon atmosphere, Compound 3-I was dissolved in 15 mL of 1,4-dioxane. 87 mg (0.632 ml-mole) of 1-butyl sulfonamide and 0.188 mL (1.20 mmoles) of DBU were added, and the mixture was stirred for 14 hours at 90° C. When the reaction had ended, the solvent was removed under reduced pressure and the residue was diluted with ethyl acetate. The residue was sequentially washed with 1N hydrochloric acid aqueous solution and saturated brine and dried with anhydrous sodium sulfate. The solvent was then removed under reduced pressure. The residue was purified by silica gel column chromatography, yielding 85 mg (a yield of 22 percent, 2 steps) of Compound 4-I.

Embodiment 5-I

Synthesis of Compound 5-I

Compound 4-1 was synthesized in the same manner using Compound 2-I.

Embodiment 6-I

Synthesis of Compound 6-I

Under argon atmosphere, 3 mL of thionyl chloride was added to 659 mg (1.71 mmoles) of quinoline carboxylic acid, the synthetic intermediate of Embodiment 3-I, and the mixture was stirred for 1.5 hours at 60° C. The thionyl chloride was then removed under reduced pressure. The residue was dissolved in 20 mL of methylene chloride, the solution was added dropwise at 0° C. to a 10 mL pyridine solution of 294 mg (1.71 mmoles) of 2-aminobenzenesulfonamide, and the mixture was stirred for 19 hours at room temperature. The pyridine was then removed under reduced pressure. The residue was dissolved in ethyl acetate, sequentially washed with 2N HCl aqueous solution and saturated brine, and dried with anhydrous sodium sulfate. The solvent was removed under reduced pressure. The residue was then purified by silica gel column chromatography, yielding 61 mg (a yield of 66 percent) of Compound 6-I.

Embodiment 7-I

Synthesis of Compound 7-1

Under argon atmosphere, 58 mg (0.108 mmole) of Compound 6-I was dissolved in 10 mL of tetrahydrofuran, 26 mg (0.216 mmole) of 4,4-dimethylaminopyridine and 0.018 mL (0.129 mmole) of n-hexanoyl chloride were added, and the mixture was stirred for one hour at 60° C. When the reaction had ended, the reaction solution was diluted with 25 mL of ethyl acetate, sequentially washed with 2N HCl aqueous solution and saturated brine, and dried with anhydrous sodium acetate. The solvent was then removed under reduced pressure. The residues was purified by recrystallization, yielding 29 mg (a yield of 42 percent) of Compound 7-I.

Embodiment 8-I

Synthesis of Compound 8-I

Ester compound 1, the synthetic intermediate of Embodiment 3-I, was resynthesized as Compound 8-I.

Embodiment 9-I

Synthesis of Compound 9-I

Under argon atmosphere, 2 mL of thionyl chloride was added to 227 mg (0.68 mmole) of the corresponding quinoline carboxylic acid compound and the mixture was stirred for three hours at 70° C. The thionyl chloride was then removed under reduced pressure. The residue was dissolved in 3 mL of methylene chloride, the solution was added dropwise at 0° C. to a 5 mL pyridine solution of 113 mg (0.68 mmole) of ethyl 2-aminobenzoate, and the mixture was stirred for three hours at room temperature. The pyridine was then removed under reduced pressure. The residue was dissolved in ethyl acetate, sequentially washed with 2N HCl aqueous solution and saturated brine, and dried with anhydrous sodium sulfate. The solvent was then distilled off under reduced pressure. The residue was purified by recrystallization, yielding 46 mg (a yield of 14 percent) of Compound 9-I.

Embodiment 10-I

Synthesis of Compound 10-I

Under argon atmosphere, 2 mL of thionyl chloride was added to 64 mg (0.19 mmole) of the corresponding quinoline carboxylic acid compound and the mixture was stirred for three hours at 60° C. The thionyl chloride was then removed under reduced pressure. The residue was dissolved in 3 mL of methylene chloride, the solution was added dropwise at 0° C. to a 5 mL pyridine solution of 33 mg (0.19 mmole) of 2-aminobenzenesulfonamide, and the mixture was stirred for 18 hours at room temperature. The pyridine was removed under reduced pressure. The residue was dissolved in ethyl acetate, washed sequentially in 2N HCl aqueous solution and saturated brine, and dried with anhydrous sodium sulfate. The solvent was then removed under reduced pressure. The residue was purified by recrystallization, yielding 17 mg (a yield of 18 percent) of Compound 10-I.

Embodiment 11-I

Synthesis of Compound 11-I

Under argon atmosphere, 43 mg (0.09 mmole) of Embodiment Compound 9-I was dissolved in 5 mL, of tetrahydrofuran and 2 mL of methanol, 1 mL of 2N sodium hydroxide solution was added, and the mixture was stirred for 15 hours. When the reaction had ended, 2N hydrochloric acid was added. Following neutralization, the reaction m was concentrated. The precipitating crystals were washed with water, yielding 32 mg (a yield of 79 percent) of Compound 11-I.

Embodiment 12-I

Synthesis of Compound 12-I

Under argon atmosphere, 16 mg (0.03 mmole) of Compound 10-I was dissolved in 1 mL of tetrahydrofuran, 8 mg (0.06 mmole) of 4,4-dimethylaminopyridine and 0.005 mL (0.4 mmole) of n-hexanoyl chloride were added, and the mixture was stirred for 15 hours at 60° C. When the reaction had ended, the reaction product was diluted with 25 mL of ethyl acetate, sequentially washed with 2N HCl aqueous solution and saturated brine, and dried with anhydrous sodium sulfate. The solvent was then removed under reduced pressure. The residue was purified by recrystallization, yielding 3.6 mg (a yield of 19 percent) of Compound 12-I.

Embodiment 13-I

Synthesis of Compound 13-I

Under argon atmosphere, 30 mg (0.07 mmole) of Compound 11-I was dissolved in a mixed solution of 2 mL of tetrahydrofuran and 2 mL of chloroform, 20 mg (0.08 mmole) of 2-chloro-1-methylpyridinium iodide and 0.022 mL (0.16 mmole) of triethylamine were added, and the mixture was stirred for 15 hours. The solvent was then removed under reduced pressure. The residue was dissolved in ethyl acetate, sequentially washed in water and saturated brine, and dried with anhydrous sodium sulfate. The solvent was then removed under reduced pressure. The solution was dissolved in 1,4-dioxane, 9.1 mg (0.07 mmole) of n-butyl sulfonamide and 20 mg (0.14 mmole) of 1,8-diazabicyclo[5.4.0]undec-7-ene were added, and the mixture was stirred for 15 hours under argon atmosphere at 90° C. The reaction solution was concentrated, dissolved in ethyl acetate, sequentially washed with water and saturated brine, and dried with anhydrous sodium sulfate. The solvent was then removed under reduced pressure. The residue was purified by recrystallization, yielding 15 mg (a yield of 40 percent) of Compound 13-I.

Embodiment 14-I

Synthesis of Compounds 14-I, 16-I, 19-I to 26-I, 28-I to 31-I, 35-I to 45-I, 47-I, 48-I, 55-I, 57-I to 59-I, 61-I to 68-I, 95-I to 97-I, 99-I, 100-I, 101-I, 104-I to 106-I, and 111-I The corresponding compounds were obtained in the same manner as the syntheses of Embodiments 3-I, 4-I, and 5-I.

Embodiment 15-I

Synthesis of Compounds 15-I, 17-I, 18-I, 33-I, 34-I, 83-I, 85-I, 103-I, and 107-I to 110-I The corresponding compounds were obtained in the same manner as the syntheses of Embodiments 6-1 and 7-I.

Embodiment 16-I

Synthesis of Compound 50-I 443 mg of quinoline carboxylic acid, the synthetics intermediate of Embodiment 3-I, was dissolved in 2 mL of DMF and 5 mL of dichloromethane; 60 mg of DMAP, 561 mg of PS-TFP resin made by Argonaut Corp., and 0.575 mL of diisopropylcarbodiimide were added; and the mixture was stirred for 10 hours at room temperature. The mixture was sequentially washed five times each with 60 mL each of dichloromethane, DMF, and dichloromethane. The resin was then dried. To the obtained resin were added 194 mg of 3-amino-3-cyclohexyl-propionic acid methyl ester, 5 mL of dichloromethane, 0.216 mL of N,N-diisopropylethylamine, and 8 mg of triethylamine hydrochloride and the mixture was stirred at room temperature for 12 hours. The reaction solution was concentrated and diluted with ethyl acetate and washed with 1N hydrochloric acid aqueous solution. The ethyl acetate layer was dried with anhydrous sodium sulfate and the solvent was removed under reduced pressure, yielding 350 mg of ester compound.

The obtained ester compound was dissolved in 2 mL of tetrahydrofuran and 2 mL of methanol, excess 2N sodium hydroxide aqueous solution was added, and the mixture was stirred for three hours at room temperature. When the reaction had ended, the reaction solution was acidified with 1N hydrochloric acid aqueous solution and the methanol was removed. The residue was diluted with ethyl acetate, sequentially washed with 1N hydrochloric acid aqueous solution and saturated brine, and dried with anhydrous sodium sulfate. The solvent was removed under reduced pressure, yielding 415 mg of carboxylic acid.

The obtained carboxylic acid was dissolved in a mixed solution of 5 mL of chloroform and 5 mL of tetrahydrofuran; 239 mg of 1-aminopyridium iodide and 0.263 mL of triethylamine were added, and the mixture was stirred for 12 hours at room temperature. The solvent was removed under reduced pressure. The residue was dissolved in 10 mL of 1,4-dioxane; 0.233 mL of DBU and 155 mg of 4isopropylbenzenesulfonamide were added, and the mixture was stirred for one hour at 90° C. To this was added 1N hydrochloric acid aqueous solution. When the reaction had ended, the solvent was removed under reduced pressure. The residue was diluted with ethyl acetate, washed with 1N hydrochloric acid aqueous solution and the ethyl acetate layer was dried with anhydrous sodium sulfate. The solvent was then removed under reduced pressure. The residue was purified by silica gel column chromatography, yielding 109 mg of Compound 50-I.

Embodiment 17-I

Synthesis of Compounds 32-I, 49-I to 54-I, 56-I, 60-I, 79-I, 86-I, 92-I to 94-I

The corresponding compounds were obtained in the same manner as the synthesis of Embodiment 16-I.

Embodiment 18-I

Synthesis of compound 112-I 495 mg (1.78 mmole) of quinoline carboxylic acid, the synthetic intermediate of Embodiment 3-I, was dissolved in 10 mL of tert-butanol; 0.387 mL (1.80 mmoles) of diphenylphosphanaazide and 0.358 mL (2.57 mmoles) of triethylamine were added, and the mixture was refluxed overnight. When the reaction had ended, the solvent was removed under reduced pressure, 5 mL of 4N HCl/1,4-dioxane was added to the residue, and the mixture was stirred overnight at room temperatures. When the reaction had ended, the solvent was removed under reduced pressure, ethyl acetate and 1N NaOH aqueous solution were added to the residue, the mixture was extracted with ethyl acetate, and hexane was added to the organic layer. The obtained crystals were separated by filtration, yielding 220 mg of amine compound. 50 mg (0.140 mmole) of the obtained amine compound was dissolved in 2 mL of toluene, 41 mg (0.280 mmole) of phthalic anhydride was added, and the mixture was stirred overnight at room temperature. When the reaction had ended, the solvent was removed under reduced pressure and the residue was purified by recrystallization, yielding 48 mg of Compound 112-I.

Embodiment 19-I

Synthesis of Compound 113-I 50 mg (0.140 mmole) of amine compound, the synthetic intermediate of Embodiment 18-I, was dissolved in 2 mL of toluene, 52 mg (0.280 mmole) of 2-sulfobenzoic acid anhydride was added, and the mixture was stirred overnight at room temperature. When the reaction had ended, the solvent was removed under reduced pressure and the residue was purified by recrystallization, yielding 68 mg of Compound 113-I.

Embodiment 20-I

Synthesis of Compound 114-I 460 mg (1.19 mmole) of quinoline carboxylic acid, the synthetic intermediate of Embodiment 3-I, was dissolved in 2 mL of thionyl chloride and the mixture was stirred for four hours at 40° C. The solvent was removed under reduced pressure, the residue was dissolved in 5 mL of 1,4-dioxane, 2 mL of 27 percent ammonium aqueous solution was added, and the mixture was stirred overnight at room temperature. When the reaction had ended, the solvent was removed under reduced pressure, ethyl acetate and 1N NaOH aqueous solution were added to the residue, and the mixture was extracted with ethyl acetate. The organic layer was washed with saturated brine and dried with anhydrous sodium sulfate. The solvent was removed under reduced pressure and the residue was purified by silica gel column chromatography, yielding 102 mg of amide compound.

102 mg (0.260 mmole) of the obtained amide compound was dissolved in 5 mL of THF, 69 mg (0.312 mmole) of phosphorus pentasulfide was added, and the mixture was stirred overnight at room temperature. When the reaction had ended, the solvent was removed under reduced pressure. The residue was purified by silica gel column chroinatography, yielding 90 mg of thioamide compound.

90 mg (2.25 mmole) quantity of the obtained thioamide compound was dissolved in 5 mL of THF, 69 mg (0.269 mmole) of 2-(2-bromoacetyl) benzoic acid methyl ester was added, and the mixture was stirred for two nights at 60° C. When the reaction had ended, 5 mL of MeOH was added to the reaction solution 1 mL of 1N NaOH aqueous solution was then added and the mixture was stirred for four hours at room temperature. When the reaction had ended, the solvent was removed under reduced pressure, ethyl acetate and 1N HCl aqueous solution were added to the residue, and the mixture was extracted with ethyl acetate. The organic layer was washed with saturated brine and dried with anhydrous sodium sulfate. The solvent was removed under reduced pressure. The obtained residue was subjected to reverse-phase high-performance liquid chromatography employing silica gel of the chemically bonded octadodecyl group type as packing material and eluted with a mixed solution of water and acetonitrile containing 0.1 percent (v/v) trifluoroacetic acid. The target fraction was freeze-dried, yielding 50 mg of Compound 114-I.

Embodiment 21-I

Synthesis of Compound 115-I 33 mg (0.0606 mmole) of Compound 114-I was dissolved in 1 mL of DMF and 0.016 ml (0.145 mmole) of dimethylsulfamoyl chloride was added. To this was added a separately prepared 1 mL DMF solution of 15 mg (0.0727 mmole) of 4-isopropylbenzenesulfonamide, 0.031 mL (0.218 mmole) of butyldimethylamine, and 8 mg (0.0606 mmole) of dimethylaminopyridine, and the mixture was stirred for three days at 50° C. The solvent was removed under reduced pressure. The residue was subjected to reverse-phase high-performance liquid chromatography employing silica gel of the chemically bonded octadodecyl group type as packing material and eluted with a mixed solution of water and acetonitrile containing 0.1 percent (v/v) trifluoroacetic acid. The target fraction was freeze-dried, yielding 3 mg of Compound 115-I.

NMR analysis values of representative compounds among synthesized compounds are shown in Table 2-I.

TABLE 2-I

| Compound No. | NMR | SOLVENT |
|---|---|---|
| 4 | 0.80(3H, t, J=7.5Hz), 1.27-1.68(4H, m), 3.15-3.42(2H, m), 7.13-7.16(2H, m), 7.48-7.50(1H, m), 8.02-8.08(1H, m), 8.26-9.17(8H, m), 11.54(1H, S) | DMSO-d6 |
| 7 | 0.77(3H, t, J=6.6Hz), 1.09-1.20(4H, m), 1.38-1.44(2H, m), 2.23(2H, t, J=7.2Hz), 7.41-7.47(1H, m), 7.76-8.00(1H, m), 8.31-8.34(3H, m), 8.39-8.42(1H, m),, 8.58-8.76(3H, m), 8.99(2H, s), 10.67(1H, s) | DMSO-d6 |
| 9 | 4.88(3H, s), 7.55-7.65(3H, m), 7.94-7.97(2H, m), 8.12-8.45(5H, m), 8.59(1H, m), 8.96-9.00(2H, m) | CDCl3 |
| 10 | 7.55-7.60(3H, m), 7.94-7.97(2H, m), 8.11(1H, m), 8.22-8.37(5H, m), 8.67-8.70(2H, m) | CDCl3 |
| 11 | 7.27(1H, m), 7.56(1H, m), 7.68-7.77(2H, m), 8.09(1H, m), 8.29-8.39(5H, m), 8.69-8.75(3H, m) | DMSO-d6 |
| 12 | 0.78(3H, t, J=6.3Hz), 1.14-1.18(4H, m), 1.39-1.44(2H, m), 2.21(2H, t, J=6.9Hz), 7.44(1H, m), 7.57(1H, m), 7.72-7.77(2H, m), 7.97(1H, m), 8.23-8.48(6H, m), 8.67-8.72(2H, m) | DMSO-d6 |
| 13 | :0.79(3H, t, J=6.3Hz), 1.31-1.39(2H, m), 1.60-1.65(2H, m), 2.49-2.50(2H, m), 7.11(1H, m), 7.45-7.71(2H, m), 7.73(1H, m), 8.10-8.50(5H, m), 8.83-8.86(2H, m), 9.10(1H, m) | DMSO-d6 |

Pharmacological Test Example 1

Measurement of ACC Inhibition Activity (1. Purification of ACC)

A male SD rat was deprived of food for two days and then fed a high-sucrose diet (component) for two days. While anesthetized with ether, the descending vena cava was cut upon, the animal was bled, and the liver was rapidly recovered. In an ice-cooled buffer solution A (225 mM mannitol, 75 mM sucrose, 10 mM Tris-HCl (pH 7.5), 0.05 mM EDTA, 5 mM potassium citrate, 2.5 mM MgCl2, 10 mg/L pepstatin A, 10 mg/L leupeptin, 1 mM PMSF), the liver was homogenized with a polytone homogenizer. A quantity of buffer A nine times the weight of the liver was added, the mixture was centrifuged for 10 minutes at 1,000 g, the supernatant was recovered, and the supernatant was centrifuged for another 10 minutes at 17,000 g.

Ammonium sulfate was added to 35 percent saturation to the obtained supernatant. The mixture was stirred for 45 minutes and then centrifuged for 10 minutes at 17,000 g. Buffer solution B (100 mM Tris-HCl (pH 7.5), 500 mM NaCl, 1 mM EDTA, 0.1 mM DTT, 10 percent glycerol, 10 mg/L pepstatin A, 10 mg/L leupeptin, 0.5 mM PMSF) was added to the obtained precipitate and dissolved. The solution was then centrifuged for 20 minutes at 40,000 g. The supernatant was dialyzed overnight against buffer C (100 mM Tris-HCl (pH 7.5), 500 mM NaCl, 1 mM EDTA, 0.1 mM DTT, 5 percent glycerol).

The dialyzed supernatant was passed through a 5 µM filter, applied to a monomeric avidin sepharose column, and washed with buffer B. The ACC was eluted with buffer B containing 2 mM d-biotin.

(2 Measurement of ACC Inhibition Activity)

The compounds synthesized in the above-described embodiments were dissolved in DMSO and charged to glass vials. 250 µL of ACC-containing reaction solution (40 mM Tris-HCl (pH 7.5), 40 mM MgCl2, 40 mM sodium citrate, and 2 mM DTT) was added. The mixture was heated for 30 minutes at 37° C. in a thermostatic chamber and then cooled with ice. To reaction solution 1 was added 250 µL of reaction solution 2 containing [14C]—NaHCO3 (40 mM Tris-HCl (pH 7.5), 2 mM DTT, 8 mM ATP, 0.5 mM acetyl CoA) and the mixture was heated for 10 minutes at 37° C. 100 µL of 1N HCl was added to stop the reaction. Water in the reaction solution was removed with a centrifugal evaporator, a scintillator was added, the solid component was dissolved, and the 14C radioactivity was measured with a liquid scintillation counter. The ACC inhibition activity of each compound was calculated from the following equation and converted to the ACC inhibition activity rate (%) at 1 µM. The results are given in Table 3-I.

ACC inhibition rate (%)=(1−(a−c)/(b−c))×100
a. Radioactivity when test drug added
b: Radioactivity when test drug not added
c: Blank*

*Reaction solution 1 to which 100 µL of 1N HCl was added before mixing reaction solution 1 and reaction solution 2

TABLE 3-I

| Compound No. | ACC Inhibition (%) |
|---|---|
| 3 | 53 |
| 4 | 78 |
| 7 | 72 |
| 13 | 48 |
| 49 | 62 |
| 50 | 87 |
| 54 | 45 |
| 55 | 70 |
| 56 | 47 |
| 57 | 59 |
| 58 | 46 |
| 59 | 74 |
| 82 | 34 |
| 83 | 98 |
| 94 | 50 |
| 102 | 45 |
| 103 | 50 |
| 107 | 90 |
| 108 | 94 |
| 109 | 61 |
| 110 | 50 |
| 115 | 97 |

Embodiments of the compounds of Mode 2 of the present invention are described below.

Embodiment 1-II

Synthesis of Compound 1-II

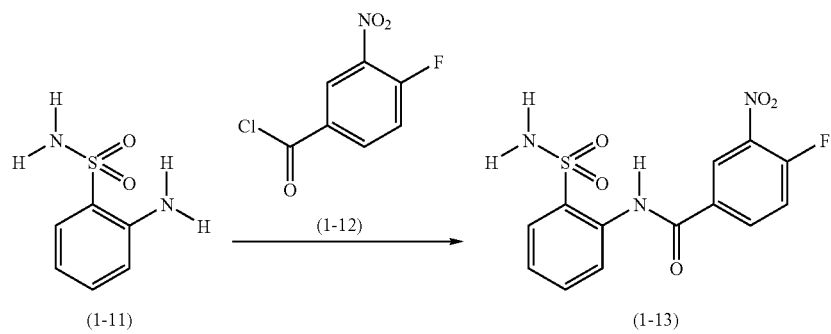

(1-11)  (1-12)  (1-13)

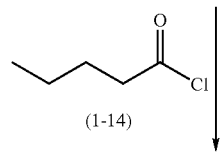

(1-14)

-continued

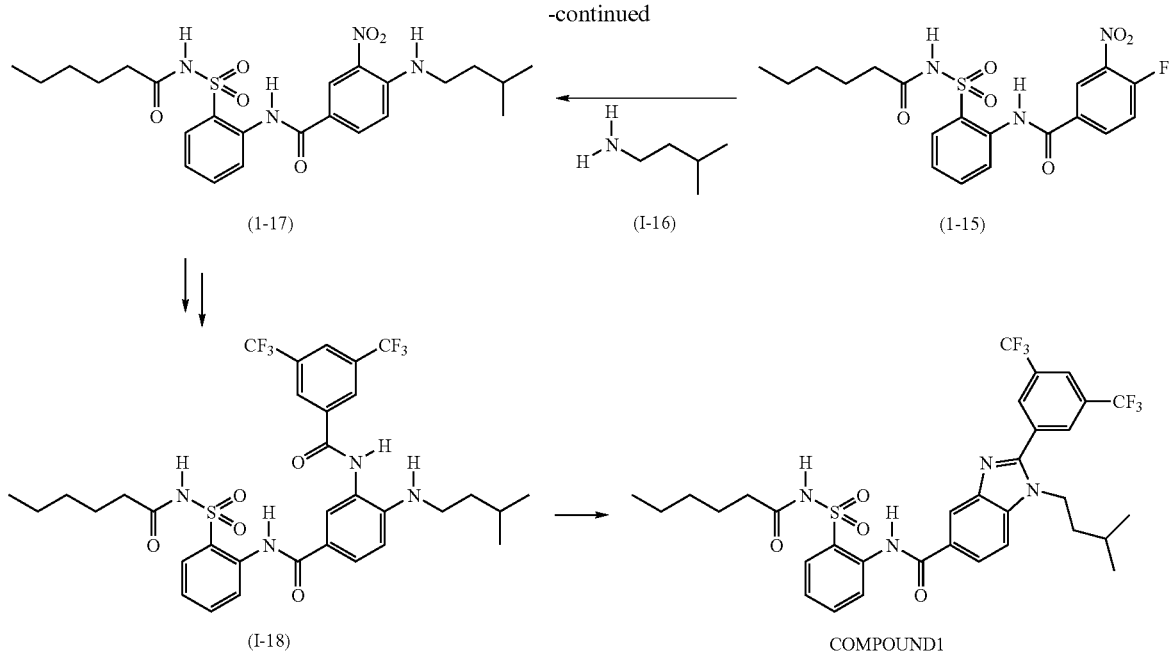

(I-17)  (I-16)  (I-15)

(I-18)  COMPOUND1

18.0 g quantity of 2-aminobenzenesulfonamide (I-11) was dissolved in 100 mL of pyridine and ice-cooled under an argon flow. A reaction solution, obtained by dissolving in 100 mL of tetrahydrofuran the acid chloride (I-12) prepared from 17.7 g of corresponding benzoic acid using thionyl chloride, was added dropwise. The mixture was stirred for three hours at room temperature and the reaction solution was removed under reduced pressure. Methanol was added to the residue and the white precipitate that formed was separated by filtration, washed with water, and dried, yielding 25.0 g of sulfonamide compound (I-13). The obtained sulfonamide compound (I-13) was dissolved in 150 mL of tetrahydrofuran, 11 mL of acid chloride (1A-14) and 0.2 g of 4-dimethylaminopyridine were added, followed by 30 mL of tetrahydrofuran. The mixture was stirred for three hours at room temperature, and 100 mL of water was added to end the reaction. NaHCO3 was added in small increments to neutralize the reaction solution, which was then extracted with 200 mL of ethyl acetate. The ethyl acetate layer was then subjected to reduced pressure to remove the solvent. The product was also extracted with ethyl acetate from the aqueous layer, the solvent was removed under reduced pressure, and this residue was combined with the residue that had been obtained earlier by concentration. Methanol was added to the combined residues. The white precipitate that formed was separated by filtration, washed with water; and dried, yielding 14.57 of nitrobenzene compound (I-15).

5 mL of amine (I-16) and 5 mL of dimethylsulfoxide were added to 504 mg of nitrobenzene compound (I-15) and the mixture was heated to 60° C. and vigorously stirred for two hours. The reaction solvents were removed under reduced pressure and 100 mL of ethyl acetate and 10 mL of 6 M/HCl aqueous solution were added. The precipitate that formed was separated by filtration, purified with methanol and normal hexane, and dried, yielding 547 mg of aniline compound (I-17).

400 mg of iron powder was added to acetic acid under an argon flow and heated to 60° C. 500 mg of aniline compound (I-17) was added incrementally, the mixture was stirred for 1.5 hours, and the iron powder was separated with a cotton plug. NaCHO3 was added in small quantities to the obtained reaction solution until pH 7 was reached. The precipitate that formed was separated by filtration, washed with water, and dried. 180 mg of the obtained powder was dissolved in 5 mL of tetrahydrofuran. 0.08 mL of 3,5-ditrifluoromethylbenzoyl chloride, 24 mg of 4-dimethylaminopyridine, and 0.5 mL of pyridine were added. The mixture was stirred for 15 minutes at room temperature and 20 mL of water was added to end the reaction. NaHCO3 was added incrementally to neutralize the reaction solution. The product was extracted with 40 mL of ethyl acetate and the ethyl acetate layer was subjected to reduced pressure to remove the solvent. The product was also extracted with ethyl acetate from the aqueous layer and the solvent was removed under reduced pressure. The residue was then combined with the residue that had been obtained earlier by concentration. Methanol was added to the combined residues. The white precipitate that formed was separated by filtration, washed with water, and dried, yielding 165 mg of aniline compound (I-18).

Aniline compound (I-18) was dissolved in 15 mL of acetic acid, heated to 50° C., and stirred for three hours. A 50 mL quantity of water was added. The white precipitate that formed was separated by filtration, washed with water, and dried, yielding 135 mg of Compound 1-II.

Embodiment 2-II

Synthesis of Compound 2-II

Synthesis was conducted with corresponding reagents in the same manner as the synthesis of Embodiment 1-II. 540 mg of corresponding Compound 2-II was obtained.

Embodiment 3-II

Synthesis of Compound 3-II

Synthesis was conducted with corresponding reagents in the same manner as the synthesis of in Embodiment 1-II. 90.4 mg of corresponding Compound 3-II was obtained.

Embodiment 4-II

Synthesis of Compound 4-II

Synthesis was conducted with corresponding reagents in the same manner as the synthesis of Embodiment 1-II. 9.7 mg of corresponding Compound 4-II was obtained.

Embodiment 5-II

Synthesis of Compound 5-II

Synthesis was conducted with corresponding reagents in the same manner as the synthesis of in Embodiment 1-II. 6.8 mg of corresponding Compound 5-II was obtained.

Embodiment 6-II

Synthesis of Compound 6-II

Synthesis was conducted with corresponding reagents in the same manner as the synthesis of Embodiment 1-II. 3.3 mg of corresponding Compound 6-II was obtained.

Embodiment 7-II

Synthesis of Compound 7-II

Step 1

2.07 g (10.4 mmole) of 4-fluoro-3-nitrobenzoic acid methyl ester was dissolved in 30 mL of diisopropylethylamine, 3.87 mL (31.2 mmole) of 4-aminobenzotrifluoride was added, and the mixture was stirred overnight at 120° C.

When the reaction had ended, the solvent was removed under reduced pressure, ethyl acetate and 1N HCl aqueous solution were added to the residue, and the residue was extracted with ethyl acetate. The obtained organic layer was washed with saturated brine and dried with anhydrous sodium sulfate, after which the solvent was removed under reduced pressure. Next, the residue was dissolved in 30 mL of MeOH, a catalytic amount of Pd/C was added, and the mixture was stirred for two hours under a hydrogen atmosphere. When the reaction had ended, the reaction solution was filtered and the solvent was removed under reduced pressure. The obtained residue was purified by silica gel column chromatography, yielding 4.34 g of diphenylamine compound.

Step 2

830 mg (2.44 mmole) of the aniline compound obtained in step 1 was dissolved in 10 mL of pyridine, 0.340 mL (2.93 mmoles) of benzoylchloride was added, and the mixture was stirred overnight at room temperature. When the reaction had ended, the solvent was removed under reduced pressure. Ethyl acetate and 1N HCl aqueous solution were added to the residue. The mixture was extracted with ethyl acetate. The obtained organic layer was washed with saturated brine and dried with anhydrous sodium sulfate. The solvent was removed under reduced pressure, yielding 1.11 g of N-benzoylaniline compound.

Step 3

10 mL of acetic acid was added to 1.10 g (2.26 mmoles) of the compound obtained in step 2 and the mixture was stirred overnight at 130° C. When the reaction had ended, the solvent was removed under reduced pressure, the residue was dissolved in MeOH (10 mL) and THF (10 mL), 10 mL of 1N NaOH was added, and the mixture was stirred overnight at room temperature. When the reaction had ended, the solvent was removed under reduced pressure, ethyl acetate and 1N HCl aqueous solution were added to the residue, and the mixture was extracted with ethyl acetate. The obtained organic layer was washed with saturated brine and dried with anhydrous sodium sulfate. The solvent was removed under reduced pressure, yielding 675 mg of benzimidazole compound.

Step 4

649 mg (1.69 mmole) of the compound obtained in step 3 was dissolved in tert-butanol, 0.51 mL (2.37 mmoles) of diphenylphosphanaazide and 0.471 mL (3.38 mmoles) of triethylamine were added, and the mixture was refluxed for five hours. When the reaction had ended, the solvent was removed under reduced pressure, 5 mL of 4N HCl/1,4-dioxane were added to the residue, and the mixture was stirred overnight at room temperature. When the reaction had ended, the solvent was removed under reduced pressure, ethyl acetate and 1N NaOH aqueous solution were added, and the mixture was extracted with ethyl acetate. Hexane was added to the organic layer to obtain crystals. These crystals were filtered out, yielding a quantitative amount of benzimidazole compound.

Step 5

35 mg, (0.100 mmole) of the compound obtained in Step 4 was dissolved in 2 mL of toluene, 37 mg (0.200 mmole) of 2-sulfobenzoic acid anhydride was added, and the mixture was stirred overnight. When the reaction had ended, the solvent was removed under reduced pressure. The residue was subjected to reverse-phase high-performance liquid chromatography employing silica gel of the chemically bonded octadodecyl group type as packing material and eluted with a mixed solution of water and acetonitrile containing 0.1 percent (v/v) trifluoroacetic acid. The target fraction was freeze-dried, yielding 9 mg of Compound 7-II.

Embodiment 8-II

Synthesis of Compound 8-II

Step 1

147 mg (1.00 mmole) of 3-cyanobenoic acid was dissolved in acetone, 1 mL (2.00 mmoles) of 2.0 M-trimethylsilyl diazomethane in hexane was added, and the mixture was stirred for one hour at room temperature. The solvent was removed under reduced pressure, the residue was dissolved in 5 mL of ethanol, 0.123 mL (2.00 mmoles) of 50 percent NH2OH aqueous solution was added, and the mixture was stirred overnight at 50° C. When the reaction had ended, the reaction solution was filtered and washed with hexane, yielding 100 mg of amideoxime compound.

Step 2

38 mg (0.100 mmole) of the benzimidazole compound of Embodiment 7 was dissolved in 2 mL of DMF, 19 mg (0.100 mmole) of the compound of Step 1 in Embodiment 8-II and 19 mg (0.100 mmole) of WSC.HCl were added, and the mixture was stirred for four hours at room temperature and then overnight at 100° C. When the reaction had ended, ethyl acetate and 1N HCl aqueous solution were added to the residue and the mixture was extracted with ethyl acetate. The obtained organic layer was washed with saturated brine and dried with anhydrous sodium sulfate. The solvent was then removed under reduced pressure. The residue was dissolved in 1 mL of MeOH and 1 mL of THF, 1 mL of 1N NaOH aqueous solution was added, and the mixture was stirred overnight at room temperature. When the reaction had ended, the solvent was removed under reduced pressure. The residue was subjected to reverse-phase high-performance liquid chromatography employing silica gel of the chemically bonded octadodecyl group type as packing material and eluted with a mixed solution of water and acetonitrile containing 0.1 percent (v/v) trifluoroacetic acid. The target fraction was freeze-dried, yielding 5 mg of Compound 8-II.

Table 1-II gives the molecular structures and mass spectrometry results for the compounds (1-II to 8-II) synthesized in embodiments 1-II to 8-II, and Table 2-II gives NMR analysis values for representative compounds.

TABLE 1-II

| Compound No. | | MS (ESI)(MH+) |
|---|---|---|
| 1 | | 697 |
| 2 | | 771 |
| 3 | | 573 |
| 4 | | 635 |

TABLE 1-II-continued
| Compound No. | | MS (ESI)(MH+) |
|---|---|---|
| 5 | 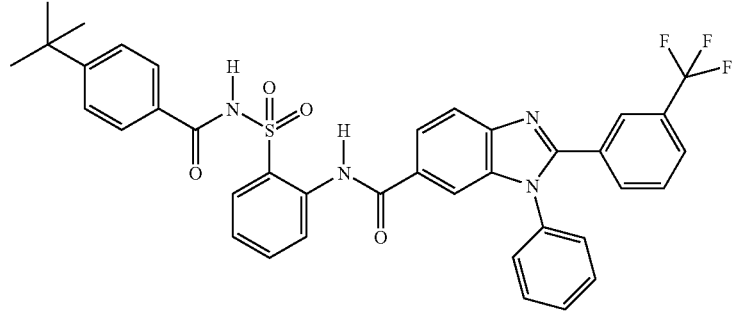 | 697 |
| 6 | 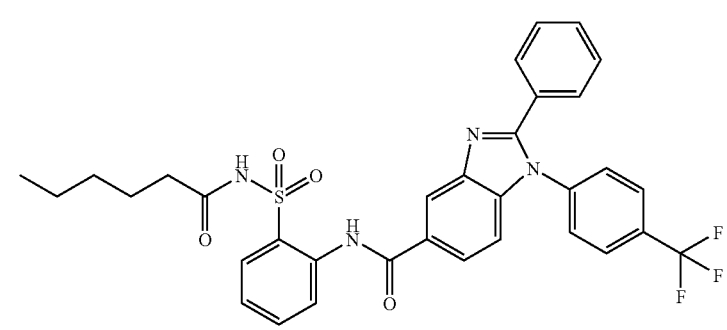 | 635 |
| 7 | 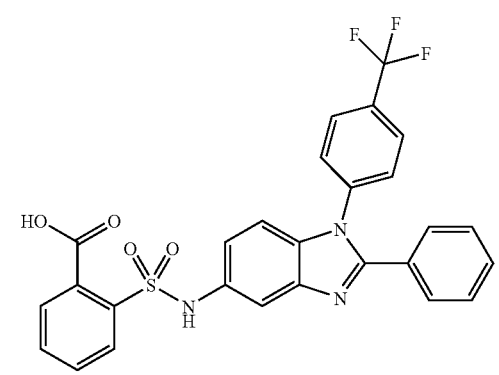 | 538 |
| 8 | 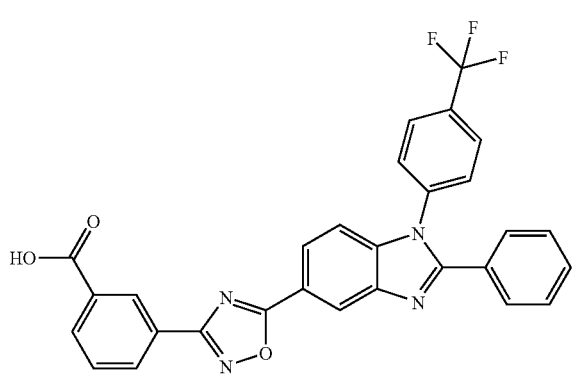 | 527 |

TABLE 2-II

| Compound No. | NMR | SOLVENT |
| --- | --- | --- |
| 1 | δ 0.77(3H, t, J=7.0Hz), 0.81(6H, d, J=6.4Hz), 1.07-1.23(4H, m), 1.42(2H, pseudo quint., J=7.3Hz), 1.54(1H, pseudo nonatet, J=6.6Hz), 1.65(2H, dd, 15.5, 7.0Hz), 2.25(2H, t, J=7.3Hz), 4.40(2H, t, J=7.8Hz), 7.40(1H, ddd, J=7.6, 7.6, 1.2Hz), 7.77(1H, ddd, J=7.8, 7.8, 1.5Hz), 7.93(1H, d, J=8.8Hz), 7.95(1H, dd, J=8.2, 1.5Hz), 8.02(1H, dd, J=8.5, 1.5Hz), 8.40(1H, s), 8.53(2H, s), 8.54(1H, d, J=8.8Hz), 10.59(1H, s), 12.6(1H, br.s). | DMSO-d6 |
| 2 | δ 0.77(3H, t, J=7.0Hz), 1.06-1.22(4H, m), 1.43(2H, pseudo quint., J=7.4Hz), 2.26(2H, t, J=7.2Hz), 7.41(1H, dd, J=7.3, 7.3Hz), 7.56(1H, d, J=8.5Hz), 7.78(1H, dd, J=7.8, 7.8Hz), 7.84(2H, d, J=8.5Hz), 7.95(1H, dd, J=7.9, 1.5Hz), 8.03(2H, d, J=8.5Hz), 8.07(2H, s), 8.25(1H, s), 8.52-8.55(2H, m), 10.65(1H, s), 12.6(1H, br.s). | DMSO-d6 |
| 3 | δ 0.77(3H, t, J=7.0Hz), 1.04-1.21(4H, m), 1.41(2H, pseudo quint., J=7.3Hz), 2.24(2H, t, J=7.3Hz), 2.53(3H, s), 7.38(2H, d, J=8.5Hz), 7.39(1H, dd, J=7.8, 7.8Hz), 7.76(1H, dd, J=7.8, 7.8Hz), 7.88-7.95(4H, m), 8.05(2H, d, J=8.5Hz), 8.30(1H, s), 8.52(1H, d, J=8.5Hz), 10.55(1H, s), 12.6(1H, br.s). | DMSO-d6 |
| 4 | δ 0.70(3H, t, J=7.6Hz), 1.00-1.10(4H, m), 1.42-1.50(2H, m), 2.26(2H, t, J=7.6Hz), 7.16-7.28(4H, m), 7.46-7.55(4H, m), 7.64-7.73(3H, m), 7.84(1H, d, J=7.9Hz), 7.88(1H, d, J=8.2Hz), 8.02(1H, d, J=8.8Hz), 8.66(1H, s), 8.78(1H, d, J=8.2Hz), 10.83(1H, s). | DMSO-d6 |

In the same manner, as described in Pharmacological Test Example 1, the ACC inhibition activity of the compound of Mode 2 of the present invention was calculated and the ACC inhibition activity rate was determined. The results are given in Table 3-II.

TABLE 3-II

| Compound No. | ACC Inhibition (%) |
| --- | --- |
| 1 | 50 |
| 2 | 92 |
| 4 | 54 |
| 5 | 89 |
| 8 | 57 |

Embodiments of the compound of Mode 3 of the present invention will be described next.

Embodiment 1-III

Synthesis of Compound 16-III)

To a 27 mL diethylamine solution of 3.0 g (13.7 mmoles) of iodoaniline, 52 mg (0.274 mmole) of copper iodide, and 96 mg (0.137 mmole) of dichlorobis(triphenyl-phosphine)palladium was added 3.5 g (20.5 mmoles) of 3-ethynyl-α,α,α-trifluorotoluene and the mixture was stirred for 15 hours at 50° C. Ethyl acetate was added to the reaction solution, the mixture was filtered, water was added to the filtrate, and the filtrate was extracted. The organic layer was sequentially washed with a saturated sodium hydrogencarbonate aqueous solution and saturated brine, and then dried with anhydrous magnesium sulfate. The solvent was removed under reduced pressure. The residue was purified by basic silica gel column chromatography, yielding 3.4 g (95 percent) of aniline compound.

71 mg (0.383 mmole) of 2-sulfobenzoic anhydride was added to a 2 mL toluene solution of 100 mg (0.383 mmole) of the aniline compound and the mixture was stirred for one hour at room temperature. The solvent was removed under reduced pressure and the residue was purified by thin-layer chromatography, yielding 68 mg (40 percent) of Compound 16-III.

Embodiment 2-III

Synthesis of Compounds 2-III, 3-III, 5-III, 6-III, 9-III, 19-III to 23-III, 60-III, 77-III to 78-III, 81-III, 82-III, 85-III, 87-III, 91-III, 92-III, and 98-III Compounds 2-III, 3-III, 5-III, 6-III, 9-III, 19-III to 23-III, 60-III, 77-III to 78-III, 81-III, 82-III, 85-III, 87-III, 91-III, 92-III, and 98-III were synthesized by the method described in Embodiment 1-III above (the method of subjecting aniline compounds to the various sulfonyl chlorides). Functional group conversion was conducted for compounds requiring substituent conversion, yielding corresponding compounds.

Embodiment 3-III

Synthesis of Compound 17-III 114 mg (0.766 mmole) of phthalic anhydride was added to a 4 mL toluene solution of 200 mg (0.766 mmole) of the synthetic intermediate of Embodiment 1-III and the mixture was stirred for 13 hours at room temperature. The solvent was removed under reduced pressure and the residue was purified by silica gel column chromatography, yielding 228 mg (73 percent) of Compound 17-III.

Embodiment 4-III

Synthesis of Compound 18-III 82 mg (0.362 mmole) of zinc bromide was added to a 3 mL toluene solution of 148 mg (0.362 mmole) of Embodiment 3-III and the mixture was heated to 80° C. While still at 80° C., a 1 mL toluene solution of 88 mg (0.543 mmole) of hexamethyldisilazane was added dropwise over 10 minutes and the mixture was stirred for another two hours. After cooling the mixture to room temperature, 1N hydrochloric acid was added and the mixture was extracted with ethyl acetate. The organic layer was sequentially washed with saturated sodium hydrogencarbonate aqueous solution and saturated brine and dried with anhydrous magnesium sulfate. The solvent was then removed under reduced pressure. The residue was slurry washed with methylene chloride and diethylether, yielding 128 mg (90 percent) of Embodiment Compound 18-III.

Embodiment 5-III

Synthesis of Compound 19-III 0.16 mL (1.15 mmole) of triethylamine and 126 mg (0.576 mmole) of 3-chlorosulfonylbenzoic acid were added to a 2 mL dichloromethane solution of 50 mg (0.192 mmole) of the aniline compound which is the synthetic intermediate of Embodiment 1-III, the mixture was stirred for five hours at room temperature, 1N hydrochloric acid was added to the reaction solution, and the mixture was extracted with ethyl acetate. The organic layer was dried with anhydrous magnesium sulfate and the solvent was removed under reduced pressure. The residue was purified by thin-layer chromatography, yielding 24 mg (28 percent) of Compound 19-III.

Embodiment 6-III

Synthesis of Compound 20-III

Employing 50 mg (0.192 mmole) of aniline compound as starting material, 19 mg (22 percent) of Embodiment Compound 20-III was obtained by the same procedure as in Embodiment 5-III.

Embodiment 7-III

Synthesis of Compound 21-III

Employing 5.0 g (22.6 mmole) of 4-iodoaniline as starting material, 5.8 mg (98 percent) of aniline compound was obtained by the same procedure as in Embodiment 1-III.

Employing 50 mg (0.192 mmole) of aniline compound as starting material, 38 mg (44 percent) of Embodiment Compound 21-III was obtained by the same procedure as in Embodiment 5-III.

Embodiment 8-III

Synthesis of Compound 22-III

Employing 50 mg (0.192 mmole) of the aniline compound which is the intermediate of Embodiment 7-III as starting material, 66 mg (77 percent) of Embodiment Compound 22-III was obtained by the same procedure as in Embodiment 5-III.

Embodiment 9-III

Synthesis of Compound 23-III 233 mg (2.79 mmole) of 36 percent formalin and 175 mg (2.79 mmoles) of sodium cyanoborohydride were added to a 10 mL methanol solution of 560 mg (2.15 mmoles) of the synthetic intermediate of Embodiment 8-III at 0° C. and the mixture was stirred for 10 minutes while still at 0° C. A saturated sodium hydrogencarbonate aqueous solution was added to the reaction solution and the mixture was extracted with ethyl acetate. The organic layer was washed with saturated brine and dried with anhydrous magnesium sulfate, then the solvent was removed under reduced pressure. The residue was purified by silica gel column chromatography, yielding 52 mg (9 percent) of N-methylaniline compound.

Employing 50 mg (0.182 mmole) of N-methylaniline as starting material, 81 mg (97 percent) of Embodiment Compound 23-III was obtained by the same procedure as in Embodiment 1-III.

Embodiment 10-III

Synthesis of Compound 24-III

Employing 79 mg (0.287 mmole) of the synthetic intermediate of Embodiment 9-III as starting material, 29 mg (24 percent) of Embodiment Compound 24-III was obtained by the same procedure as in Embodiment 3-III.

Embodiment 11-III

Synthesis of Compound 25-III

Employing 26 mg (0.10 mmole) of the synthetic intermediate of Embodiment 7-III as starting material, 21 mg (51 percent) of Embodiment Compound 25-III was obtained by the same procedure as in Embodiment 3-III.

Embodiment 12-III

Synthesis of Compound 26-III

Employing 26 mg (0.10 mmole) of the synthetic intermediate of Embodiment Compound 21-III as starting material, 35 mg (85 percent) of Embodiment Compound 26-III was obtained by the same procedure as in Embodiment 3-III.

Embodiment 13-III

Synthesis of Compound 27-III

Employing 229 mg (0.10 mmole) of 4-iodobenzonitrile as starting material, 259 mg (96 percent) of benzonitrile compound was obtained by the same procedure as in the synthesis of the synthetic intermediate of Embodiment Compound 16-III.

0.045 mL (0.738 mmole) of 50 percent hydroxylamine was added to a 4 mL ethanol solution of 100 mg (0.369 mmole) of the above intermediate and the mixture was stirred for 16 hours at 60° C. Water was added to the reaction solution and the mixture was extracted with ethyl acetate. The organic layer was washed with saturated brine and dried with anhydrous magnesium sulfate. The solvent was removed under reduced pressure, yielding 110 mg (98 percent) of amideoxime compound.

36 mg (0.197 mmole) of isophthalic acid monomethyl ester and 38 mg (0.197 mmole) of 1-ethyl-3-(3-dimethylaminopropyl)carbodiimide hydrochloride were added to a 2 mL N,N-dimethylformamide solution of 30 mg (0.099 mmole) of above intermediate 2-III and the mixture was stirred for one hour at room temperature and then for 17 hours at 80° C. The solvent was removed under reduced pressure, ethyl acetate and water were added, and the mixture was extracted. The organic layer was sequentially washed with saturated sodium hydrogencarbonate aqueous solution and saturated brine and then dried with anhydrous magnesium sulfate. The solvent was removed under reduced pressure. The residue was slurry washed with diethylether and hexane, yielding 23 mg (52 percent) of ester compound.

1 mL of 1N lithium hydroxide was added to a mixed solution (2 mL of methanol and 1 mL of tetrahydrofuran) of 22 mg (0.049 mmole) of the intermediate of 3-III and the mixture was stirred for one hour at 50° C. The mixture was cooled to room temperature and then neutralized with 1 mL of 1N hydrochloric acid. Next, 10 percent monosodium dihydrogen phosphate aqueous solution was added to adjust the pH to 3-4 and the mixture was extracted with ethyl acetate. The organic layer was dried with anhydrous magnesium sulfate and the solvent was removed under reduced pressure, yielding 17 mg (80 percent) of Embodiment Compound 27-III.

Embodiment 14-III

Synthesis of Compound 28-III

Employing 30 mg (0.099 mmole) of the synthetic intermediate of Embodiment 13-III as starting material, 36 mg (81 percent) of ester compound was obtained by the same procedure as in Embodiment 13-III.

Employing 35 mg (0.078 mmole) of the above synthetic intermediate as starting material, 28 mg (83 percent) of Embodiment Compound 28-III was obtained by the same procedure as in Embodiment 13-III.

Embodiment 15-III

Synthesis of Compound 29-III

Employing 30 mg (0.099 mmole) of the synthetic intermediate of Embodiment 13-II as starting material, 12 mg (5 percent) of ester compound was obtained by the same procedure as in Embodiment 13-III.

Employing 11 mg (0.025 mmole) of the above synthetic intermediate as starting material, 10 mg (92 percent) of Embodiment Compound 29-III was obtained by the same procedure as in Embodiment 13-III.

Embodiment 16-III

Synthesis of Compound 30-III 4 mg (0.032 mmole) of morpholine and 6 mg (0.032 mmole) of 1-ethyl-3-(3-dimethylaminopropyl)carbodiimide hydrochloride were added to a 1 mL N,N-dimethylformamide solution of 7 mg (0.016 mmole) of Compound 27-III and the mixture was stirred for 15 hours at room temperature. Water was added to the reaction solution and the mixture was extracted with ethyl acetate. The organic layer was washed with saturated brine and dried with anhydrous magnesium sulfate. The solvent was removed under reduced pressure. The residue was purified by silica gel column chromatography, yielding 7 mg (88 percent) of Embodiment Compound 30-III.

Embodiment 17-III

Synthesis of Compound 31-III

Employing 14 mg (0.032 mmole) of Compound 28-III as starting material, 13 mg (81 percent) of Embodiment Compound 31-III was obtained by the same procedure as in Embodiment 16-III.

Embodiment 18-III

Synthesis of Compound 32-III 5.00 g (22.8 mmole) of 4-iodoaniline was dissolved in 40 mL of diethylamine; 4.29 mL (29.7 mmoles) of 3-ethynyl-α,α,α-trifluorotoluene, 160 mg (0.0228 mmole) of PdCl2(PPh3)2, and 87 mg (0.456 mmole) of CuI were added, and the mixture was stirred overnight at 50° C. The solvent was removed, ethyl acetate was added to the residue, and the organic layer was sequentially washed with 1N HCl aqueous solution and 1N NaOH aqueous solution. The obtained organic layer was washed with saturated brine and dried with anhydrous sodium sulfate. The solvent was removed under reduced pressure. The residue was purified by silica gel column chromatography, yielding a quantitative amount of aniline compound.

447 mg (1.83 mmole) of the obtained aniline compound was dissolved in CH2Cl2 and cooled to 0° C. Next, 0.409 mL (2.74 mmoles) of diethylaniline and 0.275 mL (2.19 mmoles) of phenyl chloroformate were added and the mixture was stirred for two hours at 0° C. After the reaction had ended, 1N HCl aqueous solution was added to the reaction solution, the mixture was extracted with ethyl acetate, and the obtained organic layer was washed with saturated brine and dried with anhydrous sodium sulfate. The solvent was removed under reduced pressure. The residue was washed with hexane, yielding 607 mg of phenylcarbamate compound.

76 mg (0.200 mole) of the obtained phenylcarbamate compound was dissolved in CHCl3, 0.060 mL (0.400 mmole) of DBU and 0.031 mL (0.200 mmole) of ethyl nipecotate were added, and the mixture was stirred for two hours at room temperature.

After the reaction had ended, 1N HCl aqueous solution was added to the reaction solution and the mixture was extracted with ethyl acetate. The obtained organic layer was washed with saturated brine and dried with anhydrous sodium sulfate. The solvent was removed under reduced pressure. The residue was purified by silica gel column chromatography, yielding 79 mg of Embodiment Compound 32-III.

Embodiment 19-III

Synthesis of Compound 33-III 70 mg (0.157 mmole) of Compound 32-III was dissolved in 3 mL of THF and 3 mL of MeOH. 3 mL of 1N NaOH aqueous solution was added, and the mixture was stirred for one hour at room temperature. After the reaction had ended, 1N HCl aqueous solution was added to the reaction solution and the mixture was extracted with ethyl acetate. The obtained organic layer was washed with saturated brine and dried with anhydrous sodium sulfate. The solvent was removed under reduced pressure, yielding 50 mg of Compound 33-III.

Embodiment 20-III

Synthesis of Compound 34-III 20 mg (0.048 mmole) of Compound 33-III was dissolved in 1 mL of DMF, 0.009 mL (0.096 mmole) of morpholine and 18.4 mg (0.096 mmole) of WSC.HCl were added, and the mixture was stirred overnight at room temperature. After the reaction had ended, the solvent was removed under reduced pressure. The obtained residue was subjected to reverse-phase high-performance liquid chromatography employing silica gel of the chemically bonded octadodecyl group type as packing material and eluted with a mixed solution of water and acetonitrile containing 0.1 percent (v/v) trifluoroacetic acid. The target fraction was freeze-dried, yielding 10 mg of Compound 34-III.

Embodiment 21-III

Synthesis of Compound 35-III 1.5 mL (3.0 mmole) of 2M trimethylsilyldiazomethane in hexane was gradually added dropwise at 0° C. to a mixed solution (1 mL of methanol, and 9 mL of benzene) of 328 mg (2.0 mmoles) of 2-acetylbenzoic acid. The solvent was removed under reduced pressure. The residue was purified by silica gel column chromatography, yielding 330 mg (93 percent) of a methyl ester compound.

793 mg (2.04 mmole) of benzyl trimethyl ammonium tribromide was added to a 10 mL tetrahydrofuran solution of 330 mg (1.85 mmoles) of the above intermediate and the mixture was stirred for 14 hours at room temperature. Sodium hydrogencarbonate aqueous solution was added to the reaction solution and the mixture was extracted with ethyl acetate. The organic layer was washed with saturated brine and dried with anhydrous magnesium sulfate. The solvent was removed under reduced pressure, yielding 890 mg of crude phenylbromide compound. This compound was employed without purification in the subsequent reaction.

Employing 250 mg (0.922 mmole) of the synthetic intermediate of Embodiment 13-III as starting material, 302 mg (quant.) of thioamide compound was obtained by the same procedure as in Embodiment 62-III.

Employing 63 mg (0.246 mmole) of the above intermediate and 50 mg (0.164 mmole) of the above intermediate as starting materials, 39 mg (51 percent) of thiazole compound was obtained by the same procedure as in Embodiment 38-III.

Employing 31 mg (0.067 mmole) of the above intermediate as starting material, 17 mg (57 percent) of Compound 35-III was obtained by the same procedure as in Embodiment 13-III.

Embodiment 22-III

Synthesis of Compound 36-III

Employing 192 mg (1.0 mmole) of ethyl 4-acetylbenzoate as starting material, 303 mg of crude phenacylbromide compound was obtained by the same procedure as in Embodiment 21-III.

Employing 49 mg (0.180 mmole) of the above synthetic intermediate and 50 mg (0.164 mmole) of the thioamide intermediate compound obtained in the synthesis of Embodiment 21-III as starting materials, 90 mg (quant.) of thiazole compound was obtained by the same procedure as in Embodiment 38-III.

Employing 83 mg (0.174 mmole) of the above synthetic intermediate as starting material, 65 mg (83 percent) of Embodiment Compound 36-III was obtained by the same procedure as in Embodiment 13-III.

Embodiment 23-III

Synthesis of Compound 37-III 0.2 mL of N,N-dimethylformamide was added to a 2 mL dichloromethane solution of 89 mg (0.4 mmole) of 9-anthracene carboxylic acid, the mixture was cooled to 0° C., 0.03 mL (0.4 mmole) of thionyl chloride was added, and the mixture was stirred for one hour at room temperature. The mixture was further cooled to 0° C., a mixed solution (2 mL of dichloromethane and 1 mL of triethylamine) of 52 mg (0.2 mmole) of the synthetic intermediate of Embodiment 1-III was gradually added dropwise, and the mixture was stirred for 1.5 hours at room temperature. Water was added to the reaction solution and the mixture was extracted with ethyl acetate. The organic layer was sequentially washed with saturated sodium hydrogencarbonate aqueous solution and saturated brine and dried with anhydrous magnesium sulfate. The solvent was removed under reduced pressure. The residue was purified by silica gel column chromatography yielding 27 mg (29 percent) of Compound 37-III.

Embodiment 24-III

Synthesis of Compound 38-III

Employing 52 mg (0.2 mmole) of the synthetic intermediate of Embodiment 7-III as starting material, 7 mg (8 percent) of Embodiment Compound 38-III was obtained by the same procedure as in Embodiment 23-III.

Embodiment 25-III

Synthesis of Compound 39-III

Employing 50 mg (0.168 mmole) of 4-(5-trifluoromethylpyridine-2-yloxy) thiobenzamide and 65 mg (0.252 mmole) of the synthesis intermediate of Embodiment 21-III as starting materials, 78 mg (quant.) of thiazole compound was obtained by the same procedure as in Embodiment 38-III.

Employing 68 mg (0.149 mmole) of the above synthetic intermediate as starting material, 43 mg (68 percent) of Compound 39-III was obtained by the same procedure as in Embodiment 13-III.

Embodiment 26-III

Synthesis of Compound 40-III

Employing 50 mg (0.168 mmole) of 4-(5-trifluoromethylpyridine-2-yloxy)thiobenzamide and 50 mg (0.185 mmole) of the synthetic intermediate of Embodiment 22-III as starting materials, 47 mg (60 percent) of thiazole compound was obtained by the same procedure as in Embodiment 38-III.

Employing 40 mg (0.085 mmole) of the above synthetic intermediate as starling material, 32 mg (85 percent) of Embodiment Compound 40-III was obtained by the same procedure as in Embodiment 38-III.

Embodiment 27-III

Synthesis of Compound 41-III

Employing 12 mg (0.027 mmole) of Compound 35-III as starting material, 6 mg (43 percent) of Compound 41-III was obtained by the same procedure as in Embodiment 16-III.

Embodiment 28-III

Synthesis of Compound 42-III

Employing 33 mg (0.073 mmole) of Compound 0.36 as starting material, 24 mg (63 percent) of Compound 42-III was obtained by the same procedure as in Embodiment 16-III.

Embodiment 29-III

Synthesis of Compound 49-III)

295 mg (45 percent) of thiazole compound was obtained from 410 mg (2.0 insoles) of 4-trifluoromethyl thiobenzamide and 538 mg (2.4 mmoles) of α-bromo-4'-cyanoacetophenone by the same procedure as in Embodiment 38-III.

Employing 280 mg (0.848 mmole) of the above synthetic intermediate as starting material, 302 mg (98 percent) of amideoxime compound was obtained by the same procedure as in Embodiment 13-III.

Employing 130 mg (0.358 mmole) of the above synthetic intermediate as starting material, 87 mg (48 percent) of ester compound was obtained by the same procedure as in Embodiment 13-III.

Employing 80 mg (0.158 mmole) of the above synthetic intermediate as starting material, 65 mg (83 percent) of Compound 49-III was obtained by the same procedure as in Embodiment 13-III.

Embodiment 30-III

Synthesis of Compound 50-III

Employing 70 mg (0.193 mmole) of the synthetic intermediate of Embodiment 29-III as starting material, 57 mg (58 percent) of ester compound was obtained by the same procedure as in Embodiment 13-III.

Employing 48 mg (0.095 mmole) of the above intermediate as starting material, 36 mg (77 percent) of Compound 50-III was obtained by the same procedure as in Embodiment 13-III.

Embodiment 31-III

Synthesis of Compound 51-III

Employing 70 mg (0.193 mmole) of the synthetic intermediate of Embodiment 29-III as starting material, 38 mg (39 percent) of an ester compound was obtained by the same procedure as in Embodiment 13-III.

Employing 30 mg (0.059 mmole) of the above intermediate as starting material, 21 mg (72 percent) of Compound 51-III was obtained by the same procedure as in Embodiment 13-III.

Embodiment 32-III

Synthesis of Compound 52-III

Employing 100 mg (0.398 mmole) of the synthetic intermediate of Embodiment 1-III as starting material, 61 mg (42 percent) of Compound 52-III was obtained by the same procedure as in Embodiment 3-III.

Embodiment 33-III

Synthesis of Compound 53-III

Employing 100 mg (0.398 mmole) of the synthetic intermediate of Embodiment 1-III as starting material, 87 mg (61 percent) of Compound 53-III was obtained by the same procedure as in Embodiment 3-III.

Embodiment 34-III

Synthesis of Compound 54-III

Employing 100 mg (0.398 mmole) of the synthetic intermediate of Embodiment 1-III as starting material, 89 mg (53 percent) of Compound 54-III was obtained by the same procedure as in Embodiment 3-III.

Embodiment 35-III

Synthesis of Compound 57-III

Employing 100 mg (0.398 mmole) of the synthetic intermediate of Embodiment 11-III as starting material, 69 mg (42 percent) of Compound 57-III was obtained by the same procedure as in Embodiment 3-III.

Embodiment 36-III

Synthesis of Compound 58-III 0.13 mL (0.768 mmole) of diisopropyl ethyl amine and 76 mg (0.287 mmole) of 1,2-bis(bromomethyl)benzene were added to a 2 mL dichloromethane solution of 50 mg (0.192 mmole) of the synthetic intermediate of Embodiment 1-III and the mixture was stirred for three hours at 50° C. Water was added to the reaction solution and the mixture was extracted with ethyl acetate. The organic layer was washed with saturated brine and dried with anhydrous magnesium sulfate. The solvent was removed under reduced pressure. The residue was purified by silica gel column chromatography, yielding 35 mg (50 percent) of Compound 58-III.

Embodiment 37-III

Synthesis of Compound 59-III

Employing 50 mg (0.192 mmole) of the synthetic intermediate of Embodiment 7-III as starting material, 26 mg (37 percent) of Compound 59-III was obtained by the same procedure as in Embodiment 36-III.

Embodiment 39-III

Synthesis of Compound 60-III 10.0 g (40.97 mmole) of α-bromo-4'-nitroacetophenone was added to a 200 mL methanol solution of 5.62 g (40.97 mmoles) of thiobenzamide and the mixture was stirred for 15 hours at 50° C. Methylene chloride was added to the reaction solution to conduct slurry washing, yielding 11.0 g (95 percent) of thiazole compound.

3.3 g of 10 percent Pd—C (wet) was added to a mixed solution (150 mL of tetrahydrofuran and 150 mL of ethanol) of 11.0 g (39.0 mmoles) of the thiazole compound and the mixture was stirred for 16 hours under a hydrogen flow. When the reaction had ended, the reaction product was filtered with celite and the solvent was removed under reduced pressure. Ethyl acetate and hexane were added to the residue to conduct slurry washing, yielding 8.8 g (90 percent) of an aniline compound.

Employing 50 mg (0.198 mmole) of the above intermediate as starting material, 53 mg (61 percent) of Compound 60-III was obtained by the same procedure as in Embodiment 1-III.

Embodiment 39-III

Synthesis of Compound 61-III

Employing 71 mg (0.282 mmole) of the synthetic intermediate of Embodiment 1-III as starting material, 108 mg (96 percent) of Embodiment Compound 61-III was obtained by the same procedure as in Embodiment 3-III.

Embodiment 40-III

Synthesis of Compound 62-III

Employing 55 mg (0.152 mmole) of Embodiment Compound 52-III as starting material, 42 mg (81 percent) of Embodiment Compound 62-III was obtained by the same procedure as in Embodiment 18-III.

Embodiment 41-III

Synthesis of Compound 63-III

Employing 80 mg (0.222 mmole) of Compound 53-III as starting material, 41 mg (54 percent) of Compound 63-III was obtained by the same procedure as in Embodiment 4-III.

Embodiment 42-III

Synthesis of Compound 64-III

Employing 59 mg (0.142 mmole) of Compound 57-III as starting material, 49 mg (87 percent) of Compound 64-III was obtained by the same procedure as in Embodiment 4-III.

Embodiment 43-III

Synthesis of Compound 69-III

Employing 30 mg (0.075 mmole) of Compound 61-III as starting material, 21 mg (73 percent) of Compound 69-III was obtained by the same procedure as in Embodiment 4-III.

Embodiment 44-III

Synthesis of Compound 70-III

A mixture of 50 mg (0.192 mmole) of the intermediate of Embodiment 1-III, 1.5 g of imidazole, 46 mg (0.229 mmole) of 1,8-napthalic anhydride, and 21 mg (0.096 mmole) of zinc acetate dihydrate was stirred for 2 hours at 130° C. After cooling the mixture to room temperature, 1N hydrochloric acid was added and the mixture was extracted with methylene chloride. The organic layer was sequentially washed with saturated sodium hydrogencarbonate aqueous solution and saturated brine and then dried with anhydrous magnesium sulfate. The solvent was removed under reduced pressure. The residue was purified by silica gel column chromatography, yielding 31 mg (37 percent) of Compound 70-III.

Embodiment 45-III

Synthesis of Compound 71-III

Employing 50 mg (0.192 mmole) of the synthetic intermediate of Embodiment 1-III as starting material, 53 mg (63 percent) of Compound 71-III was obtained by the same procedure as in Embodiment 3-III.

Embodiment 46-III

Synthesis of Compound 72-III

Employing 47 mg (0.108 mmole) of the synthetic intermediate of Embodiment 47-III as starting material, 16 mg (36 percent) of Compound 72-III was obtained by the same procedure as in Embodiment 4-III.

Embodiment 47-III

Synthesis of Compound 73-III 29 mg (0.23 mmole) of 2,3-dimethylmaleic anhydride and 86 mg (0.384 mmole) of zinc bromide were added to a 2 mL toluene solution of 50 mg (0.192 mmole) of the synthetic intermediate of Embodiment 1-III and the mixture was heated to 80° C. While still at 80° C., 0.068 mL (0.324 mmole) of hexamethyldisilazane was gradually added and the mixture was stirred for two hours. After cooling the mixture to room temperature, it was filtered with celite and the solvent was removed under reduced pressures. The residue was purified by thin-layer chromatography, yielding 15 mg (21 percent) of Compound 73-III.

Embodiment 48-III

Synthesis of Compound 74-III

Employing 50 mg (0.192 mmole) of the synthetic intermediate of Embodiment 1-III as starting material, 39 mg (41 percent) of Compound 74-III was obtained by the same procedure as in Embodiment 47-III.

Embodiment 49-III

Synthesis of Compound 75-III)

19 mg (0.093 mmole) of 4-isopropylbenzenesulfonamide, 11 mg (0.093 mmole) of 4-(N,N-dimethylamino)pyridine, and 18 mg (0.093 mmole) of 1-ethyl-3-(3-dimethylaminopropyl)carbodiimide hydrochloride were added to a solution 1 mL N,N-dimethylformamide of 23 mg (0.047 mmole) of Compound 49-III and the mixture was stirred for 22 hours at room temperature. Water was added to the reaction solution and the mixture was extracted with ethyl acetate. The organic layer was washed with saturated brine and dried with anhydrous magnesium sulfate. The solvent was removed under reduced pressure. The residue was purified by thin-layer chromatography, yielding 9 mg (28 percent) of Compound 75-III.

Embodiment 50-III

Synthesis of Compound 79-III 30 mg (0.119 mmole) of the synthetic intermediate of Embodiment 38-II was dissolved in 2 mL of DMF and 60 mg (0.375 mmole) of K2CO3 and 66 mg (0.375 mmole) of 4-bromomethylbenzoic acid methyl ester were added, and the mixture was stirred overnight at 75° C. When the reaction had ended, the solvent was removed under reduced pressure. The obtained residue was subjected to reverse-phase high-performance liquid chromatography employing silica gel of the chemically bonded octadodecyl group type as packing material and eluted with a mixed solution of water and acetonitrile containing 0.1 percent (v/v) trifluoroacetic acid. The target fraction was freeze-dried, yielding 15 mg of Compound 79-III.

Embodiment 51-III

Synthesis of Compound 80-III

Compound 80-III was obtained employing the corresponding arylbromide by the sale procedure as in Embodiment 50-III.

Embodiment 52-III

Synthesis of Compound 83-III 1.85 g (71 percent) of thiazole compound was obtained from 1.37 g (10 mmoles) of thiobenzamide and 2.24 g (10 mmoles) of α-bromo-4'-cyanoacetophenone by the same procedure as in Embodiment 38-III.

Employing 262 mg (1.0 mmole) of the above intermediate as starting material, 228 mg (98 percent) of an amideoxime compound was obtained by the same procedure as in Embodiment 13-III.

Employing 285 mg (0.966 mmole) of the above intermediate as starting material, 163 mg (38 percent) of an ester compound was obtained by the same procedure as in Embodiment 13-III.

Employing 157 mg (0.358 mmole) of the above intermediate as starting material, 151 mg (99 percent) of Compound 83-III was obtained by the same procedure as in Embodiment 13-III.

Embodiment 53-III

Synthesis of Compound 86-III 25 mg (0.152 mmole) of carbonyl diimidazole was added to a 3 mL 1,2-dichlotoethane solution of 43 mg (0.101 mmole) of Compound 83-III and the mixture was stirred for 12 hours at 50° C. 62 mg (0.404 mmole) of 1,8-diazabicyclo [5.4.0]undec-7-ene and 60 mg (0.303 mmole) of 4-isopropylbenzenesulfonamide were added and the mixture was stirred for 11 hours. The solvent was removed under reduced pressure. The residue was purified by silica gel column chromatography and slurry washed with acetonitrile and water, yielding 40 mg (65 percent) of Compound 86-III.

Embodiment 54-III

Synthesis of Compound 88-III

Two drops from a Pasteur pipet of triethylamine and 14 mg (0.077 mmole) of N-benzylpiperadine were added to a 2 mL dichloromethane solution of 19 mg (0.051 mmole) of the corresponding phenylcarbamate compound and the mixture was stirred for 19 hours at room temperature. The solvent was removed under reduced pressure. The residue was purified by silica gel column chromatography, yielding 21 mg (91 percent) of Compound 88-III.

Embodiment 55-III

Synthesis of Compound 89-III

Employing 37 mg (0.100 mmole) of the corresponding phenylcarbamate as starting material, 93 mg of crude urea compound was obtained by the same procedure as in Embodiment 54-III.

0.1 mL of trimethylamine and 44 mg (0.200 mmole) of 4-isopropylbenzenesulfonyl chloride were added to a 2 mL dichloromethane solution of 0.100 mmole of the above intermediate and the mixture was stirred for 15 hours. Water was added to the reaction solution and the mixture was extracted with ethyl acetate. The organic layer was washed with saturated brine and dried with anhydrous magnesium sulfate. The solvent was removed under reduced pressure. The residue was purified by silica gel column chromatography, yielding 23 mg (42 percent for 2 steps) of Compound 89-III.

Embodiment 56-III

Synthesis of Compound 90-III

Employing 37 mg (0.100 mmole) of the corresponding phenylcarbamate as starting material, 63 mg of crude urea compound was obtained by the same procedure as in Embodiment 55-III.

Employing the above intermediate (0.100 mmole) as starting material, 36 mg (64 percent) of Compound 90-III was obtained by the same procedure as in Embodiment 55-III.

Embodiment 57-III

Synthesis of Compound 93-III 100 mg (0.355 mmole) of the synthetic intermediate of Embodiment 38-III and 179 mg (0.711 mmole) of the synthetic intermediate of Embodiment 20-III were dissolved in 10 mL of CH2Cl2, 0.248 mL (1.78 mmoles) of triethylamine and 136 mg (0.711 mmole) of WSC.HCl were added, and the mixture was stirred overnight at room temperature. Ethyl acetate was added to the residue. The organic layer was washed with 1N HCl aqueous solution, 1N NaOH aqueous solution, and saturated brine, and then dried with anhydrous sodium sulfate, then the solvent was removed under reduced pressure. The residue was dissolved in 1 mL of MeOH and 1 mL of THF, 1 mL of 1N NaOH aqueous solution was added, and the mixture was stirred overnight at room temperature. The residue was subjected to reverse-phase high-performance liquid chromatography employing silica gel of the chemically bonded octadodecyl group type as packing material and eluted with a mixed solution of water and acetonitrile containing 0.1 percent (v/v) trifluoroacetic acid. The target fraction was freeze-dried, yielding 107 mg of Compound 93-III.

Embodiment 58-III

Synthesis of Compounds 94-III and 95-III

Using the corresponding amine, Compounds 94-III and 95-III were obtained by the same procedure as in Embodiment 57-III.

Embodiment 59-III

Synthesis of Compounds 96-III and 97-III 401 mg (1.5 mmole) of 2-benzoyloxycarbonylaminosuccinic acid and 383 mg (2.0 mmoles) of 1-ethyl-3-(3-dimethylaminopropyl) carbodiimide hydrochloride were added to a 5 mL N,N-dimethylformamide solution of 252 mg (1.0 mmole) of the synthetic intermediate of Embodiment 38-III, the mixture was stirred for 24 hours at room temperature, 0.5 N hydrochloric acid was added to the reaction solution, and the mixture was extracted with ethyl acetate. The organic layer was dried with anhydrous magnesium sulfate and the solvent was removed under reduced pressure. The residue was purified by silica gel column chromatography, yielding 41 mg (8 percent) of Compound 96-III and 22 mg (4 percent) of Compound 97-III.

Embodiment 60-III

Synthesis of Compound 98-III 2.22 g (10.0 mmole) of phosphorus pentasulfide was added to a 50 mL tetrahydrofuran solution of 2.07 g (10.0 mmoles) of 2-fluoro-5-trifluoromethylbenzamide and the mixture was stirred for five hours at room temperature. Ethyl acetate was added to the reaction solution, the mixture was filtered with celite, and the solvent was removed under reduced pressure, yielding crude thioamide. The present compound was employed in the following reaction without purifications.

Employing 223 mg (1.0 mmole) of the above intermediate as starting material, 239 mg (65 percent) of thiazole compound was obtained by the same procedure as in Embodiment 38-III.

Employing 226 mg (0.614 mmole) of the above intermediate as starting material, 204 mg (98 percent) of aniline compound was obtained by the same procedure as in Embodiment 38-III.

Employing 50 mg (0.148 mmole) of the above intermediate as starting material, 51 mg (66 percent) of Compound 98-III was obtained by the same procedure as in Embodiment 1-III.

Embodiment 61-III

Synthesis of Compound 99-III

Employing 50 mg (0.148 mmole) of the above synthesis intermediate of Embodiment 60-III as starting material, 56 mg (78 percent) of Compound 99-III was obtained by the same procedure as in the synthesis of Embodiment 3-III.

Embodiment 62-III

Synthesis of Compound 100-III

A mixed solution (3 mL of dithiophosphoric acid diethyl ester and 0.1 mL of water) of 605 mg (50 mmoles) of 2-fluorobenzonitrile was stirred for 46 hours at room temperature. Water was added to the reaction solution and the mixture was extracted with ethyl acetate. The organic layer was sequentially washed with saturated sodium hydrogencarbonate and saturated brine and dried with anhydrous magnesium sulfate, after which the solvent was removed under reduced pressure. The residue was purified by silica gel column chromatography, yielding 680 mg (88 percent) of thioamide compound. Employing 660 mg (4.26 mmoles) of the above intermediate as starting material, 1.14 g (89 percent) of thiazole compound was obtained by the same procedure as in the synthesis of Embodiment Compound 60-III.

Employing 1.1 g (3.67 mmoles) of the above intermediate as starting material, 969 mg (98 percent) aniline compound was obtained by the same procedure as in Embodiment 38-III.

Employing 50 mg (0.148 mmole) of the above intermediate as starting material, 68 mg (88 percent) of Compound 100-III was obtained by the same procedure as in Embodiment 1-III.

Embodiment 63-III

Synthesis of Compound 101-III

Employing 50 mg (0.185 mmole) of the synthetic intermediate of Embodiment 62-III as starting material, 68 mg (88 percent) of Compound 101-III was obtained by the same procedure as in Embodiment 3-III.

Embodiment 64-III

Synthesis of Compound 102-III 252 mg (1.00 mmole) of the synthetic intermediate of Embodiment 38-III was dissolved in CH2Cl2 and cooled to 0° C. Next, 0.239 mL (1.50 mmoles) of diethylaniline and 0.151 mL (1.20 mmoles) of phenyl chloroformate were added and the mixture was stirred overnight at room temperature. When the reaction had ended, 1N HCl aqueous solution was added to the reaction solution and the mixture was extracted with CH2Cl2. The obtained organic layer was washed with saturated brine and dried with anhydrous sodium sulfate. The solvent was removed under reduced pressure. The residue was washed with hexane, yielding 361 mg of phenylcarbamate compound.

100 mg (0.268 mmole) of the obtained phenylcarbamate compound was dissolved in CH2Cl2, 0.082 mL (0.590 mmole) of TEA and 64 mg (0.295 mmole) of L-Phe-OMe HCl were added, the mixture was stirred overnight at room temperature, and the solvent was removed under reduced pressure. The obtained residue was dissolved in 1 mL of MeOH and 1 mL of THF, 1 mL of 1N NaOH aqueous solution was added, the mixture was stirred overnight at room temperature, 1N HCl aqueous solution was added to the reaction solution, and the solution was neutralized. The obtained white solid was filtered out, yielding 73 mg of Compound 102-III.

Embodiment 65-III

Synthesis of Compound 103-III

Employing the corresponding amino acid ethyl ester. Compound 103-III was obtained by the same procedure as in the synthesis of Embodiment 64-III.

Embodiment 66-III

Synthesis of Compound 104-III

Employing 100 mg (0.397 mmole) of the synthetic intermediate of Embodiment 38-III as starting material, 155 mg (68 percent) of amide compound was obtained by the same procedure as in Embodiment 59-III.

2.5 mL of 4N HCl in dioxan-e was added to 143 mg (0.250 mmole) of the above intermediate and the mixture was stirred for 20 hours at room temperature. Water was added to the reaction solution and the mixture was extracted with ethyl acetate. The organic layer was dried with anhydrous magnesium sulfate and the solvent was removed under reduced pressure. The residue was slurry washed with ethyl acetate and hexane, yielding 80 mg (62 percent) of Compound 104-III.

Embodiment 67-III

Synthesis of Compound 105-III

Employing 17 mg (0.038 mmole) of Compound 36-III as starting material, 9 mg (38 percent) of Compound 105-III was obtained by the same procedure as in Embodiment 53-III.

Embodiment 68-III

Synthesis of Compound 106-III 1 mL N,N-dimethylformamide solution of 13.3 mg (0.067 mmole) of 4-isopropylbenzenesulfonamide, 7.5 mg (0.061 mmole) of 4-(N,N-dimethylamino)pyridine, 19 mg (0.183 mmole) of butyldimethylamine, and 17.5 mg (0.122 mmole) of dimethylsulfamoyl chloride was added to a 1 mL N,N-dimethylformamide solution of 30 mg (0.061 mmole) of Compound 50-III, the mixture was stirred for four hours at 50° C., 1N hydrochloric acid was added to the reaction solution, and the mixture was extracted with ethyl acetate. The organic layer was washed with saturated brine and dried with anhydrous magnesium sulfate. The solvent was removed under reduced pressure. The residue was slurry washed with acetonitrile, yielding 14 mg (34 percent) of Compound 106-III.

Embodiment 69-III

Synthesis of Compound 107-III

Employing 30 mg (0.061 mmole) of Compound 51-III as starting material, 17 mg (41 percent) of Compound 107-III was obtained by the same procedure as in the synthesis of Embodiment 68-III.

Embodiment 70-III

Synthesis of Compound 108-III

Employing 50 mg (0.198 mmole) of the synthetic intermediate of Embodiment 38-III as starting material, 76 mg (87 percent) of Compound 108-III was obtained by the same procedure as in Embodiment 59-III.

Embodiment 71-III

Synthesis of Compound 113-III

Employing 50 mg (0.198 mmole) of the synthetic intermediate of Embodiment 38-III as starting material, crude amide compound was obtained by the same procedure as in Embodiment 59-III.

Employing the above intermediate as starting material, 82 mg (80 percent for two steps) of Compound 113-III was obtained by the same procedure as in the synthesis of Embodiment 66-III.

Embodiment 72-III

Synthesis of Compound 114-III

Employing 50 mg (0.198 mmole) of the synthetic intermediate of Embodiment 38-III as starting material, crude amide derivative was obtained by the same procedure as in Embodiment 59-III.

Employing the above intermediate as starting material, 58 mg (57 percent for two steps) of Compound 114-III was obtained by the same procedure as in Embodiment 66-III.

Embodiment 73-III

Synthesis of Compound 115-III

Employing 252 mg (1.0 mmole) of the synthetic intermediate of Embodiment 38-III as starting material, 435 mg (82 percent) of Embodiment Compound 115-III was obtained by the same procedure as in Embodiment 59-III.

Embodiment 74-III

Synthesis of Compound 116-III

Employing 252 mg (1.0 mmole) of the synthetic intermediate of Embodiment 38-III as starting material, 469 mg (71 percent) of Embodiment Compound 116-III was obtained by the same procedure as in Embodiment 59-III.

Embodiment 75-III

Synthesis of Compound 117-III

Employing 252 mg (1.0 mmole) of the synthetic intermediate of Embodiment 38-III as starting material, 248 mg (38 percent) of Embodiment Compound 117-III was obtained by the same procedure as in Embodiment 59-III.

Embodiment 76-III (Synthesis of Compound 119-III 0.5 mL of piperidine was added to a 5 mL N,N-dimethylformamide solution of 172 mg (0.323 mmole) of Compound 115-III in, the mixture was stirred for two hours at room temperature, 1N sodium hydroxide aqueous solution was added to the reaction solution, and the mixture was extracted with ethyl acetate. The organic layer was washed with saturated brine and dried with potassium carbonate, after which the solvent was removed under reduced pressure. The residue was purified by basic silica gel column chromatography, yielding 82 mg (82 percent) of Compound 119-III.

Embodiment 77-III

Synthesis of Compound 120-III 1 mL of 4N HCl in ethyl acetate was added to 30 mg (0.046 mmole) of Compound 116-III and the mixture was stirred for 14 hours at room temperature. Water was added to the reaction solution and the mixture was extracted with methylene chloride. The organic layer was dried with anhydrous magnesium sulfate and the solvent was removed under reduced pressure. The residue was slurry washed with methylene chloride, yielding 8 mg (29 percent) of Embodiment Compound 120-III.

Embodiment 78-III

Synthesis of Compound 121-III

Employing 30 mg (0.046 mmole) of Compound 117-III as starting material, 12 mg (442 percent) of Compound 121-III was obtained by the same procedure as in Embodiment 77-III.

Embodiment 79-III

Synthesis of Compound 122-III

Employing 52 mg (0.168 mmole) of Compound 119-III as starting material, 39 mg (75 percent) of Compound 122-III was obtained by the same procedure as in Embodiment 55-III.

Embodiment 80-III

Synthesis of Compound 127-III 82 mg (0.207 mmole) of the corresponding starting material was dissolved in 5 mL of THF, the solution was cooled to 0° C., 24 mg (0.620 mmole) of NaH was added, and the mixture was stirred for 10 minutes. Next, 0.074 mL (0.062 mmole) of benzylbromide was added and the mixture was stirred overnight at room temperature. When the reaction had ended, the solvent was removed under reduced pressure. The obtained residue was subjected to reverse-phase high-performance liquid chromatography employing silica gel of the chemically bonded octadodecyl group type as packing material and eluted with a mixed solution of water and acetonitrile containing 0.1 percent (v/v) trifluoroacetic acid. The target fraction was freeze-dried, yielding 2 mg of Compound 127-III.

Embodiment 80-III

Synthesis of Other Compounds

Compounds in addition to those described above were synthesized based on the above methods.

The molecular structures and mass spectrometry results of the above-synthesized compounds are given in Table 1-III

TABLE 1-III

| Compound No. | MOLSTRUCTURE | MS (ESI)(MH+) |
|---|---|---|
| 1 | 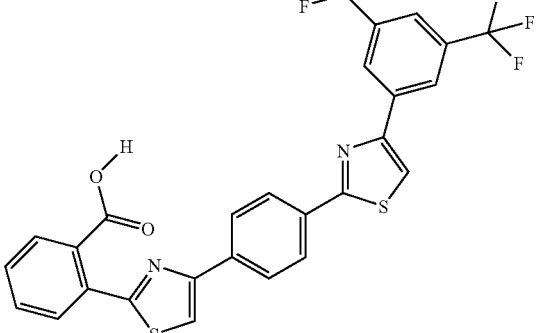 | 577 |
| 2 | 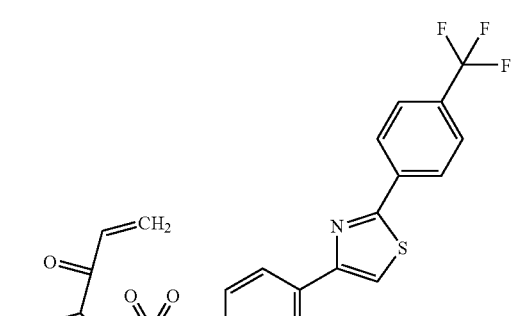 | 519 |
| 3 | 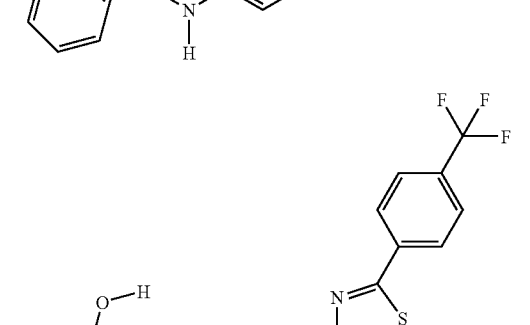 | 505 |

TABLE 1-III-continued

| Compound No. | MOLSTRUCTURE | MS (ESI)(MH+) |
|---|---|---|
| 4 | | 504 |
| 5 | | 392 |
| 6 | | 378 |
| 7 | | 445 |
| 8 | | 543 |

TABLE 1-III-continued

| Compound No. | MOLSTRUCTURE | MS (ESI)(MH+) |
|---|---|---|
| 9 | | 446 |
| 10 | | 410 |
| 11 | | 392 |
| 12 | | 445 |
| 13 | | 454 |

TABLE 1-III-continued

| Compound No. | MOLSTRUCTURE | MS (ESI)(MH+) |
| --- | --- | --- |
| 14 | | 454 |
| 15 | | 543 |
| 16 | | 446 |
| 17 | | 410 |
| 18 | | 392 |

TABLE 1-III-continued

| Compound No. | MOLSTRUCTURE | MS (ESI)(MH+) |
|---|---|---|
| 19 | | 446 |
| 20 | | 446 |
| 21 | | 446 |
| 22 | | 446 |
| 23 | | 460 |

TABLE 1-III-continued
| Compound No. | MOLSTRUCTURE | MS (ESI)(MH+) |
|---|---|---|
| 24 | 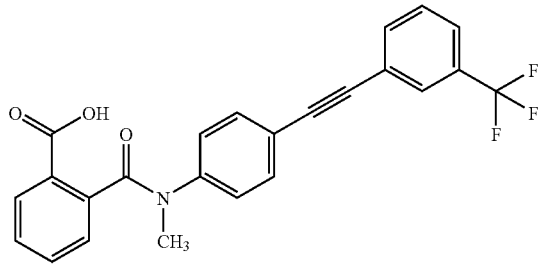 | 424 |
| 25 | 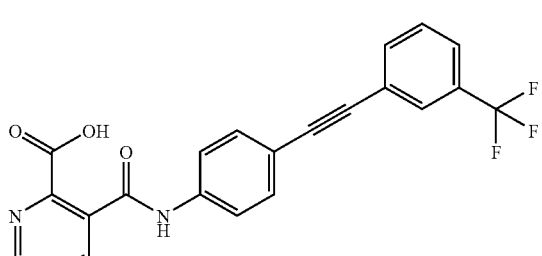 | 411 |
| 26 | 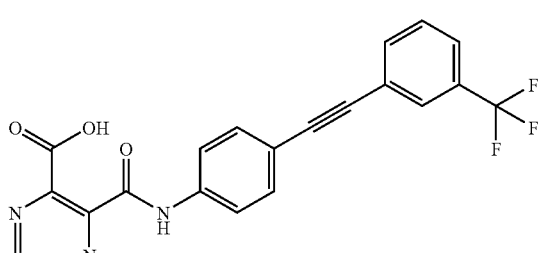 | 412 |
| 27 | 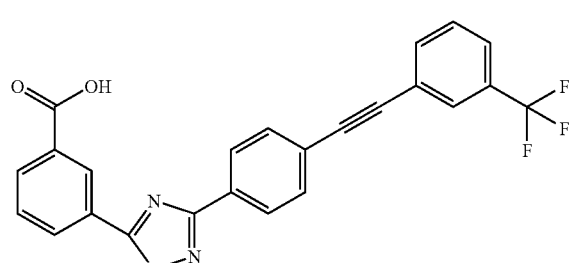 | 435 |
| 28 | 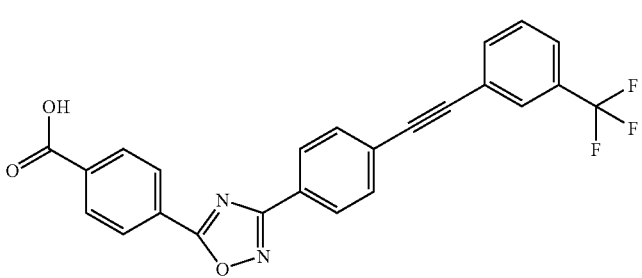 | 435 |

TABLE 1-III-continued

| Compound No. | MOLSTRUCTURE | MS (ESI)(MH+) |
| --- | --- | --- |
| 29 | | 435 |
| 30 | | 504 |
| 31 | | 504 |
| 32 | | 445 |
| 33 | | 417 |

TABLE 1-III-continued
| Compound No. | MOLSTRUCTURE | MS (ESI)(MH+) |
|---|---|---|
| 34 | 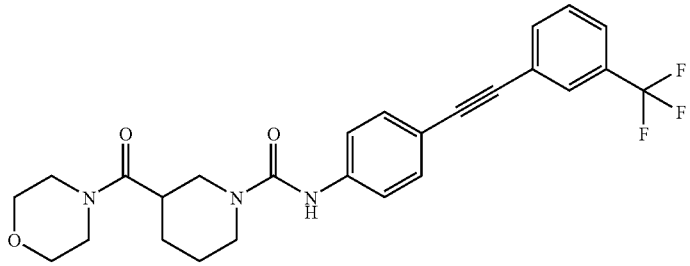 | 486 |
| 35 | 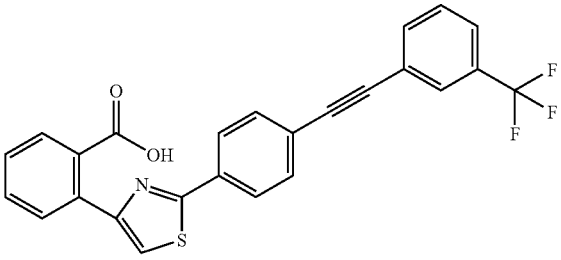 | 450 |
| 36 | 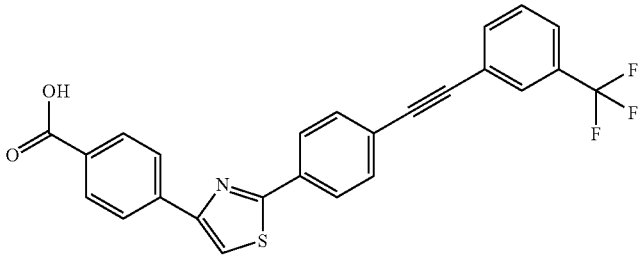 | 450 |
| 37 | 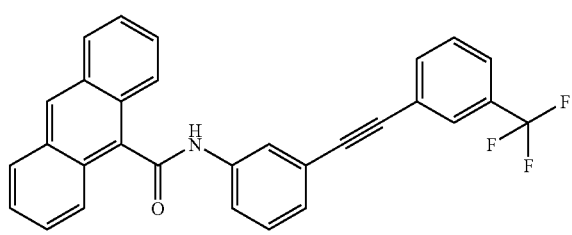 | 466 |
| 38 | 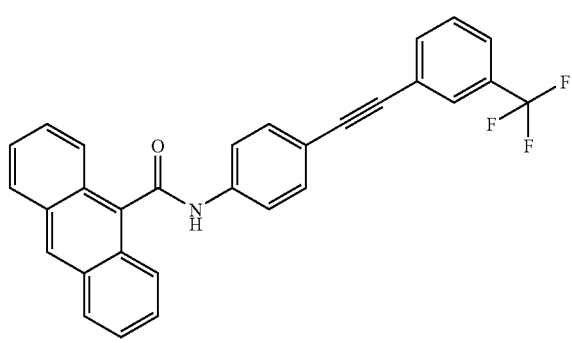 | 466 |

TABLE 1-III-continued

| Compound No. | MOLSTRUCTURE | MS (ESI)(MH+) |
|---|---|---|
| 39 | | 443 |
| 40 | | 443 |
| 41 | | 519 |
| 42 | | 519 |
| 43 | | 363 |
| 44 | | 349 |

TABLE 1-III-continued

| Compound No. | MOLSTRUCTURE | MS (ESI)(MH+) |
|---|---|---|
| 45 | | 349 |
| 46 | | 469 |
| 47 | | 545 |
| 48 | | 451 |
| 49 | | 494 |

TABLE 1-III-continued

| Compound No. | MOLSTRUCTURE | MS (ESI)(MH+) |
|---|---|---|
| 50 | | 494 |
| 51 | | 494 |
| 52 | | 362 |
| 53 | | 360 |
| 54 | | 847 |

TABLE 1-III-continued

| Compound No. | MOLSTRUCTURE | MS (ESI)(MH+) |
|---|---|---|
| 55 | | 843 |
| 56 | | 616 |
| 57 | | 416 |
| 58 | | 364 |
| 59 | | 364 |

TABLE 1-III-continued

| Compound No. | MOLSTRUCTURE | MS (ESI)(MH+) |
| --- | --- | --- |
| 60 | | 437 |
| 61 | | 401 |
| 62 | | 344 |
| 63 | | 342 |
| 64 | | 398 |
| 65 | | 363 |

TABLE 1-III-continued

| Compound No. | MOLSTRUCTURE | MS (ESI)(MH+) |
|---|---|---|
| 66 | | 453 |
| 67 | | 393 |
| 68 | | 405 |
| 69 | | 383 |
| 70 | | 442 |
| 71 | | 871 |

TABLE 1-III-continued

| Compound No. | MOLSTRUCTURE | MS (ESI)(MH+) |
| --- | --- | --- |
| 72 | | 418 |
| 73 | | 370 |
| 74 | | 494 |
| 75 | | 675 |

TABLE 1-III-continued

| Compound No. | MOLSTRUCTURE | MS (ESI)(MH+) |
|---|---|---|
| 76 | | 385 |
| 77 | | 438 |
| 78 | | 424 |
| 79 | | 387 |
| 80 | | 387 |
| 81 | | 408 |

TABLE 1-III-continued

| Compound No. | MOLSTRUCTURE | MS (ESI)(MH+) |
|---|---|---|
| 82 | | 438 |
| 83 | | 426 |
| 84 | | 431 |
| 85 | | 408 |
| 86 | | 607 |
| 87 | | 438 |

TABLE 1-III-continued

| Compound No. | MOLSTRUCTURE | MS (ESI)(MH+) |
|---|---|---|
| 88 | | 455 |
| 89 | | 547 |
| 90 | | 561 |
| 91 | | 408 |
| 92 | | 590 |

TABLE 1-III-continued

| Compound No. | MOLSTRUCTURE | MS (ESI)(MH+) |
| --- | --- | --- |
| 93 | | 422 |
| 94 | | 410 |
| 95 | | 458 |
| 96 | | 484 |
| 97 | | 502 |
| 98 | | 523 |

TABLE 1-III-continued

| Compound No. | MOLSTRUCTURE | MS (ESI)(MH+) |
|---|---|---|
| 99 | | 487 |
| 100 | | 455 |
| 101 | | 419 |
| 102 | | 444 |
| 103 | | 444 |
| 104 | | 516 |

TABLE 1-III-continued

| Compound No. | MOLSTRUCTURE | MS (ESI)(MH+) |
|---|---|---|
| 105 | | 631 |
| 106 | | 675 |
| 107 | | 675 |
| 108 | | 444 |

TABLE 1-III-continued
| Compound No. | MOLSTRUCTURE | MS (ESI)(MH+) |
|---|---|---|
| 109 | 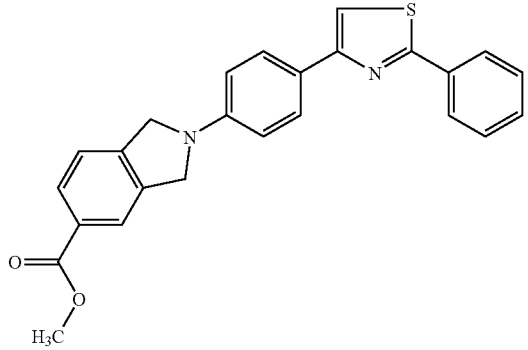 | 413 |
| 110 | 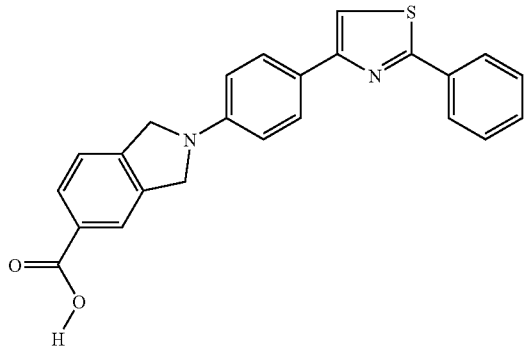 | 399 |
| 111 | 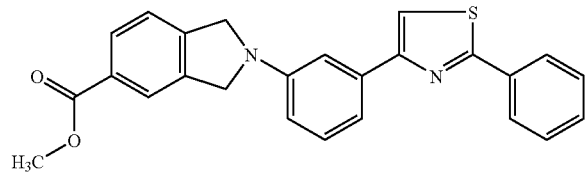 | 413 |
| 112 | 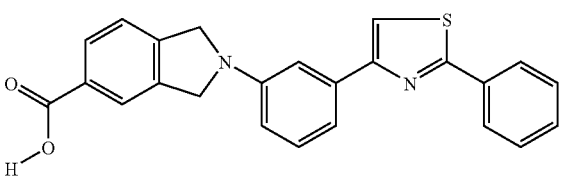 | 399 |
| 113 | 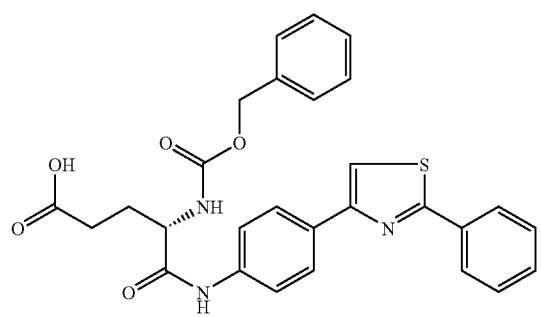 | 516 |

TABLE 1-III-continued

| Compound No. | MOLSTRUCTURE | MS (ESI)(MH+) |
| --- | --- | --- |
| 114 | | 516 |
| 115 | | 532 |
| 116 | | 660 |
| 117 | | 660 |

TABLE 1-III-continued

| Compound No. | MOLSTRUCTURE | MS (ESI)(MH+) |
| --- | --- | --- |
| 118 | | 580 |
| 119 | | 310 |
| 120 | | 604 |
| 121 | | 604 |
| 122 | | 492 |

TABLE 1-III-continued

| Compound No. | MOLSTRUCTURE | MS (ESI)(MH+) |
|---|---|---|
| 123 | | 580 |
| 124 | | 553 |
| 125 | | 553 |
| 126 | | 398 |
| 127 | | 578 |
| 128 | | 474 |

TABLE 1-III-continued

| Compound No. | MOLSTRUCTURE | MS (ESI)(MH+) |
|---|---|---|
| 129 | | 474 |
| 130 | | 625 |

The ACC inhibiting activity of the compound of Mode 3 of the present invention were calculated and the ACC inhibiting activity rate was determined in the same manner as described for Pharmacological Test Example 1. The results are given in Table 2-III.

TABLE 2-III

| Compound No. | ACC Inhibition (%) |
|---|---|
| 1 | 62 |
| 9 | 60 |
| 10 | 61 |
| 13 | 51 |
| 18 | 60 |
| 27 | 56 |
| 28 | 58 |
| 35 | 50 |
| 36 | 54 |
| 49 | 62 |
| 50 | 55 |
| 51 | 53 |
| 55 | 73 |
| 65 | 64 |
| 66 | 73 |
| 70 | 62 |
| 74 | 66 |
| 75 | 98 |
| 77 | 64 |
| 78 | 55 |
| 82 | 63 |
| 86 | 99 |
| 91 | 65 |
| 99 | 52 |
| 103 | 63 |
| 104 | 66 |
| 105 | 99 |
| 106 | 97 |
| 107 | 100 |
| 118 | 60 |
| 130 | 88 |

Embodiments of compounds of Mode 4 of the present invention are described below.

The present invention is described in greater detail below through these embodiments; however, the present invention is not limited in any manner thereby. Synthesis embodiments and pharmacological test embodiments are described below.

The molecular structure of the compounds synthesized in the following synthesis embodiments, mass analysis results for representative compounds, and NMR results for representative compounds are given in Table 1-IV, 2-IV, and 3-IV.

TABLE 1-IV

| Compd. No. | MOLSTRUCTURE |
|---|---|
| 1 | |
| 2 | |
| 3 | |
| 4 | |
| 5 | |
| 6 | |

TABLE 1-IV-continued
| Compd. No. | MOLSTRUCTURE |
|---|---|
| 7 | 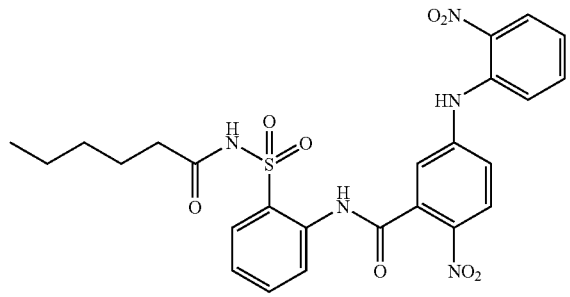 |
| 8 | 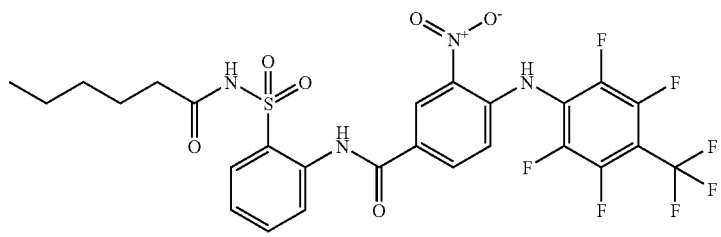 |
| 9 | 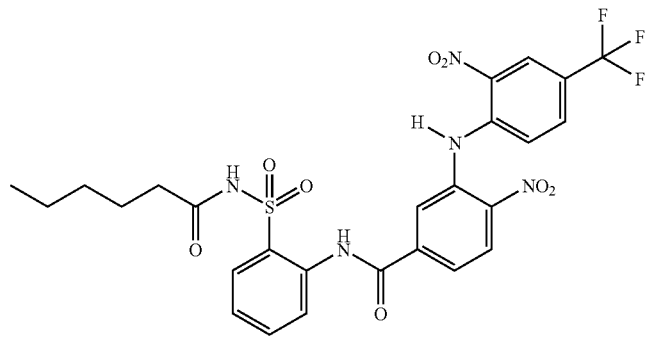 |
| 10 | 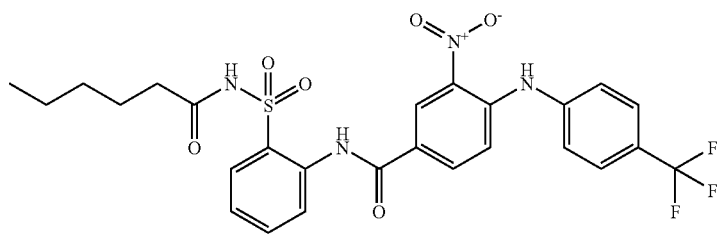 |
| 11 | 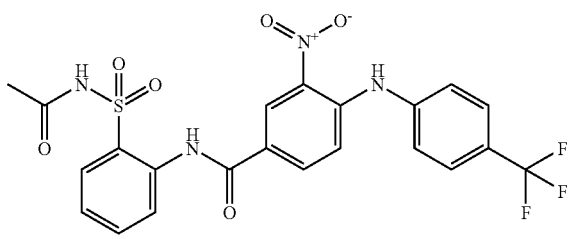 |

TABLE 1-IV-continued

| Compd. No. | MOLSTRUCTURE |
|---|---|
| 12 | |
| 13 | |
| 14 | |
| 15 | |
| 16 | |

TABLE 1-IV-continued
| Compd. No. | MOLSTRUCTURE |
| --- | --- |
| 17 | 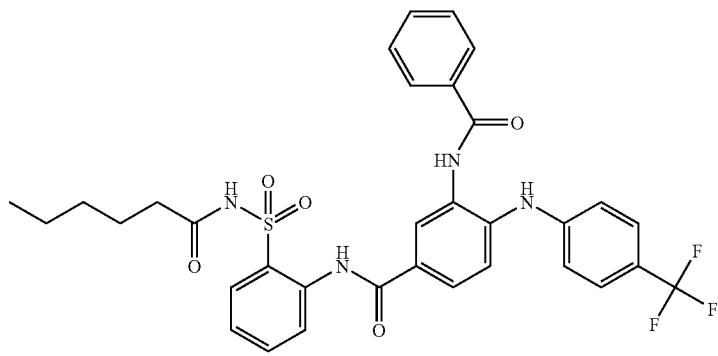 |
| 18 | 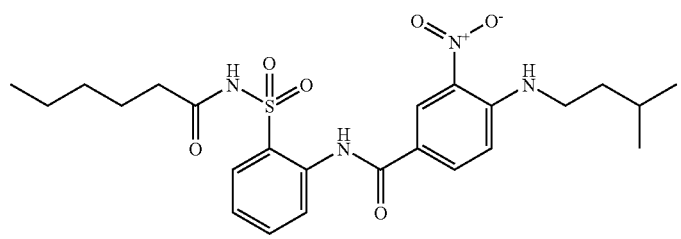 |
| 19 | 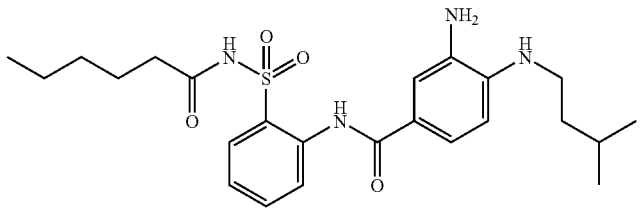 |
| 20 | 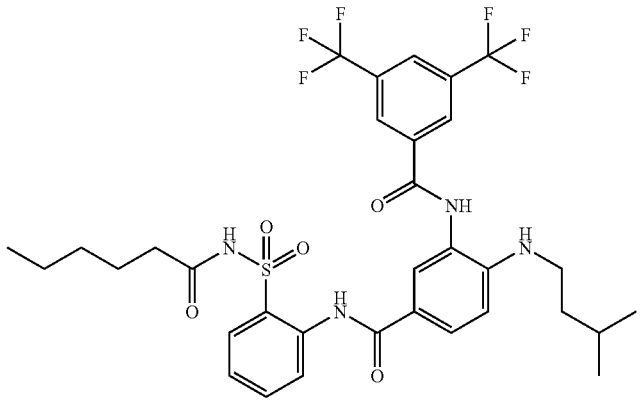 |

TABLE 1-IV-continued
| Compd. No. | MOLSTRUCTURE |
|---|---|
| 23 | 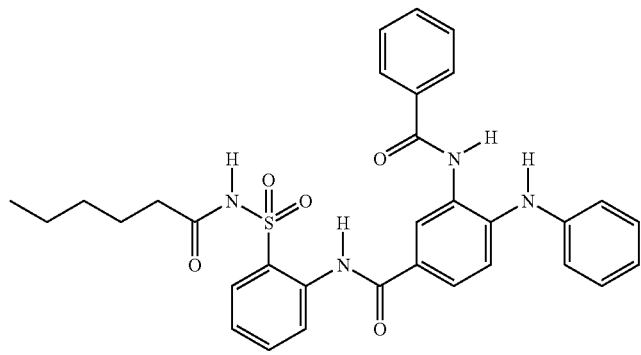 |
| 24 | 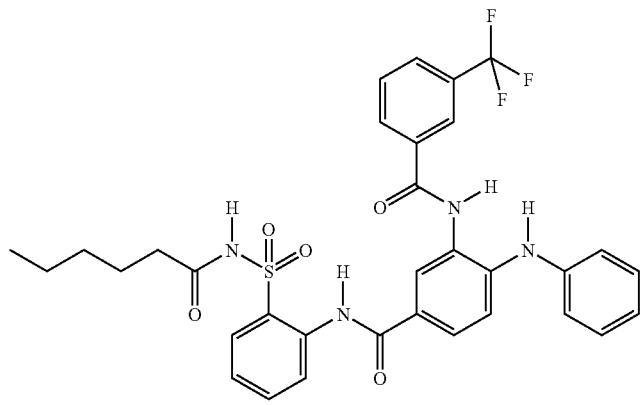 |
| 25 | 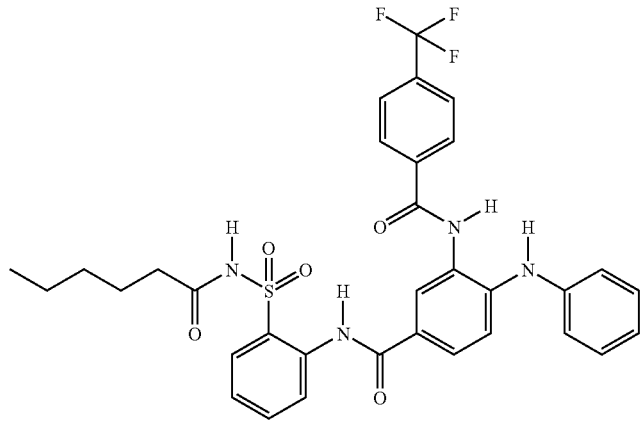 |

TABLE 1-IV-continued

| Compd. No. | MOLSTRUCTURE |
|---|---|
| 26 | |
| 27 | |
| 28 | |
| 29 | |

TABLE 1-IV-continued
| Compd. No. | MOLSTRUCTURE |
|---|---|
| 30 | 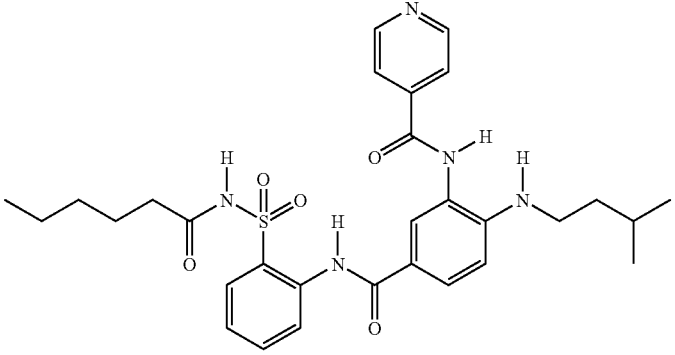 |
| 31 | 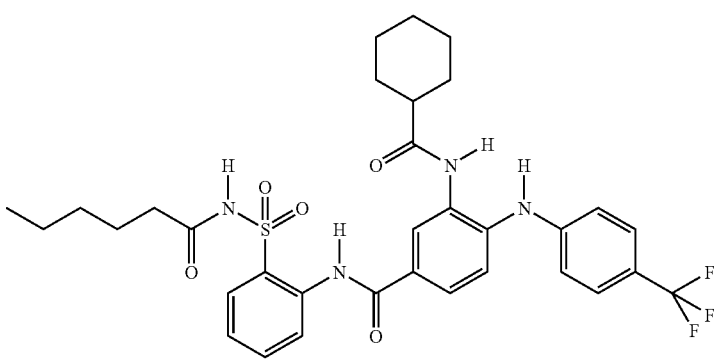 |
| 32 | 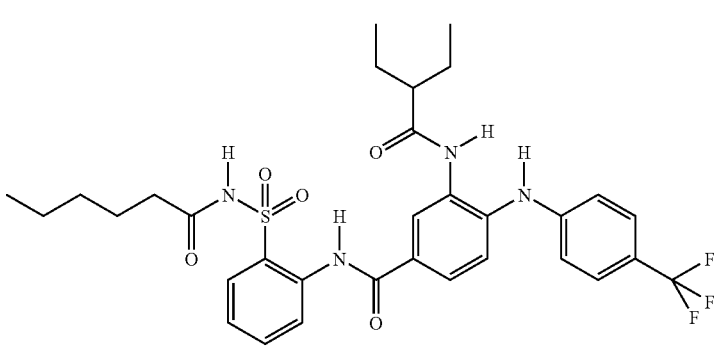 |
| 33 | 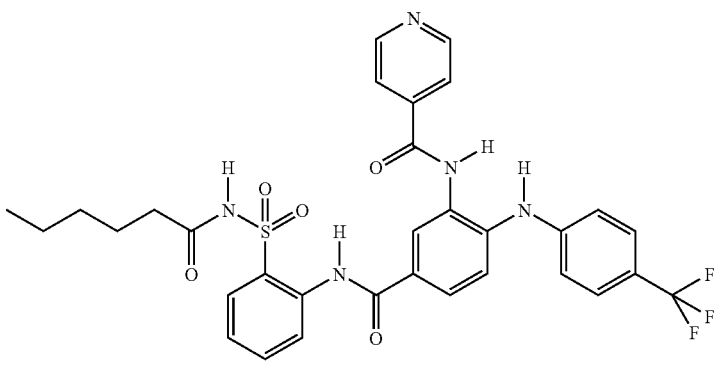 |

TABLE 1-IV-continued
| Compd. No. | MOLSTRUCTURE |
|---|---|
| 34 | 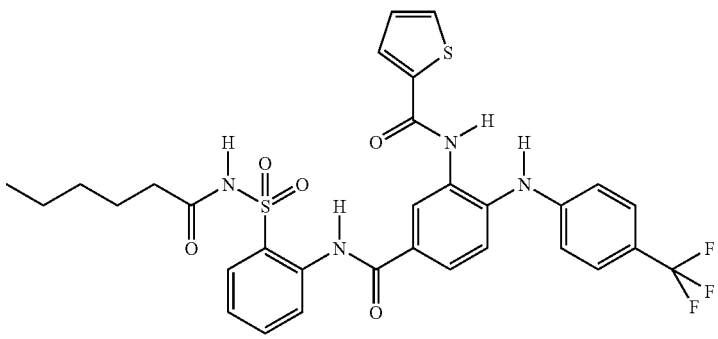 |
| 35 | 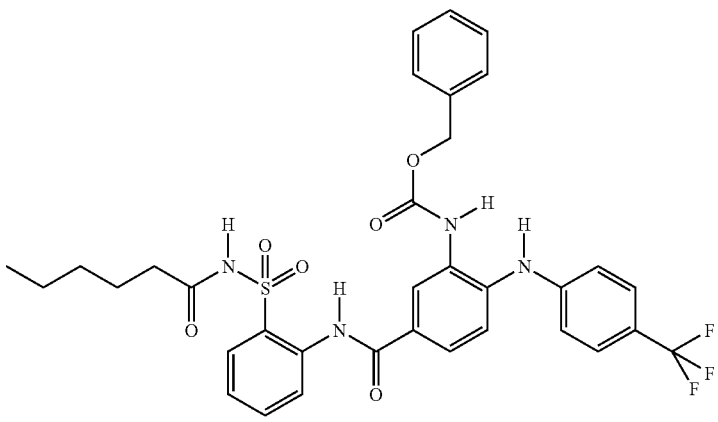 |
| 36 | 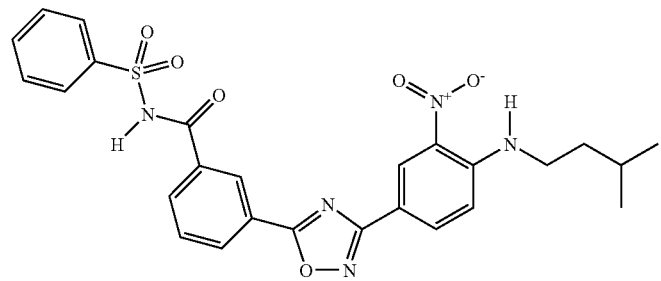 |
| 37 | 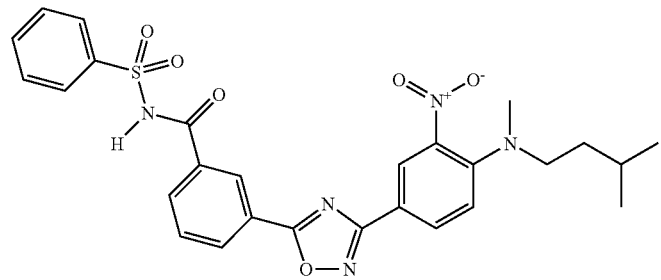 |

TABLE 1-IV-continued

| Compd. No. | MOLSTRUCTURE |
|---|---|
| 38 | |
| 39 | |
| 40 | |
| 41 | |

TABLE 1-IV-continued

| Compd. No. | MOLSTRUCTURE |
| --- | --- |
| 42 | |
| 43 | |
| 44 | |
| 45 | |

TABLE 1-IV-continued

| Compd. No. | MOLSTRUCTURE |
|---|---|
| 46 | |
| 47 | |
| 48 | |
| 49 | |
| 50 | |

TABLE 1-IV-continued
| Compd. No. | MOLSTRUCTURE |
| --- | --- |
| 51 | 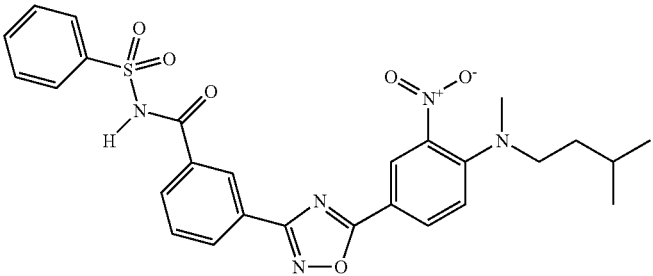 |
| 52 | 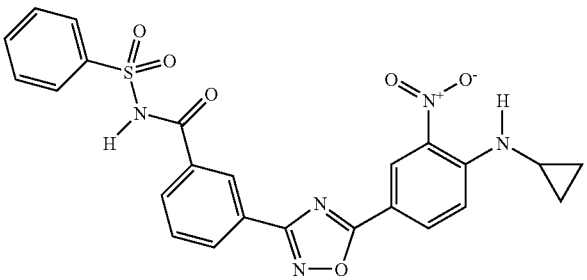 |
| 53 | 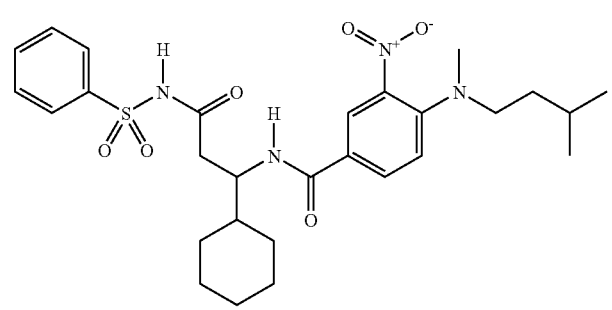 |
| 54 | 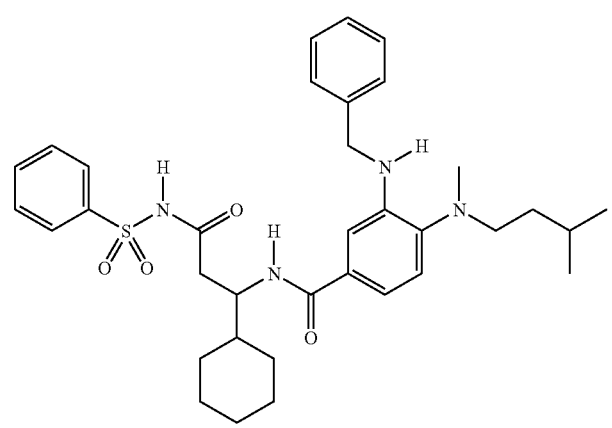 |

TABLE 1-IV-continued
| Compd. No. | MOLSTRUCTURE |
| --- | --- |
| 55 | 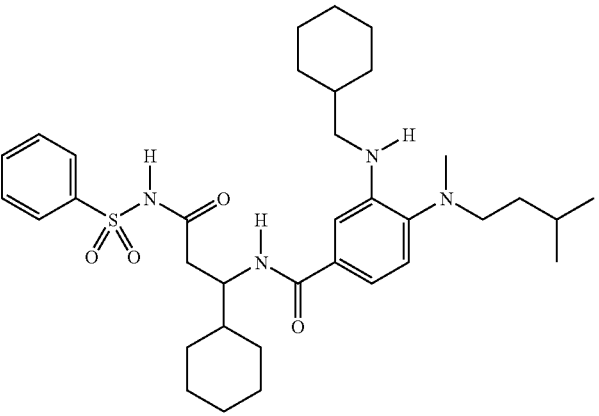 |
| 56 | 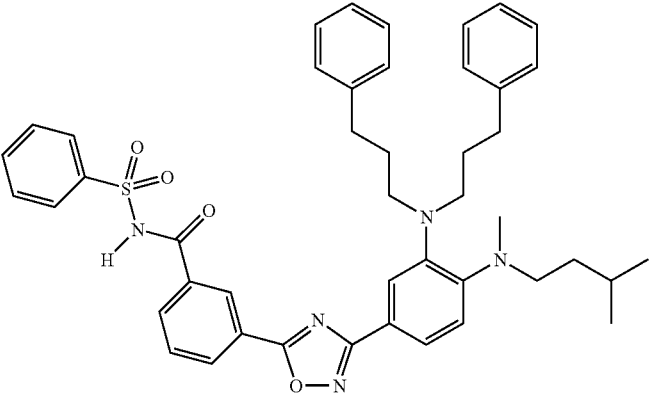 |
| 57 | 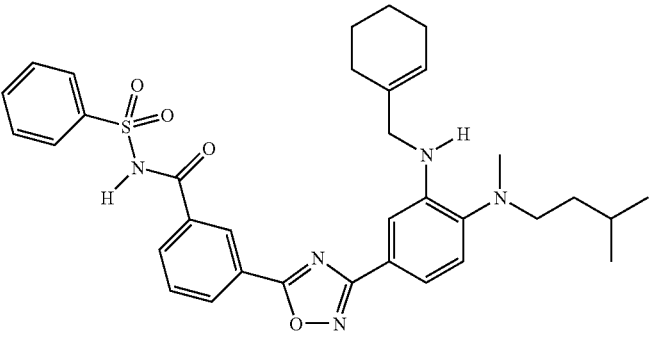 |
| 58 | 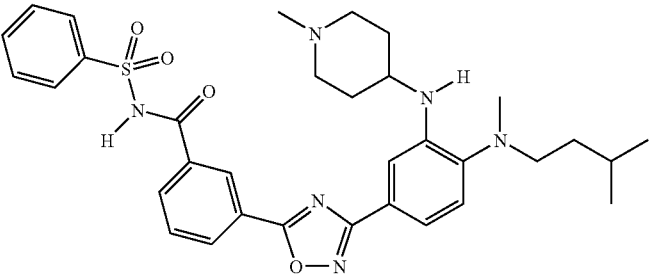 |

TABLE 1-IV-continued
| Compd. No. | MOLSTRUCTURE |
|---|---|
| 59 | 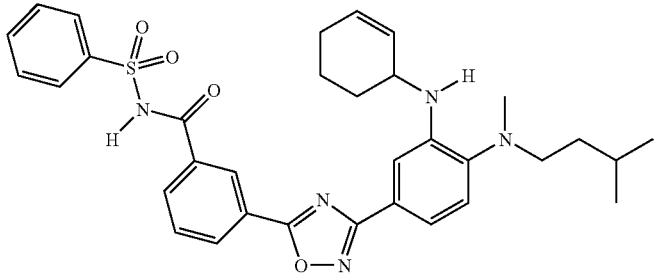 |
| 60 | 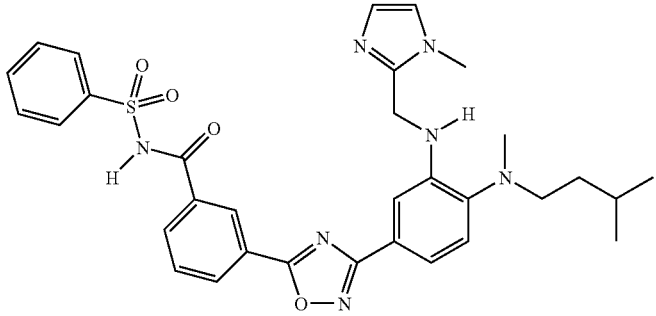 |
| 61 | 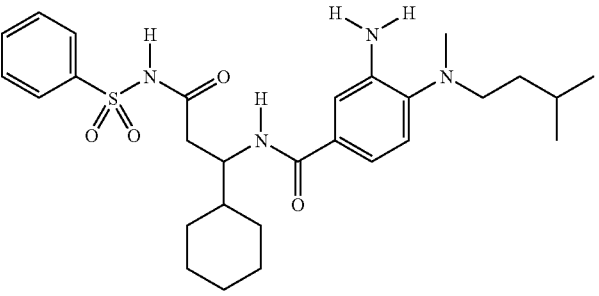 |
| 62 | 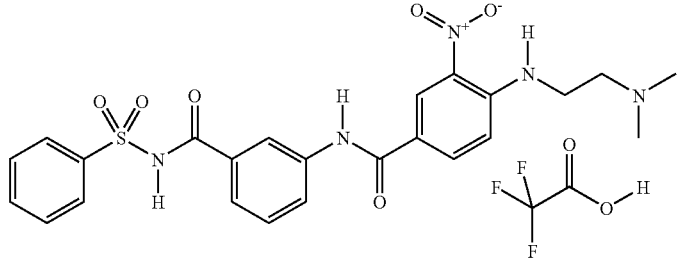 |
| 63 | 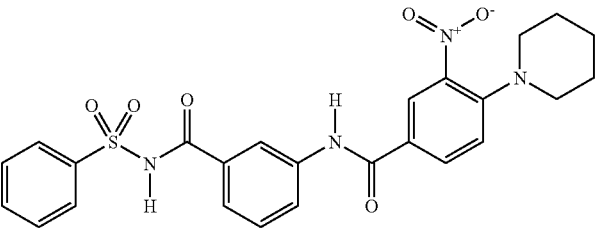 |

TABLE 1-IV-continued
| Compd. No. | MOLSTRUCTURE |
|---|---|
| 64 | 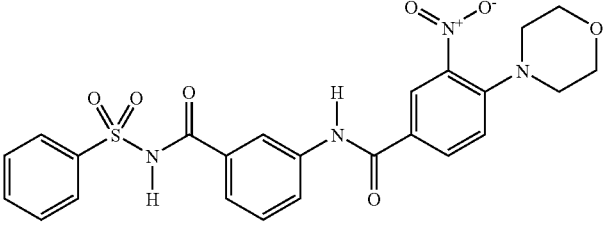 |
| 65 | 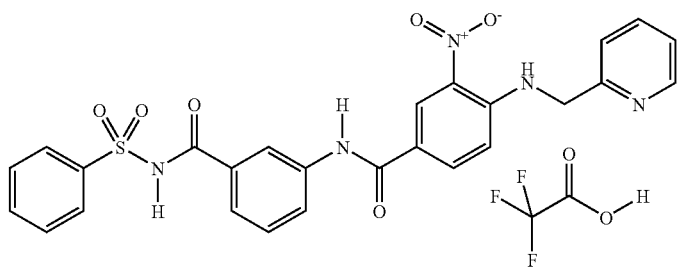 |
| 66 | 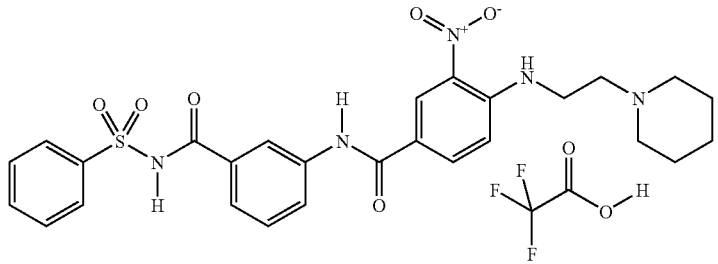 |
| 67 | 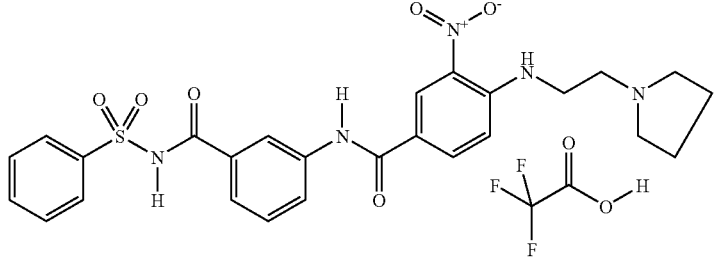 |
| 68 | 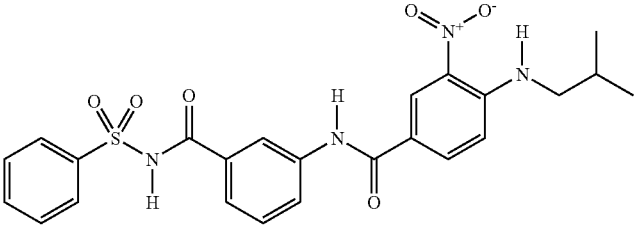 |
| 69 | 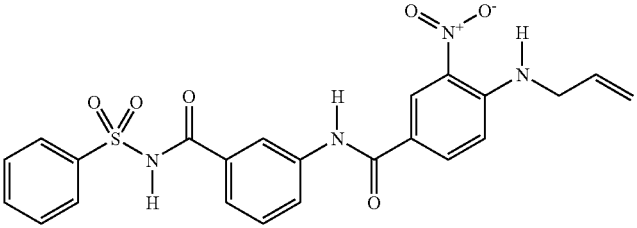 |

TABLE 1-IV-continued
| Compd. No. | MOLSTRUCTURE |
|---|---|
| 70 | 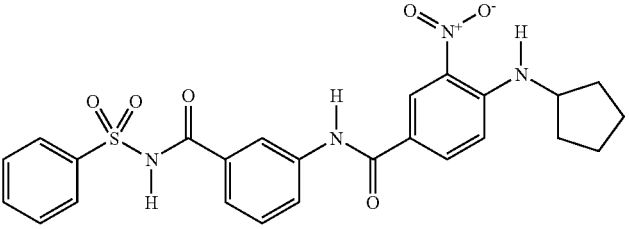 |
| 71 | 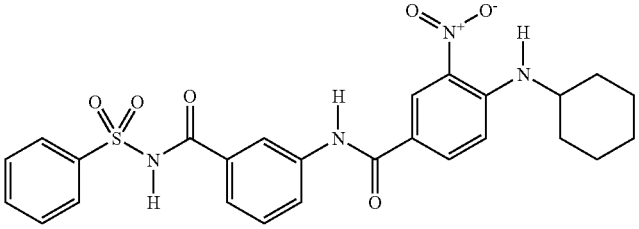 |
| 72 | 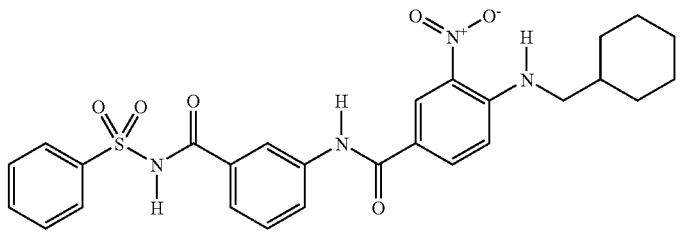 |
| 73 | 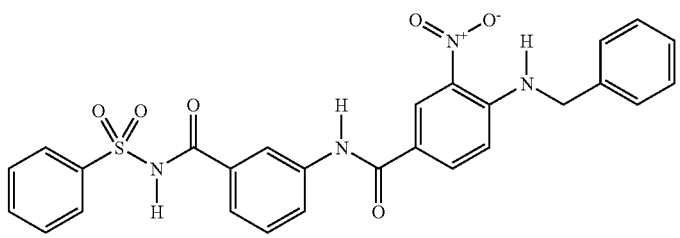 |
| 74 | 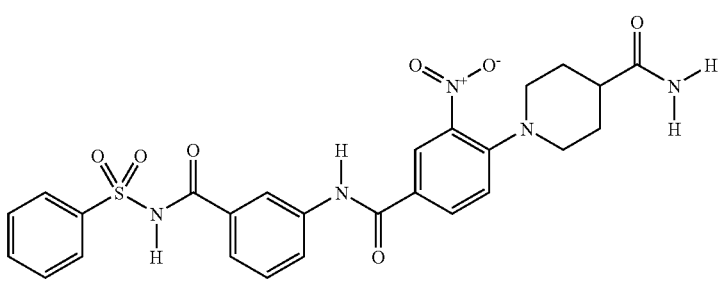 |
| 75 | 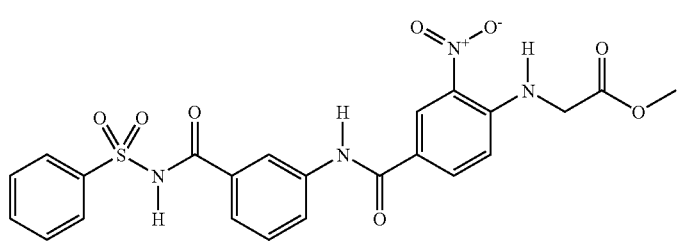 |

TABLE 1-IV-continued

| Compd. No. | MOLSTRUCTURE |
|---|---|
| 76 | |
| 77 | |
| 78 | |
| 79 | |
| 80 | |
| 81 | |

TABLE 1-IV-continued
| Compd. No. | MOLSTRUCTURE |
|---|---|
| 82 | 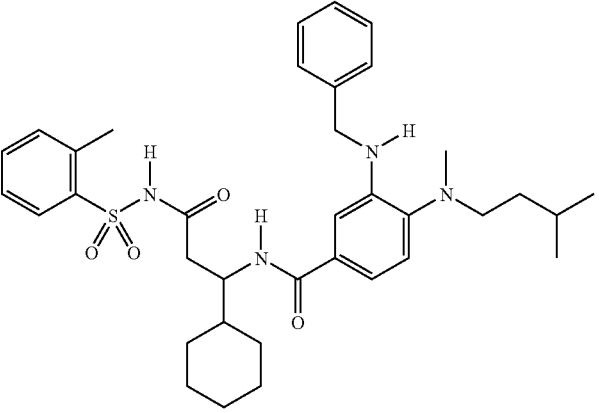 |
| 83 | 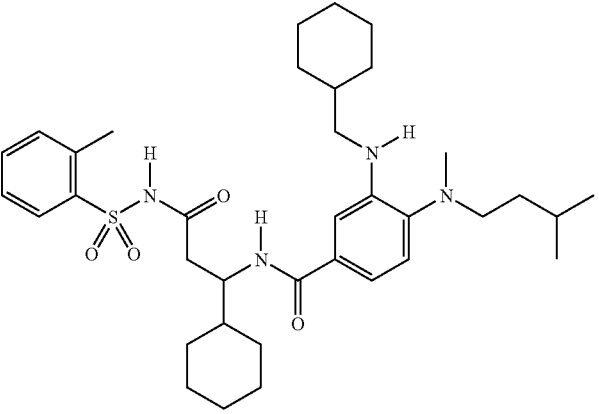 |
| 84 | 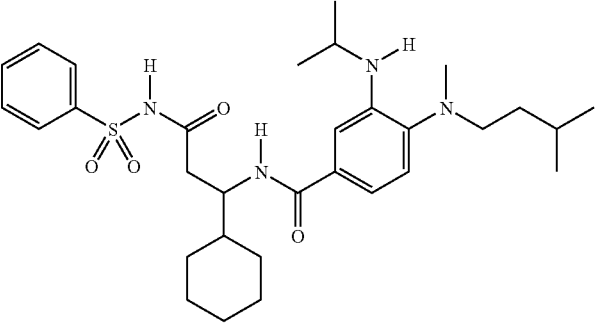 |
| 85 | 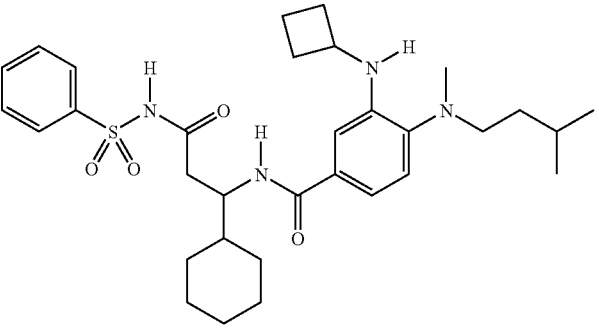 |

TABLE 1-IV-continued
| Compd. No. | MOLSTRUCTURE |
|---|---|
| 86 | 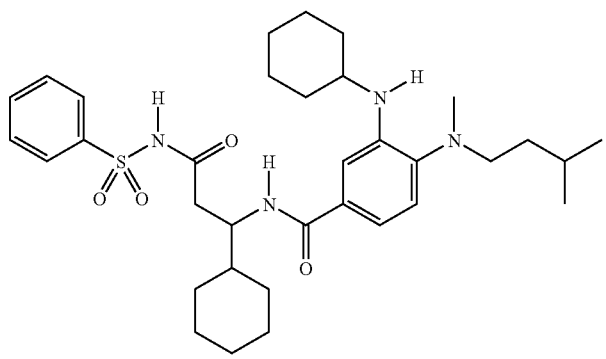 |
| 87 | 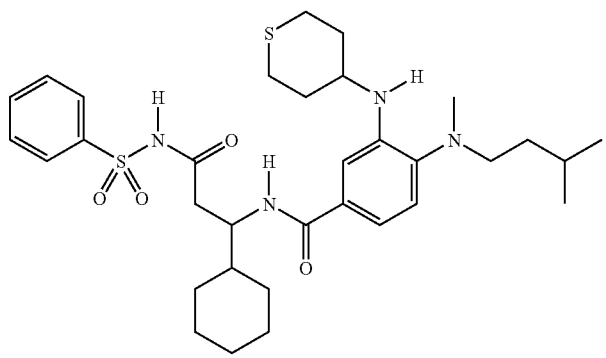 |
| 88 | 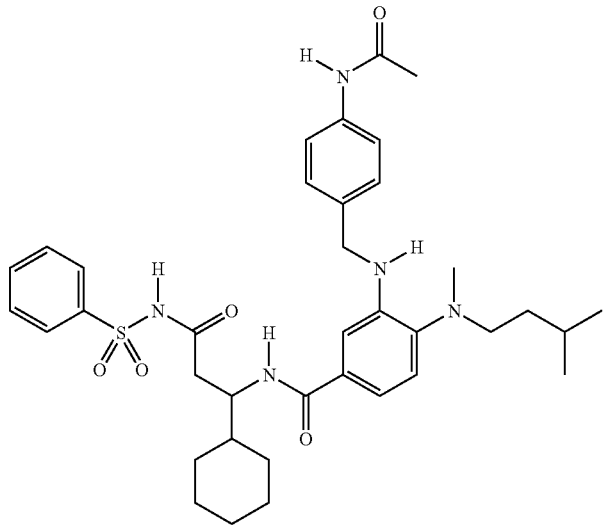 |

TABLE 1-IV-continued
| Compd. No. | MOLSTRUCTURE |
|---|---|
| 89 | 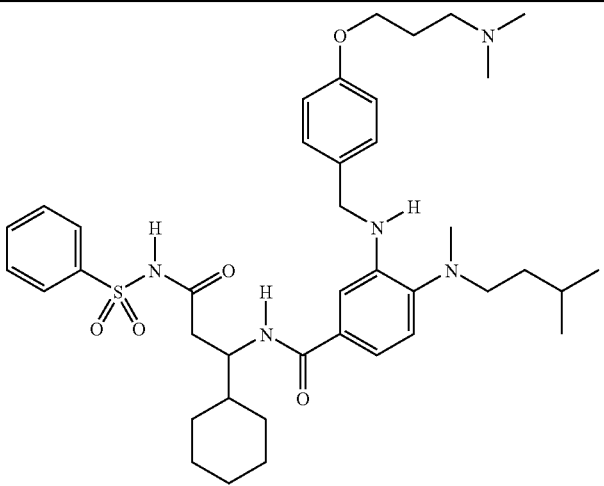 |
| 90 | 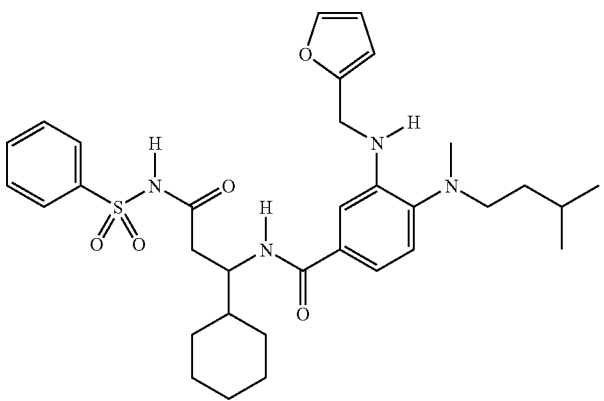 |
| 91 | 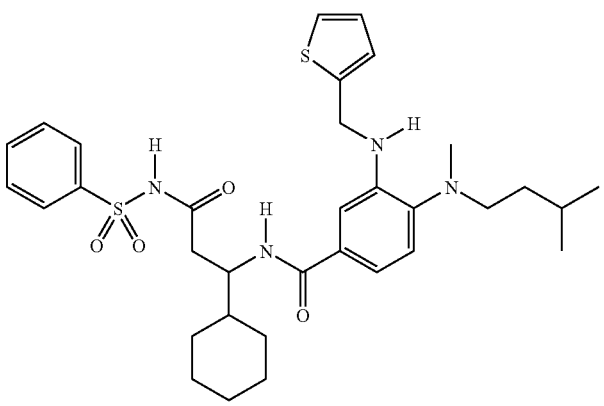 |

TABLE 1-IV-continued
| Compd. No. | MOLSTRUCTURE |
|---|---|
| 92 | 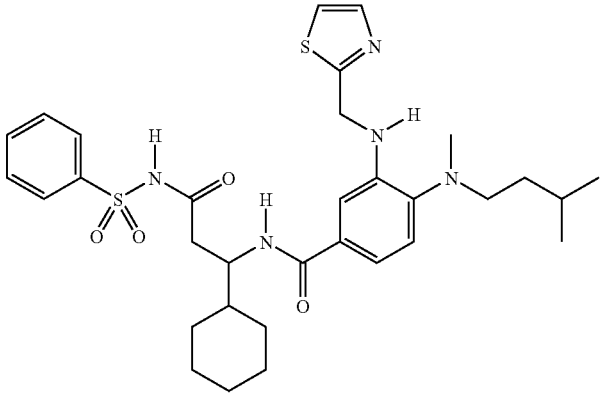 |
| 93 | 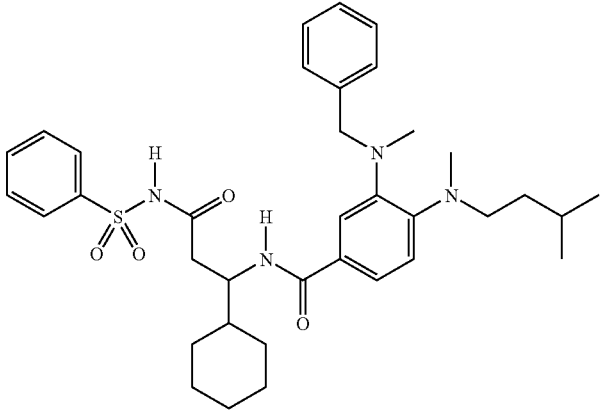 |
| 94 | 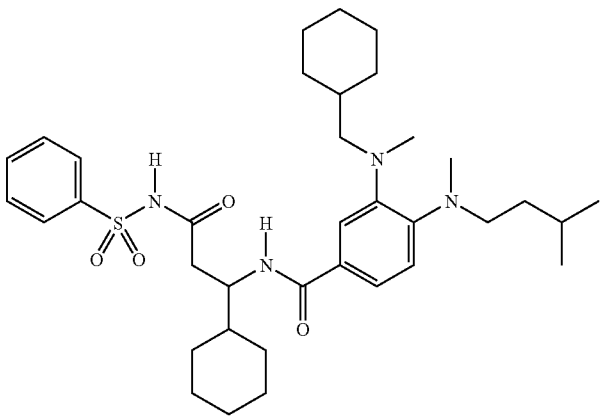 |

TABLE 1-IV-continued
| Compd. No. | MOLSTRUCTURE |
| --- | --- |
| 95 | 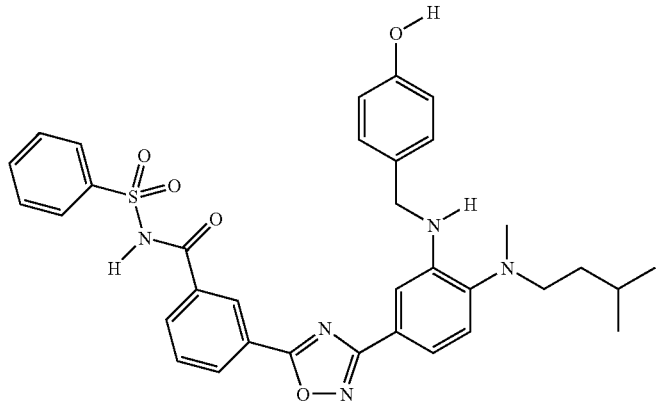 |
| 96 | 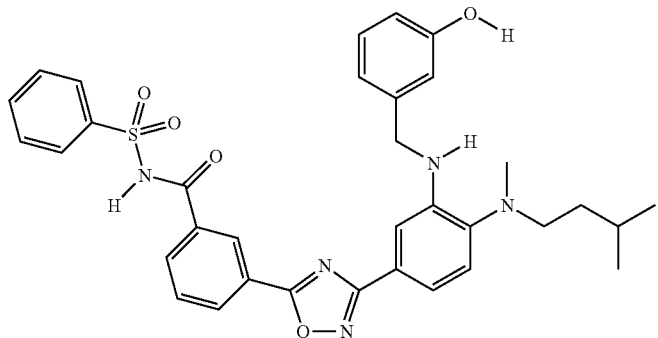 |
| 97 | 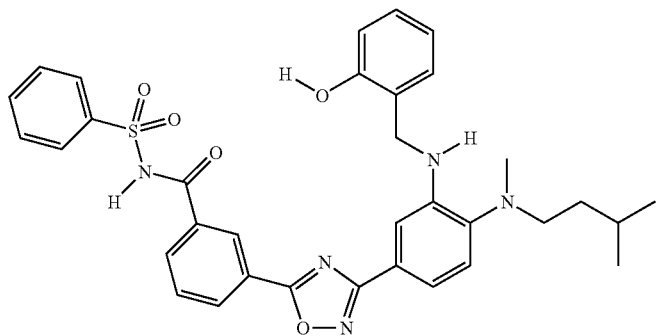 |
| 98 | 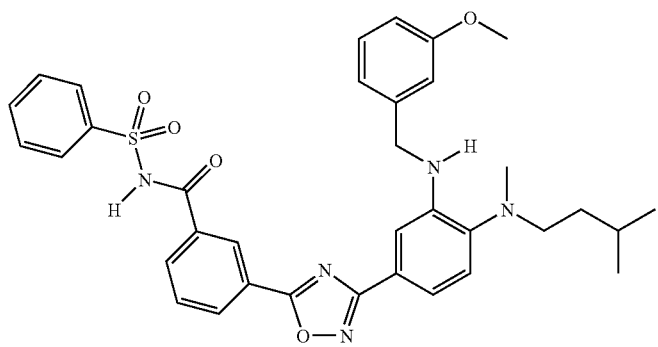 |

TABLE 1-IV-continued
| Compd. No. | MOLSTRUCTURE |
|---|---|
| 99 | 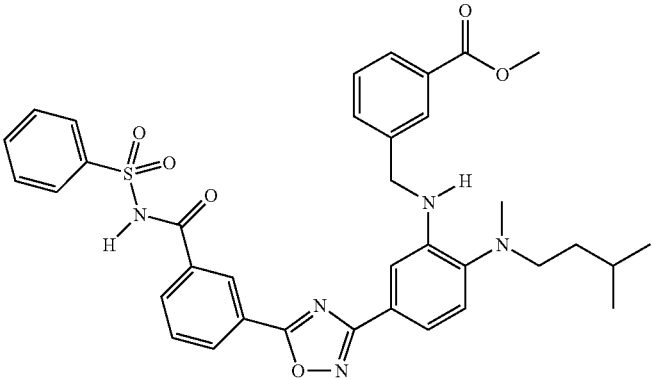 |
| 100 | 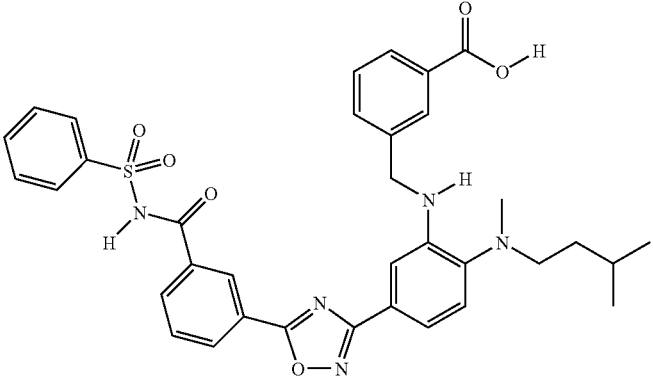 |
| 101 | 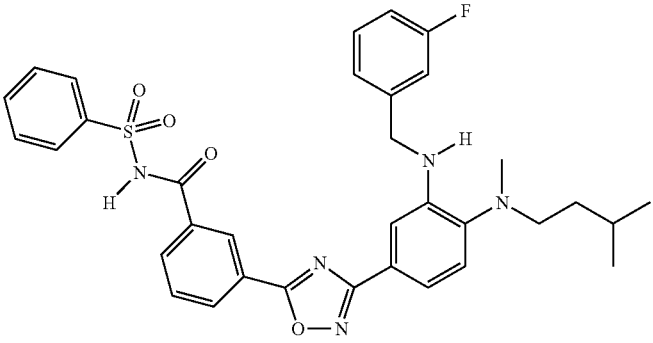 |
| 102 | 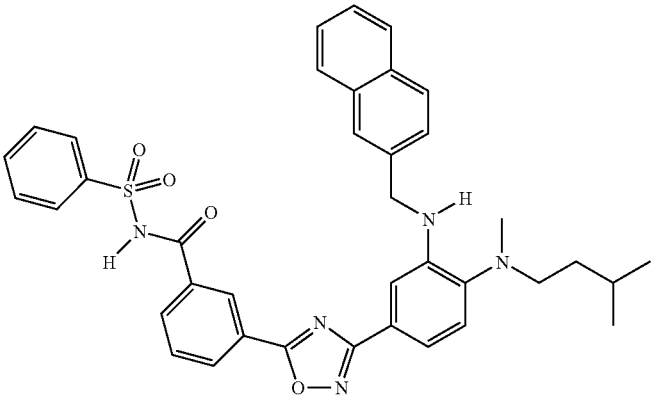 |

TABLE 1-IV-continued
| Compd. No. | MOLSTRUCTURE |
|---|---|
| 103 | 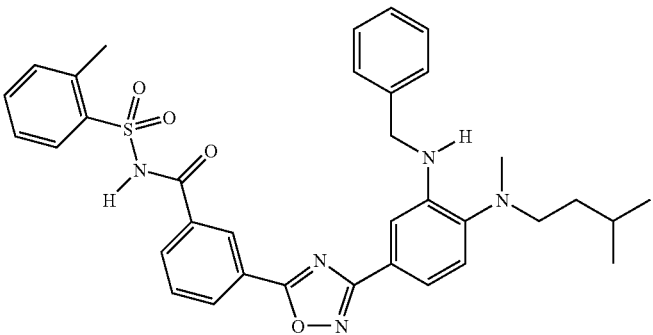 |
| 104 | 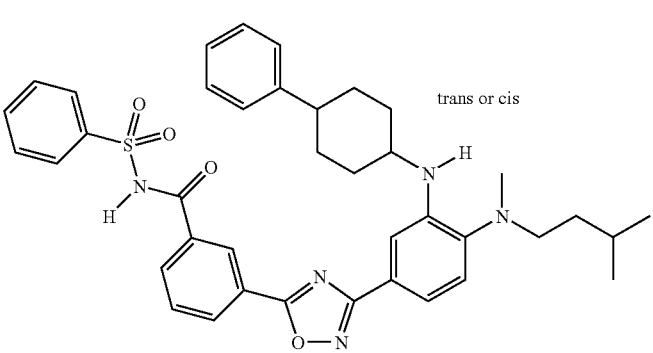 trans or cis |
| 105 | 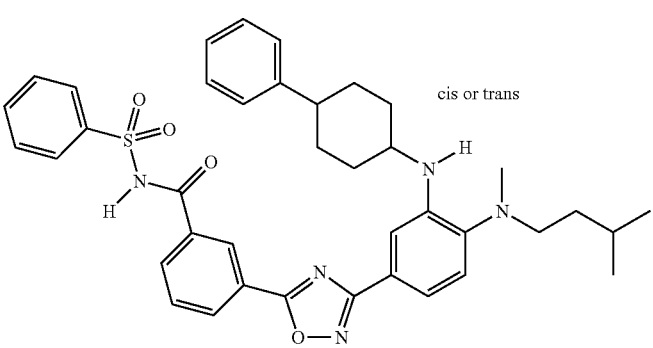 cis or trans |
| 106 | 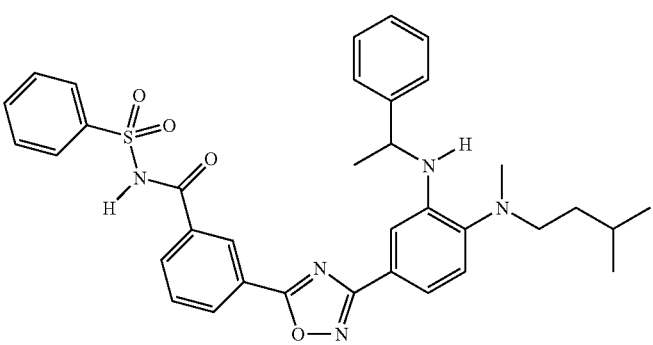 |

TABLE 1-IV-continued
| Compd. No. | MOLSTRUCTURE |
|---|---|
| 107 | 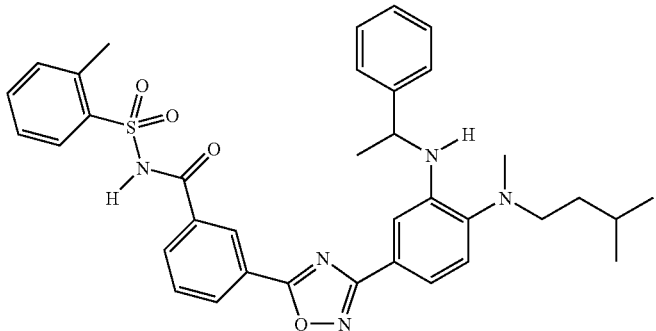 |
| 108 | 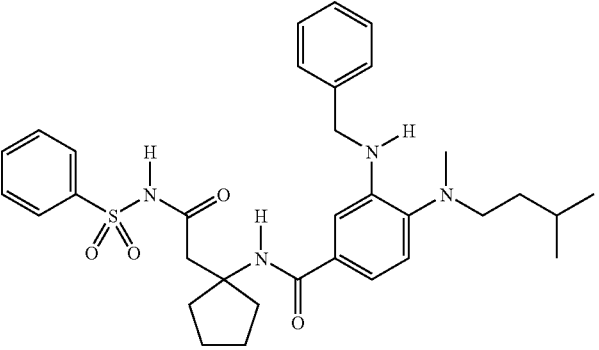 |
| 109 | 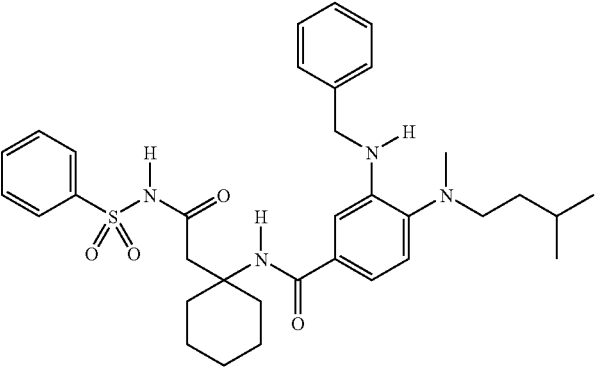 |
| 110 | 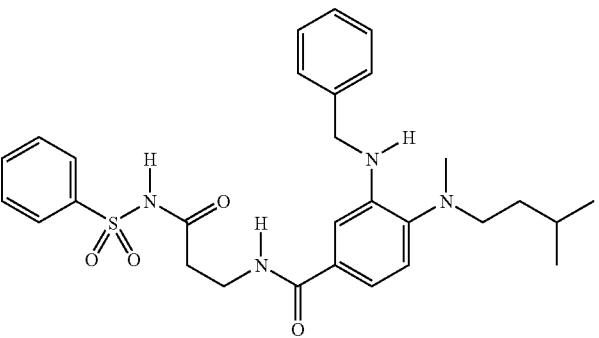 |

TABLE 1-IV-continued
| Compd. No. | MOLSTRUCTURE |
|---|---|
| 111 | 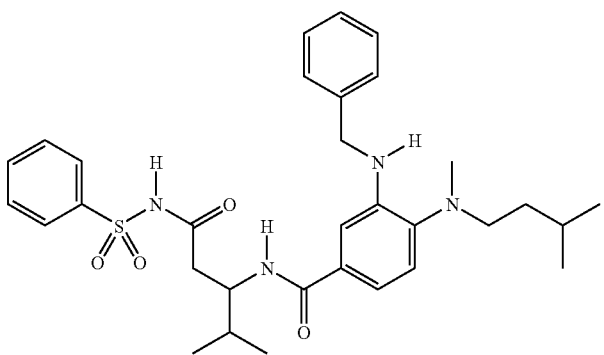 |
| 112 | 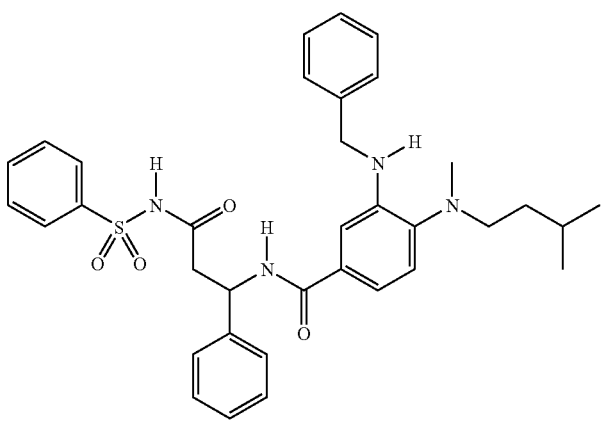 |
| 113 | 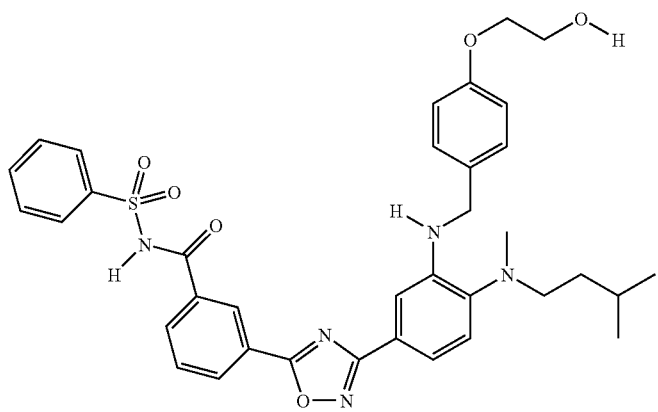 |
| 114 | 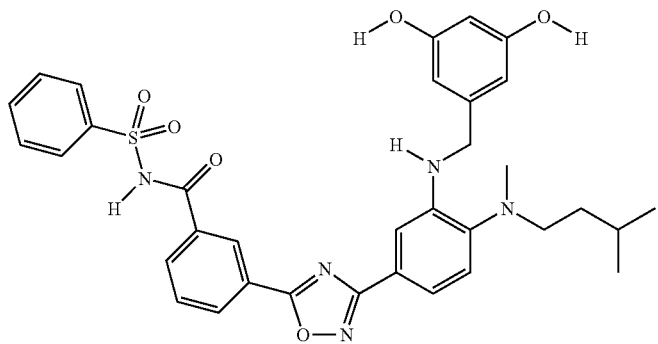 |

TABLE 1-IV-continued

| Compd. No. | MOLSTRUCTURE |
|---|---|
| 115 | |
| 116 | |
| 117 | |
| 118 | |

TABLE 1-IV-continued
| Compd. No. | MOLSTRUCTURE |
| --- | --- |
| 119 | 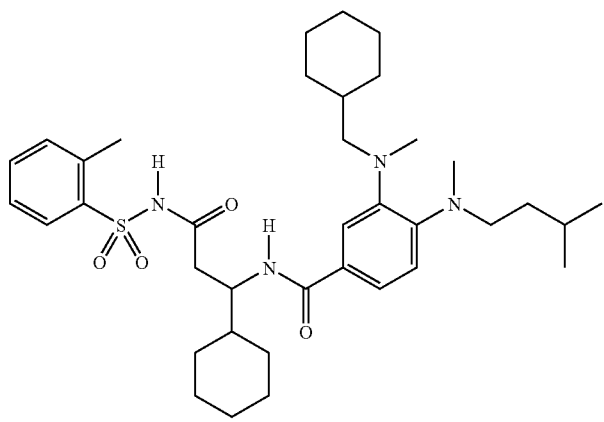 |
| 120 | 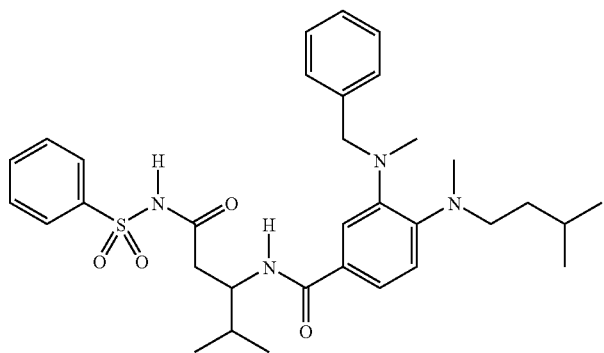 |
| 121 | 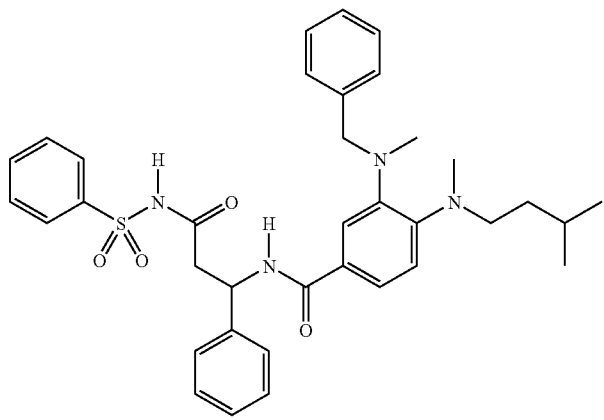 |

TABLE 1-IV-continued

| Compd. No. | MOLSTRUCTURE |
|---|---|
| 122 | |
| 123 | |
| 124 | |

TABLE 1-IV-continued
| Compd. No. | MOLSTRUCTURE |
| --- | --- |
| 125 | 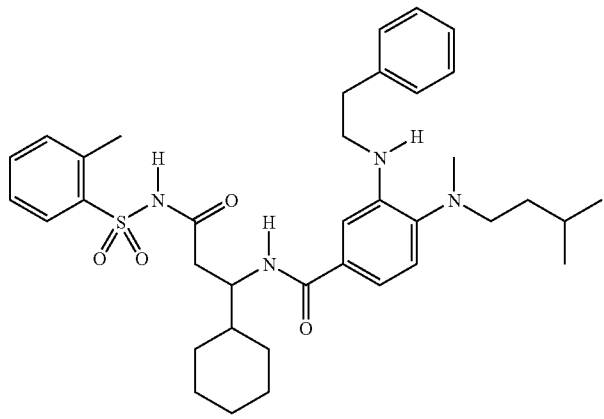 |
| 126 | 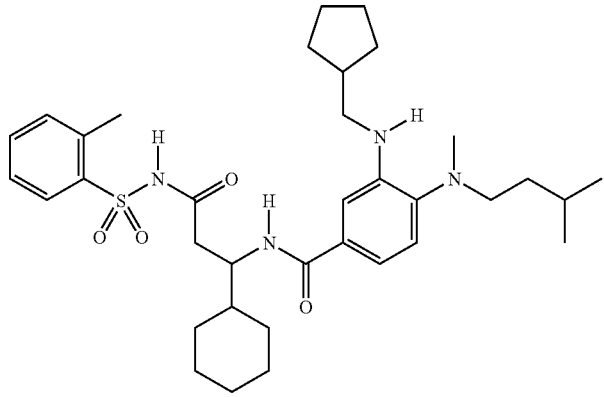 |
| 127 | 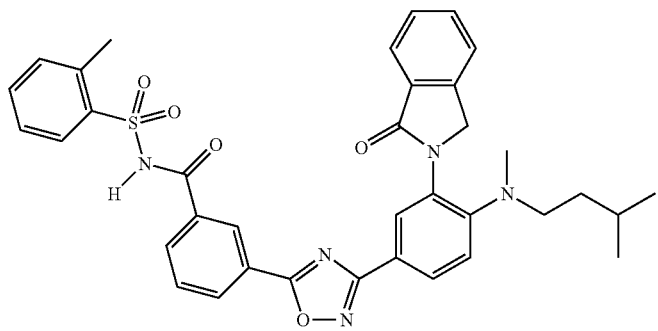 |
| 128 | 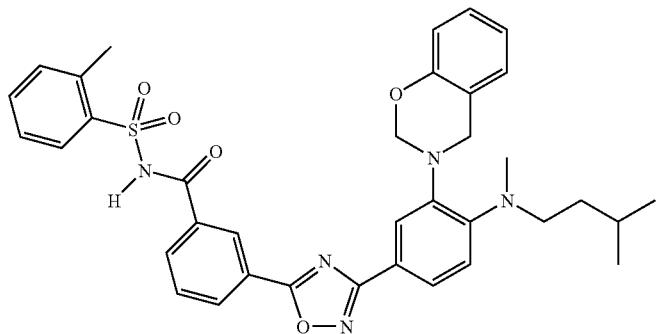 |

TABLE 1-IV-continued

| Compd. No. | MOLSTRUCTURE |
|---|---|
| 129 | |
| 130 | |
| 131 | |
| 132 | |

TABLE 1-IV-continued
| Compd. No. | MOLSTRUCTURE |
|---|---|
| 133 | 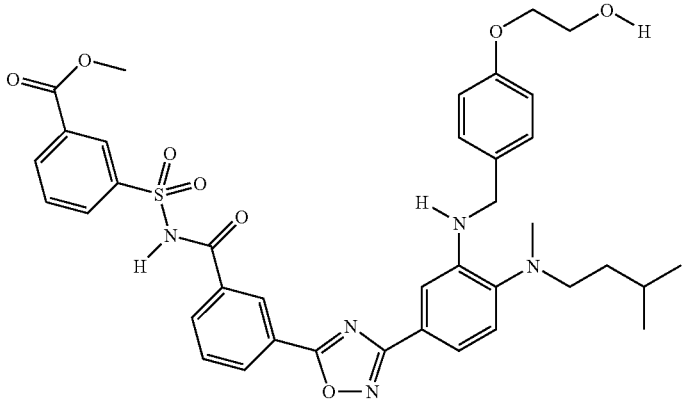 |
| 134 | 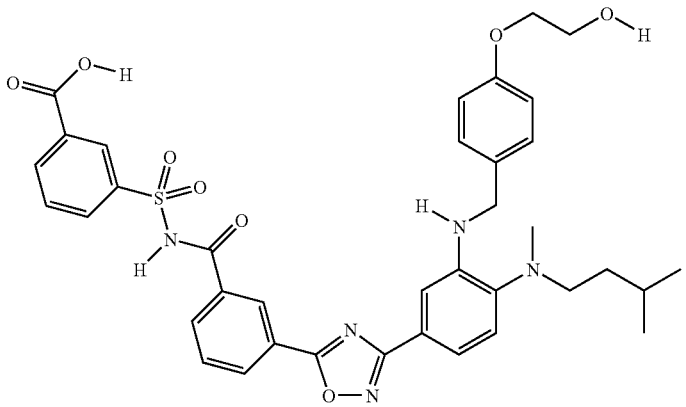 |
| 135 | 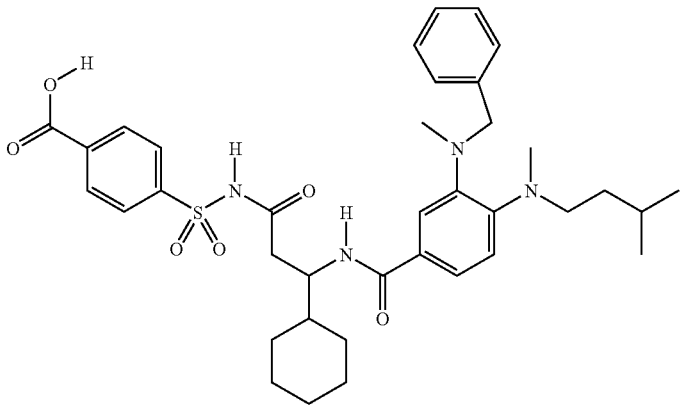 |
| 136 | 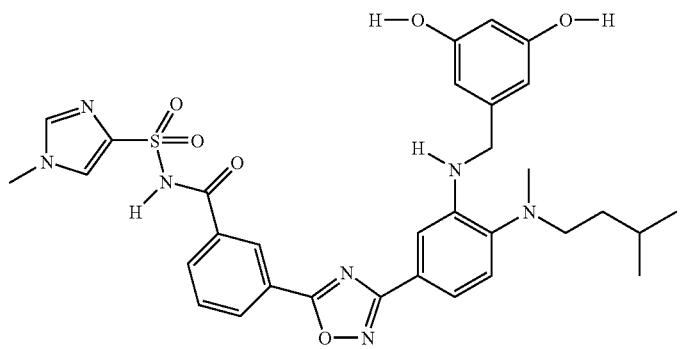 |

TABLE 1-IV-continued
| Compd. No. | MOLSTRUCTURE |
|---|---|
| 137 | 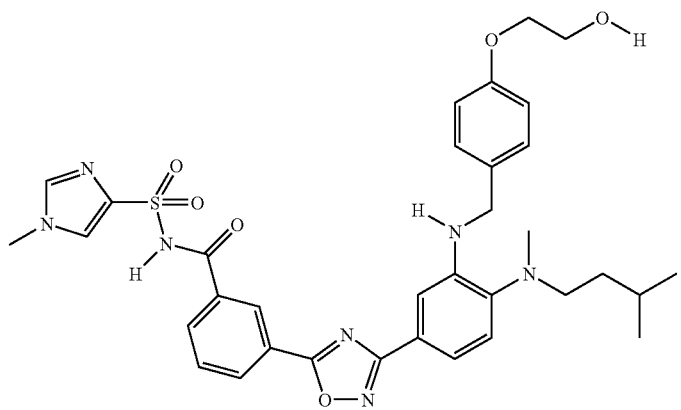 |
| 138 | 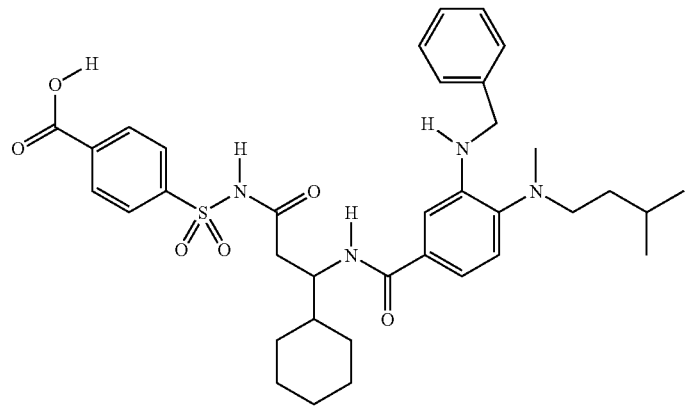 |
| 139 | 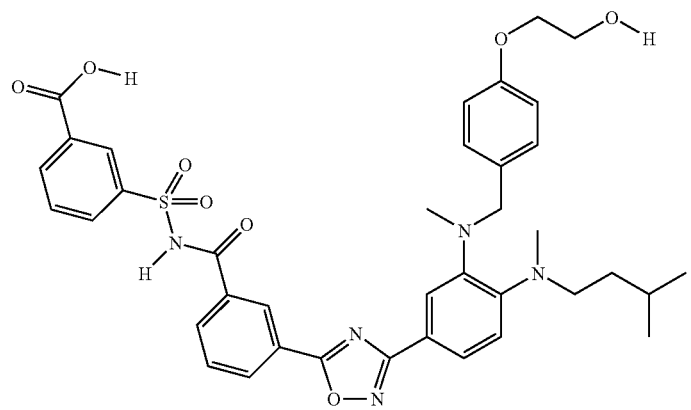 |

TABLE 1-IV-continued
| Compd. No. | MOLSTRUCTURE |
|---|---|
| 140 | 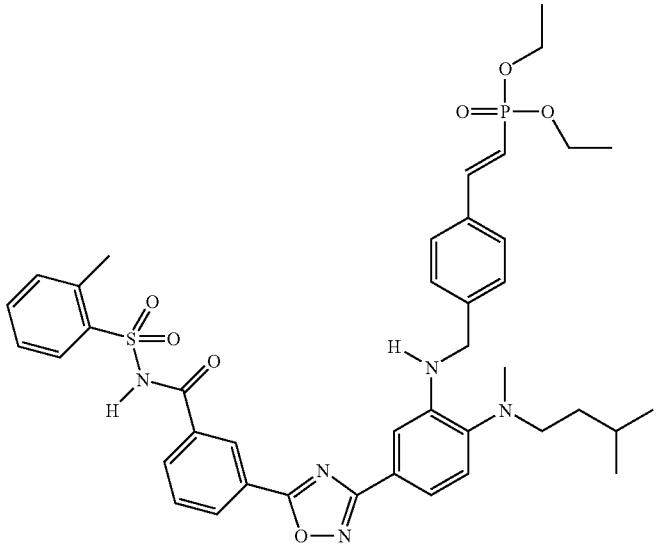 |
| 141 | 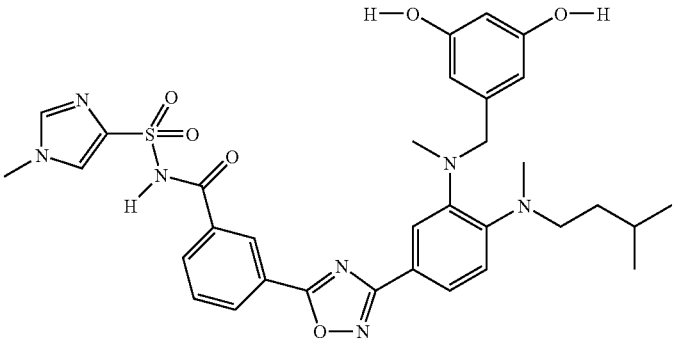 |
| 142 | 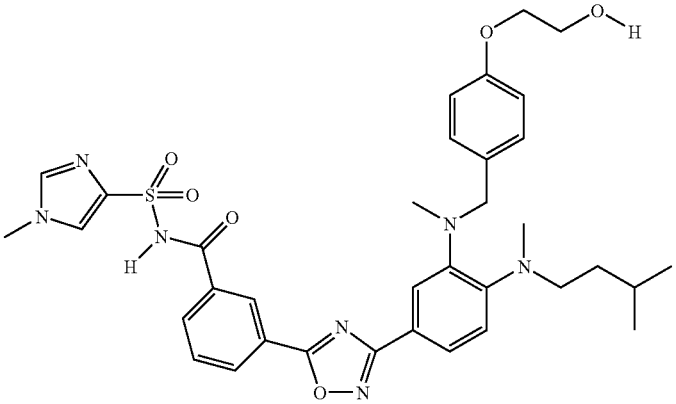 |

TABLE 1-IV-continued

| Compd. No. | MOLSTRUCTURE |
|---|---|
| 143 | |
| 144 | |
| 145 | |
| 146 | |

TABLE 1-IV-continued
| Compd. No. | MOLSTRUCTURE |
| --- | --- |
| 147 | 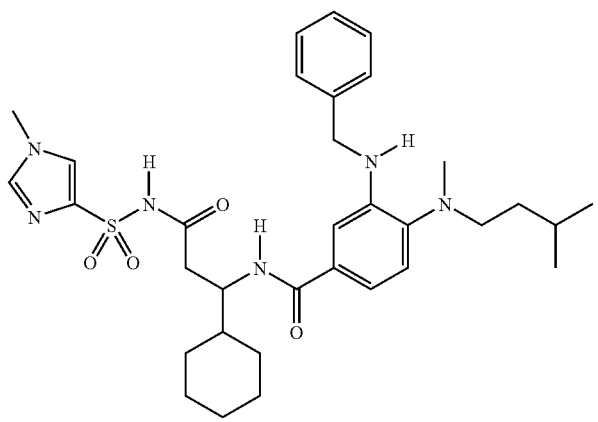 |
| 148 | 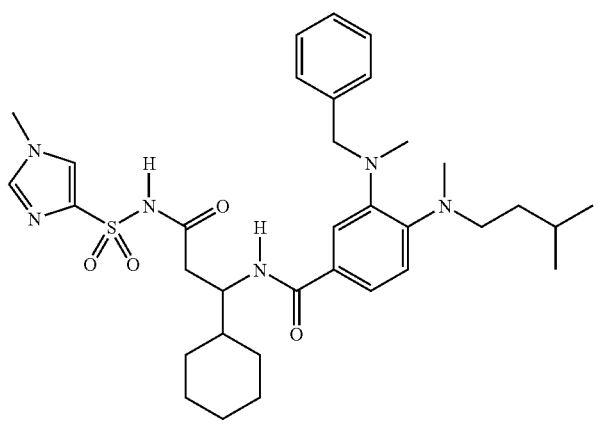 |
| 149 | 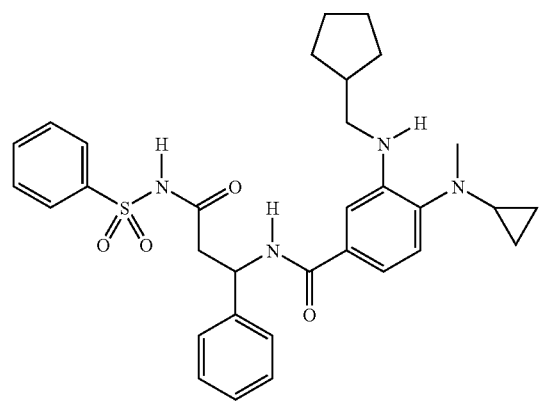 |

TABLE 1-IV-continued
| Compd. No. | MOLSTRUCTURE |
|---|---|
| 150 | 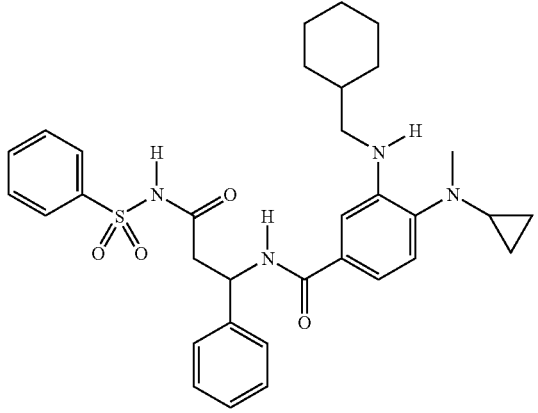 |
| 151 | 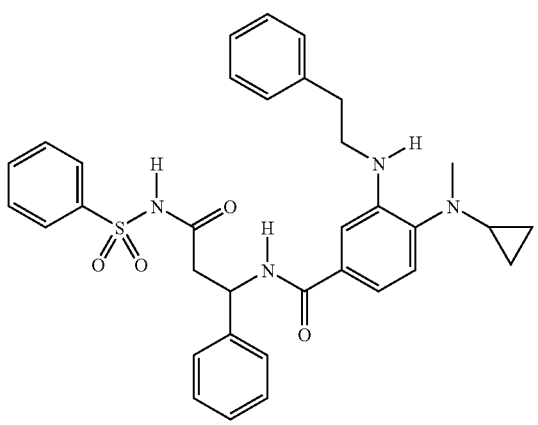 |
| 152 | 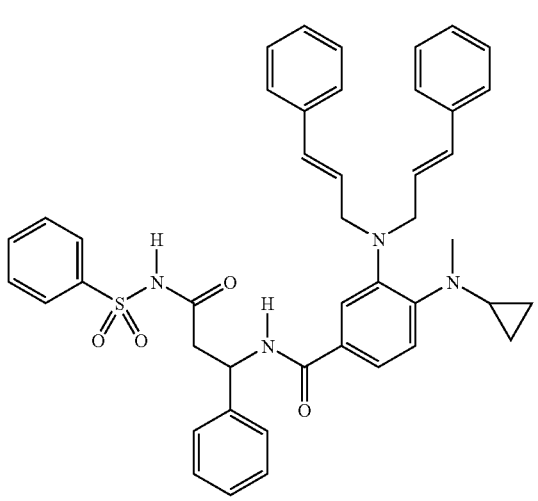 |

TABLE 1-IV-continued
| Compd. No. | MOLSTRUCTURE |
|---|---|
| 153 | 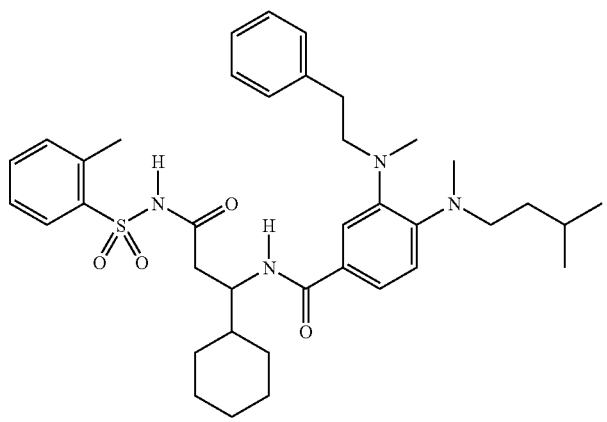 |
| 154 | 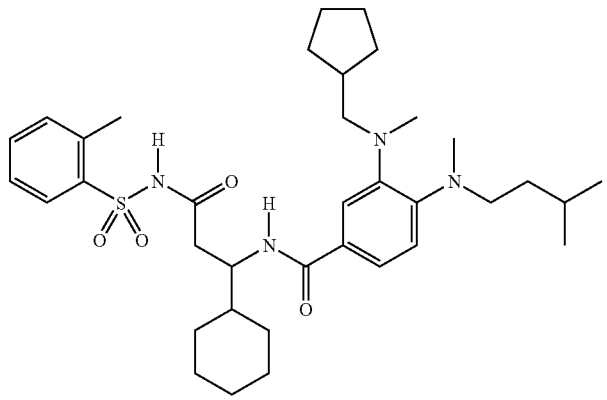 |
| 155 | 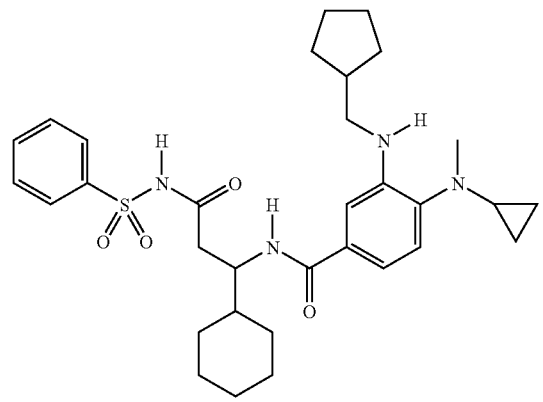 |

TABLE 1-IV-continued

| Compd. No. | MOLSTRUCTURE |
| --- | --- |
| 156 | |
| 157 | |
| 158 | |

TABLE 1-IV-continued
| Compd. No. | MOLSTRUCTURE |
|---|---|
| 159 | 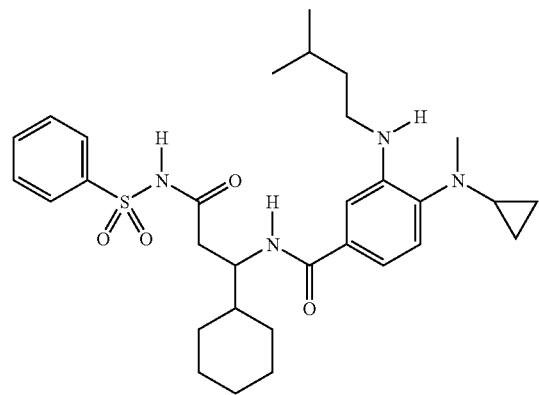 |
| 160 | 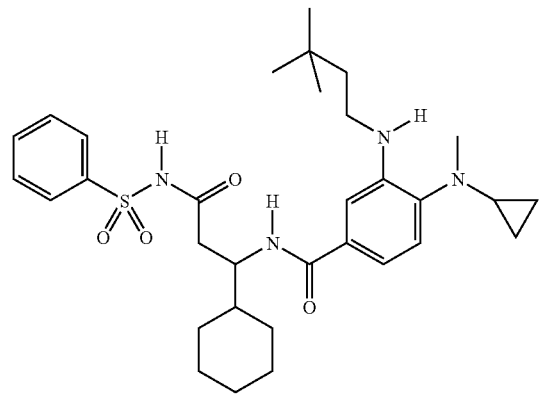 |
| 161 | 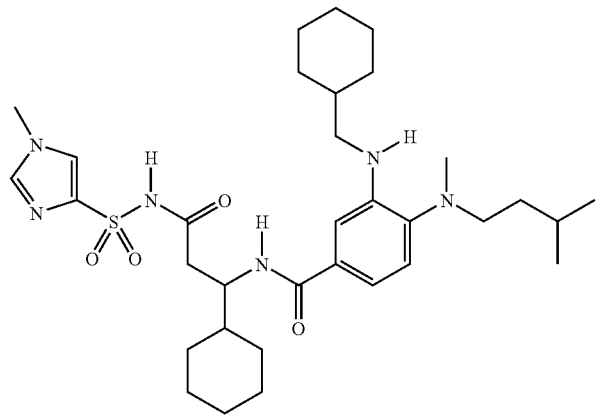 |

TABLE 1-IV-continued
| Compd. No. | MOLSTRUCTURE |
|---|---|
| 162 | 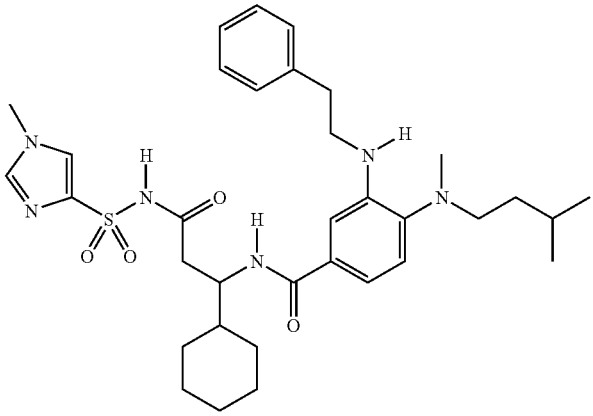 |
TABLE 2-IV
| Compound No. | MS(ESI)(MH+) |
|---|---|
| 1 | 579 |
| 2 | 593 |
| 3 | 624 |
| 4 | 556 |
| 5 | 638 |
| 6 | 624 |
| 7 | 556 |
| 8 | 651 |
| 9 | 624 |
| 10 | 579 |
| 11 | 523 |
| 12 | 597 |
| 13 | 544 |
| 14 | 594 |
| 15 | 549 |
| 16 | 789 |
| 17 | 653 |
| 18 | 505 |
| 19 | 475 |
| 20 | 715 |
| 23 | 585 |
| 24 | 563 |
| 25 | 653 |
| 26 | 721 |
| 27 | 721 |
| 28 | 721 |
| 29 | 559 |
| 30 | 580 |
| 31 | 659 |
| 32 | 647 |
| 33 | 654 |
| 34 | 659 |
| 35 | 683 |
| 36 | 536 |
| 37 | 550 |
| 38 | 520 |
| 39 | 692 |
| 40 | 624 |
| 41 | 630 |
| 42 | 618 |
| 43 | 630 |
| 44 | 654 |
| 45 | 610 |
| 46 | 508 |
| 47 | 616 |
| 48 | 562 |
| 49 | 494 |
| 50 | 606 |
TABLE 2-IV-continued
| Compound No. | MS(ESI)(MH+) |
|---|---|
| 51 | 550 |
| 52 | 506 |
| 53 | 559 |
| 54 | 619 |
| 55 | 625 |
| 56 | 756 |
| 57 | 614 |
| 58 | 617 |
| 59 | 600 |
| 60 | 614 |
| 61 | 529 |
| 62 | 626 |
| 63 | 509 |
| 64 | 511 |
| 65 | 646 |
| 66 | 666 |
| 67 | 652 |
| 68 | 497 |
| 69 | 481 |
| 70 | 509 |
| 71 | 523 |
| 72 | 537 |
| 73 | 531 |
| 74 | 552 |
| 75 | 513 |
| 76 | 555 |
| 77 | 492 |
| 78 | 521 |
| 79 | 663 |
| 80 | 566 |
| 81 | 573 |
| 82 | 633 |
| 83 | 639 |
| 84 | 571 |
| 85 | 583 |
| 86 | 611 |
| 87 | 629 |
| 88 | 676 |
| 89 | 720 |
| 90 | 609 |
| 91 | 625 |
| 92 | 626 |
| 93 | 633 |
| 94 | 639 |
| 95 | 626 |
| 96 | 626 |
| 97 | 626 |
| 98 | 640 |

TABLE 2-IV-continued

| Compound No. | MS(ESI)(MH+) |
|---|---|
| 99 | 668 |
| 100 | 654 |
| 101 | 628 |
| 102 | 660 |
| 103 | 624 |
| 104 | 678 |
| 105 | 678 |
| 106 | 624 |
| 107 | 638 |
| 108 | 691 |
| 109 | 605 |
| 110 | 537 |
| 111 | 579 |
| 112 | 613 |
| 113 | 670 |
| 114 | 642 |
| 115 | 656 |
| 116 | 638 |
| 117 | 551 |
| 118 | 647 |
| 119 | 653 |
| 120 | 593 |
| 121 | 627 |
| 122 | 649 |
| 123 | 649 |
| 124 | 678 |
| 125 | 647 |
| 126 | 625 |
| 127 | 650 |
| 128 | 652 |
| 129 | 669 |
| 130 | 682 |
| 131 | 661 |
| 132 | 659 |
| 133 | 728 |
| 134 | 714 |
| 135 | 677 |
| 136 | 646 |
| 137 | 674 |
| 138 | 663 |
| 139 | 728 |
| 140 | 786 |
| 141 | 660 |
| 142 | 688 |
| 143 | 691 |
| 144 | 591 |
| 145 | 605 |
| 146 | 605 |
| 147 | 623 |
| 148 | 637 |
| 149 | 575 |
| 150 | 589 |
| 151 | 597 |
| 152 | 725 |
| 153 | 661 |
| 154 | 639 |
| 165 | 581 |
| 156 | 595 |
| 157 | 603 |
| 158 | 633 |
| 159 | 569 |
| 160 | 583 |
| 161 | 629 |
| 162 | 637 |

TABLE 3-IV

| Compd. No. | NMR | SOLVENT |
|---|---|---|
| 1 | δ0.77(3H, t, J=7.0Hz), 1.01-1.21(4H, m), 1.41(2H, pseudo quint., J=7.3Hz), 2.24(2H, t, J=7.3Hz), 7.40(1H, ddd, J=7.8, 7.8, 1.2Hz), 7.51(1H, d, J=7.9Hz), 7.55(2H, d, J=8.5Hz), 7.76(1H, ddd, J=7.8, 7.8, 1.6Hz), 7.85(1H, dd, J=9.1, 2.1Hz), 7.94(1H, dd, J=8.2, 1.5Hz), 8.02(2H, d, J=8.8Hz), 8.40(1H, d, J=1.2Hz), 8.46(1H, d, J=7.9Hz), 9.82(1H, s), 10.44(1H, s), 12.5(1H, br.s). | DMSO-d6 |
| 3 | δ0.85(3H, t, J=6.7Hz), 1.23-1.28(4H, m), 1.55-1.63(2H, m), 2.29(2H, t, J=7.5Hz), 7.30(1H, dd, J=7.9, 7.9Hz), 7.69-7.79(4H, m), 7.96(1H, dd, J=7.9, 1.5Hz), 8.27(1H, dd, J=8.9, 1.9Hz), 8.54(1H, s), 8.70(1H, d, J=8.5Hz), 9.04(1H, d, J=2.3Hz), 10.68(1H, s), 11.44(1H, s). | CDCl3 |
| 4 | δ0.76(3H, t, J=7.0Hz), 1.03-1.21(4H, m), 1.39(2H, pseudo quint., J=7.3Hz), 2.20(2H, t, J=7.3Hz), 7.36-7.44(2H, m), 7.56(1H, d, J=9.1Hz), 7.72-7.80(3H, m), 7.94(1H, dd, J=8.2, 1.5Hz), 8.11(1H, dd, J=8.9, 2.2Hz), 8.20(1H, dd, J=8.8, 1.2Hz), 8.27(1H, dd, J=8.4, 1.0Hz), 8.81(1H, d, J=2.1Hz), 10.48(1H, s), 10.76(1H, s), 12.4(1H, br.s). | DMSO-d6 |
| 6 | δ0.74(3H, t, J=7.0Hz), 1.02-1.20(4H, m), 1.29(2H, pseudo quint., J=7.3Hz), 2.11(2H, t, J=7.6Hz), 7.44(1H, dd, J=7.6, 7.6Hz), 7.58(1H, d, J=9.6Hz), 7.66(1H, s), 7.74-7.79(2H, m), 7.87(1H, d, J=7.9Hz), 7.93(1H, d, J=7.3Hz), 8.16(1H, d, J=8.2Hz), 8.21(1H, d, J=8.8Hz), 8.41(1H, s), 9.94(1H, s), 10.06(1H, s), 12.3(1H, br.s). | DMSO-d6 |
| 7 | δ0.74(3H, t, J=7.2Hz), 1.01-1.18(4H, m), 1.31(2H, pseudo quint., J=7.4Hz), 2.12(2H, t, J=7.3Hz), 7.25-7.45(4H, m), 7.65(1H, s), 7.76(1H, dd, J=6.9, 6.9Hz), 7.92(1H, dd, J=7.9, 1.5Hz), 8.10(1H, d, J=8.5Hz), 8.14(1H, d, J=9.1Hz), 8.18(1H, br.d, J=xHz), 9.58(1H, s), 9.95(1H, s), 12.3(1H, br.s). | DMSO-d6 |
| 8 | δ0.75(3H, t, J=7.0Hz), 1.01-1.19(4H, m), 1.38(2H, pseudo quint., J=7.3Hz), 2.19(2H, t, J=7.5Hz), 7.27(1H, dd, J=8.8, 2.1Hz), 7.42(1H, ddd, J=7.8, 7.8, 1.2Hz), 7.75(1H, ddd, J=7.8, 7.8, 1.4Hz), 7.93(1H, dd, J=7.9, 1.5Hz), 8.06(1H, dd, J=8.8, 2.1Hz), 8.24(1H, dd, J=8.2, 0.9Hz), 8.77(1H, d, J=2.3Hz), 9.72(1H, s), 10.46(1H, s), 12.4(1H, br.s). | DMSO-d6 |

TABLE 3-IV-continued

| Compd. No. | NMR | SOLVENT |
|---|---|---|
| 8 | 19F-NMR δ−144.02(m), −142.44(m), −55.68(CF3, t, 4JFF=20.8Hz). | DMSO-d6 |
| 9 | δ0.74(3H, t, J=7.3Hz), 0.98-1.18(4H, m), 1.28(2H, pseudo quint., J=7.0Hz); 7.46(1H, dd, J=7.8, 7.8Hz), 7.76(1H, d, J=8.5Hz), 7.77(1H, dd, J=7.8, 7.8Hz), 7.88(2H, d, J=9.4Hz), 7.95(1H, d, J=7.9Hz), 8.22(1H, d, J=8.8Hz), 8.23(1H, s), 8.39(1H, d, J=8.8Hz), 8.47(1H, s), 10.54(1H, s), 10.75(1H, s), 12.4(1H, br.s). | DMSO-d6 |
| 10 | δ0.77(3H, t, J=7.0Hz), 1.04-1.21(4H, m), 1.41(2H, pseudo quint., J=7.3Hz), 2.22(2H, t, J=7.3Hz), 7.42(1H, ddd, J=7.8, 7.8, 1.2Hz), 7.49(1H, d, J=9.1Hz), 7.57(2H, d, J=8.5Hz), 7.76(1H, ddd, J=7.6, 7.8, 1.5Hz), 7.78(2H, d, J=8.5Hz), 7.95(1H, dd, J=7.9, 1.5Hz), 8.07(1H, dd, J=8.9, 2.2Hz), 8.31(1H, d, J=7.3Hz), 8.78(1H, d, J=2.1Hz), 9.81(1H, s), 10.46(1H, s), 12.4(1H, br.s). | DMSO-d6 |
| 11 | δ1.96(3H, s), 7.43(1H, dd, J=7.8, 7.8Hz), 7.50(1H, d, J=9.1Hz), 7.56(2H, d, J=8.5Hz), 7.76(1H, dd, J=7.8, 7.8Hz), 7.78(2H, d, J=8.5Hz), 7.95(1H, dd, J=8.2, 1.5Hz), 8.07(1H, dd, J=8.9, 1.9Hz), 8.28(1H, d, J=7.3Hz), 8.77(1H, d, J=2.1Hz), 9.80(1H, s), 10.46(1H, s), 12.5(1H, br.s). | DMSO-d6 |
| 12 | δ0.78(3H, t, J=6.9Hz), 1.04-1.22(4H, m), 1.41(2H, pseudo quint., J=7.1Hz), 2.22(2H, t, J=7.2Hz), 7.33(1H, d, J=8.2Hz), 7.41-7.47(2H, m), 7.67(1H, d, J=8.8Hz), 7.73-7.79(2H, m), 7.95(1H, d, J=8.5Hz), 8.12(1H, dd, J=8.5, 1.5Hz), 8.29(1H, d, J=8.2Hz), 8.76(1H, d, J=2.1Hz), 9.78(1H, s), 10.50(1H, s), 12.5(1H, br.s). | DMSO-d6 |
| 12 | 19F{1H}-NMR(DMSO-d6)δ−59.7(CF3, d, 4JFF=11.9Hz), −114.4(F, q, 4JFF=11.9Hz). | DMSO-d6 |
| 13 | δ0.77(3H, t, J=6.9Hz), 1.04-1.22(4H, m), 1.41(2H, pseudo quint., J=7.3Hz), 2.22(2H, t, J=7.3Hz), 3.3(1H, br.s), 5.6(1H, br.s), 6.41(1H, ddd, 3JFF=8.5Hz, J=8.5, 2.9Hz), 6.57(1H, dd, 3JFF=11.4Hz, J=2.9Hz), 6.61(1H, d, J=9.1Hz), 7.09(1H, dd, 4JFF=6.2Hz, J=8.5Hz), 7.39(1H, dd, J=7.6, 7.6, 1.2Hz), 7.74(1H, ddd, J=7.9, 7.9, 1.5Hz), 7.91-7.97(2H, m), 8.35(1H, d, J=8.2Hz), 8.80(1H, d, J=2.3Hz), 9.33(1H, s), 10.41(1H, s). | DMSO-d6 |
| 14 | δ0.76(3H, t, J=7.0Hz), 1.04-1.24(4H, m), 1.41(2H, pseudo quint., J=7.3Hz), 2.22(2H, t, J=7.2Hz), 3.35(1H, br.s), 5.97(1H, br.s), 6.58(1H, d, J=8.8Hz), 6.91(1H, d, J=8.8Hz), 7.37-7.42(2H, m), 7.75(1H, dd, J=7.9, 7.9Hz), 7.93(1H, dd, J=8.1, 1.6Hz), 7.97(1H, dd, J=9.1, 2.1Hz), 8.35(1H, d, J=8.5Hz), 8.81(1H, d, J=2.1Hz), 9.46(1H, s), 10.42(1H, s), 12.5(1H, br.s). | DMSO-d6 |
| 15 | δ0.76(3H, t, J=7.0Hz), 1.01-1.20(4H, m), 1.40(2H, pseudo quint., J=7.4Hz), 2.22(2H, t, J=7.3Hz), 6.95(2H, d, J=8.5Hz), 7.16-7.23(2H, m), 7.35(1H, ddd, J=7.7, 7.7, 1.0Hz), 7.41(1H, d, J=1.5Hz), 7.50(2H, d, J=8.5Hz), 7.73(1H, ddd, J=7.8, 7.8, 1.6Hz), 7.91(1H, dd, J=8.1, 1.6Hz), 8.01(1H, s), 8.50(1H, d, J=7.3Hz), 9.46(1H, s), 10.28(1H, s). | DMSO-d6 |
| 16 | δ0.72(3H, t, J=7.0Hz), 1.01-1.14(4H, m), 1.38(2H, pseudo quint., J=7.1Hz), 2.22(2H, t, J=7.3Hz), 7.19(2H, d, J=8.5Hz), 7.38(1H, ddd, J=7.8, 7.8, 1.2Hz), 7.52(1H, d, J=8.2Hz), 7.55(2H, d, J=8.5Hz), 7.75(1H, ddd, J=7.9, 7.9, 1.5Hz), 7.85(1H, dd, J=8.5, 2.1Hz), 7.93(1H, dd, J=8.2, 1.5Hz), 8.12(1H, d, J=2.3Hz), 8.36(1H, s), 8.42(1H, dd, J=8.5, 1.4Hz), 8.50(2H, s), 8.63(1H, s), 10.39(1H, s), 10.45(1H, s), 12.5(1H, br.s). | DMSO-d6 |
| 82 | 0.89(6H, d), 1.02-1.20(3H, m), 1.32-1.40(2H, m), 1.42-1.76(7H, m), 2.48-2.72(9H, m), 2.89(2H, t), 4.01(1H, brs), 4.35(2H, s), 4.92(2H, brs), 5.11(1H, brs), 6.42(1H, brs), 6.96(2H, d), 7.12-7.52(8H, m), 8.02(1H, d), 8.13(1H, d) | CDCl3 |
| 83 | 0.90(6H, d), 0.91-2.05(25H, m), 2.53-2.75(6H, m), 2.88(2H, t), 2.92-3.05(2H, m), 4.07(1H, brs), 4.98(2H, s), 6.50-6.64(1H, m), 6.88-7.05(2H, m), 7.14-7.52(5H, m), 8.01(1H, d)m 8.15(1H, d) | CDCl3 |
| 93 | 0.89(6H, d), 1.01-1.22(2H, m), 1.32-1.83(8H, m), 2.58(2H, s), 2.68(3H, s), 2.91(3H, s), 3.22-3.43(2H, m), 3.93-4.11(1H, m), 4.30(2H, d), 4.42-4.59(1H, m), 6.41(1H, brs), 6.80-7.00(2H, m), 7.09-7.68(9H, m), 7.88(1H, d), 8.00(1H, d) | CDCl3 |
| 94 | 0.90(6H, d), 0.93-1.40(13H, m), 1.44-1.91(13H, m), 2.30-2.42(1H, m), 2.63-2.82(5H, m), 2.92-3.07(2H, m), 3.29(3H, s), 3.47(2H, m), 4.40(1H, brs), 7.36-7.59(3H, m), 7.88-8.07(3H, m), 8.38-8.74(2H, m) | CDCl3 |

Synthesis Embodiment 1-IV

Synthesis Example of Compound No. 1-IV

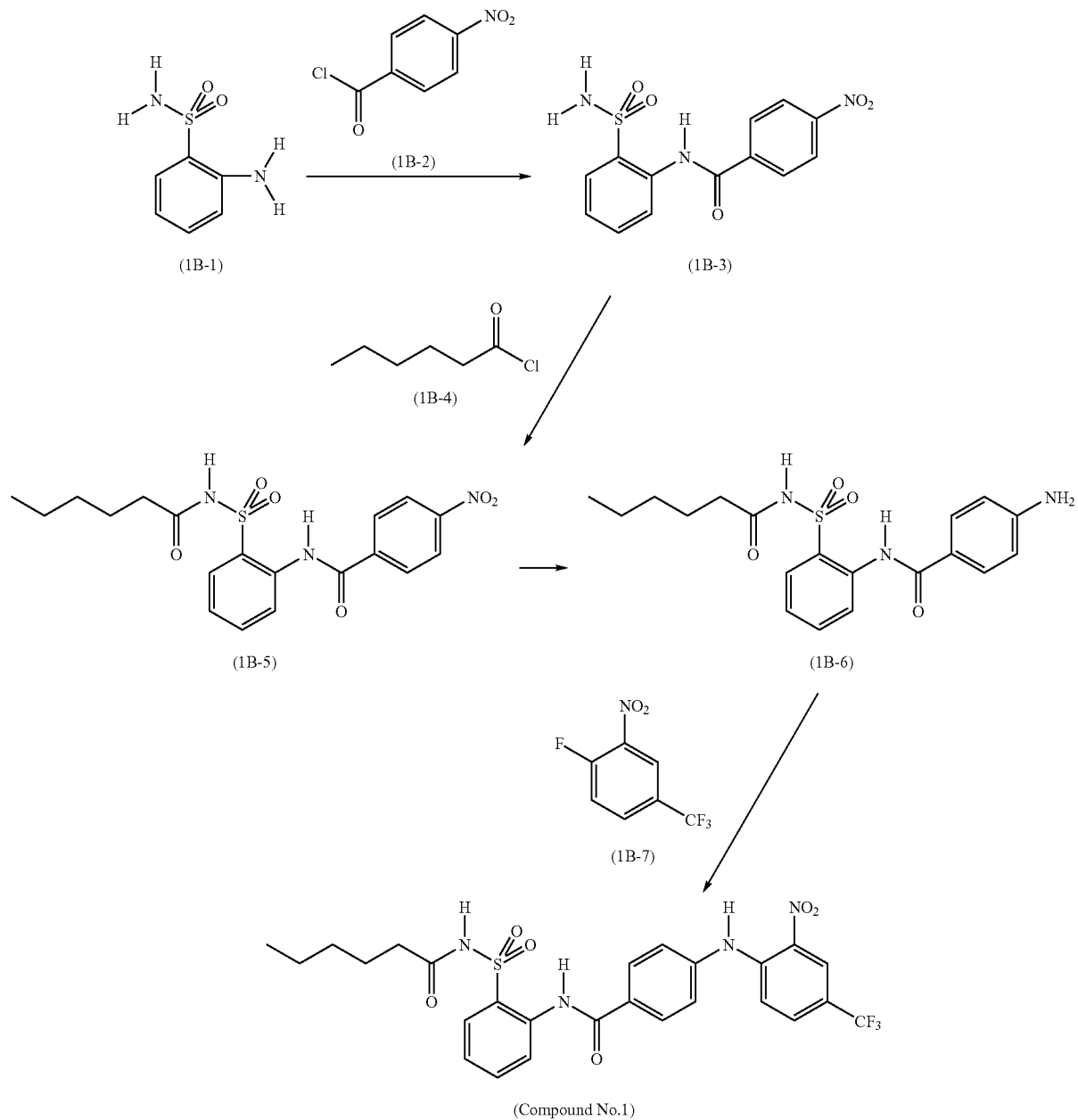

(Compound No.1)

26.0 g of 2-aminobenzenesulfonamide (1B-1) was dissolved in 100 mL of pyridine, the mixture was cooled on ice under an argon flow, a 100 mL tetrahydrofuran solution of 25.3 g of acid chloride (1B-2) was added dropwise, and the mixture was stirred for three hours at room temperature. The solvent was removed under reduced pressure. Methanol was added to the residue, the white precipitate that formed was recovered by filtration, washed with water, and dried, yielding 27.4 g of sulfonamide compound (1B-3). The obtained sulfonamide compound (1B-3) was dissolved in 150 mL of tetrahydrofuran, 13 mL of acid chloride (1B-4) and 15.0 g of 4-dimethylaminopyridine were added, another 30 mL of tetrahydrofuran was added, and the mixture was stirred for three hours at room temperature. Water was added to end the reaction, NaHCO3 was added in small increments to neutralize the reaction solution, and the product was extracted with 200 mL of ethyl acetate. The solvent was removed under reduced pressure. Product was also extracted with ethyl acetate from the aqueous layer, the solvent was removed under reduced pressure, and the residue was added to the concentrated residue obtained earlier. Methanol was added to the combined residues and the white precipitate that formed was recovered by filtration, washed with water, and dried, yielding 34.5 g of acyl sulfonamide compound (1B-5).

12.6 g of iron powder was added to acetic acid under an argon flow, the mixture was heated to 70° C., and 25.3 g of nitrobenzene compound (1B-5) was added in small increments. One hour later, the iron powder was separated with a cotton plug and NaHCO3 was added in small increments at about pH 5 to the obtained reaction solution. The precipitate that formed was recovered by filtration, washed with water, and dried, yielding 17.0 g of aniline compound (1B-6).

28 mL of fluoronitrobenzene (1B-7), 50 mL of N,N-diisopropylethylamine, and 150 mL of triethylamine were added to 17.0 g of the aniline compound (1B-6). The mixture was heated to 120° C. and stirred vigorously for six hours. The solvent was removed under reduced pressure and 100 mL of ethyl acetate and 10 mL of 6M HCl aqueous solution were added. The precipitate that formed was recovered by filtration, washed with methanol and normal hexane, and dried, yielding 17.3 g of the target compound of Embodiment 1-IV (Compound No. 1-IV).

Synthesis of the Compounds of Embodiments 2-IV to 14-IV and 18-IV

Synthesis Examples of Compound Nos. 2-IV to 14-IV and 18-IV

The synthetic intermediate fluorobenzene compound (1B-8) employed was synthesized in the same manner as synthetic intermediate (1B-5) in the compound of Synthesis Embodiment 1-IV.

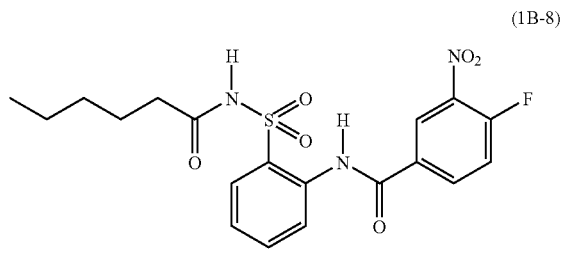

(1B-8)

The compounds of Embodiments 2-IV and 18-IV (Compound Nos. 2-IV and 18-IV) were synthesized by the same procedure as in the synthesis of Embodiment 1-IV using corresponding starting materials. The compound of Embodiment 3-IV (Compound No. 3-IV) was synthesized by an SNAr reaction in the same manner as the synthesis of the compounds of Embodiments 1-IV and 2-IV. 1 mL of dimethylsulfoxide was added to 63.2 mg of the corresponding fluoronitrobenzene acyl sulfonamide compound, 63.4 mg of corresponding aniline compound, and 67.3 mg of potassium carbonate. The mixture was heated to 50° C. and vigorously stirred for five hours. The mixture was then diluted with 10 mL of ethyl acetate, washed with saturated brine, and dried with anhydrous sodium sulfate. The residue was purified by silica gel column chromatography, yielding 43.8 mg of the compound of Embodiment 3-IV.

The compounds of Embodiments 4-IV to 14-IV (Compound Nos. 4-IV to 14-IV) were synthesized in the same manner as the compound of Embodiment 3-IV (Compound No. 3-IV). 39.5 mg of the compound of Embodiment 4-IV (Compound No. 4-IV), 41.4 mg of the compound of Embodiment 5-IV (Compound No. 5-IV), 53.2 mg of the compound of Embodiment 6-IV (Compound No. 6-IV), 27.2 mg of the compound of Embodiment 7-IV (Compound No. 7-IV), and 50.7 mg of the compound of Embodiment 8-IV (Compound No. 8-IV) were obtained employing the corresponding aniline compounds.

Synthesis of the Compounds of Embodiments 15-IV and 19-IV

Compound Nos. 15-IV and 19-IV 668 mg of iron powder was added to acetic acid under an argon flow and the mixture was heated to 60° C. 1.1 g of the compound of Embodiment 15-IV (Compound No. 15-IV) was added in small increments. The mixture was stirred for three hours, the iron powder was separated with a cotton pad, and NaHCO3 was added in small quantities to the obtained reaction solution until reaching about pH 5. The precipitate that formed was recovered by filtration, washed with water, diluted with 100 mL of ethyl acetate, washed with saturated brine, and dried with anhydrous sodium sulfate. The solvent was removed under reduced pressure. The residue was purified by silica gel column chromatography, yielding 665 mg of the compound of Embodiment 15-IV (Compound No. 15-IV). The compound of Embodiment 19-IV (Compound No. 19-IV) was synthesized by the same procedure as in Embodiment 15-IV using corresponding starting materials.

Synthesis of the Compounds of Embodiments 16-IV, 17-IV, and 20-IV

Compound Nos. 16-IV, 17-IV, and 20-IV

The compound of Embodiment 15-IV (Compound No. 15-IV) was dissolved in 100 mL of pyridine and ice cooled under an argon flow. 29.2 mg of 4-dimethylaminopyridine was added, a further 5 mL of tetrahydrofuran was added, and the mixture was stirred for 10 hours at room temperature. 0.24 mL of 3,5-ditrifluoromethyl-benzoylchloride was added and the mixture was stirred for one hour at room temperature. The mixture was diluted with 30 mL of ethyl acetate and 1N HCl aqueous solution and saturated brine were added. The precipitate that formed was recovered by filtration, washed with water, and dried, yielding 609 mg of the compound of Embodiment 16-IV (Compound No. 16-IV).

The compounds of Embodiment 17-IV and 20-IV (Compound Nos. 17-IV and 20-IV) were obtained by the same procedure as in Embodiment 16-IV using benzoyl chloride.

Synthesis of the Compounds of Embodiments 23-IV to 35-IV

Compound Nos. 23-IV to 35-IV

Synthesis of Embodiment 23-IV 0.46 mL (5.0 mmole) of aniline was added to a 10 mL diisopropylethylamine solution of 437 mg (1.0 mmole) of fluoronitrobenzene compound (1B-8) and the mixture was stirred for 16 hours at 120° C. The solvent was removed under reduced pressure, 1N hydrochloride was added, and the mixture was extracted with ethyl acetate. The organic layer was washed with saturated brine and dried with anhydrous magnesium sulfate. The solvent was removed under reduced pressure, yielding 496 mg (97 percent) of nitrobenzene compound (1B-9).

(1B-9)

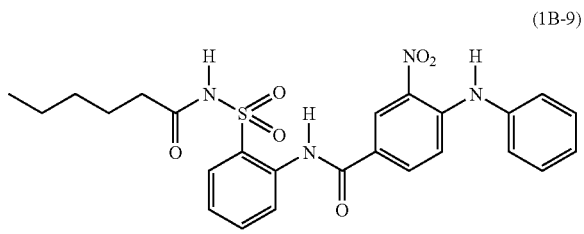

100 mg of 10 percent Pd—C (wet) was added to a mixed solution (10 mL of tetrahydrofuran and 10 mL of methanol) of the nitrobenzene compound (1B-9), then the mixture was stirred for 17 hours under a hydrogen gas flow. The mixture was filtered with celite and the solvent was removed under reduced pressure, yielding aniline compound (1B-10).

(1B-10)

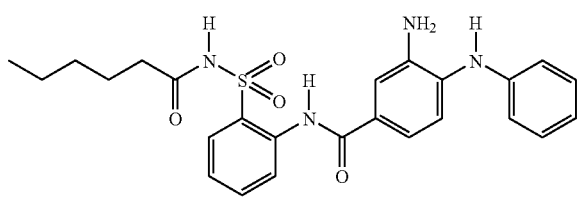

0.5 mL of pyridine, 22 uL, (0.183 mmole) of benzoyl chloride, and catalytic amount of 4-(N,N-dimethylamine)pyridine were sequentially added to a 2 mL tetrahydrofuran solution of 80 mg (0.166 mmole) of aniline compound (1B-10) and the mixture was stirred for one hour at room temperature. To the reaction solution was added 1N hydrochloric acid and the mixture was extracted with ethyl acetate. The organic layer was sequentially washed with saturated sodium hydrogencarbonate aqueous solution and saturated brine and then dried with anhydrous magnesium sulfate. The solvent was removed under reduced pressure. The residue was slurry washed with ethyl acetate-hexane, yielding 83 mg (86 percent) of the compound of Embodiment 23-IV (Compound No. 23-IV).

The compounds of Embodiments 24-IV to 35-IV (Compound Nos. 24-IV to 35-IV) were obtained by the same procedure as in Embodiment 23-IV (Compound No. 23-IV), yielding: 85 mg (a yield of 79 percent) of the compound of Embodiment 24-IV (Compound No. 24-IV); 97 mg (a yield of 90 percent) of the compound of Embodiment 25-IV (Compound No. 25-IV); and 90 mg (a yield of 75 percent) of the compound of Embodiment 26-IV (Compound No. 26-IV).

Synthesis of the Compound of Embodiment 36-IV

Compound No. 36-IV 1 mL of isoamylamine was added to a 2 mL diisopropylethylamine solution of 182 mg (1.0 mmole) of 4-chloro-3-nitrobenzonitrile, the mixture was stirred for 15 hours at 90° C., 1N hydrochloric acid was added to the reaction solution, and the mixture was extracted with ethyl acetate. The organic layer was sequentially washed with saturated sodium hydrogencarbonate aqueous solution and saturated brine and dried with anhydrous magnesium sulfate. The solvent was removed under reduced pressure, yielding 250 mg of aniline compound (1B-11).

(1B-11)

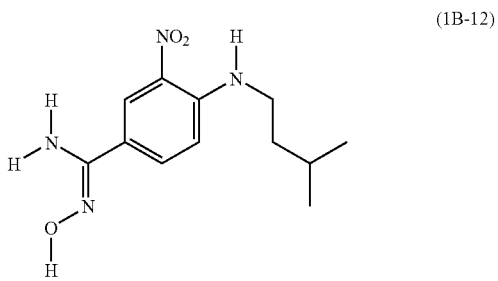

0.3 mL (50 mmole) of 50 percent hydroxylamine aqueous solution was added to a mixed solution (2 mL of tetrahydrofuran and 8 mL ethanol) of 240 mg (1.0 mmole) of aniline compound (1B-9) and the mixture was stirred for 14 hours at 50° C. The solvent was removed under reduced pressure. The residue was subjected to silica gel column chromatography, and 256 mg (a yield of 96 percent) of amideoxime compound (1B-12) was obtained from the ethyl acetate-hexane (1:1) fraction.

(1B-12)

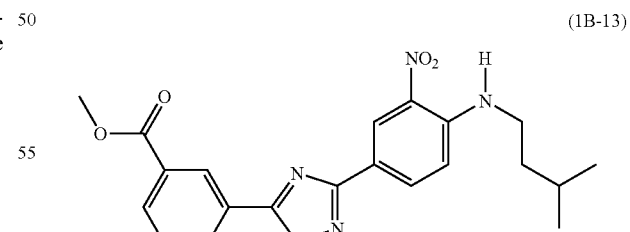

221 mg (1.23 mmole) of isophthalic acid monomethyl ester and 217 mg (1.13 mmoles) of WSC hydrochloride were added to a 10 mL dioxane solution of 251 mg (0.943 mmole) of the above amideoxime. The mixture was stilled for 3 hours at room temperature and then stirred for 18 hours at 95° C. Water was added to the reaction solution and the mixture was extracted with ethyl acetate. The organic layer was sequentially washed with saturated sodium hydrogencarbonate aqueous solution and saturated brine and then dried with anhydrous magnesium sulfate. The solvent was removed under reduced pressure. The residue was subjected to silica gel column chromatography, and 319 mg (an 83 percent yield) of oxadiazole compound (1B-13) was obtained from the ethyl acetate-hexane (1:3) fraction.

(1B-13)

2 mL of 1N lithium hydroxide was added to a solution (2 mL of methanol and 5 mL of tetrahydrofuran) of 319 mg (0.366 mmole) of the above oxadiazole compound (1B-13), the mixture was stirred for 15 hours at room temperature, 1N hydrochloric acid was added to the reaction solution, and the mixture was extracted with ethyl acetate. The organic layer was washed with saturated brine and dried with anhydrous magnesium sulfate. The solvent was removed under reduced pressure, yielding 137 mg (a 97 percent yield) of benzoic, acid compound (1B-14).

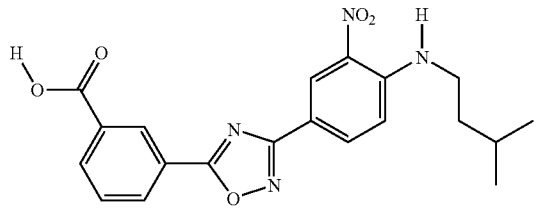

(1B-14)

To a solution of 130 mg (0.328 mmole) of benzoic acid compound (1B-14) in 2 mL of N,N-dimethylformamide were sequentially added 13 uL (0.122 mmole) of dimethylsulfamoyl chloride, 26 uL (0.183 mmole) of butyldimethylamine, 4 mg (0.030 mmole) of pyridine, and 21 mg (0.122 mmole) of benzenesulfonamide and the mixture was stirred for 14 hours at room temperature. The solvent was removed under reduced pressure, after which 1N hydrochloric acid was added and the mixture was extracted with ethyl acetate. The organic layer was washed with saturated brine and dried with anhydrous magnesium sulfate. The solvent was removed under reduced pressure. The residue was subjected to silica gel column chromatography and 78 mg (a 44 percent yield) of the compound of Embodiment 36-IV was obtained from the ethyl acetate-hexane (2:1) fraction.

Synthesis of the Compound of Embodiment 37-IV

Compound No. 37-IV 1.00 g (4.29 mmole) of 4-(3-methylbutylamino)-3-nitrobenzonitrile was dissolved in 10 mL of DMF, 0.205 g (5.14 mmoles) of NaH was added, and the mixture was stirred for 10 minutes at room temperature. 0.5 mL (5.14 mmole) of methyl iodide was added and the mixture was stirred overnight at room temperature. When the reaction had ended, the solvent was removed under reduced pressure, and water was added to the residue. The mixture was extracted with ethyl acetate. The residue was washed with saturated brine and dried with anhydrous sodium sulfate. The solvent was removed under reduced pressure, yielding a nitrobenzene intermediate. Next, the nitrobenzene intermediate was dissolved in 20 mL of ethanol, 50 percent NH2OH aqueous solution was added, and the mixture was stirred overnight at 50° C. When the reaction had ended, the solvent was removed under reduced pressure. The residue was purified by silica gel column chromatography, yielding 1.46 g of amideoxime intermediate.

500 mg (1.79 mmole) of the amideoxime intermediate was dissolved in 10 mL of DMF and 322 mg (1.79 mmoles) of monomethyl isophthalate, 0.251 mL (1.79 mmoles) of triethylamine, and 343 mg (1.79 mmoles) of WSC.HCl were added. The mixture was then stirred for eight hours at room temperature and then stirred overnight at 100° C. When the reaction had ended, the solvent was removed under reduced pressure and water was added to the residue. The mixture was extracted with ethyl acetate, washed with saturated brine, and dried with anhydrous sodium sulfate. The solvent was removed under reduced pressure. The residue was purified by silica gel column chromatography. The obtained compound was dissolved in 5 mL of THF and 5 mL of MeOH, 1N NaOH aqueous solution was added, and the mixture was stilled overnight at room temperature. When the reaction had ended, the solvent was removed under reduced pressure. Water was added to the residue. The mixture was extracted with ethyl acetate, washed with saturated brine, and dried with anhydrous sodium sulfate. The solvent was then removed under reduced pressure. The residue was purified by recrystallization, yielding 780 mg of carboxylic acid intermediate.

300 mg (7.32 mmole) of the carboxylic acid intermediate was dissolved in 3 mL of DMF, 0.157 mL (1.46 mmoles) of dimethylsulfamoyl chloride was added, and the mixture was stirred for 10 minutes at room temperature. A separately prepared 2 mL DMF solution of 126 mg (0.804 mmole) of benzenesulfonamide and 89 mg (0.731 mmole) of DMAP in 0.308 mL (2.19 mmoles) of butyldimethylamine was added and the mixture was stirred overnight at room temperature. When the reaction had ended, the solvent was removed under reduced pressure, 1N hydrochloric acid was added to the residue, and the mixture was extracted with ethyl acetate. The mixture was washed with saturated brine and dried with anhydrous sodium sulfate. The solvent was removed under reduced pressure. The residue was purified by recrystallization, yielding 203 mg of the compound of Embodiment 37-IV (Compound No. 37-IV).

Synthesis of the Compound of Embodiment 38-IV

Compound No. 38-IV

The compound of Embodiment 37-IV was dissolved in 10 mL of ethyl acetate and catalytic amount of 10 percent wet Pd—C was added. The reactor was backfilled with hydrogen and the mixture was stirred for five hours at room temperature. When the reaction had ended, the palladium catalyst was removed by filtration and the solvent was removed under reduced pressure. The residue obtained was subjected to reverse-phase high-performance liquid chromatography employing silica gel of the chemically bonded octadodecyl group type as packing material and eluted with a mixed solution of water and acetonitrile containing 0.1 percent (v/v) trifluoroacetic acid. The target fraction was freeze-dried, yielding 13 mg of the compound of Embodiment 38-IV (Compound No. 38-IV).

Synthesis of the Compound of Embodiment 39-IV

Compound No. 39-IV 36 mg (0.0694 mmole) of the compound of Embodiment 38-IV was dissolved in 3 mL of THF. 0.5 mL of pyridine and 0.015 mL (0.104 mmole) of 3-trifluoromethylbenzoylchloride were added and the mixture was stirred overnight at room temperature. When the reaction had ended, the solvent was removed under reduced pressure and 1N HCl aqueous solution was added to the residue the mixture was extracted with ethyl acetate, washed with saturated brine, and dried with anhydrous sodium sulfate. The solvent was then removed under reduced pressure. Next, the residue was purified by PTLC, yielding 5 ml-g of the compound of Embodiment 39-IV (Compound No. 39-IV).

Synthesis of the Compounds of Embodiments 40-IV to 44-IV

Compound Nos. 40-IV to 44-IV

The above compounds were synthesized by the same procedure as in Embodiment 39-IV from corresponding starting materials.

Synthesis of the Compound of Embodiment 45-IV

Compound No. 45-IV 10 mg (0.0193 mmole) of the compound of Embodiment 38-IV was dissolved in 3 mL of dichloromethane. 2 mg (0.0193 mmole) of benzaldehyde and catalytic amount of acetic acid were added. Subsequently, 5 mg (0.0770 mmole) of sodium cyanoborohydride was added and the mixture was stirred overnight at room temperature. When the reaction had ended, water was added, and the mixture was extracted with ethyl acetate. The mixture was washed with saturated brine and dried with anhydrous sodium sulfate. The solvent was removed under reduced pressure. The residue was purified by PTLC, yielding 2 mg of the compound of Embodiment 45-IV (Compound No. 45-IV).

Synthesis of the Compound of Embodiment 46-IV

Compound No. 46-IV

Employing 185 mg (1.0 mmole) of 4-fluoro-3-nitrobenzoic acid as starting material, aniline compound (1B-15) was obtained by the sane procedure as in the synthesis of synthesis intermediate (1B-11) of the compound of Embodiment 36-IV Employing 3-cyanobenzoic acid and benzenesulfonamide as starting materials, 6.67 g of amideoxime compound (1B-16) was obtained in a two-step reaction by the same procedure as in the synthesis of the compound of Embodiment 36-IV.

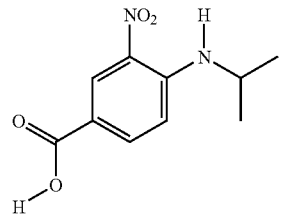
(1B-15)

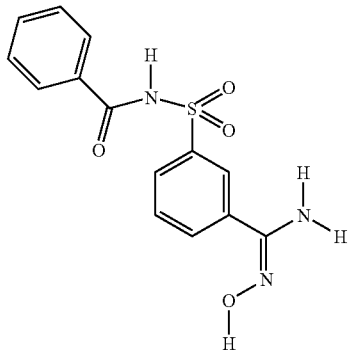
(1B-16)

0.17 mL of diisopropylethylamine and 190 mg of HBTU were added to a 4 mL N,N-dimethylformamide solution of 56 mg (0.25 mmole) of above intermediate (1B-15) and 133 mg (0.25 mmole) of above intermediate (1B-16). The mixture was irradiated with microwaves and reacted for 10 minutes at 200° C. The solvent was removed under reduced pressure and the residue was purified by HPLC, yielding 2.6 mg (2 percent) of the compound of Embodiment 46-IV (Compound No. 46-IV).

Synthesis of the Compounds of Embodiments 47-IV, 48-IV, 56-IV to 60-IV, 95-IV to 102-IV, 104-IV to 106-IV, 108-IV, 114-IV to 116-IV

Compound Nos. 47-IV, 48-IV, 56-IV to 60-IV, 95-IV to 102-IV, 104-IV to 106-IV, 108-IV, 114-IV to 116-IV The above compounds were synthesized using corresponding aldehydes and ketones by the same procedure as in synthesis of the compound of Embodiment 47-IV.

Synthesis of the Compounds of Embodiments 49-IV to 50-IV

Compound Nos. 49-IV to 50-IV 4.8 mg (4 percent) of the compound of Embodiment 49-IV (Compound No. 49-IV) and 5 mg (a yield of 3 percent) of the compound of Embodiment 50-IV (Compound No. 50-IV) were obtained by the same procedure as in synthesis of the compound of Embodiment 46-IV.

Synthesis of the Compound of Embodiment 51-IV

Compound No. 51-IV

Employing 555 mg (3.0 mmoles) of 4-fluoro-3-nitrobenzoic acid and N-methylisoamylamine as starting materials, 798 mg of aniline compound was obtained by the same procedure as in synthesis of the compound of Embodiment 46-IV.

2 mL thionyl chloride solution of 38 mg (0.142 mmole) of the aniline compound was stirred for one hour at 50° C. The solvent was removed under reduced pressure, yielding a crude chloride compound.

2 mL methylene chloride solution of the intermediate obtained above was added to a 2 mL pyridine solution of 113 mg (0.213 mmole) of amideoxime compound (1B-16) and the mixture was stirred for 56 hours at 100° C. The solvent was removed under reduced pressure and the residue was purified by HPLC (water-acetonitrile), yielding 12 mg (a yield of 15 percent) of the compound of Embodiment 51-IV (Compound No. 52-IV).

Synthesis of the Compound of Embodiment 52-IV

Compound No. 52-IV 5 mg of the compound of Embodiment 52-IV (Compound No. 52-IV) was obtained by the same procedure as in synthesis of the compound of Embodiment 51-IV.

Synthesis of the Compound of Embodiment 53-IV

Compound No. 53-IV 185 mg (1.0 mmole) of 4-fluoro-3-nitrobenzoic acid, 0.35 mL (2.5 mmoles) of triethylamine, and 211 mg (1.1 mmoles) of WSC hydrochloride were added to a 10 mL N,N-dimethylformamide solution of 263 mg (1.12 mmoles) of 3-amino-3-cyclohexylpropionic acid ethyl ester and the mixture was stirred for 56 hours at room temperature. Water was added to the reaction solution and the mixture was extracted with ethyl acetate. The organic layer was washed with saturated brine and dried with anhydrous magnesium sulfate. The solvent was removed tinder reduced pressure. The residue was subjected to silica gel column chromatography and 45 mg (12 percent) of amide compound was obtained from the ethyl acetate-hexane (1:2) fraction. N,N-Methylisoamylamino group was incorporated by SNAr reaction in the same manner as in synthesis of the compound of Embodiment 36-IV, yielding aniline compound. 1 mL of 1N lithium hydroxide as added to a mixed solution (1 mL of methanol and 3 mL of tetrahydrofuran) of 43 mg (0.117 mmole) of the obtained aniline compound and the mixture was stirred for 16 hours at room temperature. To the reaction solution was added 1N hydrochloric acid and the mixture was extracted with ethyl acetate. The organic layer was washed with saturated brine and dried with anhydrous magnesium sulfate. The solvent was removed under reduced pressure. The residue was purified by HPLC (water-acetonitrile), yielding 20 mg (a yield of 35 percent) of carboxylic acid compound.

0.1 mL (0.75 mmole) of triethylamine and 96 mg (0.375 mmole) of 2-chloro-1-methylpyridinium iodide were added to a mixed solution of 131 mg (0.313 mmole) of the obtained carboxylic acid compound in 5 mL of chloroform and 5 mL of tetrahydrofuran and the mixture was stirred for 13 hours at room temperature. The solvent was removed under reduced pressure, water was added, and the mixture was extracted with ethyl acetate. The organic layer was washed with saturated brine and dried with anhydrous magnesium sulfate. The solvent was removed under reduced pressure. To a 5 mL dioxane solution of the residue were added 0.112 mL (0.75 mmole) of diazabicyclo[5.4.0]undeca-7-ene and 59 mg (0.375 mmole) of benzenesulfonamide and the mixture was stirred for three hours at 90° C. The solvent was removed under reduced pressure, 1N hydrochloric acid was added, and the mixture was extracted with ethyl acetate. The organic layer was washed with saturated brine and dried with anhydrous magnesium sulfate, then the solvent was removed under reduced pressure. The residue was subjected to silica gel column chromatography and 164 mg (a yield of 94 percent) of the compound of Embodiment 53-IV (Compound No. 53-IV) was obtained from the ethyl acetate-hexane (2:1) fraction.

Synthesis of the Compounds of Embodiments 54-IV and 61-IV

Compound No. 51-IV and 61-IV 50 mg of 10 percent Pd—C (wet) was added to a mixed solution (3 mL of tetrahydrofuran and 6 mL of methanol) of 161 mg (0.289 mmole) of the compound of Embodiment 53-IV and the mixture was stirred for 12 hours under a hydrogen flow. The mixture was filtered with celite and the solvent was removed under reduced pressure. The residue was subjected to silica gel column chromatography, yielding 66 mg (a yield of 43 percent) of the compound of Embodiment 61-IV (Compound No. 61-IV) from the ethyl acetate-hexane (1:1) fraction.

0.5 mL of acetic acid, 0.019 mL (0.189 mmole) of benzaldehyde and 24 mg (0.38 mmole) of sodium cyanoborohydride were added to a 2 mL methylene chloride solution of the compound of Embodiment 61-IV and the mixture was stirred for two hours at room temperature. The solvent was removed under reduced pressure and the residue was slurry washed with water-acetonitrile, yielding 11 mg (a 47 percent yield) of the compound of Embodiment 54-IV (Compound No. 54-IV).

Synthesis of the Compound of Embodiment 55-IV

Compound No. 55-IV 15 mg (a yield of 63 percent) of the compound of Embodiment 55-IV (Compound No. 55-IV) was obtained by the same procedure as in the synthesis of the compound of Embodiment 54-IV.

Synthesis of the Compounds of Embodiments 62-IV to 80-IV

Compound Nos. 62-IV to 80-IV

Employing 1.67 g (10 mmoles) of 3-nitrobenzoic acid as starting material, 2.25 g (a yield of 74 percent) of nitrobenzene compound (1B-17) was obtained by the same procedure as in synthesis of the compound of Embodiment 36-IV.

500 mg of 10 percent Pd—C (wet) was added to a mixed solution of 2.25 g (7.35 mmoles) of nitrobenzene compound (1B-17) in 10 mL, of tetrahydrofuran and 20 mL of methanol and the mixture was stirred for 14 hours under a hydrogen flow. The mixture was filtered with celite and the solvent was removed under reduced pressure, yielding 2.15 g of aniline compound (1B-18).

0.87 mL (10.8 mmole) of pyridine and 956 mg (4.35 mmoles) of 4-chloro-3-nitrobenzoylchloride were added to a 30 mL tetrahydrofuran solution of 1.0 g (3.6 mmoles) of aniline compound (1B-18) and the mixture was stirred for one hour at room temperature. To the reaction solution was added 1N hydrochloric acid and the mixture was extracted with ethyl acetate. The organic layer was washed with saturated brine and dried with anhydrous magnesium sulfate, then the solvent was removed under reduced pressure. The residue was slurry washed with ethyl acetate-hexane, yielding 1.41 g (a yield of 85 percent) of nitrobenzene compound (1B-19).

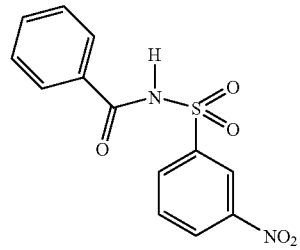

(1B-17)

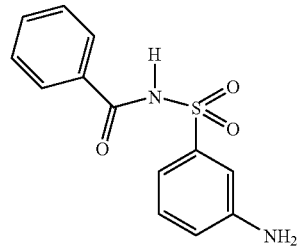

(1B-18)

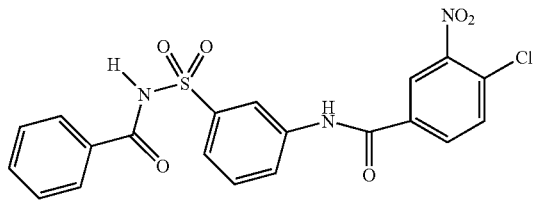

(1B-19)

Employing nitrobenzene compound (1B-19) as starting material, the compound of Embodiment 62-IV (Compound No. 62-IV) was obtained by the same procedure as in synthesis of the compound of Embodiment 36-IV.

The compounds of Embodiments 63-IV to 80-IV were synthesized by the same procedure as in synthesis of the compound of Embodiment 62-IV.

11 mg of Compound No. 63-IV, 7 mg of Compound No. 64-IV, 5 mg of Compound No. 65-IV, 6 mg of Compound No. 66-IV, 7 mg of Compound No. 67-IV, 7 mg of Compound No. 68-IV, 5 mg of Compound No. 69-IV. 10 mg of Compound No. 70-IV, 7 mg of Compound No. 71-IV, 18 mg of Compound No. 72-IV, 9 mg of Compound No. 73-IV, 15 mg of Compound No. 74-IV, 3 mg of Compound No. 75-IV, 1 mg of Compound No. 76-IV, 9 mg of Compound No. 77-IV, 5 mg of Compound No. 78-IV, 7 mg of Compound No. 79-IV, and 4 mg of Compound No. 80-IV were obtained.

Synthesis of the Compound of Embodiment 81-IV

Compound No. 81-IV 951 mg of the compound of Embodiment 81-IV (Compound No. 81-IV) was obtained by the same procedure as in synthesis of the compound of Embodiment 53-IV.

Synthesis of the Compound of Embodiment 82-IV

Compound No. 82-IV

Employing 951 mg (1.66 mmoles) of the compound of Embodiment 81-IV as starting material, 868 mg (96 percent) of aniline compound was obtained by the same procedure as in synthesis of the compound of Embodiment 61-IV.

Employing 30 mg (0.055 mmole) of the obtained aniline compound as starting material, 24 mg (68 percent) of the compound of Embodiment 82-IV was obtained by the same procedure as in synthesis of the compound of Embodiment 54-NV.

Synthesis of the Compounds of Embodiments 83-IV to 92-IV

Compound Nos. 83-IV to 92-IV

Employing 30 mg (0.055 mmole) of the aniline compound which is the synthetic intermediate of Embodiment Compound 82-IV as starling material, 17 mg (a yield of 49 percent) of the compound of Embodiment 83-IV (Compound No. 83-IV) was obtained by the same procedure as in the synthesis of Embodiment 54-IV. The compounds of Embodiments 84-IV to 92-IV were synthesized by the same procedure as in synthesis of the compound of Embodiment 83-IV.

4.3 mg of Compound No. 84-IV, 3.0 mg of Compound No. 85-IV, 5 mg of Compound No. 86-IV, 4.2 mg of Compound No. 87-IV, 0.9 mg of Compound No. 88-IV, 2.4 mg of Compound No. 89-IV, 2.2 mg of Compound No. 90-IV, 08 mg of Compound No. 91-IV, and 4.6 mg of Compound No. 92-IV were obtained.

Synthesis of the Compounds of Embodiments 93-IV and 94-IV

Compound Nos. 93-IV and 94-IV

Formalin and 10 mg of sodium cyanoborohydride were added to a mixed solution of 17 mg (0.027 mmole) of the compound of Embodiment 54-IV in 1 mL of methylene chloride and 1 mL of methanol and the mixture was stirred for seven hours at room temperature. The solvent was removed under reduced pressure. The residue was purified by HPLC (water-acetonitrile), yielding 2.7 mg of the compound of Embodiment 93-IV (Compound No. 93-IV).

Employing 11 mg (0.017 mmole) of the compound of Embodiment 55-IV as starting material, 1.0 mg of the compound of Embodiment 94-IV (Compound No. 94-IV) was obtained by the same procedure as in the synthesis of Embodiment 9)-IV.

Synthesis of the Compound of Embodiment 103-IV

Compound No. 103-IV

A catalytic amount of 10 percent Pd—C (wet.) was added to a solution of the compound of Embodiment 37-IV, the reactor was backfilled with hydrogen, and the mixture was stirred overnight at room temperature, yielding 350 mg of reduced aniline intermediate.

10 mg (0.0193 mmole) of the obtained aniline intermediate was dissolved in 3 mL of dichloromethane, 2 mg (0.0193 mmole) of benzaldehyde and catalytic amount of acetic acid were added, followed by the addition of 5 mg (0.0770 mmole) of sodium cyanoborohydride, and the mixture was stirred overnight at room temperature. When the reaction had ended, water was added and the mixture was extracted with ethyl acetate. The mixture was washed with saturated brine and dried with anhydrous sodium sulfate. The solvent was removed under reduced pressure. Next, the obtained residue was subjected to reverse-phase high-performance liquid chromatography employing silica gel of the chemically bonded octadodecyl group type as packing material and eluted with a mixed solution of water and acetonitrile containing 0.1 percent (v/v) trifluoroacetic acid. The target fraction was freeze-dried, yielding 2 mg of the compound of Embodiment 103-IV (Compound No. 103-IV).

Synthesis of the Compounds of Embodiments 107-IV, 129-IV, 130-IV, 133-IV, 136-IV, and 137-IV Compound Nos. 107-IV, 129-IV, 130-IV, 133-IV, 136-IV, and 137-IV These compounds were synthesized with corresponding sulfonamides, aldehydes, and ketones by the same procedure as in synthesis of the compound of Embodiment 103-IV.

Synthesis of the Compounds of Embodiments 109-IV to 113-IV and 117-IV to 126-IV

Compound Nos. 109-IV to 113-IV and 117-IV to 126-IV

These compounds were synthesized by the same procedure as in synthesis of the compound of Embodiment 54-IV.

Synthesis of the Compound of Embodiment 127-IV

Compound No. 127-IV 30 mg (0.0561 mmole) of the synthesis intermediate of Embodiment 103-IV was dissolved in 4 mL of dichloromethane and 1 mL of MeOH, excess methyl-2-formylbenzoate and catalytic amount of acetic acid were added, followed by the addition of excess sodium cyanoborohydride, and the mixture was stirred overnight at room temperature. When the reaction had ended, water was added and the mixture was extracted with ethyl acetate. The mixture was washed with saturated brine and dried with anhydrous sodium sulfate. The solvent was removed under reduced pressure. The residue was dissolved in 3 mL of toluene and the mixture was stirred overnight at 100° C. When the reaction had ended, the solvent was removed under reduced pressure. The obtained residue was subjected to reverse-phase high-performance liquid chromatography employing silica gel of the chemically bonded octadodecyl group type as packing material and eluted with a mixed solution of water and acetonitrile containing 0.1 percent (v/v) trifluoroacetic acid. The target fraction was freeze-dried, yielding 10 mg of the compound of Embodiment 127-IV (Compound No. 127-IV).

Synthesis of the Compound of Embodiment 128-IV

Compound No. 128-IV 30 mg (0.0561 mmole) of the aniline compound which is the synthetic intermediate of Embodiment 103-IV was dissolved in 4 mL of dichloromethane and 1 mL of MeOH, excess salicyl aldehyde and catalytic amount of acetic acid were added, followed by the addition of excess sodium cyanoborohydride, and the mixture was stirred overnight. When the reaction had ended, water was added and the mixture was extracted with ethyl acetate. The mixture was washed with saturated brine and dried with anhydrous sodium sulfate. The solvent was removed under reduced pressure. The residue was dissolved in 3 mL of methanol, then 0.1 mL of 37 percent formaldehyde and catalytic amount of acetic acid were added. The mixture was stirred overnight at room temperature. When the reaction had ended, the solvent was removed under reduced pressure. The obtained residue was subjected to reverse-phase high-performance liquid chromatography employing silica gel of the chemically bonded octadodecyl group type as packing material and eluted with a mixed solution of water and acetonitrile containing 0.1 percent (v/v) trifluoroacetic acid. The target fraction was freeze-dried, yielding 11 mg of the compound of Embodiment 128-IV (Compound No. 128-IV).

Synthesis of the Compounds of Embodiments 131-IV and 132-IV

Compound Nos. 131-IV and 132-IV

These compounds were synthesized by the same procedure as in synthesis of the compound of Embodiment 128-IV.

Synthesis of the Compound of Embodiment 134-IV

Compound No. 134-IV 90 mg of the compound of Embodiment 133-IV was dissolved in 1 mL of THF and 1 mL of MeOH, 1 mL of 1N NaOH aqueous solution was added, and the mixture was stirred overnight at room temperature. When the reaction had ended, 1N hydrochloric acid was added, the mixture was extracted with ethyl acetate, washed with saturated brine, and dried with anhydrous sodium sulfate. The solvent was removed under reduced pressure. The residue was subjected to reverse-phase high-performance liquid chromatography employing silica gel of the chemically bonded octadodecyl group type as packing material and eluted with a mixed solution of water and acetonitrile containing 0.1 percent (v/v) trifluoroacetic acid. The target fraction was freeze-dried, yielding 50 mg of the compound of Embodiment 134-IV (Compound No. 134-IV).

Synthesis of the Compounds of Embodiments 135-IV, 139-IV, 141-IV, and 142-IV

Compound Nos. 135-IV, 139-IV, 141-IV, and 142-IV 20 mg of Embodiment Compound 134-IV was dissolved in 3 mL of dichloromethane, 1 mL of 37 percent formaldehyde and catalytic amount of acetic acid were added, followed by the addition of excess sodium cyanoborohydride, and the mixture was stirred overnight at room temperature. When the reaction had ended, the solvent was removed under reduced pressure. The residue was then subjected to reverse-phase high-performance liquid chromatography employing silica gel of the chemically bonded octadodecyl group type as packing material and eluted with a mixed solution of water and acetonitrile containing 0.1 percent (v/v) trifluoroacetic acid. The target fraction was freeze-dried, yielding 9 mg of the compound of Embodiment 139-IV (Compound No. 139-IV).

The compounds of Embodiments 135-IV, 141-IV, and 142-IV were synthesized from corresponding starting materials by the same procedure as in synthesis of the compound of Embodiment 139-IV.

Synthesis of the Compound of Embodiment 138-IV

Compound No. 138-IV 247 mg (0.516 mmole) of the carboxylic compound which is the synthetic intermediate of Embodiment 135-IV was dissolved in 10 mL of chloroform, 0.174 mL (1.24 mmoles) of triethylamine and 158 mg (0.619 mmole) of 2-chloro-1-methylpyridinium iodide were added, and the mixture was stirred for two hours at room temperature. Water was added to the reaction solution and the mixture was extracted with ethyl acetate. The mixture was then washed with saturated brine and dried with anhydrous sodium sulfate. The solvent was removed under reduced pressure. The residue was dissolved in 10 mL of 1,4-dioxane, 111 mg (0.516 mmole) of 4-sulfamoylbenzoic acid methyl ester and 0.154 mL (1.03 mmoles) of DBU were added, and the mixture was stirred for two hours at 70° C. When the reaction had ended, the solvent was removed under reduced pressure. The residue was then dissolved in 10 mL of THF and 10 mL of MeOH, 2 mL of 1N NaOH aqueous solution was added, and the mixture was stirred overnight at room temperature. When the reaction had ended, 1N hydrochloric acid was added and the mixture was extracted with ethyl acetate. The mixture was washed with saturated brine and dried with anhydrous sodium sulfate, after which the solvent was removed under reduced pressure. The residue was subjected to reverse-phase high-performance liquid chromatography employing silica gel of the chemically bonded octadodecyl group type as packing material and eluted with a mixed solution of water and acetonitrile containing 0.1 percent (v/v) trifluoroacetic acid. The target fraction was freeze-dried, yielding 148 mg of the compound of Embodiment 138-IV (Compound No. 138-IV).

Synthesis of the Compound of Embodiment 140-IV

Compound No. 140-IV 40 mg (0.0772 mmole) of the aniline compound which is the synthetic intermediate of Embodiment 103-IV was dissolved in 3 mL of dichloromethane and 1 mL of MeOH, excess 4-iodobenzaldehyde and catalytic amount of acetic acid were added, followed by the addition of excess sodium cyanoborohydride, and the mixture was stirred overnight at room temperature. When the reaction had ended, water was added and the mixture was extracted with ethyl acetate. The mixture was washed with saturated brine and dried with anhydrous sodium sulfate. The solvent was removed under reduced pressure. The residue was purified by PTLC, yielding 50 mg of iodobenzene intermediate.

50 mg (0.0668 mmole) of the obtained iodobenzene intermediate was dissolved in 2 mL of DMF; 0.012 mL (0.0802 mmole) of diethylvinyl phosphonate, 0.019 mL (0.134 mmole) of triethylamine, and catalytic amount of palladium acetate were added, and the mixture was stirred overnight at 100° C. When the reaction had ended, the solvent was removed under reduced pressure. The residue was subjected to reverse-phase high-performance liquid chromatography employing silica gel of the chemically bonded octadodecyl group type as packing material and eluted with a mixed solution of water and acetonitrile containing 0.1 percent (v/v) trifluoroacetic acid. The target fraction was freeze-dried, yielding 24 mg of the compound of Embodiment 140-IV (Compound No. 140-IV).

Synthesis of the Compounds of Embodiments 143-IV and 144-IV

Compound Nos. 143-IV and 144-IV

Employing cis-1-amino-2-cyclopentanecarboxylic acid as starting material, 3.4 mg of the compound of Embodiment 143-IV (Compound No. 143-IV) and 10 mg of the compound of Embodiment 144-IV (Compound No. 144-IV) were obtained by the same procedure as in synthesis of the compound of Embodiment 108-IV.

Synthesis of the Compounds of Embodiments 145-IV and 146-IV

Compound Nos. 145-IV and 146-IV 7.6 mg of the compound of Embodiment 145-IV (Compound No. 145-IV) and 12 mg of the compound of Embodiment 145-IV (Compound No. 146-IV) were obtained by the same procedure as in synthesis of the compound of Embodiment 143-IV.

Synthesis of the Compound of Embodiment 147-IV

Compound No. 147-IV

Employing 639 mg (1.45 mmoles) of the carboxylic acid which is the synthetic intermediate of Embodiment 135-IV as starting material, 645 mg of the compound of Embodiment 147-IV (Compound No. 147-IV) was obtained by the same procedure as in synthesis of the compound of Embodiment 53-IV.

Synthesis of the Compound of Embodiment 148-IV

Compound No. 148-IV

Employing 100 mg (0.161 mmole) of the compound of Embodiment 147-IV as starting material, 30 mg of the compound of Embodiment 148-IV (Compound No. 148-IV) was obtained by the same procedure as in synthesis of the compound of Embodiment 135-IV.

Synthesis of the Compounds of Embodiments 149-IV to 152-IV

Compound Nos. 149-IV to 152-IV 3 mg of the compound of Embodiment 150-IV (Compound No. 150-IV), 6 mg of the compound of Embodiment 151-IV (Compound No. 151-IV), and 2 mg of the compound of Embodiment 152-IV (Compound No. 152-IV) were obtained by the same procedure as in synthesis of the compound of Embodiment 108-IV.

Synthesis of the Compound of Embodiment 153-IV

Compound No. 153-IV

Employing 50 mg of the compound of Embodiment 125-IV as starting material, 6 mg of the compound of Embodiment 153-IV (Compound No. 153-IV) was obtained by the same procedure as in synthesis of the compound of Embodiment 135-IV.

Synthesis of the Compound of Embodiment 154-IV

Compound No. 154-IV

Employing 50 mg of the compound of Embodiment 126-IV as starting material, 8 mg of the compound of Embodiment 154-IV (Compound No. 154-IV) was obtained by the same procedure as in synthesis of the compound of Embodiment 135-IV.

Synthesis of the Compound of Embodiment 155-IV

Compound No. 155-IV 4 mg of the compound of Embodiment 155-IV (Compound No. 155-IV) was obtained by the same procedure as in synthesis of the compound of Embodiment 108-IV.

Synthesis of the Compounds of Embodiments 156-IV to 160-IV

Compound Nos. 156-IV to 160-IV 4 mg of the compound of Embodiment 156-IV (Compound No. 156), 5 mg of the compound of Embodiment 157-IV (Compound No. 157-IV), 6 mg of the compound of Embodiment 158-IV (Compound No. 158-IV), 5 mg of the compound of Embodiment 159-IV (Compound No. 159-IV), and 6 mg of the compound of Embodiment 160-IV (Compound No. 160-IV) were obtained by the same procedure as in synthesis of the compound of Embodiment 108-IV.

Synthesis of the Compound of Embodiment 161-IV

Compound No. 161-IV 50 mg of 20 percent palladium hydroxide was added to a mixed solution (3 mL of chloroform and 6 mL of methanol) of 118 mg (0.19 mmole) of the compound of Embodiment 147-IV and the mixture was stirred for 18 hours under a hydrogen flow. The mixture was filtered with celite and the solvent was removed under reduced pressure. The residue was purified by HPLC (water-acetonitrile), yielding 43 mg (43 percent) of aniline compound.

Employing 21 mg of the obtained aniline compound as starting material, 3 mg of the compound of Embodiment 161-IV (Compound No. 161-IV) was obtained by the same procedure as in synthesis of the compound of Embodiment 54.

Synthesis of the Compound of Embodiment 162-IV

Compound No. 162-IV

Employing 21 mg of the aniline compound which is the synthetic intermediate of the compound of Embodiment 161-IV as starting material, 6 mg of the compound of Embodiment 162-IV (Compound No. 162-IV) was obtained by the same procedure as in synthesis of the compound of Embodiment 54-IV.

The ACC inhibition activity of the compounds of Mode 4 of the present invention was measured and the ACC inhibition activity rate was calculated in the same manner as described in Pharmacological Test Example 1. Table 4-IV gives the results

TABLE 4-IV

| Compd. No. | ACC Inhibition (%) |
| --- | --- |
| 8 | 50 |
| 16 | 86 |
| 20 | 85 |
| 23 | 74 |
| 24 | 89 |
| 25 | 97 |
| 26 | 78 |
| 27 | 91 |
| 28 | 92 |
| 31 | 72 |
| 33 | 61 |
| 34 | 67 |
| 35 | 91 |
| 36 | 87 |
| 37 | 86 |
| 39 | 99 |
| 40 | 87 |
| 41 | 85 |
| 42 | 76 |
| 43 | 83 |
| 44 | 100 |
| 45 | 100 |
| 47 | 100 |
| 48 | 87 |
| 51 | 76 |
| 52 | 59 |
| 54 | 87 |
| 55 | 90 |
| 56 | 100 |
| 57 | 100 |
| 59 | 100 |
| 60 | 61 |
| 62 | 53 |
| 67 | 58 |
| 82 | 56 |
| 83 | 92 |
| 84 | 52 |
| 85 | 59 |
| 86 | 54 |
| 90 | 62 |
| 91 | 70 |
| 92 | 49 |
| 93 | 84 |
| 94 | 96 |
| 95 | 100 |
| 96 | 95 |
| 97 | 98 |
| 98 | 100 |
| 100 | 72 |
| 101 | 100 |
| 102 | 100 |
| 103 | 100 |
| 106 | 100 |
| 107 | 100 |
| 108 | 52 |
| 112 | 75 |
| 113 | 97 |
| 114 | 77 |
| 115 | 100 |
| 118 | 93 |
| 119 | 94 |
| 121 | 90 |
| 122 | 67 |
| 124 | 64 |
| 125 | 98 |
| 126 | 91 |
| 127 | 92 |
| 128 | 100 |
| 129 | 100 |
| 133 | 99 |
| 134 | 89 |
| 137 | 79 |
| 138 | 63 |
| 139 | 100 |
| 140 | 100 |
| 142 | 93 |
| 144 | 94 |
| 145 | 57 |
| 146 | 72 |
| 147 | 68 |
| 148 | 63 |
| 153 | 86 |
| 157 | 69 |
| 158 | 65 |
| 161 | 71 |
| 162 | 85 |

Further embodiments of the compound of Modes 2 and 3 of the present invention are described below.

The molecular structures and mass spectroscopy results of the synthesized compounds (Compounds 9-II, 131-III to 147-III) and NMR measurements of representative compounds are given in Tables 1-A, 2-A, and 3-A.

TABLE 1-A
| Compd. No. | MOLSTRUCTURE |
|---|---|
| 131-111 | 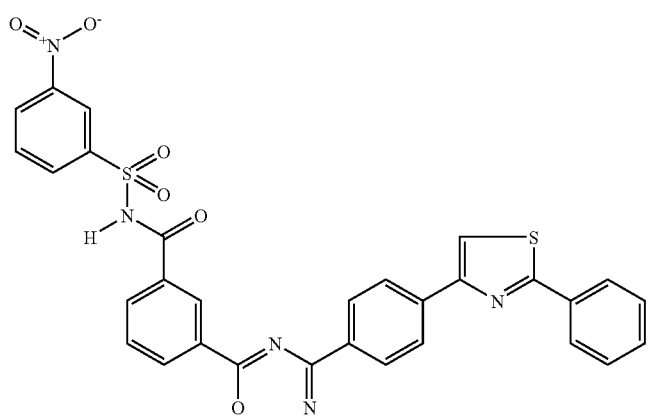 |
| 132-111 | 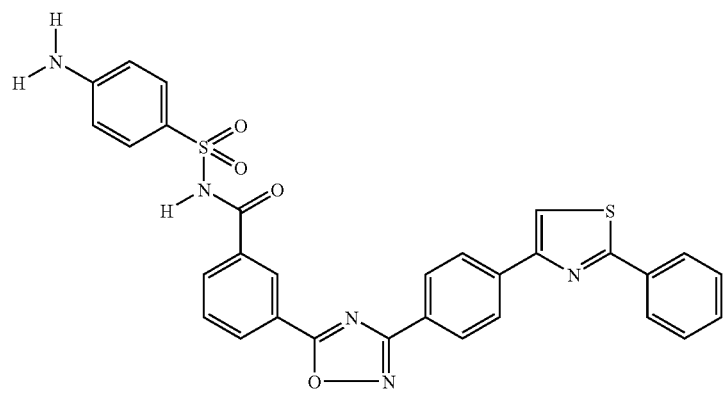 |
| 133-111 | 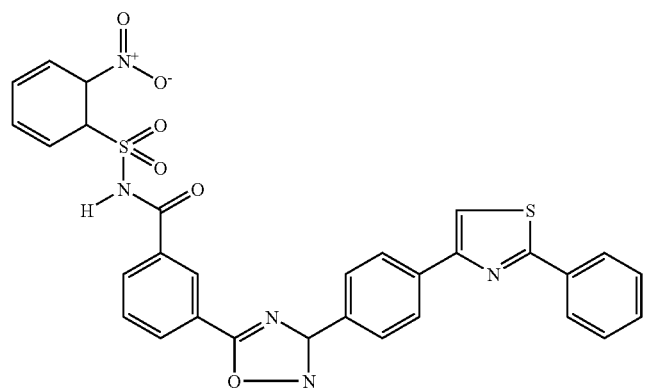 |

TABLE 1-A-continued

| Compd. No. | MOLSTRUCTURE |
|---|---|
| 134-111 | |
| 135-111 | |
| 136-111 | |
| 137-111 | |
| 138-111 | |

TABLE 1-A-continued
| Compd. No. | MOLSTRUCTURE |
|---|---|
| 139-111 | 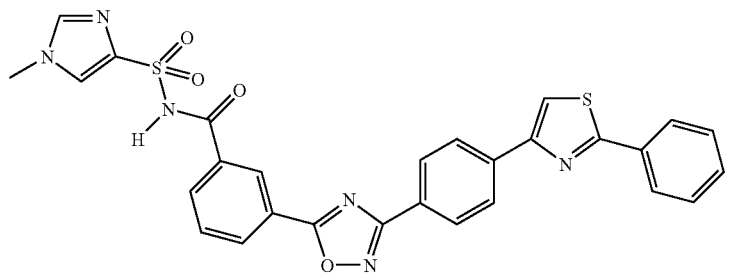 |
| 140-111 | 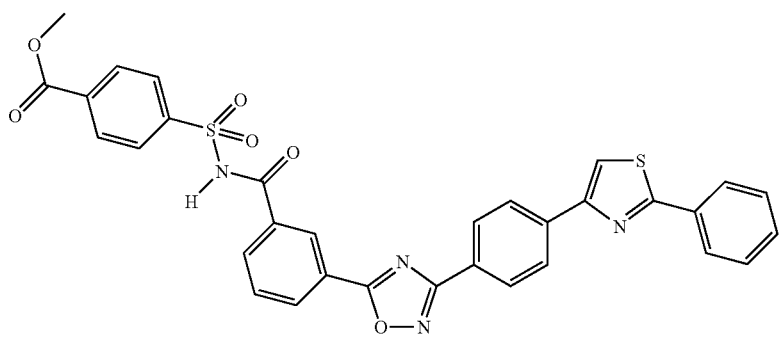 |
| 141-111 | 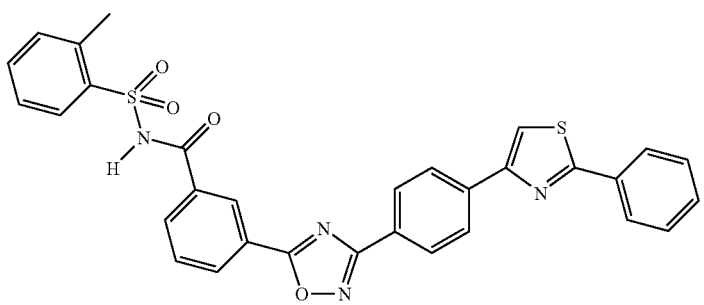 |
| 9-111 | 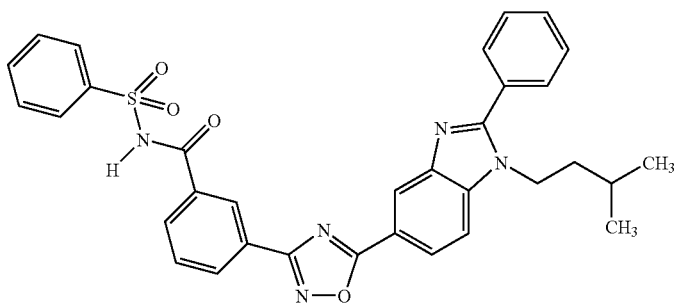 |
| 142-111 | 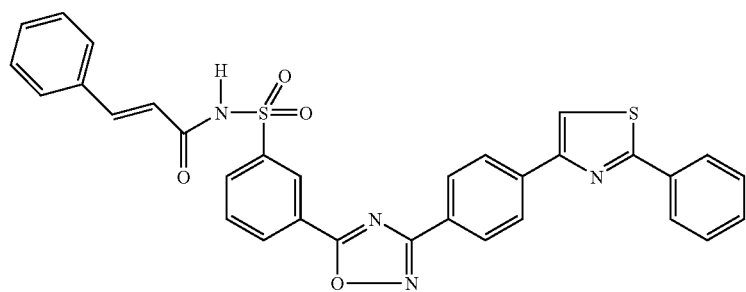 |

TABLE 1-A-continued
| Compd. No. | MOLSTRUCTURE |
|---|---|
| 143-111 | 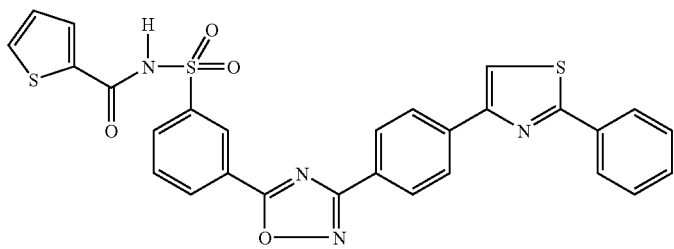 |
| 144-111 | 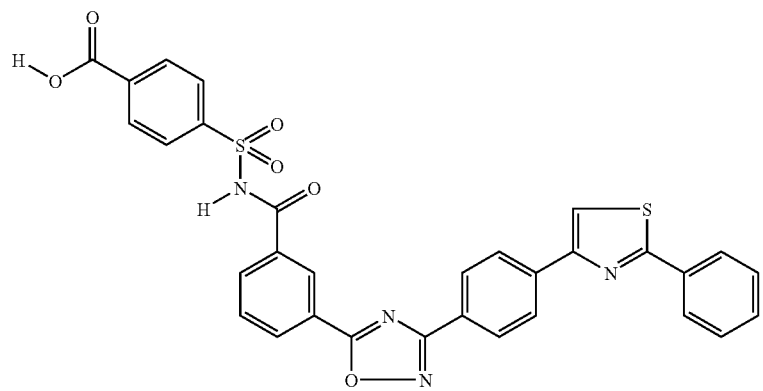 |
| 145-111 | 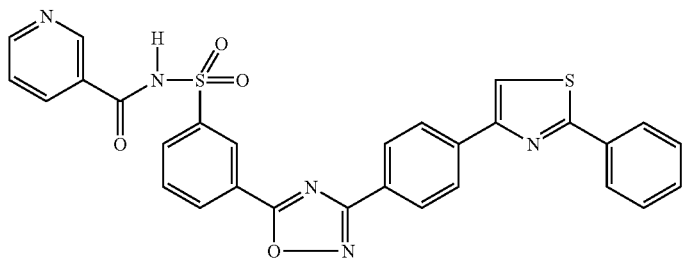 |
| 146-111 | 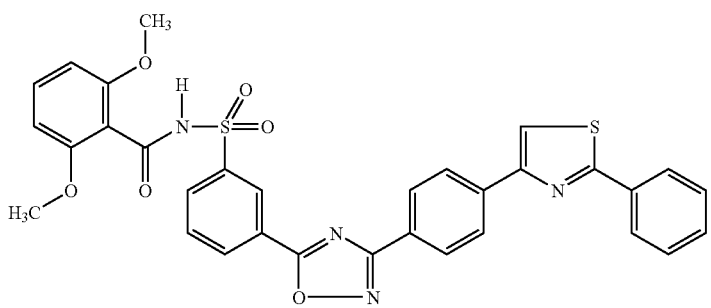 |
| 147-111 | 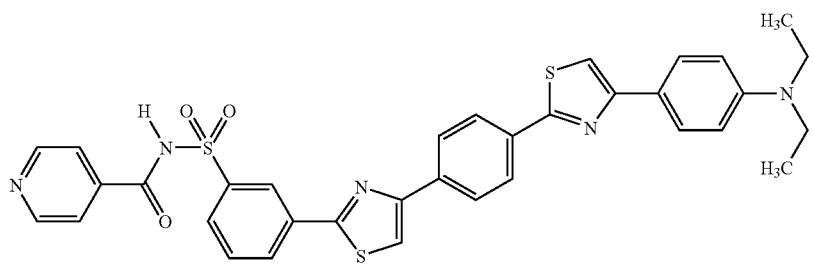 |

TABLE 2-A

| Compound No. | MS(ESI)(MH+) |
|---|---|
| 131-III | 610 |
| 132-III | 580 |
| 133-III | 610 |
| 134-III | 608 |
| 135-III | 565 |
| 136-III | 565 |
| 137-III | 580 |
| 138-III | 631 |
| 139-III | 569 |
| 140-III | 623 |
| 141-III | 579 |
| 9-II | 592 |
| 142-III | 591 |
| 143-III | 571 |
| 144-III | 609 |
| 145-III | 566 |
| 146-III | 625 |
| 147-III | 652 |

TABLE 3-A

| Compound No. | NMR | SOLVENT |
|---|---|---|
| 135-III | δ8.40(s, 1H), 8.32-8.26(m, 7H), 8.08 (d, 3H), 7.91(d, 2H), 7.56(d, 2H), 7.55 (br, 1H), 7.39-7.30(m, 3H). | DMSO-d6 |
| 136-III | δ8.67(br, 1H), 8.41(s, 1H), 8.32-8.23(m, 4H), 8.16(d, 1H), 8.09-8.06(m, 1H), 8.02-7.96(m, 1H), 7.91(d, 2H), 7.73(t, 1H), 7.60-7.50 (m, 4H), 7.40-7.30(m, 4H). | DSMO-d6 |
| 138-III | δ8.68(s, 1H), 8.41(s, 1H), 8.31-8.23(m, 4H), 8.20(d, 2H), 8.16 1H), 8.08(d, 2H), 8.02(d, 2H), 7.79(br, 1H), 7.72(t, 1H), 7.62(d, 2H), 7.59-7.54(m, 2H), 7.10 (s, 1H), 6.95(d, 2H). | DSMO-d6 |

Embodiment A

Synthesis of Compound No. 131-III

A thiazole compound was obtained from benzenesulfonamide and α-bromo-4'-cyanoacetophenone, and 302 mg (98 percent) of amideoxime compound was obtained by the usual procedure. This was reacted with the corresponding benzene di-carboxylic acid derivative to obtain an oxadiazole ring product (ester compound), which was hydrolyzed by the usual method to obtain a carboxylic acid serving as a synthetic intermediate.

30 mg (0.608 mmole) of the obtained synthetic intermediate was dissolved in 1 mL of DMF, 0.013 mL (0.12 mmole) of dimethylsulfamoyl chloride was added, and the mixture was stirred for 10 hours at room temperature. A separately prepared solution of 14 mg (0.0669 mole) of 2-nitrobenzenesulfonamide and 7 mg (0.0608 mmole) of DMAP in 0.26 ml (0.182 mmole) of butyldimethylamine and 1 mL of DMF was added and the mixture was stirred overnight at 60° C. When the reaction had ended, 1N hydrochloric acid was added and the mixture was extracted with ethyl acetate. The mixture was washed with saturated brine and dried with anhydrous sodium sulfate, after which the solvent was removed under reduced pressure. The residue was purified by recrystallization, yielding 40 mg of Compound No. 131-III.

Synthesis of Compound No. 132-III

Using corresponding starting materials, Compound Non 132-III was synthesized by the same procedure as Compound No. 131-III.

Synthesis of Compound No. 133-III

Employing 82 mg (0.406 mmole) of 2-nitrobenzenesulfonamide as starting material, 62 mg of Compound No. 133-III was obtained by the same method as in synthesis of Compound No. 131-III.

Synthesis of Compound No. 134-III

Employing corresponding starting materials, Compound No. 1 34-III was synthesized by the same procedure as Compound No. 131-III.

Synthesis of Compound No. 135-III

The para position was employed as the substitution position of the free carboxyl group on the synthesis intermediate of Compound No. 131, and a synthesis intermediate in which the carboxyl group had been replaced with a sulfonamide group was synthesized by the usual methods. 50 mg (0.11 mmole) of this synthetic intermediate, 27 mg (0.22 mmole) of 4-(dimethylamino)pyridine, 45 μL (0.33 mmole) of triethylamine, and 32 μL (0.26 mmole) of benzoyl chloride were added to 5 mL of dehydrated 1,4-dioxane and the mixture was stirred for 3 hours at room temperatures. The solvent was removed under reduced pressure and the residue was distributed in ethyl acetate/water (2/1). The organic layer was washed with saturated brine (10 mL×1) and dried with anhydrous magnesium sulfate. The product was filtered and then concentrated under reduced pressure. The obtained crude residue was purified by silica gel column chromatography, yielding 16 mg (0.0283 mmole, 26.0 percent) of targeted Compound No. 135-III.

Synthesis of Compound No. 136-III 26 mg of iron was added to a mixed solution (2 mL of methanol, 2 mL of tetrahydrofuran, and 2 mL of acetic acid) of 57 mg (0.093 mmole) of Compound No. 133-III and the mixture was stirred for 3 hours at 50° C. The mixture was filtered with celite and the solvent was removed under reduced pressure. Water-acetonitrile was added to the residue and the mixture was slurry washed, yielding 12 mg (22 percent) of Compound No. 137-III.

Synthesis of Compound No. 138-III 83 mg (0.441 mmole) of (1H-imidazole-1-yl)benzoic acid and 10 μL of dimethylformamide were added to 4 mL of thionyl chloride and the mixture was stirred for 2 hours at 80° C. The thionyl chloride was removed under reduced pressure and the residue was suspended in 10 mL of 1,4-dioxane. 163 mg (0.353 mmole) of the synthetic intermediate of Compound No. 137-III, 151 μL (1.08 mmole) of triethylamine, 60 mg (0.48 mmole) of 4-dimethylaminopyridine, and 10 mL of 1,4-dioxane were charged to a separate reactor, and while stirring this mixture, the earlier prepared acid chloride solution was gradually added. The mixture was then stirred for 24 hours at room temperature. The solvent was removed under reduced pressure and the residue was distributed in dichloromethane/water (7/3, 100 mL). The organic layer was dried with anhydrous magnesium sulfate, filtered, and concentrated under reduced pressure. The obtained residue was slurry washed with ethyl acetate (5 mL×4), yielding 89.7 mg of Compound No. 138-III.

Synthesis of Compound Nos. 139-III and 140-III

Employing corresponding starting materials, Compound Nos. 139-III and 140-III were synthesized by the same 4procedure as Compound No. 131-III.

Synthesis of Compound No. 141-III

Employing corresponding starting materials, 281 mg (83 percent) of Compound No. 141-III was obtained by the same procedure as Compound No. 131-III.

Synthesis of Compound No. 9-II 20 mL of N-methylpiperidone, 1.25 mL (15.8 mmoles) of pyridine, and 1.37 mL (9.6 mmoles) of 2,6-dichlorobenzoyl chloride were added to 2.0 g (2.4 mmoles) of Wang resin and 1.78 g (9.6 mmoles) of 4-fluoro-3-nitrobenzoic acid and the mixture was stirred for seven hours at room temperature. The mixture was sequentially washed with N,N-dimethylformamide, ethanol, and methylene chloride, yielding Wang resin ester.

2 mL of dimethylsulfoxide, 0.35 mL (2.0 mmoles) of diisopropylethylamine, and 0.464 mL (4.0 mmoles) of isoamylamine were added to 200 mg (0.2 mmole) of the above ester and the mixture was stirred for 13 hours. The mixture was sequentially washed with N,N-dimethylformamide, methanol, and methylene chloride, yielding nitroaniline compound.

812 mg (3.6 mmole) of stannous chloride dihydrate, 1.9 mL of N-methylpiperidone, and 0.1 mL of ethanol were added to 19.3 mg (0.18 mmole) of the nitroaniline compound and the mixture was stirred for 20 hours at room temperature.

The mixture was sequentially washed with N,N-dimethylformamide, methanol, and methylene chloride, yielding 186 mg of aniline compound.

186 mg (0.179 mmole) of the aniline compound, 119 mg (0.900 mmole) of benzoic acid, 122 mg (0.900 mmole) of HOAt, 69 uL (0.45 mmole) of diisopropylcarbodiimide, and 2 mL of N-methylpiperidone were added and the mixture was stirred for 18 hours at room temperature. The mixture was sequentially washed with N,N-dimethylformamide, ethanol, and methylene chloride; 2 mL of trifluoroacetic acid was added, and the mixture was stirred for 30 minutes, yielding 77 mg of amide compound.

Employing 77 mg (0.2 mmole) of the amide compound as starting material, 5 mg of Compound No. 9-II was obtained by the same procedure as in the synthesis of Compound No. 131-III.

Synthesis of Compound Nos. 142-III, 143-III, 145-III, 146-III, and 147-III

Compound Nos. 142-III, 143-III, 145-III, 146-III, and 147-III were synthesized using corresponding starting materials by the same procedure as Compound No. 131-III.

Synthesis of Compound No. 144-III

An ester compound was obtained using corresponding starting materials by the same method as in Compound No. 131-III. 0.5 mL of 1N-sodium hydroxide aqueous solution was added to a solution of 32 mg (0.051 mmole) of the obtained ester compound in 8 mL, of tetrahydrofuran and 2 mL of methanol and the mixture was stirred for 16 hours at room temperature. To the reaction solution was added 1N hydrochloric acid and the precipitating crystals were recovered by filtration (washed with methanol), yielding 30 mg (97 percent) of Compound No. 144-III.

The ACC inhibition activity of the compounds of Modes 2 and 3 of the present invention was measured and the ACC inhibition activity rate was calculated in the same manner as described for Pharmacological Test Example 1. The results are given in Table 4-A.

TABLE 4-A

| Compound No. | ACC Inhibition (%) | Compound No. | ACC Inhibition (%) |
|---|---|---|---|
| 131-III | 100 | 140-III | 92 |
| 132-III | 96 | 141-III | 100 |
| 133-III | 99 | 9-II | 72 |
| 134-III | 70 | 142-III | 100 |
| 135-III | 98 | 143-III | 83 |
| 136-III | 94 | 144-III | 97 |
| 137-III | 96 | 145-III | 84 |
| 138-III | 100 | 146-III | 79 |
| 139-III | 96 | 147-III | 65 |

INDUSTRIAL APPLICABILITY

The benzene compounds of the present invention and analogs thereof, which function by a different mechanism from conventional anti-obesity agents and insulin resistance-combating agents, can be used to treat the following: obesity; hyperlipemia (especially obesity-induced hyperlipemia) fatty liver; hyperglycemia, impaired glucose tolerance (especially insulin resistance-induced glucose tolerance impairment), diabetes, diabetic complications (diabetic peripheral neuropathy, diabetic nephropathy, diabetic retinopathy, and diabetic macroangiopathy), hypertension, and arteriosclerosis. They are extremely useful as drug treatments for these diseases.

The invention claimed is:

1. A compound of formula (1A-IV), or a pharmaceutically acceptable salt thereof:

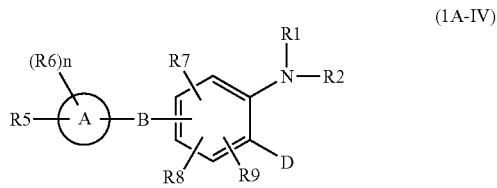

(1A-IV)

wherein ring A represents a benzene ring which is substituted with R5 and (R6)n, or an imidazole ring which is substituted with R5 and (R6)n;

B represents formula (ix):

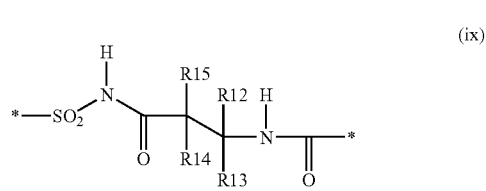

(ix)

wherein B is attached para to the NR1R2 substituent on the phenyl ring, and each of R12, R13, R14, and R15 represents a hydrogen atom, an unsubstituted alkyl group with 1 to 12 carbon atoms, an unsubstituted phenyl group or a cyclic alkyl group with 3 to 12 carbon atoms, or R12 and R13 may join together to make a five- or six-membered) ring;

D represents a nitro group, or an amino group substituted with R3 and R4;

each of R1, R2, R3, and R4 represents a) a hydrogen atom, b) an unsubstituted alkyl group with 1 to 12 carbon atoms, c) a substituted alkyl group with 1 to 12 carbon atoms which is substituted with 1) a phenyl group which may have further one or more substituents, 2) a naphthyl group, 3) a cyclic alkyl aroup with 3 to 6 carbon atoms, 4) a thienyl group, 5) a furyl group, 6) a thiazolyl group, 7) an isothiazolyl group, 8) an imidazolyl group, 9) a pyridyl group, or 10) a benzyloxy group, d) an unsubstituted alkenyl group with 2 to 12 carbon atoms, e) a substituted alkenyl group with 2 to 12 carbon atom which is substituted with phenyl group, f) an unsubstituted alkynyl group with 2 to 12 carbon atoms, g) a substituted alkynyl group with 2 to 12 carbon atom which is substituted with phenyl group, h) a phenyl group which may have further one or more substituents, i) an unsubstituted naphthyl group, j) an substituted acyl group with 1 to 18 carbon atoms, k) an unsubstituted pyridyl group, furyl group, or thienyl group, l) a cyclic alkyl group with 3 to 6 carbon atoms, or m) a tetrahydrothiapyrane-4-yl group; with R1, R2, R3, and R4 being the same or different, proviso that neither R1 and R2 nor R3 and R4 are joined together to form a five-, six-, or seven-membered ring which may comprise nitrogen atoms, oxygen atoms, or sulfur atoms;

wherein each of said one or more substituents on said phenyl group in c) and h) is halogen atom, alkyl group with 1 to 20 carbon atom, alkoxy group with 1 to 20 carbon atom, thiol group, nitro group, alkylamino group with 1 to 20 carbon atom, amino group, cyano group, hydroxyl group, alkylthio group with 1 to 20 carbon atom, carboxyl group, alkoxycarbonyl group with 1 to 20 carbon atom, acetamide group, or dimethylaminopropoxy group;

R5 represents an unsubstituted alkyl group with 1 to 12 carbon atoms, a hydrogen atom, or a carboxyl group;

R6 in (R6)n (wherein n is the number of substitutions of R6 and represents 1, 2, 3, 4, or 5) represents a hydrogen atom; and each of R7, R8, and R9 represents a hydrogen atom.

2. A pharmaceutical composition comprising i) a compound according to claim 1, or a pharmaceutically acceptable salt thereof, and ii) a pharmaceutical acceptable carrier.

3. The compound or pharmaceutically acceptable salt thereof according to claim 1, wherein each of R1 and R2 represents a) a hydrogen atom, b) an unsubstituted alkyl group with 1 to 12 carbon atoms, or l) a cyclic alkyl group with 3 to 6 carbon atoms, and each of R3 and R4 represents a) a hydrogen atom, b) an unsubstituted alkyl group with 1 to 12 carbon atoms, c) a substituted alkyl group with 1 to 12 carbon atoms which is substituted with 1) a phenyl group which may have further substituents, 3) a cyclic alkyl group with 3 to 6 carbon atoms, 4) a thienyl group, 5) a furyl group, 6) a thiazolyl group, or 10) a benzyloxy group, e) a substituted alkenyl group with 2 to 12 carbon atom which is substituted with phenyl group, h) a phenyl group which may have further substituents, l) a cyclic alkyl group with 3 to 6 carbon atoms, or m) a tetrahydrothiapyrane-4-yl group.

4. The compound or pharmaceutically acceptable salt thereof according to claim 3, wherein each of said one or more substituents on said phenyl group in c) and h) is nitro group, hydroxyl group, aceramide group, or dimethylaminopropoxy group.

5. The compound or pharmaceutically acceptable salt thereof according to claim 1, which has the structure:

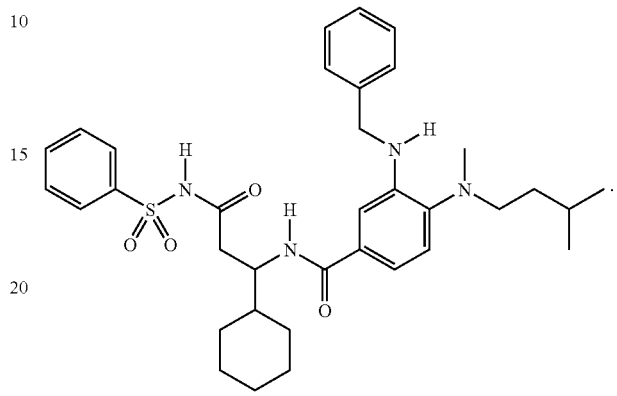

6. The compound or pharmaceutically acceptable salt thereof according to claim 1, which has the structure:

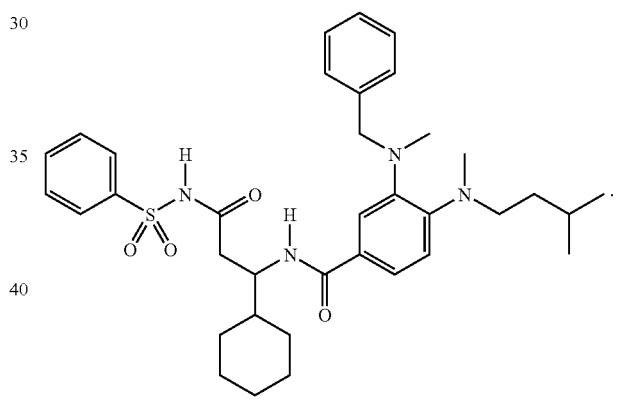

7. The compound or pharmaceutically acceptable salt thereof according to claim 1, which has the structure:

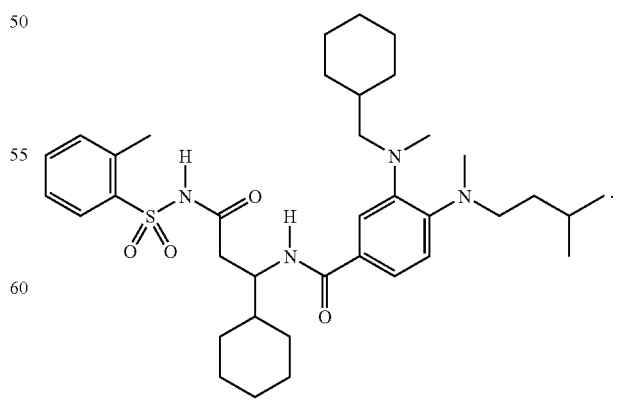

* * * * *